US012128035B2

United States Patent
Ericsson et al.

(10) Patent No.: US 12,128,035 B2
(45) Date of Patent: Oct. 29, 2024

(54) ACTIVATING PYRUVATE KINASE R

(71) Applicant: Novo Nordisk Health Care AG, Zurich (CH)

(72) Inventors: Anna Ericsson, Shrewsbury, MA (US); Neal Green, Newton, MA (US); Gary Gustafson, Ridgefield, CT (US); David R. Lancia, Jr., Boston, MA (US); Gary Marshall, Watertown, MA (US); Lorna Mitchell, Cambridge (NZ); David Richard, Littleton, MA (US); Zhongguo Wang, Lexington, MA (US); Sanjeev Forsyth, Milton, MA (US); Patrick F. Kelly, Concord, MA (US); Madhu Mondal, Winchester, MA (US); Maria Ribadeneira, Cambridge, MA (US); Patricia Schroeder, Somerville, MA (US)

(73) Assignee: Novo Nordisk Health Care AG, Zurich (CH)

(*) Notice: Subject to any disclaimer, the term of this patent is extended or adjusted under 35 U.S.C. 154(b) by 0 days.

(21) Appl. No.: 17/698,505

(22) Filed: Mar. 18, 2022

(65) Prior Publication Data
US 2022/0304987 A1     Sep. 29, 2022

Related U.S. Application Data

(60) Provisional application No. 63/163,362, filed on Mar. 19, 2021.

(51) Int. Cl.
 A61K 31/436 (2006.01)
 A61P 9/00 (2006.01)

(52) U.S. Cl.
 CPC .............. *A61K 31/436* (2013.01); *A61P 9/00* (2018.01)

(58) Field of Classification Search
 CPC .................................................. A61K 31/436
 See application file for complete search history.

(56) References Cited

U.S. PATENT DOCUMENTS

| | | |
|---|---|---|
| 4,602,093 A | 7/1986 | Baldwin et al. |
| 4,918,073 A | 4/1990 | Ruger et al. |
| 5,030,631 A | 7/1991 | Bauer |
| 5,037,467 A | 8/1991 | Cho et al. |
| 5,059,605 A | 10/1991 | Clough et al. |
| 5,089,621 A | 2/1992 | Kim et al. |
| 5,091,384 A | 2/1992 | Kim et al. |
| 5,180,719 A | 1/1993 | White et al. |
| 5,250,544 A | 10/1993 | Lavielle et al. |
| 5,336,772 A | 8/1994 | Saiki et al. |
| 5,480,899 A | 1/1996 | Yano et al. |
| 5,672,601 A | 9/1997 | Cignarella |
| 5,714,625 A | 2/1998 | Hada et al. |
| 5,747,502 A | 5/1998 | Hanaoka et al. |
| 5,962,703 A | 10/1999 | Moszner et al. |
| 6,214,879 B1 | 4/2001 | Abraham et al. |
| 6,534,501 B2 | 3/2003 | Abraham et al. |
| 6,710,052 B2 | 3/2004 | Pease et al. |
| 6,878,715 B1 | 4/2005 | Klein et al. |
| 7,138,401 B2 | 11/2006 | Kasibhatla et al. |
| 7,160,885 B2 | 1/2007 | Currie et al. |
| 7,875,603 B2 | 1/2011 | Rathinavelu et al. |
| 8,501,953 B2 | 8/2013 | Salituro et al. |
| 8,552,050 B2 | 10/2013 | Cantley et al. |
| 8,692,001 B2 | 4/2014 | Becker et al. |
| 8,742,119 B2 | 6/2014 | Salituro et al. |
| 8,785,450 B2 | 7/2014 | Salituro et al. |
| 8,841,305 B2 | 9/2014 | Thomas et al. |
| 8,877,791 B2 | 11/2014 | Cantley et al. |
| 8,889,667 B2 | 11/2014 | Salituro et al. |
| 8,952,171 B2 | 2/2015 | Xu et al. |
| 9,012,450 B2 | 4/2015 | Metcalf et al. |
| 9,018,210 B2 | 4/2015 | Metcalf et al. |
| 9,108,921 B2 | 8/2015 | Cianchetta et al. |
| 9,181,231 B2 | 11/2015 | Su |
| 9,221,792 B2 | 12/2015 | Salituro et al. |
| 9,248,199 B2 | 2/2016 | Metcalf |
| 9,328,077 B2 | 5/2016 | Salituro et al. |
| 9,394,257 B2 | 7/2016 | Ho et al. |
| 9,422,279 B2 | 8/2016 | Metcalf et al. |
| 9,458,132 B2 | 10/2016 | Cianchetta et al. |

(Continued)

FOREIGN PATENT DOCUMENTS

| | | |
|---|---|---|
| CN | 101812063 A | 8/2010 |
| CN | 102206217 A | 10/2011 |

(Continued)

OTHER PUBLICATIONS

Abbady M.A., et al., Synthesis and biological activity of some new 4-(2-pyrazolin-3-yl)-, 4-(2-isoxazolin-e-yl)- and 4-(1,2,5,6-tetrahydro-2-thioxopyrimidin-4-yl)phenyl aminophenyl sulfides and sulfones., *Egyptian Journal of Pharmaceutical Sciences*, vol. 27, No. 1-4, (1986), Abstract Only.

Abraham DJ, Mehanna AS, Wireko FC, et al. "Vanillin, a potential agent for the treatment of sickle cell anemia." *Blood*. 1991;77(6):1334-41.

Adakveo [package insert]. East Hanover, New Jersey, Novartis Pharmaceuticals Corporation (Nov. 2019), 10 pgs.

Agios First Quarter 2020 Financial Results (Apr. 30, 2020), pp. 1-22.

Agrawal RK, Patel RK, Shah V, Nainiwal L, Trivedi B. "Hydroxyurea in sickle cell disease: drug review." *Indian J Hematol Blood Transfus*. Jun. 2014, 30(2):91(2)96.

(Continued)

*Primary Examiner* — Paul V Ward
(74) *Attorney, Agent, or Firm* — Jianjie Hu

(57) ABSTRACT

The compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a pharmaceutically acceptable salt thereof, is useful to increase the affinity of hemoglobin for oxygen. Methods and compositions for the treatment of a hemoglobinopathies are provided herein, including certain pharmaceutical compositions for activating PKR.

21 Claims, 65 Drawing Sheets

(56) References Cited

U.S. PATENT DOCUMENTS

| | | | |
|---|---|---|---|
| 9,458,139 B2 | 10/2016 | Xu et al. |
| 9,604,999 B2 | 3/2017 | Harris et al. |
| 9,708,267 B2 | 7/2017 | Boxer et al. |
| 9,744,145 B1 | 8/2017 | Liu et al. |
| 9,776,960 B2 | 10/2017 | Xu et al. |
| 9,802,900 B2 | 10/2017 | Li et al. |
| 9,957,250 B2 | 5/2018 | Metcalf et al. |
| 9,981,939 B2 | 5/2018 | Metcalf et al. |
| 10,004,725 B2 | 6/2018 | Dufu et al. |
| 10,017,491 B2 | 7/2018 | Metcalf et al. |
| 10,034,879 B2 | 7/2018 | Metcalf et al. |
| 10,077,249 B2 | 9/2018 | Li et al. |
| 10,100,040 B2 | 10/2018 | Li et al. |
| 10,100,043 B2 | 10/2018 | Metcalf et al. |
| 10,208,052 B1 | 2/2019 | Zheng et al. |
| 10,266,551 B2 | 4/2019 | Li et al. |
| 10,315,991 B2 | 6/2019 | Xu et al. |
| 10,377,741 B2 | 8/2019 | Metcalf et al. |
| 10,435,393 B2 | 10/2019 | Xu et al. |
| 10,450,269 B1 | 10/2019 | Xu et al. |
| 10,472,371 B2 | 11/2019 | Zheng et al. |
| 10,493,035 B2 | 12/2019 | Dalziel et al. |
| 10,577,345 B2 | 3/2020 | Li et al. |
| 10,675,274 B2 | 6/2020 | Ericsson et al. |
| 10,683,285 B2 | 6/2020 | Li |
| 10,695,330 B2 | 6/2020 | Li et al. |
| 10,836,771 B2 | 11/2020 | Zheng et al. |
| 11,014,927 B2 | 5/2021 | Ericsson et al. |
| 11,071,725 B2 | 7/2021 | Ericsson et al. |
| 11,396,513 B2 | 7/2022 | Zheng et al. |
| 11,649,242 B2 | 5/2023 | Ericsson et al. |
| 11,844,787 B2 | 12/2023 | Ericsson et al. |
| 11,980,611 B2 | 5/2024 | Ericsson et al. |
| 2004/0077648 A1 | 4/2004 | Timmer et al. |
| 2004/0102458 A1 | 5/2004 | Chiosis et al. |
| 2005/0002861 A1 | 1/2005 | Krause et al. |
| 2005/0049263 A1 | 3/2005 | Kasibhatla et al. |
| 2005/0059663 A1 | 3/2005 | Martin et al. |
| 2005/0181305 A1 | 8/2005 | Shibuya |
| 2005/0256103 A1 | 11/2005 | Suzuki et al. |
| 2006/0074121 A1 | 4/2006 | Chen et al. |
| 2006/0211737 A1 | 9/2006 | Huang et al. |
| 2007/0015752 A1 | 1/2007 | Hangauer, Jr. |
| 2007/0270433 A1 | 11/2007 | Brinkman et al. |
| 2008/0058315 A1 | 3/2008 | Cai et al. |
| 2008/0184495 A1 | 8/2008 | Brun et al. |
| 2008/0253965 A1 | 10/2008 | Chiosis et al. |
| 2008/0269234 A1 | 10/2008 | Gandhi et al. |
| 2009/0042966 A1 | 2/2009 | Coleman et al. |
| 2009/0163545 A1 | 6/2009 | Goldfarb |
| 2009/0291921 A1 | 11/2009 | Jabri et al. |
| 2010/0029575 A1 | 2/2010 | Junien et al. |
| 2010/0120863 A1 | 5/2010 | Biftu et al. |
| 2010/0144594 A1 | 6/2010 | Zoller et al. |
| 2010/0144722 A1 | 6/2010 | Alexander et al. |
| 2010/0152157 A1 | 6/2010 | Puech et al. |
| 2010/0179154 A1 | 7/2010 | Almario Garcia et al. |
| 2010/0216774 A1 | 8/2010 | Bender et al. |
| 2010/0324030 A1 | 12/2010 | Dale et al. |
| 2011/0059089 A1 | 3/2011 | Swagemakers et al. |
| 2011/0085969 A1 | 4/2011 | Rollo et al. |
| 2011/0104054 A1 | 5/2011 | Chiosis et al. |
| 2012/0134979 A1 | 5/2012 | Xia et al. |
| 2012/0252818 A1 | 10/2012 | Chiosis et al. |
| 2013/0109684 A1 | 5/2013 | Blagg et al. |
| 2013/0116430 A1 | 5/2013 | Fujiwara et al. |
| 2013/0155489 A1 | 6/2013 | Kato et al. |
| 2013/0190315 A1 | 7/2013 | Metcalf et al. |
| 2013/0190316 A1 | 7/2013 | Metcalf et al. |
| 2014/0228360 A1 | 8/2014 | Duncan et al. |
| 2014/0242602 A1 | 8/2014 | Chiosis et al. |
| 2015/0246025 A1 | 9/2015 | Desai et al. |
| 2016/0106728 A1 | 4/2016 | Shen et al. |
| 2016/0200681 A1 | 7/2016 | Yu et al. |
| 2017/0121338 A1 | 5/2017 | Zhang et al. |
| 2017/0216434 A1 | 8/2017 | Hines et al. |
| 2017/0217964 A1 | 8/2017 | Li |
| 2018/0215765 A1 | 8/2018 | Di Giorgio et al. |
| 2018/0282369 A1 | 10/2018 | Desai et al. |
| 2019/0218221 A1 | 7/2019 | Zheng et al. |
| 2020/0031839 A1 | 1/2020 | Zheng et al. |
| 2020/0069643 A1 | 3/2020 | Ericsson |
| 2020/0085798 A1 | 3/2020 | Ericsson |
| 2020/0087309 A1 | 3/2020 | Lancia, Jr. |
| 2020/0129485 A1* | 4/2020 | Ericsson ............ A61K 31/436 |
| 2020/0253939 A1 | 8/2020 | Ericsson et al. |
| 2021/0017184 A1 | 1/2021 | Zheng et al. |
| 2021/0246143 A1 | 8/2021 | Ericsson et al. |
| 2022/0031671 A1 | 2/2022 | Ericsson et al. |
| 2022/0378755 A1 | 12/2022 | Luke et al. |
| 2022/0378756 A1 | 12/2022 | Ericsson et al. |
| 2024/0083901 A1 | 3/2024 | Ericsson et al. |
| 2024/0131011 A1 | 4/2024 | Luke et al. |

FOREIGN PATENT DOCUMENTS

| | | |
|---|---|---|
| CN | 102952139 A | 3/2013 |
| CN | 103570722 A | 2/2014 |
| CN | 104736534 A | 6/2015 |
| CN | 105037367 A | 11/2015 |
| CN | 105085528 A | 11/2015 |
| CN | 105153119 A | 12/2015 |
| CN | 105254628 A | 1/2016 |
| CN | 105294694 A | 2/2016 |
| CN | 105348286 A | 2/2016 |
| CN | 106928222 A | 7/2017 |
| CN | 109912610 A | 6/2019 |
| DE | 102008010661 A1 | 9/2009 |
| EP | 0007529 A1 | 2/1980 |
| EP | 0036711 A2 | 9/1981 |
| EP | 0264883 A2 | 4/1988 |
| EP | 0273534 A2 | 7/1988 |
| EP | 0338372 A2 | 10/1988 |
| EP | 0363212 A2 | 4/1990 |
| EP | 0378255 A2 | 7/1990 |
| EP | 0424850 A1 | 5/1991 |
| EP | 0424851 A1 | 5/1991 |
| EP | 0424852 A1 | 5/1991 |
| EP | 0486022 A2 | 5/1992 |
| EP | 0520277 A2 | 12/1992 |
| EP | 0590415 A2 | 4/1994 |
| EP | 0737670 A1 | 10/1996 |
| EP | 1096310 A2 | 5/2001 |
| EP | 1099692 A1 | 5/2001 |
| EP | 1249233 A1 | 10/2002 |
| EP | 1952800 A2 | 8/2008 |
| EP | 3141542 A1 | 3/2017 |
| EP | 2797416 B1 | 8/2017 |
| EP | 3483164 A1 | 5/2019 |
| IN | 1809/MUM/2013 | 5/2013 |
| IN | 2013/MU01809 | 3/2015 |
| JP | S 61 200544 | 9/1986 |
| JP | 3 13040 B2 | 2/1991 |
| JP | 3 275666 | 12/1991 |
| JP | 04 054181 A | 2/1992 |
| JP | 05125050 A | 5/1993 |
| JP | 05 196976 | 8/1993 |
| JP | 7 164400 | 6/1995 |
| JP | 1 110376 | 1/1999 |
| JP | 2001261653 A | 9/2001 |
| JP | 2003514673 | 4/2003 |
| JP | 2004175674 A | 6/2004 |
| JP | 2007246885 A | 9/2007 |
| JP | 2007328090 A | 12/2007 |
| JP | 2008031064 A | 2/2008 |
| JP | 2008063256 A | 3/2008 |
| JP | 2009149707 A | 7/2009 |
| JP | 2009212473 A | 9/2009 |
| JP | 2010192782 A | 9/2010 |
| JP | 2011246649 A | 12/2011 |
| JP | 2012188474 A | 10/2012 |
| JP | 2012188475 A | 10/2012 |
| JP | 2013171968 A | 9/2013 |
| KR | 20110096442 A | 8/2011 |

(56) References Cited

FOREIGN PATENT DOCUMENTS

| | | |
|---|---|---|
| LB | 11379 | 7/2018 |
| RU | 2517693 C2 | 4/2011 |
| RU | 2472794 C1 | 11/2012 |
| WO | WO 1993/011106 | 6/1993 |
| WO | WO 1993/022298 A1 | 11/1993 |
| WO | WO 1995/019353 A1 | 7/1995 |
| WO | WO 1998/038239 | 9/1998 |
| WO | WO 1998/050364 A1 | 11/1998 |
| WO | WO 1999/001442 A1 | 1/1999 |
| WO | WO 1999/002493 A1 | 1/1999 |
| WO | WO 1999/047489 A1 | 9/1999 |
| WO | WO 1999/047516 A1 | 9/1999 |
| WO | WO 1999/048461 A2 | 9/1999 |
| WO | WO 1999/048490 A1 | 9/1999 |
| WO | WO 1999/065895 A1 | 12/1999 |
| WO | WO 1999/065901 | 12/1999 |
| WO | WO 2000/004023 A1 | 1/2000 |
| WO | WO 2000/021951 A1 | 4/2000 |
| WO | WO 2000/053591 A1 | 9/2000 |
| WO | WO 2001/010842 A2 | 2/2001 |
| WO | WO 2001/032764 | 5/2001 |
| WO | WO 2001/043744 A1 | 6/2001 |
| WO | WO 2001/053288 A2 | 7/2001 |
| WO | WO 2001/057037 A2 | 8/2001 |
| WO | WO 2001/085728 A2 | 11/2001 |
| WO | WO 2002/030358 | 4/2002 |
| WO | WO 2002/034754 A2 | 5/2002 |
| WO | WO 2002/060902 A1 | 8/2002 |
| WO | WO 2002/076989 A1 | 10/2002 |
| WO | WO 2002/095063 A1 | 11/2002 |
| WO | WO 2003/015769 A1 | 2/2003 |
| WO | WO 2003/037860 A2 | 5/2003 |
| WO | WO 2003/063794 | 8/2003 |
| WO | WO 2003/067332 A2 | 8/2003 |
| WO | WO 2003/084948 A1 | 10/2003 |
| WO | WO 2004/002490 A2 | 1/2004 |
| WO | WO 2004/007770 A2 | 1/2004 |
| WO | WO 2004/009600 A1 | 1/2004 |
| WO | WO 2004/013144 A1 | 2/2004 |
| WO | WO 2004/014374 A1 | 2/2004 |
| WO | WO 2004/014382 | 2/2004 |
| WO | WO 2004/024676 A1 | 3/2004 |
| WO | WO 2004/080457 A1 | 9/2004 |
| WO | WO 2004/089470 A2 | 10/2004 |
| WO | WO 2004/089947 A2 | 10/2004 |
| WO | WO 2004/104000 A1 | 12/2004 |
| WO | WO 2005/000098 A2 | 1/2005 |
| WO | WO 2005/002577 A1 | 1/2005 |
| WO | WO 2005/009965 A1 | 2/2005 |
| WO | WO 2005/011653 A2 | 2/2005 |
| WO | WO 2005/011656 A2 | 2/2005 |
| WO | WO 2005/016915 A1 | 2/2005 |
| WO | WO 2005/023761 A2 | 3/2005 |
| WO | WO 2005/049570 | 6/2005 |
| WO | WO 2005/058869 | 6/2005 |
| WO | WO 2005/058870 | 6/2005 |
| WO | WO 2005/058871 | 6/2005 |
| WO | WO 2005/058873 | 6/2005 |
| WO | WO 2005/058874 | 6/2005 |
| WO | WO 2005/084667 A1 | 9/2005 |
| WO | WO 2005/094251 A2 | 10/2005 |
| WO | WO 2005/094834 A1 | 10/2005 |
| WO | WO 2005/103015 A1 | 11/2005 |
| WO | WO 2006/002100 A2 | 1/2006 |
| WO | WO 2006/009886 A1 | 1/2006 |
| WO | WO 2006/018279 A2 | 2/2006 |
| WO | WO 2006/018280 A2 | 2/2006 |
| WO | WO 2006/021448 A1 | 3/2006 |
| WO | WO 2006/023608 A2 | 3/2006 |
| WO | WO 2006/034315 A2 | 3/2006 |
| WO | WO 2006/038172 A1 | 4/2006 |
| WO | WO 2006/060122 A2 | 6/2006 |
| WO | WO 2006/084030 A2 | 8/2006 |
| WO | WO 2006/086445 A2 | 8/2006 |
| WO | WO 2006/099884 A1 | 9/2006 |
| WO | WO 2006/101521 A2 | 9/2006 |
| WO | WO 2006/110390 A1 | 10/2006 |
| WO | WO 2006/123121 A1 | 11/2006 |
| WO | WO 2006/130469 A1 | 12/2006 |
| WO | WO 2006/137485 A1 | 12/2006 |
| WO | WO 2007/006926 A2 | 1/2007 |
| WO | WO 2007/007069 A1 | 1/2007 |
| WO | WO 2007/019344 A1 | 2/2007 |
| WO | WO 2007/027734 A2 | 3/2007 |
| WO | WO 2007/042325 A1 | 4/2007 |
| WO | WO 2007/083119 A2 | 7/2007 |
| WO | WO 2007/087231 A2 | 8/2007 |
| WO | WO 2007/088123 A2 | 8/2007 |
| WO | WO 2007/097931 A2 | 8/2007 |
| WO | WO 2007/098418 A1 | 8/2007 |
| WO | WO 2007/126745 A2 | 11/2007 |
| WO | WO 2007/136603 A2 | 11/2007 |
| WO | WO 2007/138351 A2 | 12/2007 |
| WO | WO 2008/005937 A2 | 1/2008 |
| WO | WO 2008/019139 A2 | 2/2008 |
| WO | WO 2008/032905 A1 | 3/2008 |
| WO | WO 2008/057608 A2 | 5/2008 |
| WO | WO 2008/083027 A1 | 7/2008 |
| WO | WO 2008/094203 A2 | 8/2008 |
| WO | WO 2008/115719 A1 | 9/2008 |
| WO | WO 2008/120003 A1 | 10/2008 |
| WO | WO 2008/135141 A1 | 11/2008 |
| WO | WO 2008/139585 A1 | 11/2008 |
| WO | WO 2009/001126 A1 | 12/2008 |
| WO | WO 2009/004356 A1 | 1/2009 |
| WO | WO 2009/025781 A1 | 2/2009 |
| WO | WO 2009/025784 A1 | 2/2009 |
| WO | WO 2009/063244 A1 | 5/2009 |
| WO | WO 2009/077527 A1 | 6/2009 |
| WO | WO 2009/093032 A1 | 7/2009 |
| WO | WO 2009/112677 | 9/2009 |
| WO | WO 2009/121623 A2 | 10/2009 |
| WO | WO 2009/136889 A1 | 11/2009 |
| WO | WO 2009/153554 A1 | 12/2009 |
| WO | WO 2010/002802 A1 | 1/2010 |
| WO | WO 2010/021717 A2 | 2/2010 |
| WO | WO 2010/028761 A1 | 3/2010 |
| WO | WO 2010/042867 A2 | 4/2010 |
| WO | WO 2010/058318 A1 | 5/2010 |
| WO | WO 2010/092181 A1 | 8/2010 |
| WO | WO 2010/105243 A1 | 9/2010 |
| WO | WO 2010/108268 A1 | 9/2010 |
| WO | WO 2010/115688 A1 | 10/2010 |
| WO | WO 2010/118063 | 10/2010 |
| WO | WO 2010/129596 | 11/2010 |
| WO | WO 2010/132599 A1 | 11/2010 |
| WO | WO 2010/135524 A1 | 11/2010 |
| WO | WO 2010/151797 | 12/2010 |
| WO | WO 2011/002816 | 1/2011 |
| WO | WO 2011/002817 | 1/2011 |
| WO | WO 2011/025690 A1 | 3/2011 |
| WO | WO 2011/037793 A1 | 3/2011 |
| WO | WO 2011/050210 | 4/2011 |
| WO | WO 2011/050211 | 4/2011 |
| WO | WO 2011/060321 A1 | 5/2011 |
| WO | WO 2011/063055 A2 | 5/2011 |
| WO | WO 2011/103256 A1 | 8/2011 |
| WO | WO 2011/116282 A2 | 9/2011 |
| WO | WO 2011/137089 A1 | 11/2011 |
| WO | WO 2011/146358 A1 | 11/2011 |
| WO | WO 2012/002577 A1 | 1/2012 |
| WO | WO 2012/007861 A1 | 1/2012 |
| WO | WO 2012/007868 A2 | 1/2012 |
| WO | WO 2012/007877 A2 | 1/2012 |
| WO | WO 2012/019426 A1 | 2/2012 |
| WO | WO 2012/019427 A1 | 2/2012 |
| WO | WO 2012/056319 A1 | 5/2012 |
| WO | WO 2012/068096 A2 | 5/2012 |
| WO | WO 2012/071519 A1 | 5/2012 |
| WO | WO 2012/071684 A1 | 6/2012 |
| WO | WO 2012/080729 A2 | 6/2012 |
| WO | WO 2012/083246 | 6/2012 |
| WO | WO 2012/088314 | 6/2012 |
| WO | WO 2012/092426 A1 | 7/2012 |

(56) References Cited

FOREIGN PATENT DOCUMENTS

| | | |
|---|---|---|
| WO | WO 2012/092442 | 7/2012 |
| WO | WO 2012/092485 A1 | 7/2012 |
| WO | WO 2012/151440 A1 | 11/2012 |
| WO | WO 2012/151448 A1 | 11/2012 |
| WO | WO 2012/151450 A1 | 11/2012 |
| WO | WO 2012/151451 A1 | 11/2012 |
| WO | WO 2012/151452 A1 | 11/2012 |
| WO | WO 2012/160392 | 11/2012 |
| WO | WO 2012/160447 A1 | 11/2012 |
| WO | WO 2012/174126 | 12/2012 |
| WO | WO 2013/003249 A1 | 1/2013 |
| WO | WO 2013/003250 A1 | 1/2013 |
| WO | WO 2013/021054 A1 | 2/2013 |
| WO | WO 2013/038390 A1 | 3/2013 |
| WO | WO 2013/056153 | 4/2013 |
| WO | WO 2013/102142 A1 | 7/2013 |
| WO | WO 2013/102826 A1 | 7/2013 |
| WO | WO 2013/118805 A1 | 8/2013 |
| WO | WO 2013/126856 A1 | 8/2013 |
| WO | WO 2013/127266 A1 | 9/2013 |
| WO | WO 2013/155223 A1 | 10/2013 |
| WO | WO 2013/177224 A1 | 11/2013 |
| WO | WO 2013/184794 A2 | 12/2013 |
| WO | WO 2014/008458 A2 | 1/2014 |
| WO | WO 2014/014050 A1 | 1/2014 |
| WO | WO 2014/018355 A1 | 1/2014 |
| WO | WO 2014/023814 A1 | 2/2014 |
| WO | WO 2014/044356 A1 | 3/2014 |
| WO | WO 2014/048865 A1 | 4/2014 |
| WO | WO 2014/061031 A1 | 4/2014 |
| WO | WO 2014/062838 A2 | 4/2014 |
| WO | WO 2014/074848 | 5/2014 |
| WO | WO 2014/102817 A1 | 7/2014 |
| WO | WO 2014/118634 A1 | 8/2014 |
| WO | WO 2014/130890 A1 | 8/2014 |
| WO | WO 2014/139144 A1 | 9/2014 |
| WO | WO 2014/139325 A1 | 9/2014 |
| WO | WO 2014/139978 A1 | 9/2014 |
| WO | WO 2014/144715 A1 | 9/2014 |
| WO | WO 2014/150276 A1 | 9/2014 |
| WO | WO 2014/152588 A1 | 9/2014 |
| WO | WO 2014/172638 A2 | 10/2014 |
| WO | WO 2015/030514 A1 | 3/2015 |
| WO | WO 2015/036078 | 3/2015 |
| WO | WO 2015/042397 A1 | 3/2015 |
| WO | WO 2015/048336 A2 | 4/2015 |
| WO | WO 2015/051230 A1 | 4/2015 |
| WO | WO 2015/054555 A1 | 4/2015 |
| WO | WO 2015/078374 A1 | 6/2015 |
| WO | WO 2015/093948 A2 | 6/2015 |
| WO | WO 2015/116061 A1 | 8/2015 |
| WO | WO 2015/130915 A1 | 9/2015 |
| WO | WO 2015/144605 A1 | 10/2015 |
| WO | WO 2015/172732 A1 | 11/2015 |
| WO | WO 2015/183173 A1 | 12/2015 |
| WO | WO 2015/192701 A1 | 12/2015 |
| WO | WO 2016/005576 A1 | 1/2016 |
| WO | WO 2016/005577 A1 | 1/2016 |
| WO | WO 2016/014324 A1 | 1/2016 |
| WO | WO 2016/014522 A1 | 1/2016 |
| WO | WO 2016/021815 | 2/2016 |
| WO | WO 2016/044604 A1 | 3/2016 |
| WO | WO 2016/044629 A1 | 3/2016 |
| WO | WO 2016/044650 A1 | 3/2016 |
| WO | WO 2016/046837 A1 | 3/2016 |
| WO | WO 2016/047592 A1 | 3/2016 |
| WO | WO 2016/168647 A1 | 10/2016 |
| WO | WO 2016/181408 A2 | 11/2016 |
| WO | WO 2016/196816 | 12/2016 |
| WO | WO 2016/201227 A1 | 12/2016 |
| WO | WO 2017/006270 | 1/2017 |
| WO | WO 2017/050791 A1 | 3/2017 |
| WO | WO 2017/050792 A1 | 3/2017 |
| WO | WO 2017/191274 A2 | 11/2017 |
| WO | WO 2017/214002 A1 | 12/2017 |
| WO | WO 2018/049263 A1 | 3/2018 |
| WO | WO 2018/109277 A1 | 6/2018 |
| WO | WO 2018/175474 A1 | 9/2018 |
| WO | WO 2019/035863 A1 | 2/2019 |
| WO | WO 2019/035864 A1 | 2/2019 |
| WO | WO 2019/035865 A1 | 2/2019 |
| WO | WO 2019/099651 A1 | 5/2019 |
| WO | WO 2019/104134 | 5/2019 |
| WO | WO 2019/113359 | 6/2019 |
| WO | WO 2020/061252 | 3/2020 |
| WO | WO 2020/061255 | 3/2020 |
| WO | WO 2020/061261 | 3/2020 |
| WO | WO 2020/061378 | 3/2020 |
| WO | 2020139916 A1 | 7/2020 |
| WO | WO 2020/191022 | 9/2020 |

OTHER PUBLICATIONS

Agrawal, R. K. et al., "Hydroxyurea in Sickle Cell Disease: Drug Review", *Indian J. Hematol Blood Transfus*, 30(2), pp. 91-96, (Apr.-Jun. 2014).

Aiuti, A. et al, Progress and prospects: gene therapy clinical trials (part 2), *Gene Ther*, 14(22): 1555-1563 (2007).

Al-Hakim, A.K. et al., 14-3-3 cooperates with LKB1 to regulate the activity and localization of QSK and SIK, *Journal of Cell Science* 118 (23), pp. 5661-5673 (Aug. 2005).

Al-Hakim, A.K. et al., "Control of AMPK-related kinases by USP9X and atypical Ly529/Ly533-linked polyubiquitin chains", *Biochemical Journal*, 411 (2), pp. 249-260, (Feb. 2008).

Alves-Filho, J.C. & Palsson-Mcdermott, E.M., Pyruvate Kinase M2: A Potential Target for Regulating Inflammation, *Frontiers in Immunology*, 7(145): Article 145 (2016).

Ambrus, J. et al., Studies on the vasoocclusive crisis of sickle cell disease. III. In vitro and in vivo effect of the pyrimido-pyrimidine derivative, RA-233: studies on its mechanism of action, *J Med*, 18(3-4):165-198 (1987).

Amer, J. et al., Red blood cells, platelets and polymorphonuclear neutrophils of patients with sickle cell disease exhibit oxidative stress that can be ameliorated by antioxidants, *British Journal of Haematology*, 132(1):108-113 (2006).

Andresen, C.A. et al., "Protein Interaction Screening for the Ankyrin Repeats and Suppressor of Cytokine Signaling (SOCS) Box (ASB) Family Identify Asb11 as a Novel Endoplasmic Reticulum Resident Ubiquitin Ligase", *The Journal of Biological Chemistry*, vol. 289, No. 4, pp. 2043-2054, (Jan. 24, 2014).

Ataga KI, Kutlar A, KanterJ, Liles D, Cancado R, Friedrisch J, Guthrie TH, Knight-Madden J, Alvarez OA, Gordeuk VR, Gualandro S, Colella MP, Smith WR, Rollins SA, Stocker JW, Rother RP. "Crizanlizumab for the prevention of pain crises in sickle cell disease." *N Engl J Med*. Feb. 2, 2017, 376(5):429-439.

Atkinson, Peter J., et al., 3,4-Dihydro-2H-benzoxazinones are 5-HT1A receptor antagonists with potent 5-HT reuptake inhibitory activity, *BioOrganic & Medicinal Chemistry Letters*, 15(3), pp. 737-741 (2005).

Austin, Nigel E., et al., "Novel 2,3,4,5-tetrahydro-1H-3-benzazepines with high affinity and selectivity for the dopamine D3 receptor", *BioOrganic & Medicinal Chemistry Letters*, 10(22), pp. 2553-2555, (2000).

Bailey, S.D. et al., "Variation at the NFATCZ Locus Increases the Risk of Thiazolidinedione-Induced Edema in the Diabetes Reduction Assessment with Ramipril and rosiglitazone Medication (DREAM) Study", *Diabetes Care*, vol. 33, No. 10, pp. 2250-2254, (Oct. 2010).

Bakshi N, Sinha CB, Ross D, Khemani K, Loewenstein G, Krishnamurti L. "Proponent or collaborative: Physician perspectives and approaches to disease modifying therapies in sickle cell disease." *PLoS One*. Jul. 20, 2017, 12(7):e0178413.

Balakin, Konstantin V. et al., Comprehensive Computational Assessment of ADME Properties using Mapping Techniques, *Current Drug Discovery Technologies*, 2(2), pp. 99-113 (2005).

Banerjee, S. et al., "Interplay between Polo kinase, LKB1-activated NUAK1 kinase, PP1β phosphatase complex and the SCFβ$^{TrCP}$ E3 ubiquitin ligase", *Biochem. J.* 461, pp. 233-245, (2014).

(56) References Cited

OTHER PUBLICATIONS

Banerjee, T. and Kuypers F.A., Reactive oxygen species and phosphatidylserine externalization in murine sickle red cells, *British Journal of Haematology*, 124:391-402 (2004).
Barbier AJ, Bodie S, Connor G, et al. "Safety, tolerability, pharmacokinetics and pharmacodynamics of multiple doses of AG-519, an allosteric activator of pyruvate kinase-R, in healthy subjects." *Blood*. 2016, 128:1264.
Barua, A.K., et al., Chemistry and Industry Communications to the Editor 1376 24 (Oct. 1970).
Bennett, Eric J., et al., "Dynamics of Cullin-RING Ubiquitin Ligase Network Revealed by Systematic Quantitative Proteomics", *Cell* 143, pp. 951-965, (Dec. 10, 2010).
Betz T, Lenz M, Joanny JF, Sykes C. "ATP-dependent mechanics of red blood cells." *Proc Natl Acad Sci USA*. 2009;106(36):15320-5.
Beutler, E. and Gelbart, T., "Estimating the prevalence of pyruvate kinase deficiency from the gene frequency in the general white population", *Blood*, 95(11): 3585-3588 (2000).
Bianchi, P. and Zanella, A., "Hematologically important mutations: red cell pyruvate kinase", (Third update), *Blood Cells Mol Dis.*, 26(1): 47-53 (2000).
Biftu, T. et al., "Omarigliptin (MK-3102): A Novel Long-Acting DPP-4 Inhibitor for Once-Weekly Treatment of Type 2 Diabetes", *Journal of Medicinal Chemistry*, 57, pp. 3205-3212, (2014).
Bouwmeester, T. et al., "A physical and functional map of the human TNF-α/NF-κB signal transduction pathway", *Nature Cell Biology*, vol. 6, No. 2, pp. 97-105, (Feb. 2004).
Boxer, M.B. et al., "Evaluation of Substituted N,N$^1$-Diarylsulfonamides as Activators of the Tumor Cell Specific M2 Isoform of Pyruvate Kinase", *J. Med. Chem.*, 53: pp. 1048-1055 (2010).
Brajenovic, M. et al., "Comprehensive Proteomic Analysis of Human Par Protein Complexes Reveals an Interconnected Protein Network", *The Journal of Biological Chemistry*, vol. 275, No. 13, pp. 12804-12811 (Mar. 2004).
Brehme, M. et al., "Charting the molecular network of the drug target Bcr-Abl", *PNAS*, vol. 106, No. 18, pp. 7414-7419, (May 2009).
Bridges, C.R., et al., "USP9X deubiquitylating enzyme maintains RAPTOR protein levels, mTORC1 signalling and proliferation in neural progenitors", *Scientific Reports* 7:391, pp. 1-15, (Mar. 2017).
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *Blood* (2020) 136 (Supplement 1):19-20, Nov. 4, 2020.
Brown, R. Clark, et al., "FT-4202, an Allosteric Activator of Pyruvate Kinase-R, Demonstrates Proof of Mechanism and Proof of Concept after a Single Dose and after Multiple Daily Doses in a Phase 1 Study of Patients with Sickle Cell Disease," *ASH* 2020, Dec. 7, 2020.
Budzikiewicz, Herbert et al., "Vincetene, a benzopyrroloisoquinoline alkaloid, from *Cynanchum vincetoxicum* (L.) Pers. (Asclepiadaceae)", Liebigs Annalen Der Chemie, (8), pp. 1212-1231 (1979).
Buontempo P, Jubin RG, Buontempo C, Real R, Kazo F, O'Brien S, Adeel F, Abuchowski A. "Pegylated carboxyhemoglobin bovine (SANGUINATE) restores RBCs roundness and reduces pain during a sickle cell vaso-occlusive crisis." *Blood*. 2017, 130:969
Cabrales, P. et al., "A look inside the mechanistic black box: Are red blood cells the critical effectors of RRx-001 cytotoxicity?", *Med Oncol.*, 33(7):63 (2016).
CAS Registry No. 1208929-16-1, Tert-Butyl 1H,2H,3H,4H,5H,6H-Pyrrolo[3,4-C]Pyrrole-2-Carboxylate Hydrochloride (Mar. 11, 2010).
Castilhos, L. et al., "Altered E-NTPDase/E-ADA activities and CD39 expression in platelets of sickle cell anemia patients", *Biomed Pharmacother.*, 79:241-246 (2016).
Castilhos, L. et al., "Increased oxidative stress alters nucleosides metabolite levels in sickle cell anemia", *Redox Rep.*, 22(6):451-459 (2017).
Castilhos, L. et al., "Sickle cell anemia induces changes in peripheral lymphocytes E-NTPDase/E-ADA activities and cytokines secretion in patients under treatment", *Biomedicine & Pharmacotherapy* 73 (2015), pp. 102-108.
Castro, O., Viability and function of stored sickle erythrocytes, *Transfusion*, 20(6):695-703 (1980).
Cazzola, M., Pyruvate kinase deficiency, Haematologica, 90(1): 1-2 (2005).
Charache, S. et al., Effect of 2,3-Diphosphateglycerate on oxygen affinity of blood in sickle, Cell Anemia, Journal of Clinical Investigation, 49(4):806-812 (1970).
Chaudhary, Neelam & Maddika, Subbareddy, "WWPZ-WWP1 Ubiquitin Ligase Complex Coordinated by PPM1G Maintains the Balance Between Cellular p73 and ΔNp73 Levels", Mol. Cell. Biol. (Oct. 2014).
Chen, Yue et al.—Preclinical Pharmacokinetic/Pharmacodynamic Relationships for AG-348, An Investigational Small-Molecule Activator of Pyruvate Kinase, European Hematology Association, Jun. 13, 2015.
Cheung, Yiu-Yin et al., Solution-Phase Parallel Synthesis and SAR of Homopiperazinyl Analogs as Positive Allosteric Modulators of MGlu$_4$, ACS Comb Sci. 13(2), pp. 159-165, (Mar. 2011).
Chiosis et al., Development of a Purine-Scaffold Novel Class of Hsp90 Binders that Inhibit the Proliferation of Cancer Cells and Induce the Degradation of Her2 Tyrosine Kinase, BioOrganic & Medicinal Chemistry, vol. 10, Iss 11, (Nov. 2002), pp. 3555-3564.
Chiou WL, Barve A. "Linear correlation of the fraction of oral dose absorbed of 64 drugs between humans and rats." *Pharm Res*. Nov. 1998, 15(11):1792-5.
Chonat, S. et al.,—Improvement in Red Blood Cell Physiology in Children With Sickle Cell Anemia Receiving Voxelotor—Childrens Healthcare of Atlanta (Dec. 2019).
Choudhury, N.R., et al., "RNA-binding activity of TRIM25 is mediated by its PRY/SPRY domain and is required for ubiquitination", BMC Biology 15:105, pp. 1-20, (2017).
Christensen, R.D. et al., Siblings with Severe Pyruvate Kinase Deficiency and a Complex Genotype, American Journal of Medical Genetics, Part A, (2016), pp. 2449-2452.
Chubukov V, Johnson K, Kosinski PA, et al. "Characterization of metabolic response to AG-348, an allosteric activator of red cell pyruvate kinase, in healthy volunteers and pyruvate kinase deficiency patients." Poster presented at: 58th American Society of Hematology Annual Meeting and Exposition; Dec. 4, 2016; San Diego, California. http://investor.agios.com/staticfiles/e1e9fd70-c84b-4472-bff3-bef0ecf05482 Accessed Jul. 28, 2017.
Chung, J.Y.L. et al., "Evolution of a Manufacturing Route to Omarigliptin, A Long-Acting DPP-4 Inhibitor for the Treatment of Type 2 Diabetes", Organic Process Research & Development, 19, pp. 1760-1768, (2015).
Clinical Trial Study—NCT02604433—U.S. National Library of Medicine, An Efficacy and Safety Study of Luspatercept (ACE-536) Versus Placebo in Adults Who Require Regular Red Blood Cell Transfusions Due to Beta (β) Thalassemia (BELIEVE), Submitted Date: Nov. 13, 2015, 24 pgs.
ClinicalTrlals.gov, NCT03815695, (v1)—U.S. National Library of Medicine, "A SAD/MAD to Assess the Safety, Pharmacokinetics and Pharmacodynamics of FT-4202 in Healthy Volunteers and Sickle Cell Disease Patients" (Jan. 22, 2019).
Clinical Trials Study, NCT03815695, (v2)—U.S. National Library of Medicine, "A SAD/MAD to Assess the Safety, Pharmacokinetics and Pharmacodynamics of FT-4202 in Healthy Volunteers and Sickle Cell Disease Patients," (Mar. 13, 2019) pp. 1-5.
ClinicalTrlals.gov, NCT03815695, (v3)—U.S. National Library of Medicine, "A SAD/MAD to Assess the Safety, Pharmacokinetics and Pharmacodynamics of FT-4202 in Healthy Volunteers and Sickle Cell Disease Patients" (Sep. 16, 2019).
Clinical Trial Study—NCT03815695, (v4)—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Sep. 19, 2019 (v4), 5 pgs.
Clinical Trial Study NCT03815695—U.S. National Library of Medicine, "A SAD/MAD to Assess the Safety, Pharmacokinetics

(56) References Cited

OTHER PUBLICATIONS and Pharmacodynamics of FT-4202 in Healthy Volunteers and Sickle Cell Disease Patients," Submitted Date: Sep. 23, 2019 (v5), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 9, 2019 (v6), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Oct. 10, 2019 (v7), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Nov. 27, 2019 (v8), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 15, 2020 (v9 ), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Jan. 16, 2020 (v10), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Date: Feb. 21, 2020 (v11), 5 pgs.
Clinical Trial Study NCT03815695—U.S. National Library of Medicine, "A SAD/MAD to Assess the Safety, Pharmacokinetics and Pharmacodynamics of FT-4202 in Healthy Volunteers and Sickle Cell Disease Patients," Submitted Apr. 1, 2020, (v12), 12 pgs.
ClinicalTrials.gov, NCT03815695 (v13), "A SAD/MAD to Assess the Safety, Pharmacokinetics and Pharmacodynamics of FT-4202 in Healthy Volunteers and Sickle Cell Patients," Jun. 15, 2020.
ClinicalTrials.gov, NCT03815695 (v14), "A SAD/MAD to Assess the Safety, Pharmacokinetics and Pharmacodynamics of FT-4202 in Healthy Volunteers and Sickle Cell Patients," Jul. 17, 2020.
ClinicalTrials.gov, NCT03815695 (v15), "A SAD/MAD to Assess the Safety, Pharmacokinetics and Pharmacodynamics of FT-4202 in Healthy Volunteers and Sickle Cell Patients," Aug. 19, 2020.
ClinicalTrials.gov, NCT03815695 (v16), "A SAD/MAD to Assess the Safety, Pharmacokinetics and Pharmacodynamics of FT-4202 in Healthy Volunteers and Sickle Cell Patients," Sep. 1, 2020.
ClinicalTrials.gov, NCT03815695 (v17), "A SAD/MAD to Assess the Safety, Pharmacokinetics and Pharmacodynamics of FT-4202 in Healthy Volunteers and Sickle Cell Patients," Sep. 18, 2020.
ClinicalTrials.gov, NCT03815695 (v18), "A SAD/MAD to Assess the Safety, Pharmacokinetics and Pharmacodynamics of FT-4202 in Healthy Volunteers and Sickle Cell Patients," Oct. 15, 2020.
ClinicalTrials.gov, NCT03815695 (v19), "A SAD/MAD to Assess the Safety, Pharmacokinetics and Pharmacodynamices of FT-4202 in Healthy Volunteers and Sickle Cell Patients," Study Record Versions 19—Dec. 24, 2020.
ClinicalTrials.gov, NCT03815695 (v20), "A SAD/MAD to Assess the Safety, Pharmacokinetics and Pharmacodynamices of FT-4202 in Healthy Volunteers and Sickle Cell Patients," Study Record Versions 20, Jan. 8, 2021.
ClinicalTrials.gov, NCT04624659 (v1), "A Study of FT-4202 in Adults and Adolescents With Sickle Cell Disease," Study Record Version 1—Nov. 5, 2020.
ClinicalTrials.gov, NCT04624659 (v2), "A Study of FT-4202 in Adults and Adolescents With Sickle Cell Disease," Study Record Version 2—Nov. 10, 2020.
ClinicalTrials.gov, NCT04624659 (v3), "A Study of FT-4202 in Adults and Adolescents With Sickle Cell Disease," Study Record Versions 3—Dec. 10, 2020.
ClinicalTrials.gov, NCT04624659 (v4), "A Study of FT-4202 in Adults and Adolescents With Sickle Cell Disease," Study Record Versions 4, Dec. 28, 2020.
ClinicalTrials.gov, NCT04624659 (v5), "A Study of FT-4202 in Adults and Adolescents With Sickle Cell Disease," Study Record Versions 5, Jan. 7, 2021.
ClinicalTrials.gov, NCT04624659 (v6), "A Study of FT-4202 in Adults and Adolescents With Sickle Cell Disease," Study Record Versions 6, Jan. 14, 2021.
ClinicalTrials.gov, NCT04624659 (v7), "A Study of FT-4202 in Adults and Adolescents With Sickle Cell Disease,"Study Record Versions 7, Feb. 8, 2021.
Cloutier, P. et al., "R2TP/Prefoldin-like component RUVBL1/RUVBL2 directly interacts with ZNHIT2 to regulate assembly of U5 small nuclear ribonucleoprotein", Nature Communications, pp. 1-14 (May 2017).
Cole, D.C. et al., Conformationally Constrained N1-arylsulfonyltryptamine derivatives as 5-HT6 receptor antagonists, BioOrganic & Medicinal Chemistry Letters, vol. 15, No. 21, (Nov. 1, 2005), pp. 4780-4785.
Cox, J.L., et al., "The SOX2-Interactome in Brain Cancer Cell Identifies the Requirement of MSI2 and USP9X for the Growth of Brain Tumor Cell", PLOS ONE, vol. 8, Issue 5, pp. 1-13, (May 2013).
Croasdell, G., European Hematology Association—20th Annual Congress (Jun. 11-14, 2015—Vienna, Austria) Meeting Report, Drugs of Today (2015), 51(7),I pp. 441-445.
Das, A. et al., "USP9X counteracts differential ubiquitination of NPHP5 by MARCH7 and BBS11 to regulate ciliogenesis", PLOS Genetics, pp. 1-24, (May 12, 2017).
Davis, Z.H., et al., "Global Mapping of Herpesvirus-Host Protein Complexes Reveals a Transcription Strategy for Late Genes", Molecular Cell 57, pp. 349-360; (Jan. 22, 2015).
De Furia, F. et al., The effects of cyanate in vitro on red blood cell metabolism and function in sickle cell anemia, J Clin Invest., 51(3):566-574 (1972).
De Jong, K. and Kuypers, F., Sulphydryl modifications alter scramblase activity in murine sickle cell disease, British Journal of Haematology, 133(4):427-432 (2006).
De Rosa MC, Carelli Alinovi C, Galtieri A, Russo A, Giardina B. "Allosteric properties of hemoglobin and the plasma membrane of the erythrocyte: New insights in gas transport and metabolic modulation." IUBMB Life. 2008, 60(2):87-93.
Diez, A. et al., Life-threatening nonspherocytic hemolytic anemia in a patient with a null mutation in the PKLR gene and no compensatory PKM gene expression, Blood, 106:1851 (2005).
Diez-Silva M, Dao M, Han J, Lim CT, Suresh S. "Shape and biomechanical characteristics of human red blood cells in health and disease." MRS Bull. May 2010, 35(5):382-8.
Drissi, R. et al., "Quantitative Proteomics Reveals Dynamic Interactions of the Mini chromosome Maintenance Complex (MCM) in the Cellular Response to Etoposide Induced DNA Damage", Molecular & Cellular Proteomics, pp. 2002-2013, (2015).
DROXIA [package insert]. Princeton, New Jersey, Bristol-Myers Squibb Company, (Dec. 2017), 28 pgs.
DROXIA [package insert]. Princeton, New Jersey, Bristol-Myers Squibb Company (Dec. 2019), 25 pgs.
Dupont, S. et al., "FAM/USP9x, a Deubiquitinating Enzyme Essential for TGFβ Signaling, Controls Smad4 Monoubiquitination", Cell, 136, pp. 123-135, (Jan. 9, 2009).
Dzandu JK, Johnson RM. "Membrane protein phosphorylation in intact normal and sickle cell erythrocytes." J Biol Chem. Jul. 10, 1980, 255(13):6382-6.
El-Sharief, A.M., et al., Some halogenated sulfonamides with biological interest, Journal of the Indian Chemical Society, vol. 61, No. 6, (1984), pp. 537-543.
Emam, H.A., et al., Heterocyclization of sulfamido chalcones to pyrazoline, cyanopyridone, nicotinonitrile and hydrobenzo [1,2-c] pyrazole derivatives, Journal of the Serbian Chemical Society, vol. 62, No. 7, (1997), Abstract only.

(56) References Cited

OTHER PUBLICATIONS

ENDARI [package insert]. Torrance, California: Emmaus Medical, Inc., (Jul. 2017), 8 pgs.
ENDARI [package insert]. Torrance, California, Emmaus Medical, Inc., (Nov. 2019), 10 pgs.
Ernst, A. et al., "A Strategy for Modulation of Enzymes in the Ubiquitin System", Science, 339, pp. 1-15, (Feb. 2013).
Estepp, et al., Phase 1 Single (SAD) and Multiple Ascending Dose (MAD) Study of the Safety, Pharmacokinetics (PK) and Pharmacodynamics (PD) of FT-4202, A PKR-Activator, In Healthy and Sickle Cell Disease Subjects, Abstract, e-Poster, European Hematology Association Open Access Library, Presentation EHA25, (May 14, 2020), 2 pgs.
Estepp, et al., Phase 1 Single (SAD) and Multiple Ascending Dose (MAD) Study of the Safety, Phyarmacokinetics (PK) and Pharmacodynamics (PD) of FT-4202, a PKR Activator, in Healthy and Sickle Cell Disease Subjects, Poster, EP1531, (Jun. 12, 2020), 1 pg.
Estepp, J.H. et al., A clinically meaningful fetal hemoglobin threshold for children with sickle cell anemia during hydroxyurea therapy, Am J Hematol., 92:1333-1339 (2017).
Estepp, Jeremie H., et al., "Phase 1 Single (SAD) and Multiple Ascending Dose (MAD) Study of the Safety, Pharmacokinetics (PK) and Pharmacodynamics (PD) of FT-4202, a PKR Activator, in Healthy Volunteers and Patients with Sickle Cell Disease," Virtual meeting [poster EP1531] presented at the 25th Congress of the European Hematology Association; Jul. 11-21, 2020.
European Hematology Association HemaSphere Abstract Book, 15th Annual Sickle Cell & Thalassaemia & 1st EHA European Sickle Cell Conference, Oct. 26-31, 2020.
Fioravanti, R., et al., Synthesis and Biological Evaluation of N-substituted-3, 5-diphenyl—2-pyrazoline derivatives as cyclooxygenase (COX-2) inhibitors, European Journal of Medicinal Chemistry, vol. 45, No. 12, (Dec. 1, 2010), pp. 6135-6138, XP027526583.
Fitch, R. W. et al., Phantasmidine: An Epibatidine Congener from the Ecuadorian Poison Frog *Epipedobates anthonyi*', Journal of Natural Products (2010), vol. 73, No. 3, pp. 331-337.
Fleischhacker, W., et al., "Heterocyclic fused naphthalene systems from thebaine. 1", Liebigs Annalen Der Chemie, (5), pp. 844-851, (1983).
Fogeron, M.L. et al., "LGALS3BP regulates centriole biogenesis and centrosome hypertrophy in cancer cells", Nature Communications, 4:1531, pp. 1-14; (2013).
Forma Therapeutics, Press Release, "Forma Therapeutics Presents Clinical Proof-of-Concept Data at the 62nd Annual ASH Meeting Supporting the Potential of its Novel Investigational PKR Activator, FT-4202, to Treat Sickle Cell Disease (SCD)" (Dec. 7, 2020).
Forma Therapeutics, Inc., Press Release—"Forma Therapeutics Announces Positive FT-4202 600 mg Multiple Ascending Dose Cohort Data Supporting the Doses Being Evaluated in Phase 2/3 Registrational Trial, Called the Hibiscus Study", Mar. 30, 2021—2 pgs.
Frost, David A., et al., "Naturally occurring compounds related to phenalenone. V. Synthetic approaches to structures based on 8,9-dihydro-8,8,9-trimethylphenaleno [1,2-b] furan-7-one", Journal of the Chemical Society, Perkin Transactions 1: Organic and Bio-Organic Chemistry (1972-1999), pp. 2159-2169.
Gaudet, P. et al., "Phylogenetic-based propagation of functional annotations within the Gene Ontology consortium", vol. 12, No. 5, pp. 449-462; (Aug. 2011).
Giannone, R.J., et al., "The Protein Network Surrounding the Human Telomere Repeat Binding Factors TRF1, TRF2, and POT1", PLOS One, vol. 5, Issue 8, pp. 1-10, (Aug. 2010).
Gizi, A. et al., Assessment of oxidative stress in patients with sickle cell disease: The glutathione system and the oxidant-antioxidant status, Blood Cells Mol Dis., 46(3):220-225 (2011).
Gladwin, M., Adenosine recepter crossroads in sickle cell disease, Nature Medicine, 17(1):38-40, (2011).

Glombitza, S. et al., Adenosine causes cAMP-dependent activation of chick embryo red cell carbonic anhydrase and 2,3-DPG synthesis, American Journal of Physiology, 271(4):973-81 (1996).
Gomez-Bougie, P. et al., "Noxa controls Mule-dependent Mcl-1 ubiquitination through the regulation of the Mcl-1/USP9X interaction", Biochemical and Biophysical Research Communications 413, pp. 460-464, (2011).
Goncharov, T. et al., "OTUB1 modulates c-IAP1 stability to regulate signaling pathways", The EMBO Journal 32, No. 8, pp. 1103-1114, (2013).
Grace RF, Rose C, Layton DM, Yaish HM, Barcellini W, Galactéros F, Morton DH, Ravindranath Y, Kuo KHM, van Beers EJ, Kwiatkowski JL, Silver BA, Merica E, Kung C, Cohen M, Yang H, Hixon J, Kosinski PA, Silver L, Dang L, Yuan Z, Barbier AJ, Glader B. "Effects of AG_348, a pyruvate kinase activator, on anemia and hemolysis in patients with pyruvate kinase deficiency: Data from the DRIVE PK study". Blood. 2016, 128:402.
Grace, et al., Safety and Efficacy of Mitapivat in Pyruvate Kinase Deficiency, N. Engl. J. Med. 381, 10, (Sep. 5, 2019), p. 933-944.
Grasso, D. et al., "Zymophagy, a Novel Selective Autophagy Pathway Mediated by VMP1-USP9x-p62, Prevents Pancreatic Cell Death", The Journal of Biological Chemistry, vol. 286, No. 10, pp. 8308-8324, (Mar. 2011).
Greco, T.M. et al., "Nuclear Import of Histone Deacetylase 5 by Requisite Nuclear Localization Signal Phosphorylation", Molecular & Cellular Proteomics 10: , pp. 1-15, (2011).
Grou, C.P., et al., "Identification of ubiquitin-specific protease 9X (USP9X) as a deubiquitinase acting on the ubiquitin-peroxin 5 (PEX5) thioester conjugate", J. Biol. Chem., pp. 1-24; (Feb. 27, 2012).
Habata, S. et al., "BAG3-mediated Mcl-1 stabilization contributes to drug resistance via interaction with USP9X in ovarian cancer", International Journal of Oncology 49: pp. 402-410, (2016).
Han, K.J. et al., "Ubiquitin-specific Protease 9x Deubiquitinates and Stabilizes the Spinal Muscular Atrophy Protein—Survival Motor Neuron", J. Biol. Chem., pp. 1-22, (Oct. 2012).
Hanson, D. et al., "Identifying biological pathways that underlie primordial short stature using network analysis", Journal of Molecular Endocrinology, pp. 333-344, (2014).
Harada, R. et al., "Structure of pristimerine, a quinonoid triterpene", Tetrahedron Letters, pp. 603-607, (1962).
Harayama, Takashi et al., "Novel synthesis of naphthobenzazepines from N-bromobenzylnaphthylamines by regioselective C—H activation utilizing the intramolecular coordination of an amine to Pd", Synlett, (8), pp. 1141-1144, (2003).
Hauri, S. et al., "Interaction proteome of human Hippo signaling: modular control of the co-activator YAP1", Molecular Systems Biology, 9: 713, pp. 1-16 (Nov. 2013).
Havugimana, P. et al., "A Census of Human Soluble Protein Complexes", Cell 150, pp. 1068-1081, (Aug. 2012).
Hebbel RP, Eaton JW, Balasingam M, Steinberg MH. "Spontaneous oxygen radical generation by sickle erythrocytes." J Clin Invest. 1982, 70(6):1253-9.
Hein, M.Y., et al., "A Human Interactome in Three Quantitative Dimensions Organized by Stoichiometries and Abundances", Cell 163, pp. 712-723, (Oct. 2015).
Hierso, R. et al., Effects of oxidative stress on red blood cell rheology in sickle cell patients, British Journal of Haematology, 166(4):601-606 (2014).
Homan, C.C. et al., "Mutations in USP9X Are Associated with X-linked Intellectual Disability and Disrupt Neuronal Cell Migration and Growth", The American Journal of Human Genetics 94, pp. 470-478, (Mar. 2014).
Hoppe CC, Inati AC, Brown C, et al. "Initial results from a cohort in a phase 2a study (GBT440-007) evaluating adolescents with sickle cell disease treated with multiple doses of GBT440, a HbS polymerization inhibitor." Blood. 2017;130(Suppl 1): 689.
Husain, M.I., et al., Synthesis of some new N-[4-(acetyl/phenyl-5-arylpyrazolin-3-yl)phenyl]arylsulfonamides as oral hypoglycemic agents, Indian Drugs, vol. 24, No. 4, (1987), Abstract only.
Huttlin, E. L., et al., "The BioPlex Network: A Systematic Exploration of the Human Interactome", Cell 162, pp. 425-440, (Jul. 2015).

(56) References Cited

OTHER PUBLICATIONS

Huttlin, E.L., et al., "Architecture of the human interactome defines protein communities and disease networks", Nature, pp. 1-35, (May 2017).
HYDREA [package insert]. Princeton, New Jersey, Bristol-Myers Squibb Company (Jul. 2019), 29 pgs.
Imamura K, Tanaka T. "Multimolecular forms of pyruvate kinase from rat and other mammalian tissues. I Electrophoretic studies." J Biochem. 1972, 71:1043-51.
Imamura K, Tanaka T. "Pyruvate kinase isozymes from rat." Methods Enzymol. 1982, 90:150-65.
Iwasaki, Tameo et al., "Novel Selective PDE IV Inhibitors as Antiasthmatic Agents. Synthesis and Biological Activities of a Series of 1-Aryl-2,3-bis (hydroxymethyl) naphthalene Lignans", Journal of Medicinal Chemistry (1996), pp. 2696-2704.
Jendralla, H. et al., Synthesis of 1,2,3,4,5,6-Hexahydropyrrolo[3,4-c]pyrrole dihydrobromide and 1,2,3,5-Tetrahydro-2-[(4-Methyl-Phenyl)Sulfonyl]Pyrrolo[3,4-c]Pyrrole, Heterocycles, 41(6): 1291-1298 (1995).
Jin, Y. et al., Effects of gamma irradiation on red cells from donors with sickle cell trait, Transfusion, 37(8):804-808 (1997).
Johansen, L.D., et al., "IKAP localizes to membrane ruffles with filamin A and regulates actin cytoskeleton organization and cell migration", Journal of Cell Science 121, pp. 854-864, (Dec. 2007).
Jones, M.H., et al., "The *Drosophila* developmental gene fat facets has a human homologue in Xp11.4 which escapes X-inactivation and has related sequences on Yq11.2", Human Molecular Genetics, vol. 5, No. 11, pp. 1695-1701, (Aug. 1996).
Jorgensen, Eugene C., et al., "Thyroxine analogs. 20. Substituted 1- and 2-naphthyl ethers of 3,5-diiodotyrosine", Journal of Medicinal Chemistry 14(11), pp. 1023-1026, (1971).
Joshi, B., et al., Indian J. Chem., Sect. B (1983), 22B(2), Abstract only. Chemical Abstract No. 99:105146.
Joshi, P., et al., "The functional interactome landscape of the human histone deacetylase family", Molecular Systems Biology 9, 672, (2013).
Kalai, T. et al., Synthesis of Pyrroline Nitroxide Annulated Carbocycles and Heterocycles, Synthesis No. 6, pp. 831-837 (2000).
Kalfa, et al., FORMA Therapeutics, Inc., Watertown, MA, Power Pointe Presentation, Dated Nov. 6, 2019 , Phase 1 Single and Multiple Ascending Dose Study of the Safety, Tolerability, Pharmacokinetics and Pharmacodynamics of FT-4202, an Allosteric activator of Pyruvate Kinase-R, in Healthy and Sickle Cell Disease Subjects, 15 pgs.
Kalfa, T. A. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", JSCDH-D-20-0053, vol. VII, Pub. Date: Jun. 12, 2020; pp. 83-84.
Kalfa, T. et al., "Phase 1 Single (SAD) and Multiple Ascending Dose (MAD) Study of the Safety, Pharmacokinetics (PK) and Pharmacodynamics (PD) of FT-4202, a PKR Activator, in Healthy and Sickle Cell Diseases Subjects", 14th Annual Sickle Cell Disease Research and Educational Symposium/43rd National Sickle Cell Disease Scientific Meeting (Sep. 23-25, 2020).
Kalfa, T.A. et al., "616 Phase 1 Single (SAD) and Jultople Ascending Dose (MAD) Studies of the Safety, Tolerability, Pharmacokinetics (PK) and Pharmacodynamics (PD) of FT-4202, an Allosteric Activator of Pyruvate Kinase-R, in Healthy and Sickle Cell Disease Subjects", (Nov. 2019).
Kaltenbach, L.S., et al., "Huntingtin Interacting Proteins Are Genetic Modifiers of Neurodegeneration", PLOS Genetics, vol. 3, Issue 5, pp. 689-708, (May 2007).
Kasturi, Tirumalai R., et al., "Reactions of tetrahalo-1,2-benzoquinones. III. Reaction of tetrachloro-1,2-benzoquinone withtetralones and naphthols: pathway to the condensates", Journal of the Chemical Society C: Organic, (9), pp. 1257-1259, (1970).
Katzenellenbogen, R.A., et al., "NFX1-123 and Poly(A) Binding Proteins Synergistically Augment Activation of Telomerase in Human Papillomavirus Type 16 E6-Expressing Cells", Journal of Virology, vol. 81, pp. 3786-3796, (Apr. 2007).
Khafagy, M.M., Synthesis of some pyrimidine and pyrazoline derivatives, Al-Azhar Bulletin of Science, vol. 3, No. 1, (1992), Abstract only.
Kharalkar, S.S. et al., Identification of Novel Allosteric Regulators of Human-Erythrocyte Pyruvate Kinase, Chemistry & Biodiversity, vol. 4, pp. 2603-2617 (Feb. 2007).
Kim H, Kosinski P, Kung C, Dang L, Chen Y, Yang H, Chen YS, Kramer J, Liu G. "A fit-for-purpose LC-MS/MS method for the simultaneous quantitation of ATP and 2,3-DPG in human K2EDTA whole blood." J Chromatogr B Analyt Technol Biomed Life Sci. Sep. 1, 2017, 1061-1062:89-96.
Kim J, Lee H, Shin S. "Advances in the measurement of red blood cell deformability: A brief review." J Cell Biotech. 2015;1263-79.
Kim, M., et al., "Role of Angiomotin-like 2 mono-ubiquitination on YAP inhibition", EMBO reports, vol. 17, No. 1., pp. 64-78, (Nov. 23, 2015).
Kimura, K., et al., "Diversification of transcriptional modulation: Large-scale identification and characterization of putative alternative promoters of human genes", Genome Research 16, pp. 55-65, (2006).
Kirli, K., et al., "A deep proteomics perspective on CRM1-mediated nuclear export and nucleocytoplasmic partitioning", eLife, pp. 1-28; (2015).
Knauff, E.A.H., et al., "Genome-wide association study in premature ovarian failure patients suggests ADAMTS19 as a possible candidate gene", Human Reproduction, vol. 24, No. 9, pp. 2372-2379, (2009).
Kodama, K. et al., Solvent-induced dual chirality switching in the optical resolution of tropic acid via diastereomeric salt formation with (1R,2S)-2-amino-1,2-diphenylethanol, Tetrahedron 70:7923-7928 (2014).
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Blood (2020) 136 (Supplementl):23-24, Nov. 4, 2020.
Konstantinidis, Diamantis G., et al., "Ex-Vivo FT-4202 Treatment Improves Hemoglobin Oxygen Affinity and Membrane Health in Red Blood Cells of Patients with Hemoglobin SS and Hemoglobin SC Disease Irrespective of Prior Hydroxyurea Use," Presented at the 62nd American Society of Hematology (ASH) Annual Meeting, Dec. 5, 2020.
Kristensen, A.R., Gsponer, J. and Foster, L.J., "A high-throughput approach for measuring temporal changes in the interactome", Nat Methods, 9(9), pp. 1-12, (2012).
Kuehl, G. et al., In vitro interactions of 51Cr in human red blood cells and hemolysates, Vox Sang., 40(4):260-272 (1981).
Kung C, Hixon J, Kosinski PA, et al. "AG-348 enhances pyruvate kinase activity in red blood cells from patients with pyruvate kinase deficiency." Blood. 2017;130(11):1347-1356.
Kurita, R. et al., Establishment of Immortalized Human Erythroid Progenitor Cell Lines Able to Produce Enucleated Red Blood Cells, PLOS ONE, vol. 8, Iss.3, pp. 1-15 (Mar. 2013).
Kushwaha, D., et al., "USP9X inhibition promotes radiation-induced apoptosis in non-small cell lung cancer cells expressing mid-to-high MCL1", Cancer Biology & Therapy 16:3, pp. 392-401, (Mar. 2015).
Kwasna, D., et al., "Discovery and Characterization of ZUFSP/ZUP1, a Distinct Deubiquitinase Class Important for Genome Stability", Molecular Cell 70, pp. 150-164, (2018).
Le Quesne, P.W. et al., One-Step Preparation of Tetrakis(bromomethyl)ethylene from Pinacolyl Alcohol, J. Org. Chem., 40(1): 142-143 (1975).
Le, Kha et al., Population pharmacokinetics and pharmacodynamics of AG-519, a pyruvate kinase activator for the treatment of pyruvate kinase deficiency, in human healthy volunteers, Agios Pharma—1263 Poster,—58th American Society of Hematology Annual Meeting and Exposition, Dec. 3-6, 2016—San Diego, CA.
Le, Kha et al., Population pharmacokinetics and pharmacodynamics of AG-348 in healthy human volunteers guide dose selection for the treatment of pyruvate kinase deficiency, Agios Pharma—3336 Poster,—

(56) References Cited

OTHER PUBLICATIONS

57th American Society of Hematology Annual Meeting and Exposition, Dec. 5-8, 2015—Orlando, FL.
Lehrer-Graiwer J, Howard J, Hemmaway CJ, et al. "Long-term dosing in sickle cell disease subjects with GBT440, a novel HbS polymerization inhibitor." Blood, 2016:128(22): 2488.
Lehrer-Graiwer, Josh et al., Long-Term Dosinig in Sickle Cell Disease Subjects with GBT440, a Novel HbS Polymerization Inhibitor, blood, 114, Hemoglobinopathies, Excluding Thalassemia—Clinical Poster II, Dec. 2, 2016.
Lenihan, J.A., Saha, Orthis, and Young P.W., "Proteomic analysis reveals novel ligands and substrates for LNX1 E3 ubiquitin ligase", PLOS ONE, pp. 1-18; (Nov. 2017).
Li, X., et al., "Defining the protein-protein interaction network of the human protein tyrosine phosphatase family", The American Society for Biochemistry and Molecular Biology, Inc., pp. 1-54, (2016).
Litinov RI, Weisel JW. "Role of red blood cells in haemostasis and thrombosis." ISBT Sci Ser. Feb. 2017, 12(1):176-183.
Liu, X.H., et al., European Journal of Cancer, vol. 31A, No. 6, pp. 953-963, (1995).
Llauger et al., "Evaluation of 8-Arylsulfanyl, 8-Arylsulfoxyl, and 8-Arylsulfonyl Adenine Derivatives as Inhibitors of the Heat Shock Protein 90", J. Med. Chem., 48(8), pp. 2892-2905, (Mar. 25, 2005).
Llauger et al., "Synthesis of 8-arylsulfoxyl/sulfonyl adenines", Tetrahedron Letters, vol. 45, Issue 52, (Dec. 20, 2004), pp. 9549-9552.
Lochmatter, C. et al., Integrative phosphoproteomics links IL-23R signalling with metabolic adaption in lymphocytes, Scientific Reports, 6:24491 (2016).
Lockwood, S. et al., Endothelium-derived nitric oxide production is increased by ATP released from red blood cells incubated with hydroxyurea, Nitric Oxide, 38:1-7 (2014).
Loriga G. et al., Synthesis of 3,6-diazabicyclo [3.1.1]heptanes as novel ligands for the opioid receptors, Bioorganic & Medicinal Chemistry, Pergamon, GB, vol. 14, No. 3, pp. 676-691, (Feb. 1, 2006).
Lu, L., et al., "The HECT Type Ubiquitin Ligase NEDL2 Is Degraded by Anaphase-promoting Complex/Cyclosome (APC/C)-Cdh1, and Its Tight Regulation Maintains the Metaphase to Anaphase Transition", The Journal of Biological Chemistry, vol. 288, No. 50, pp. 35637-35650; (Dec. 2013).
Lucas, et al., "Facile Synthesis of a Library of 9-Alkyl-8-benzyl-9H-purin-6-ylamine Derivatives", J. Comb. Chem., 3 (6), pp. 518-520, (Sep. 21, 2001).
MacDonald, Gregor J., et al, "Design and Synthesis of trans-3-(2-(4-((3-(3-(5-Methyl-1,2,4-oxadiazolyl))-phenyl(carboxamido)cyclohexyl)ethyl)-7-methylsulfonyl-2,3,4,5-tetrahydro-1H-3-benzazepine (SB-414796): A Potent and Selective Dopamine D3 Receptor Antagonist", Journal of Medicinal Chemistry, 46(23), pp. 4952-4964 (2003).
Macdonald, Rosemary, Red cell 2,3-diphosphoglycerate and oxygen affinity, Anaesthesia, vol. 32, pp. 544-553, (1977).
Martinez-Mayorga Karina et al, Ligand/kappa-opioid receptor interactions: Insights from the X-ray crystal structure, European Journal of Medicinal Chemistry, vol. 66, pp. 114-121 (May 30, 2013).
Mathe-Allainmat, Monique et al., "Synthesis of 2-Amido-2, 3-dihydro-1H-phanalene Derivatives as New Conformationally Restricted Ligands for Melatonin Receptors", Journal of Medicinal Chemistry, 39(16), pp. 3089-3095, (1996).
McCluskey A., et al., BioOrganic & Medicinal Chemistry Letters 10 (2000), pp. 1687-1690.
McCluskey A., et al., Bioorganic & Medicinal Chemistry Letters 11 (2001), pp. 2941-2946.
McGarry, E., et al., "The deubiquitinase USP9X maintains DNA replication fork stability and DNA damage checkpoint responses by regulating CLASPIN during S-phase", Cancerres.aacrjournals.org, pp. 1-39; (2016).

Metcalf B, Chuang C, Dufu K, et al. "Discovery of GBT440, an orally bioavailable R-state stabilizer of sickle cell hemoglobin." ACS Med Chem Lett. 2017; 8(3):321-326.
Meza, N.W. et al, In vitro and in vivo expression of human erythrocyte pyruvate kinase in erythroid cells: a gene therapy approach, Hum Gene Ther, 18(6):502-514 (2007).
Middelkoop, E. et al., Studies on sickled erythrocytes provide evidence that the asymmetric distribution of phosphatidylserine in the red cell membrane is maintained by both ATP-dependent translocation and interaction with membrane skeletal proteins, Biochimica et Biophysica Acta, 937:281-288 (1988).
Misra H. Bainbridge J, Berryman J, Abuchowski A, Galvez KM, Uribe LF, Hernandez AL, Sosa NR. "A phase 1b open label, randomized, safety study of SANGUINATE™ in patients with sickle cell anemia." Rev Bras Hematol Hemoter. Jan.-Mar. 2017, 39(1):20-7.
Miwa, S. and Fujii, H., Molecular basis of erythroenzymopathies associated with hereditary hemolytic anemia: tabulation of mutant enzymes, Am J Hematol., 51(2): 122-132 (1996).
Moehrle, H., et al., "1,2,3,4-Tetrahydroquinolines as substrates for Mannich compounds", Chemical Sciences, 53(7), pp. 742-752; (1998).
Moriyama R, Lombardo CR, Workman RF, Low PS. "Regulation of linkages between the erythrocyte membrane and its skeleton by 2,3-diphosphoglycerate." J Biol Chem. May 25, 1993, 268(15):10990-6.
Mouchantaf, R., et al., "The Ubiquitin Ligase Itch Is Autoubiquitylated in Vivo and in Vitro but Is Protected from Degradation by Interacting with the Deubiquitylating Enzyme FAM/USP9X", The Journal of Biological Chemistry, vol. 281, No. 50, pp. 38738-38747, (Dec. 2006).
Murn, J. et al., "Control of a neuronal morphology program by an RNA-binding zinc finger protein, Unkempt", Genes & Development 29, pp. 501-512, (2015).
Murray, R.Z., Jolly, L.A., Wood, S.A., "The FAM Deubiquitylating Enzyme Localizes to Multiple Points of Protein Trafficking in Epithelia, where It Associates with E-cadherin and β-catenin", Molecular Biology of the Cell, vol. 15, pp. 1591-1599; (Apr. 2004).
Muzyamba, M. and Gibson, J., Effect of 1-chloro-2,4-dinitrobenzene on K+ transport in normal and sickle human red blood cells, Journal of Physiology, 547(3):903-911 (2003).
Nagai, H., et al., "Ubiquitine-like Sequence in ASK1 Plays Critical Roles in the Recognition and Stabilization by USP9X and Oxidative Stress-Induced Cell Death", Molecular Cell 36, pp. 805-818, (Dec. 2009).
Nagy, Peter I., et al., "Theoretical and Experimental Study on Ion-Pair Formation and Partitioning of Organic Salts in Octanol/Water and Dichloromethane/Water Sytems", Journal of the American Chemical Society, 122 (28), pp. 6583-6593 (2000).
Nam, Keun-Soo et al., "Synthesis of quinolone antimicrobial agents and their antibacterial activities," 5 Korean J. Med. Chem. (1995), pp. 2-5.
Narayanan, N., Wang, Z., Li, L., and Yang, Y., "Arginine methylation of USP9X promotes its interaction with TDRD3 and its antiapoptotic activities in breast cancer cells", Cell Discovery 3, pp. 1-17, (2017).
Nathan, J.A., et al., "The Ubiquitin E3 Ligase MARCH7 is Differentially Regulated by the Deubiquitylating Enzymes USP7 and USP9X", Traffic, 9, pp. 1130-1145, (2008).
Neto, E.D. et al., "Shotgun sequencing of the human transcriptome with ORF expressed sequence tags", PNAS, vol. 97, No. 7, pp. 3491-3496, (Mar. 2000).
Noma, T., et al., "Stage- and sex-dependent expressions of Usp9x, an X-linked mouse ortholog of Drosophila Fat facets, during gonadal development and oogenesis in mice", Gene Expression Patters 2, pp. 87-91, (2002).
O'Connor, H.F., et al., "Ubiquitin-Activated Interaction Traps (UBAITs) identify E3 ligase binding partners", EMBO reports, vol. 16, No. 12., (2015).
Obach RS. "Prediction of human clearance of twenty-nine drugs from hepatic microsomal intrinsic clearance data: An examination of in vitro half-life approach and nonspecific binding to microsomes." Drug Metab Dispos. Nov. 1999, 27(11):1350-9.

(56) References Cited

OTHER PUBLICATIONS

Oksenberg D, Dufu K, Patel MP, Chuang C, Li Z, Xu Q, Silva-Garcia A, Zhou C, Hutchaleelaha A, Patskovska L, Patskovsky Y, Almo SC, Sinha U, Metcalf BW, Archer DR. "GBT440 increases haemoglobin oxygen affinity, reduces sickling and prolongs RBC half-life in a murine model of sickle cell disease." Br J Haematol. Oct. 2016, 175(1):141-53.
Oliviero, G., et al., "The variant Polycomb Repressor Complex 1 component PCGF1 interacts with a pluripotency sub-network that includes DPPA4, a regulator of embryogenesis", pp. 1-11, (2015).
Olsen, J.V., et al., "Global, In Vivo, and Site-Specific Phosphorylation Dynamics in Signaling Networks", Cell 127, pp. 635-648, (Nov. 2006).
Oski, M.D., Frank A., "The Role of Organic Phosphates in Erythrocytes on the Oxygen Dissociation of Hemoglobin," Annals of Clinical Laboratory Science, vol. 1, No. 2 (Nov. 1970), pp. 162-176.
Ould Amar, A.K. et al., Assessment of qualitative functional parameters of stored red blood cells from donors with sickle cell trait (AS) or with heterozygote (AC) status, Transfus Clin Biol., 3(4):225-233 (1996).
Ouyang, W., et al., "β-catenin is regulated by USP9x and mediates resistance to TRAIL-induced apoptosis in breast cancer", Oncology Reports 35, pp. 717-724, (2016).
OXBRYTA [package insert]. San Francisco, California, Global Blood Therapeutics, Inc. (Nov. 2019), 15 pgs.
OXBRYTA Slide Show—Jan. 2020.
Paemka, L., et al., "Seizures Are Regulated by Ubiquitin-specific Peptidase 9 X-linked (USP9X), a De-Ubiquitinase", PLOS Genetics, 11(3): pp. 1-16, (Mar. 2015).
Palsson-Mcdermott, EM et al., Pyruvate kinase M2 regulates Hif-1α activity and IL-1β induction and is a critical determinant of the Warburg Effect in LPS-activated macrophages, Cell Metabolism, 21:65-80 (2015).
Papp, S.J., et al., "DNA damage shifts circadian clock time via Hausp-dependent Cry1 stabilization", eLIFE, pp. 1-19, (2015).
Park, Yoon, Jin, Hyung-seung, and Liu, Yun-Cai, "Regulation of T cell function by the ubiquitin-specific protease USP9X via modulating the Carma 1-Bcl10-Malt1 complex", PNAS, vol. 110, No. 23, pp. 9433-9438, (Jun. 2013).
Pászty C. "Transgenic and gene knock-out mouse models of sickle cell anemia and the thalassemias." Curr Opin Hematol. 1997, 4(2):88-93.
Patel, P., et al., Synthesis of some novel pyrazoline and cyanopyridine derivatives as antimicrobial agents, Il Farmaco, vol. 51, No. 1, (1996), Abstract only.
Pavagadhi, T.H., et al., 3-(3'-phenoxyphenylmethyl)-5-aryl-1-acetylpyrazolines, Journal of the Institution of Chemists (India), Vol. 73, No. 3, (2001), Abstract only.
Peddaboina, C. et al., "The downregulation of Mcl-1 via USP9X inhibition sensitizes solid tumors to Bcl-xl inhibition", BMC Cancer, 12:541, pp. 1-12, (2012).
Perez-Mancera, P.A., et al., "The deubiquitinase USP9X suppresses pancreatic ductal adenocarcinoma", Nature, 486(7402): pp. 266-270; (Dec. 2012).
Platt OS. "Hydroxyurea for the treatment of sickle cell anemia." N Engl J Med. 2008;358(13):1362-9.
Poillon W., & Kim, B., 2,3-Diphosphoglycerate and intracellular pH as interdependent determinants of the physiologic solubility of deoxyhemoglobin S, Blood, 76:1028-1036 (1990).
Poillon, W. et al., Antisickling effects of 2,3-Diphosphoglycerate Depletion, Blood, 85(11):3289-3296 (1995).
Poillon, W. et al., Intracellular hemoglobin S polymerization and the clinical severity of sickle cell anemia, Blood, 91:1777-1783 (1998).
Poillon, W. et al., The Effect of 2,3-Diphosphoglycerate on the Solubility of Deoxyhemoglobin S1, Archives of Biochemistry and Biophysics, vol. 249, No. 2, pp. 301-305, (Sep. 1986).
Press Release—"Agios Announces New Data from AG-348 and AG-519 Demonstrating Potential for First Disease-modifying Treatment for Patients with PK Deficiency" Dec. 4, 2016—Globe Newswire.

Press Release—"Agios Presents Updated Data from DRIVE PK Study Demonstrating AG-348 is Well-Tolerated and Results in Clinically Relevant, Rapid and Sustained Hemoglobin Increases in Patients with Pyruvate Kinase Deficiency" Dec. 10, 2017—Globe Newswire.
PubChem SID: 440235168, modify date Feb. 25, 2021 (Feb. 25, 2021), Version 2, p. 1-7, Structure.
PubChem SID: 440235168, date Feb. 18, 2021 (Feb. 18, 2021), Version 1 of 2, p. 1-7, Structure.
PubChem CID: 135338361, create date: Dec. 15, 2018 (Dec. 15, 2018), p. 1, formula.
PubChem CID: 135338378, create date: Dec. 15, 2018 (Dec. 15, 2018), p. 1, formula.
PubChem CID: 69203074, create date: Nov. 30, 2012 (Nov. 30, 2012), pp. 1-20, compound summary.
PubChem CID: 69203505, create date: Nov. 30, 2012 (Nov. 30, 2012), pp. 1-20, compound summary.
Rab, et al., AG-348 (Mitapivat), an allosteric activator of red blood cell pyruvate kinase, increases enzymatic activity, protein stability, and ATP levels over a broad range of PKLR genotypes, Haematologica, 105:xxx, (Jan. 23, 2020).
Rab, M.A.E. et al., Rapid and reproducible characterization of sickling during automated deoxygenation in sickle cell disease patients, Am. J. Hematol. (2019; 94; pp. 575-584.
Rabai M, Detterich JA, Wenby RB, et al. "Deformability analysis of sickle blood using ektacytometry." Biorheology. 2014;51(2-3):159-70.
Ramdani, G. and Langsley, G., ATP, an Extracellular Signaling Molecule in Red Blood Cells: A Messenger for Malaria?, Biomed Journal, 37(5):284-292 (2014).
Raththagala, M. et al., Hydroxyurea stimulates the release of ATP from rabbit erythrocytes through an increase in calcium and nitric oxide production, European Journal of Pharmacology, 645(1-3):32-38 (2010).
REBLOZYL [package insert]. Cambridge, Massachusetts, Acceleron Pharma, Inc. (2020), 27 pgs.
REBLOZYL [package insert]. Summit, New Jersey, Celgene Corporation (Nov. 2019), 16 pgs.
Rice-Evans C, Omorphos SC, Baysal E. "Cell membranes and oxidative damage." Biochem J. Jul. 1, 1986, 237(1):265-9.
Rosa, M. et al., Allosteric properties of hemoglobin and the plasma membrane of the erythrocyte: New insights in gas transport and metabolic modulation, Life, 60(2):87-93 (2008).
Ross, M.T., et al., "The DNA sequence of the human X chromosome", Nature, 434, pp. 325-337; (Mar. 2005).
Rott, Ruth, et al., "α-Synuclein fate is determined by USP9X-regulated monoubiquitination", PNAS, (2011).
Roy, R., et al., "hnRNPA1 couples nuclear export and translation of specific mRNAs downstream of FGF-2/SGK2 signalling", Nucleic Acids Research, vol. 42, No. 20, pp. 12483-12497, (Oct. 2014).
Rush, J., et al., "Immunoaffinity profiling of tyrosine phosphorylation in cancer cells", Nature Biotechnology, vol. 23, No. 1, pp. 94-101, (2005).
Sampson M, Archibong AE, Powell A, et al. "Perturbation of the developmental potential of preimplantation mouse embryos by hydroxyurea." Int J Environ Res Public Health. 2010;7(5):2033-44.
Sato, Y., et al., "Ubiquitin-specific protease 9X in host cells interacts with herpes simplex virus 1 ICP0", J. Vet. Med. Sci. 78(3), pp. 405-410; (2016).
Savio et al., "USP9X Controls EGFR Fate by Deubiquitinating the Endocytic Adaptor Eps15", Current Biology 26, pp. 173-183, (Jan. 2016).
Schwartz, R. et al., Two distinct pathways mediate the formation of intermediate density cells and hyperdense cells from normal density sickle red blood cells, Blood, 92(12):4844-4855 (1998).
Schwickart, M., et al., "Deubiquitinase USP9X stabilizes MCL1 and promotes tumour cell survival", Nature vol. 463, pp. 103-108; (Jan. 2010).
Sega, M. et al., Fluorescence assay of the interaction between hemoglobin and the cytoplasmic domain of erythrocyte membrane band 3, Blood Cells Mol Dis., 55(3):266-271 (2015).

(56) References Cited

OTHER PUBLICATIONS

Shen, G., et al., "MicroRNA-26b inhibits epithelial-mesenchymal transition in hepatocellular carcinoma by targeting USP9X," BMC Cancer 14:393, pp. 1-11, (2014).
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Blood (2020) 136 (Supplement 1):21-22, Nov. 4, 2020.
Shrestha, Archana, et al., "Oral Administration of FT-4202, an Allosteric Activator of Pyruvate Kinase-R, Has Potent Anti-Sickling Effects in a Sickle Cell Anemia (SCA) Mouse Model, Resulting in Improved RBC Survival and Hemoglobin Levels," Presented at the 62$^{nd}$ American Society of Hematology (ASH) Annual Meeting, Dec. 5, 2020.
SIKLOS [package insert]. Lannoy, France, Delpharm Lille, (May 2019), 24 pgs.
SIKLOS [package insert]. Paris, France, Addmedica, (Dec. 2017), 25 pgs.
SIKLOS [package insert]. Paris, France, Addmedica, (May 2018), 23 pgs.
Smidrkal, Jan., "Synthesis of fagaronine", Collection of Czechoslovak Chemical Communications, 53(12), pp. 3184-3192, (1988).
Sorathiya, S.D., et al., Preparation and antimicrobial activity of 3-(p-(2',5'-dibromobenzenesulfonamido)phenyl)-5-aryl-1H/acetyl/ phenyl-2-pyrazolines, Indian Journal of Chemistry, Section B: Organic, Incl. Medicinal Chemistry, vol. 36B, No. 7, (1997), Abstract only.
Soupene, E. and Kuypers, F., Identification of an erythroid ATP-dependent aminophospholipid transporter, British Journal of Haematology, 133(4):436-438 (2006).
Space SL, Lane PA, Pickett CK, Weil JV. "Nitric oxide attenuates normal and sickle red blood cell adherence to pulmonary endothelium." Am J Hematol. Apr. 2000, 63(4):200-4.
Spinella, J.F., et al., "Genomic characterization of pediatric T-cell acute lymphoblastic leukemia reveals novel recurrent driver mutations", Oncotarget, vol. 7, No. 40, pp. 65485-65503, (Sep. 2016).
Stasiuk, M. et al., Transformations of erythrocytes shape and its regulation, Postepy Biochem., 55(4):425-33 (2009). English Abstract.
St-Denis, N., et al., "Phenotypic and Interaction Profiling of the Human Phosphatases Identifies Diverse Mitotic Regulators", Cell Reports 17, pp. 2488-2501, (Nov. 2016).
Stebbins et al., Crystal Structure of an Hsp90-Geldanamycin Complex: Targeting of a Protein Chaperone by an Antitumor Agent, Cell, (Apr. 1997), 89, p. 241.
Steinberg, Martin H., Pathophysiologically based drug treatment of sickle cell disease, TRENDS in Pharmacological Sciences, vol. 27, No. 4, (Apr. 2006).
Strausberg, R.L., et al., "Generation and initial analysis of more than 15,000 full-length human and mouse cDNA sequences", PNAS vol. 99, No. 26, pp. 16899-16903, (Dec. 2002).
Sun, H., et al., "Bcr-Abl ubiquitination and Usp9x inhibition block kinase signaling and promote CML cell apoptosis", Blood, (Jan. 2011).
Sundd, Prithu et al., Pathophysiology of Sickle Cell Disease, Annual Review of Pathology: Mechanisms of Disease, (Oct. 9, 2018), pp. 261-290.
Swanson, Devin M. et al., "Identification and biological evaluation of 4-(3-trifluoromethylpyridine-2-yl) piperazine-1-c arboxylic acid (5-trifluoromethylpyridin-2-yl) amide, a high affinity TRPV1 (VR1)vanilloid receptor antagonist", Journal of Medicinal Chemistry, 48(6), pp. 1857-1872 (2005).
Taipale, M., et al., "A Quantitative Chaperone Interaction Network Reveals the Architecture of Cellular Protein Homeostasis Pathways", Cell 158, pp. 434-448, (Jul. 2014).
Takenaka, M. et al, Isolation and characterization of the human pyruvate kinase M gene, Eur J Biochem, 198(1):101-106 (1991).
Talmud, P.J., et al., "Gene-centric Association Signals for Lipids and Apolipoproteins Identified via the Human CVD Bead Chip", The American Journal of Human Genetics 85, pp. 628-642, (Nov. 2009).
Tanphaichitr, V.S. et al, Successful bone marrow transplantation in a child with red blood cell pyruvate kinase deficiency, Bone Marrow Transplant, 26(6):689-690 (2000).
Taya, S., et al., "The deubiquitinating enzyme Fam interacts with and stabilizes β-catenin", Genes to Cells 4, pp. 757-767, (1999).
Taya, S., et al., "The Ras Target AF-6 is a Substrate of the Fam Deubiquitinating Enzyme", The Journal of Cell Biology, vol. 142, No. 4, pp. 1053-1062, (Aug. 1998).
Telen, Marilyn, Malik, Punam, and Vercellotti, Gregory M., Therapeutic strategies for sickle cell disease: towards a multi-agent approach, Nature Reviews/Drug Discovery; (Dec. 4, 2018).
Terao, Y., et al., "Trifluoroacetic Acid-Catalyzed 1,3-Cycloaddition of the Simplest Iminium Ylide Leading to 3- or 3,4-Substituted Pyrrolidines and 2,5-Dihydropyrroles", Chem. Pharm. Bull., 33(7), pp. 2762-2766, (1985).
Théard, D., et al., "USP9x-mediated deubiquitination of EFA6 regulates de novo tight junction assembly", The EMBO Journal, vol. 29, No. 9, pp. 1499-1509, (2010).
Thein, Swee Lay, The Molecular Basis of β-Thalassemia, Cold Spring Harb Perspect Med. (2013).
Thompson, Alexis, M.D., M.P.H., "A Targeted Agent for Sickle Cell Disease—Changing the Protein but Not the Gene," The New England Journal of Medicine, (Jun. 14, 2019).
Tian, S., et al., Yaoxue Xueba (1993), 28(11), pp. 870-875. Chemical Abstract No. 120:299229.
Toloczko, A., et al., "Deubiquitinating Enzyme USP9X Suppresses Tumor Growth via LATS kinase and Core Components of the Hippo pathway", Cancer Research, pp. 1-37, (Jul. 2017).
Tripathi, Ashutoshi and Safo, Martin K., In Silico-Screening Approaches for Lead Generation: Identification of Novel Allosteric Modulators of Human-Erythrocyte Pyruvate Kinase, Allostery: Methods and Protocols, Methods in Molecular Biology, Chpt. 19, vol. 796, pp. 351-367 (2012).
Trivigno, D., et al., "Deubiquitinase USP9x Confers Radioresistance through Stabilization of Mcl-1 1,2", NEO Plasia, vol. 14, No. 10, pp. 893-904, (Oct. 2012).
Tsai, Y.C., et al., "Functional Proteomics Establishes the Interaction of SIRT7 with Chromatin Remodeling Complexes and Expands Its Role in Regulation of RNA Polymerase ITranscription", Molecular & Cellular Proteomics 11.5, pp. 60-76, (2012).
Tsutsumi H, Tani K, Fujii H, Miwa S. "Expression of L- and M-type pyruvate kinase in human tissues. Genomics." 1988, 2(1):86-9.
United States Securities and Exchange Commission, Form S-1 Registration Statement, Forma Therapeutics Holdings, Inc., dated Dec. 8, 2020, 374 pages.
United States Securities and Exchange Commission, Form S-1, Registration Statement—Forma Therapeutics Holdings, Inc., May 29, 2020.
Upadhyay J., et al., Studies on pyrazolines. Part III. Preparation and antimicrobial activity of 3-(4-phenylsulfonamidophenyl)-5-aryl-1-ace tyl/phenyl-4,5-dihydropyrazoles, Journal of the Indian Chemical Society, vol. 68, No. 7, (1991), pp. 413-414.
Van Zweiten, R. et al., Inborn defects in the antioxidant systems of human red blood cells, Free Radio Biol Med., 67:377-386 (2014).
Vanderah et al, Novel d-amino acid tetrapeptides produce potent antinociception by selectively acting at peripheral kappa-opioid receptors, European Journal of Pharmacology, Elsevier Science, vol. 583, No. 1, pp. 62-72 (Jan. 24, 2008).
Varjosalo, M., et al., The Protein Interaction Landscape of the Human CMGC Kinase Group, Cell Reports 3, pp. 1306-1320, (Apr. 2013).
Verma, S.K. et al., Imidazole-Catalyzed Monoacylation of Symmetrical Diamines, Organic Letters, 12(19): 4232-4235 (201).
Vichinsky, E. et al., "A Phase 3 Randomized Trial of Voxelotor in Sickle Cell Disease," N Engl J Med. DOI: 10.1056/NEJMoa1903212 (Jun. 2019).
Vichinsky, E. et al., Protocol to A Phase 3 Randomized Trial of Voxelotor in Sickle Cell Disease, (Jun. 14, 2019).
Vichinsky, E. et al., Supplementary Appendix to A Phase 3 Randomized Trial of Voxelotor in Sickle Cell Disease, (Jun. 14, 2019).
Vong, Q. P., et al., "Chromosome Alignment and Segregation Regulated by Ubiquitination of Survivin", Science, vol. 310, pp. 1499-1504, (Dec. 2, 2005).

(56) References Cited

OTHER PUBLICATIONS

Voskou S, Aslan M, Fanis P, Phylactides M, Kleanthous M. "Oxidative stress in β-thalassaemia and sickle cell disease." Redox Biol. Dec. 2015, 6:226-39.
Wagner, G. et al., Red cell vesiculation—a common membrane physiologic event, J Lab Clin., 108(4):315-324 (1986).
Wan, C., et al., "Panorama of ancient metazoan macromolecular complexes", Nature 525(7569), pp. 339-344, (Sep. 2015).
Wang, G.S., et al., Journal of Ethnopharmacology, 26 (1989), pp. 147-162.
Wang, H. et al., JMJD5 regulates PKM2 nuclear translocation and reprograms HIF-1a-mediated glucose metabolism, PNAS, 111(1):279-284 (2014).
Wang, J., et al, "TopBP1 Controls BLM Protein Level to Maintain Genome Stability", Molecular Cell 52, pp. 667-678, (Dec. 2013).
Wang, Q., et al., "The X-linked Deubiquitinase USP9X Is an Integral Component of Centrosome", The American Society for Biochemistry and Molecular Biology, Inc., pp. 1-33, (2017).
Wang, S. et al., "Ablation of the oncogenic transcription factor ERG by deubiquitinase inhibition in prostate cancer", PNAS, vol. 111, No. 11, pp. 4251-4256, (Mar. 2014).
Wang, S., et al., "The ubiquitin ligase TRIM25 targets ERG for degradation in prostate cancer", Oncotarget, vol. 7, No. 40, pp. 64921-64931, (2016).
Wang, X, et al., "Hsp90 Cochaperone Aha1 Downregulation Rescues Misfolding of CFTR in Cystic Fibrosis", Cell 127, pp. 803-815, (Nov. 2006).
Waza et al., Nature, 11, No. 10, (Oct. 2005), pp. 1088-1095.
Weatherall, D., The inherited diseases of hemoglobin are an emerging global health burden, Blood, 115(22):4331-43336 (2010).
Wei, Wan-Guo et al., "A practical procedure for multisubstituted .beta.-naphthols and their derivatives", Tetrahedron, 59(34), pp. 6621-6625, (2003).
Willcocks, J. et al., Simultaneous determination of low free Mg2+ and pH in human sickle cells using P NMR spectroscopy, The Journal of Biological Chemistry, 277(51):49911-49920 (2002).
Wood BL, Gibson DF, Tait JF. "Increased erythrocyte phosphatidylserine exposure in sickle cell disease: flow-cytometric measurement and clinical associations." Blood., 88(5):1873-80 (Sep. 1, 1996).
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease (PRAISE)," Blood (2020) 136 (Supplement 1):19-20, Nov. 4, 2020.
Wood, Kenneth W., et al., "An Adaptive, Randomized, Placebo-Controlled, Double-Blind, Multi-Center Study of Oral FT-4202, a Pyruvate Kinase Activator in Patients with Sickle Cell Disease," Presented at the 62$^{nd}$ American Society of Hematology (ASH) Annual Meeting, Dec. 7, 2020.
Woods, N.T., et al., "Charting the Landscape of Tandem BRCT Domain-Mediated Protein Interactions", Sci Signal, 5(242), pp. 1-35, (2014).
Wright, S.W. et al., A Convenient Preparation of Heteroaryl Sulfonamides and Sulfonyl Fluorides from Heteroaryl Thiols, J. Org. Chem., 71: 1080-1084 (2006).
Wu, Y., et al., "Aberrant phosphorylation of SMAD4 Thr277-mediated USP9x-SMAD4 interaction by free fatty acids promotes breast cancer matastasis", Cancer Research, pp. 1-34, (2017).
Wu, Z., et al., "Targeted Ubiquitination and Degradation of G-Protein-Coupled Receptor Kinase 5 by the DDB1-CUL4 Ubiquitin Ligase Complex", PLOS One, vol. 7, Issue 8, pp. 1-11, (Aug. 2012).
Xie, Y., et al., "Deubiquitinase FAM/USP9X Interacts with the E3 Ubiquitin Ligase SMURF1 Protein and Protects It from Ligase Activity-dependent Self-degradation", The Journal of Biological Chemistry., vol. 288, No. 5, pp. 2976-2985, (Feb. 2013).
Xu, Z., et al., "Identification of a Deubiquitinating Enzyme as a Novel AGS3-Interacting Protein", PLOS One, vol. 5, Issue 3, pp. 1-12, (Mar. 2010).
Yan, J., et al., "Usp9x- and Noxa-mediated Mcl-1 downregulation contributes to pemetrexed-induced apoptosis in human non-small-cell lung cancer cells", Cell Death and Disease 5, pp. 1-7, (2014).

Yang H, Merica E, Chen Y, Cohen M, Goldwater R, Hill C, et al. "Phase I single (SAD) and multiple ascending dose (MAD) studies of the safety, tolerability, pharmacokinetics (PK) and pharmacodynamics (PD) of AG-348, a first-in-class allosteric activator of pyruvate kinase-R, in healthy subjects." Blood. 2014, 124:4007.
Yang H, Merica E, Chen Y, et al. "Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers." Clin Pharmacol Drug Dev. Aug. 9, 2018.
Yang, H. et al., Phase 1 Single- and Multiple-Ascending-Dose Randomized Studies of the Safety, Pharmacokinetics, and Pharmacodynamics of AG-348, a First-in-Class Allosteric Activator of Pyruvate Kinase R, in Healthy Volunteers, 8 Clin. Pharmacol. Drug Dev. 246-259 (2019).
Yi, S., et al., Leukemia Research, vol. 15(10), (1991), pp. 883-886.
You, J. and Pickart, C.M., "A HECT Domain E3 Enzyme Assembles Novel Polyubiquitin Chains", vol. 276, No. 23, pp. 19871-19878, (2001).
Yu, W., et al., "Large-Scale Concatenation cDNA Sequencing", Genome Research 7, pp. 353-358, (1997).
Zanella A, Fermo E, Bianchi P, Chiarelli LR, Valentini G. "Pyruvate kinase deficiency: The genotype-phenotype association." Blood Rev. 2007, 23:217-31.
Zanella A, Fermo E, Bianchi P, Valentini G. "Red cell pyruvate kinase deficiency: molecular and clinical aspects." Br J Haematol. 2005;130(1):11-25.
Zhang, C., et al., "Synergistic anti-tumor activity of gemcitabine and ABT-737 in vitro and in vivo through disrupting the interaction of USP9X and Mcl-1", Molecular Cancer Therapeutics, (May 12, 2011).
Zhang, C., et al., "USP9X destabilizes pVHL and promotes cell proliferation", Oncotarget, vol. 7, No. 37, pp. 60519-60534, (2016).
Zhang, Y & Xia, Y., Adenosine signaling in normal and sickle erythrocytes and beyond, Microbes Infect., 14(10) (2012).
Zhang, Y. et al., Detrimental effects of adenosine signaling in sickle cell disease, Nature Medicine, 17(1):79-87 (2011).
Zhang, Yongmin et al., "Organic reactions in chiral micelles. 7. The structural effects on the asymmetric oxidation of prochiral sulfides in chiral micelles", Chinese Journal of Chemistry, (1990), pp. 89-96.
Zhao, Y., et al., "Noncanonical regulation of alkylation damage resistance by the OTUD4 deubiquitinase", EMBO Journal, vol. 34, No. 12, pp. 1687-1703, (2015).
Zhi et al., Hybrid Antibacterals. DNA Polymerase—Topoisomerase Inhibitors. J. Med. Chem., published on Web Jan. 25, 2006., vol. 49, pp. 1455-1465, especially p. 1456. Scheme 3, compound 4; p. 1457, Scheme 4, compound 13, p. 1462.
Zhou, L., et al., "The Scaffold Protein KSR1, A Novel Therapeutic Target for the Treatment of Merlin-Deficient Tumors", Oncogene 35(26), pp. 3443-3453, (Jun. 2016).
Zhou, ZH et al., Phosphorus, Sulfur and Silicon and the Related Elements (1999), 152, pp. 45-52. Chemical Abstract No. 132: 180853.
Zhu, Tong et al., Polymer-Supported Synthesis of Pyridone-Focused Libraries as Inhibitors of Anaplastic Lymphoma Kinase, Journal of Combinatorial Chemistry, 8(3), pp. 401-409.
International Search Report and Written Opinion for PCT/US2019/051831, dated Dec. 6, 2019 (06.12.2020).
International Search Report and Written Opinion for PCT/US2020/051645, dated Dec. 7, 2020 (07.12.2020).
International Search Report and Written Opinion for PCT/US2020/051579, dated Dec. 10, 2020 (10.12.2020).
International Search Report and Written Opinion for PCT/US2019/052024, dated Dec. 23, 2019 (23.12.2019).
International Search Report and Written Opinion for PCT/US2018/023405, dated Jun. 5, 2018 (05.06.2018).
Clinical Trial Study—NCT04000165 "A Dose-Finding Study of AG-348 in Sickle Cell Disease", ClinicalTrials.gov, Jun. 27, 2019, 9 pages.
Kalfa, T.A. et al., "Phase 1 Single (SAD) and Multiple Ascending Dose (MAD) Studies of the Safety, Tolerability, Pharmacokinetics (PK) and Pharmacodynamics (PD) of FT-4202, an Allosteric Acti-

(56) References Cited

OTHER PUBLICATIONS vator of Pyruvate Kinase-R, in Healthy and Sickle Cell Disease Subjects", Blood, American Society of Hematology, Nov. 13, 2019, p. 3, vol. 134.

National Center for Biotechnology Information. PubChem Substance Record for SID 377251214, SCHEMBL20511283, Source: SureChEMBL. https://pubchem.ncbi.nlm.nih.gov/substance/377251214. Accessed Nov. 3, 2020. Available Dec. 15, 2018. (Year: 2018).

Supplemental European Search Report for EP Application 20 86 4351, Aug. 2, 2023, 10 pages.

U.S. Appl. No. 16/576,720, filed Sep. 19, 2019, 47 pages.

Qian et al., "Drug-polymer solubility and miscibility: Stability consideration and practical challenges in amorphous solid dispersion development", J. Pharm. Sci., Jul. 2010, vol. 99, No. 7, pp. 2941-2947.

SurechEMBL, "Open Patent Data", 2 pages, downloaded Oct. 31, 2023 from https://www.surechembl.org/knowledgebase/75969.

Schroeder et al., "Etavopivat, a Pyruvate Kinase Activator in Red Blood Cells, for the Treatment of Sickle Cell Disease", The Journal of Pharmacology and Experimental Therapeutics, Mar. 2022, vol. 380, pp. 210-219.

\* cited by examiner

FIGURE 24A

| Cohort | Dose (mg) | Tmax (hr) | Cmax (ng/mL) | AUC0-24 (hr*ng/mL) | Half-life (hr) |
|---|---|---|---|---|---|
| SAD-1 | 200 | 0.50 [100] | 380 [69.9] | 1127 [47.2] | 11.0 [30.6] |
| SAD-2 | 400 | 1.50 [79.7] | 770 [21.1] | 2574 [24.1] | 12.7 [20.4] |
| SAD-3 | 700 | 0.53 [123] | 2204 [56.0] | 6468 [29.0] | 13.3 [28.0] |
| SAD-4 | 1000 | 0.51 [99.5] | 2452 [42.0] | 8331 [48.6] | 10.4 [22.2] |

FIGURE 24B

| Cohort | Dose | Day | Tmax (hr) | Cmax (ng/mL) | AUC0-tau (hr*ng/mL) | Ratio Day14/ Day1 Cmax | Ratio Day14 /Day1 AUC0-tau |
|---|---|---|---|---|---|---|---|
| MAD-1 | 100 mg BID | 1 | 1.00 [60.0] | 129 [62.9] | 470 [32.8] | | |
| | | 14 | | 141 [37.1] | 563 [37.5] | 1.10 [41.9] | 1.46 [5.3] |
| MAD-2 | 200 mg BID | 1 | 2.00 [55.3] | 353 [56.1] | 1016 [37.1] | | |
| | | 14 | | 299 [30.8] | 1072 [44.5] | 0.85 [50.7] | 1.27 [42.4] |
| MAD-3 | 300 mg BID | 1 | 2.00 [61.2] | 502 [62.4] | 1353 [38.7] | | |
| | | 14 | | 704 [29.5] | 2406 [6.9] | 1.40 [47.6] | 1.26 [9.2] |
| MAD-4 | 400 mg QD | 1 | 1.00 [68.8] | 760 [47.2] | 2465 [30.2] | | |
| | | 14 | | 668 [26.7] | 2962 [20.7] | 0.88 [58.2] | 1.20 [27.0] |

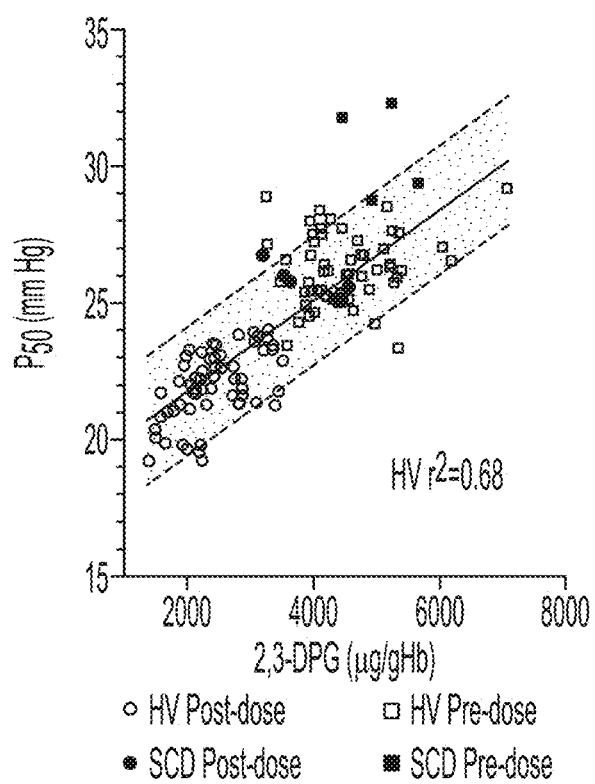

ACTIVATING PYRUVATE KINASE R

CROSS-REFERENCE TO RELATED APPLICATIONS

This application claims the benefit of U.S. Provisional Application No. 63/163,362, filed Mar. 19, 2021, which is incorporated by reference in its entirety.

TECHNICAL FIELD

This disclosure relates to therapeutic compounds, compositions and methods comprising the administration of compounds that activate pyruvate kinase R (PKR), including methods of treating hemoglobinopathy conditions by the administration of therapeutic compositions activating pyruvate kinase R (PK-R).

BACKGROUND

Hemoglobin is a tetrameric protein which binds oxygen in Red Blood Cells (RBC). Oxygen binds to the four hemes of the hemoglobin molecule. Each heme contains porphyrin and ferrous iron that reversibly binds oxygen through an iron-oxygen bond. Binding of each of four successive oxygen molecules to the heme requires less energy than the previous bound oxygen molecules. Hemoglobin has two alpha and two beta subunits symmetrically arranged to form dimers that rotate during oxygen release to open a central water cavity. An allosteric transition including movement of the alpha-beta dimer takes place between the binding of the third and fourth oxygen. In blood, hemoglobin is in equilibrium between two allosteric structures: a deoxygenated (tense, or "T" state), and an oxygenated (relaxed or "R" relaxed) state.

Pharmaceutical compositions for influencing the allosteric equilibrium of hemoglobin (e.g., by increasing the affinity of oxygen for hemoglobin) are useful for treating various diseases or conditions. For example, increasing the affinity of hemoglobin for oxygen can provide a variety of medical benefits, such as the treatment of Sickle Cell Anemia or other hemoglobinopathies. For example, therapeutic approaches that increase oxygen affinity (i.e., reduce deoxygenation) of HgbS would presumably decrease polymer formation, changes to the cell membrane, and clinical consequences associated with certain hemoglobinopathy conditions such as SCD.

Hemoglobinopathy is a diverse range of rare inherited genetic disorders that affect hemoglobin, the iron-containing protein in RBCs responsible for transporting oxygen in the blood. Normal hemoglobin is a tetramer of two beta-globin and two alpha-globin protein subunits. Mutations in either the beta- or alpha-globin genes may cause abnormalities in the production or structure of these subunits that can lead to toxicity to or reduced oxygen carrying capacity of RBCs. Collectively, disorders that arise from these mutations are referred to as hemoglobinopathies.

SCD is the most common type of hemoglobinopathy. SCD is a common single-gene disorder. SCD is a recessive disease caused by inheritance of hemoglobin S (HbS) a mutated form of the β-globin gene, together with another copy of HbS, or a different defective β-globin gene variant. Due to its chronic nature, the economic burden of SCD is high, both in terms of direct costs for lifelong management, hospitalizations and associated morbidities, and indirect costs of lost lifetime earnings and reduced productivity of both patients and caregivers. The current therapeutic treatment of SCD is inadequate. Acute painful VOC events are common, occurring on approximately 55% of days, as self-reported in SCD patients. Supportive care for the management of painful VOCs entails the use of opioids, which are effective at managing pain but are highly addictive. For most patients treatment involves the chronic use of hydroxyurea, or HU, an oral chemotherapy, which stimulates production of fetal hemoglobin, or HbF, and reduces sickle hemoglobin, or HbS, polymerization and consequent RBC sickling. While inducing HbF can be effective therapeutically, HU can suppress bone marrow function and cause birth defects. Although HU is considered to have an acceptable therapeutic index given the consequences of SCD, HU is underutilized due to safety concerns and side effects. Recent approval of voxelotor and crizanlizumab will evolve the treatment paradigm but are in early stages of adoption, and neither drug provides a complete solution, which is to address underlying anemia and to reduce clinical sequalae such as VOCs. FIG. 1 illustrates certain therapeutic strategies and approved modalities for the treatment of SCD.

Beta thalassemia is a rare genetic disease with an estimated prevalence of approximately 20,000 patients across the United States and Europe and approximately 300,000 patients globally. In beta thalassemia, mutations in the beta-globin gene cause production of a defective beta-globin subunit or the absence of a beta-globin, which results both in a reduction in the total amount of oxygen carrying by RBCs as well as an excess of alpha hemoglobin subunits that aggregate and cause RBC toxicity and destruction, or hemolysis. The spleen in these patients is often enlarged due to the high rate of chronic hemolysis. Chronic hemolysis leads to elevated levels of bilirubin which can form stones in the gall bladder that can cause obstruction. To compensate for the anemia in these patients, the bone marrow, the typical RBC producing tissue, expands, and RBC production outside of the bone marrow in organs such as the liver can occur. This expansion of the bone marrow can lead to bone deformities.

Given the current standard of care for SCD and beta thalassemia, there is a clear medical need for a noninvasive, disease-modifying therapy with appropriate safety and efficacy profiles. While there has been an increase in novel therapeutic approaches for the treatment of SCD, there remain limited treatment options for these patients and drugs with improved efficacy and tolerability are still needed to manage patients with this disease. Due to the progressive nature of SCD, early interventions that modify the disease but do not affect pediatric growth and development are needed. Emerging treatments for SCD target the mechanism of disease (HbS polymerization) or the downstream consequences of RBC deformation (e.g. vasoocculsion) or the underlying cause of disease (mutations in hemoglobin); however, these treatment strategies are limited in their outcomes and applicability, and disease-modifying therapies that are safe, effective and accessible for the majority of SCD patients are needed. Despite currently available treatment options, significant unmet needs remain as most patients with SCD suffer from significant morbidity, reduced quality of life, lifelong disability and average life expectancy that is 25 to 30 years lower than that of unaffected adults.

SUMMARY

The instant disclosure relates to the surprising discovery that once daily (QD) administration of Compound 1 is safe and effective for treating sickle cell disease (SCD) in adult and pediatric patients.

The instant disclosure further relates to the surprising discovery that Compound 1 pharmaceutical compositions may be administered in a dosing regimen that treats sickle cell disease despite resulting in extended periods of time where Compound 1 plasma concentrations are below the pharmacokinetic levels that one of ordinary skill in the art would expect are necessary for the desired pharmacodynamic outcomes. In some embodiments, 200 mg, 300 mg, 400 mg, or 600 mg of Compound 1 is administered once every 24 hours or once daily (QD). In some embodiments, the disclosure relates to a method of treating pediatric patients diagnosed with a hemoglobinopathy such as SCD or beta thalassemia, by administering a therapeutically effective amount of a Compound 1 pharmaceutical composition.

(S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one ("Compound 1") is an oral activator of pyruvate kinase R (PKR) that decreases 2,3-DPG and increases ATP in erythrocytes. Compound 1 (or a pharmaceutically acceptable salt thereof) is useful for the treatment of sickle cell disease (SCD) in adult patients 18 years of age and older. In some embodiments, Compound 1 is useful for the treatment of sickle cell disease in pediatric patients 12 to <18 years of age.

The compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one ("Compound 1") can be administered (e.g., orally) once per day (QD). The pharmacological response of Compound 1 is observed for a time period sufficient to support once daily (QD) dosing, despite reaching its maximum plasma concentration ($C_{max}$) within a few hours of administration and rapidly decreasing in concentration after $T_{max}$. For example, FIG. 41 shows the pharmacokinetic (PK) measurement of the blood concentration of Compound 1 in humans (circles) and the pharmacodynamic measurement of the resulting concentration of 2,3-DPG measured in these subjects (squares) after the administration of a single dose of Compound 1. The observed maximum 2,3-DPG decrease occurred about 16 to 24 hours post-dose and was sustained up to about 48 hours after administration. In addition, the observed increase in hemoglobin oxygen affinity in humans was comparable after once daily and twice daily administration of Compound 1. Compound 1 unexpectedly increased hemoglobin oxygen affinity in humans to a comparable degree in once daily and twice daily administration. FIG. 40 is a graph showing that the effect on oxygen affinity (measured as p50) measured 24 hours after administration of Compound 1 is similar with once daily and twice daily dosing. The PK profile of Compound 1 was biphasic with a terminal half-life of about 12-14 hours. Overall, the observed pharmacodynamic response in HVs was surprisingly durable, with 2,3-DPG depression observed long after plasma Cmax, with an apparent PD half-life supporting QD dosing. Accordingly, in some embodiments, methods of treatment comprise the once daily (QD) administration of Compound 1 (i.e., not twice per day or BID), or a pharmaceutically acceptable salt thereof, to a patient in need thereof, such as a patient diagnosed with a hemoglobinopathy such as Sickle Cell Disease (SCD).

Following 14 days of dosing in healthy subjects in the clinical trial of Example 8, the observed clearance on day 1 and day 14 was unchanged, providing clinical evidence that the PK of Compound 1 is time-independent and not a substrate of auto-induction or auto-inhibition at the doses tested.

One aspect of the disclosure relates to methods of treating a patient, such as a patient diagnosed with a hemoglobinopathy, comprising the administration of a therapeutically effective amount of a PKR Activating Compound or a pharmaceutically acceptable salt thereof. As used herein, a "PKR Activating Compound" is a compound having an $AC_{50}$ value of less than 1 micro Molar using the Luminescence Assay described in Example 2, or a pharmaceutically acceptable salt and/or other solid form thereof.

The compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one ("Compound 1") is a selective, orally bioavailable PKR Activating Compound that decreases 2,3-DPG, increases ATP, and has anti-sickling effects in disease models with a wide therapeutic margin relative to preclinical toxicity.

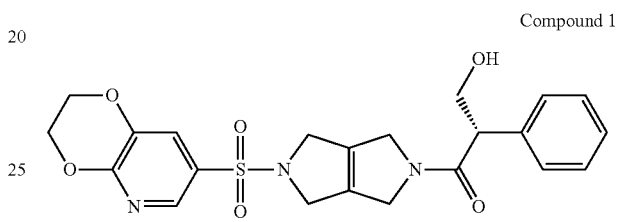

Compound 1

Compound 1 is an allosteric activator of recombinant wild type (WT) PKR and a mutant enzyme, PKR R510Q which is one of the most prevalent PKR mutations in North America. PKR exists in both a dimeric and tetrameric state, but functions most efficiently as a tetramer. Pyruvate kinase R (PKR) is the isoform of pyruvate kinase expressed in RBCs, and is the rate limiting enzyme in the glycolytic pathway. Compound 1 stabilizes the tetrameric form of PKR, thereby lowering the Michaelis-Menten constant (Km) for its substrate, phosphoenolpyruvate (P).

Compound 1 can be orally administered once per day (QD) to a patient in need thereof which is a significant benefit in a patient population requiring lifelong therapy. Compound 1 was evaluated in a randomized, placebo-controlled, double blind, single ascending and multiple ascending dose study to assess the safety, pharmacokinetics, and pharmacodynamics of Compound 1 in healthy volunteers in both single ascending dose (SAD) cohorts and in multiple ascending dose (MAD) cohorts. Four healthy SAD cohorts were evaluated at doses of 200, 400, 700, and 1000 mg, and four healthy MAD cohorts received 200 to 600 mg total daily doses for 14 days at QD or BID dosing (100 mg BID, 200 mg BID, 300 mg BID, and 400 mg QD). One SAD cohort (700 mg) and several MAD cohorts (300 mg, 400 mg QD, and 600 mg QD) are being evaluated in in SCD patients.

In some embodiments, the compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one ("Compound 1") is useful in a single daily (QD) administration to increase hemoglobin oxygen affinity in the red blood cells (RBCs) of a human subject as measured by a reduced p50 (pO2 at 50% hemoglobin saturation) measured in the RBCs at 24 hours after the administration of the compound. In some embodiments, Compound 1 can be used in daily (QD) administration for 14 consecutive days to increase hemoglobin oxygen affinity in the red blood cells (RBCs) of a human subject as measured by a reduced p50 (pO2 at 50% hemoglobin saturation)

measured in the RBCs at after 14 days of QD administration of the compound to the human subject. In some embodiments, Compound 1 is useful in reducing the 2,3-DPG concentration in the blood of the human subject by at least 30% at 24 hours after the administration of the compound. In some embodiments, Compound 1 is useful in increasing the ATP concentration in the blood of the human subject by at least 40% after administering the compound once daily to the subject for 14 consecutive days. In some embodiments, Compound 1 is useful in simultaneously activating PKR, increasing ATP, decreasing 2,3-DPG and increasing oxygen affinity (p50) in the blood of the subject for 72 hours after administering the compound to the subject.

In some embodiments, Compound 1 can be administered to a human subject diagnosed with Sickle Cell Disease (SCD). In some embodiments, the human subject is a pediatric SCD patient who is at least age 12. In some embodiments, the human subject is at least age 18.

In some embodiments, Compound 1 is useful in treating a human subject diagnosed with one of the following hemoglobin genotypes: Hgb SS, Hgb Sβ+-thalassemia, Hgb Sβ0-thalassemia, or Hgb SC.

In some embodiments, the compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is for use in the treatment of Sickle Cell Disease in a human subject having a Hgb SS or Hgb SC hemoglobin genotype.

In RBCs of the healthy volunteers, Compound 1 demonstrated a reduction in 2,3-DPG and an increase in ATP. In addition, the reduction of 2,3-DPG correlated with increased oxygen affinity with single and multiple doses of Compound 1. In the SAD cohorts, the healthy subjects' maximum decreases in 2,3-DPG levels generally occurred about 24 hours after the first dose with the reduction sustained about 48-72 hr postdose. After 14 days of Compound 1 dosing these PD effects were maintained along with an increase in ATP over baseline. The healthy volunteers who received a single dose of Compound 1 experienced a decrease in p50 measured 24-hours post-dose, relative to subjects who received the placebo. In the MAD cohorts, the subjects' maximum decrease in 2,3-DPG on Day 14 was 55% from baseline (median), and the 2,3-DPG levels reached a nadir and plateaued on Day 1 and did not return to baseline levels until 72 hours after the final dose on Day 14. Healthy subjects in the MAD cohorts who received Compound 1 experienced a decrease in blood 2,3-DPG levels, relative to subjects who received the placebo. Notably, these effects were maintained for more than one day after Compound 1 dosing was stopped at day 14. In addition, p50 (PO2 at 50% hemoglobin saturation) of healthy subjects in the MAD cohorts determined after 14 days of twice daily dosing were reduced at all dose levels tested (median reduction ranged from ~3-5 mmHg). In addition, the MAD cohort healthy subjects' blood ATP levels measured were elevated, relative to baseline, on day 14, and (notably) remained elevated for about 60 hours and returned to baseline 72 hours after the last dose.

In healthy volunteers who received single doses of Compound 1, dose normalized Cmax and AUC increased with increasing doses ≥700 mg suggesting greater than dose proportional increases in exposure at the highest doses tested (FIG. 24A). Compound 1 exhibited dose linear increase in exposure and time-independent PK, where PK parameters (Cmax, AUC) are similar after 14 days of QD dosing (FIG. 24B) and the PD activity of Compound 1 was observed at all dose levels after 24 h (decreased 2,3-DPG, $p<0.0001$) and after 14-days (increased ATP, $p<0.0001$) of dosing. The biologic consequence of this PD response was an increase in oxygen affinity (decreased p50, $p<0.0001$) within 24 h of Compound 1 dosing and a decrease in absolute reticulocyte counts ($p<0.0001$) with a slight increase in hemoglobin levels (ns) by Day 4 of the dosing period in all Compound 1 dose cohorts. Administration of Compound 1 for 3 days reduced reticulocytes ($p<0.0001$), along with increased hemoglobin (ns). Decreased reticulocyte counts may refect increased RBC lifespan in healthy volunteers.

Applicant has also discovered that the increase in oxygen affinity observed in subjects treated with Compound 1 correlated with the reduction of 2,3-DPG. That is, the observed decrease in 2,3-DPG (the independent variable) after the administration of Compound 1 was correlated with an observed increase in oxygen affinity (the dependent variable) in humans receiving Compound 1 in the clinical trial of Example 8. A positive correlative relationship between 2,3 DPG and p50 levels was observed for healthy subjects receiving various doses of Compound 1 in the SAD and MAD cohorts: the increase in oxygen affinity in subjects treated with Compound 1 correlated with the reduction of 2,3-DPG. However, the observed 2,3 DPG modulation does not track directly plasma pharmacokinetics (blood concentration of Compound 1) for healthy subjects after administration of a single dose of Compound 1 (400 mg), where the pharmacodynamic maximum (i.e., the minimum of the 2,3-DPG concentration, at time ~24 h) occurred nearly 24 h after the Cmax (i.e., maximum of the PK curve, at time ~1-2 h).

Compound 1 was evaluated in a randomized, placebo-controlled, double blind, single ascending and multiple ascending dose study to assess the safety, pharmacokinetics, and pharmacodynamics of Compound 1 in sickle cell disease (SCD) patients. Compound 1 was well tolerated and has favorable biologic effects in SCD patients tested, with evidence of pharmacodynamic activity translating into increased oxygen affinity, a shift in the Point of Sickling to lower oxygen tensions, and improved membrane deformability of sickle RBCs at low values of pO2 compared to pre-treatment baseline values. Based on the safety and PK/PD profile in healthy volunteer studies, a single 700 mg single dose was initially evaluated in patients with SCD (n=7). All patients had a Hb SS genotype and a mild VOC history but persistent anemia and ongoing hemolysis, despite hydroxyurea therapy.

Increased hemoglobin $O_2$ affinity (decreased p50) was observed after a single 700 mg dose of Compound 1 in patients with SCD, and the increased hemoglobin $O_2$ affinity correlated with a reduction in 2,3-DPG in patients with SCD. The maximum 2,3-DPG and ATP responses were observed 24 hours after administration of Compound 1. A single dose of Compound 1 resulted in an increase in Hb of 0.5 g/dL (range: 0.3, 0.9) in Compound 1-treated participants vs. a decrease in Hb of 0.4 g/dL (range: −0.5, −0.3) in placebo-treated participants (decreased Hb potentially due to phlebotomy). The decrease in Hb in placebo patients was attributed to phlebotomy performed to obtain blood for PK/PD measurements over the first 24 hour period. Thus, there was a mean Hb difference of ~0.9 g/dL in participants receiving Compound 1 or placebo. Decreased lactate dehydrogenase (LDH) was also observed in Compound 1-treated participants 72 hours after Compound 1 dosing, indicating a reduction in RBC hemolysis. Compound 1 decreased the point of sickling (the partial pressure of $O_2$ at which HbS polymerization causes stiffening of the RBC) and improved sickle RBC $O_2$-dependent deformability, as demonstrated by an increase in the minimum elongation index (Elmin) measured in the Oxygenscan. Compound 1 increased O2 affinity (decreased p50) in all participants treated. Compound 1 improved osmolality-dependent membrane function in sickle RBCs, as demonstrated by improvements (i.e., right shifts toward normal) in $O_{min}$ and $O_{hyper}$ measured with Osmoscan. Osmoscan evaluates RBC membrane function (deformability) across an osmolality gradient. The Osmoscan of SCD RBCs is differentiated from that obtained from healthy RBCs in the following ways: (1) the $O_{min}$ is reduced (shifted to the left), reflecting an increased surface/volume ratio, (2) the ratio of $EI_{max}/O_{max}$ is reduced (shifted to the left) reflecting reduced deformability and poor ion channel function, and (3) the $O_{hyper}$ is reduced (shifted to the left), reflecting increased RBC viscosity and decreased RBC cell volume. These effects were transient, returning to baseline 3 to 7 days after the single dose of Compound 1. SCD subjects who received a single dose of Compound 1 experienced increased oxygen affinity of HbS, attaining an oxygen dissociation curve similar to HbA, and also experienced a left shift in the point of sickling (PoS) with an increase in the Elmin.

Compound 1 improved oxygen affinity, decreased point of sickling and improved deformability in patients diagnosed with SCD. Compound 1 also improved membrane function, demonstrated by an improved response to an osmotic gradient under shear stress. A single dose of Compound 1 resulted in improvements in hemoglobin, RBCs, and reticulocyte counts occurred when maximum PD effects were observed. These improvements indicate a sustained 2,3-DPG reduction and increased ATP production were observed after treatment with Compound 1.

Compound 1 was well-tolerated in clinical trials and has not shown evidence of inhibition of aromatase, an enzyme involved in converting testosterone to estrogen, which may permit dosing in a broad range of patients, including both pediatric and adult populations, as it does not lead to alterations in the hormones that affect pediatric growth and development. In addition, Compound 1 demonstrated a lack of cytochrome P450, or CYP, inhibition or induction, thereby reducing risk for drug-drug interactions due to CYP's effects on pharmacokinetics of other drugs through changes in plasma concentration.

In some embodiments, pharmaceutical compositions comprising Compound 1 can be formulated for use as an oral, once-daily, potentially disease-modifying therapy for the treatment of SCD. Compound 1 can modulate RBC metabolism by impacting two critical pathways through PKR activation: a decrease in 2,3 diphosphoglycerate (2,3-DPG), which increases oxygen affinity and an increase in adenosine triphosphate, or ATP, which may improve RBC and membrane health and integrity, reducing RBC hemolysis and increasing lifespan. In some embodiments, multi-modal methods of treatment can comprise the administration of Compound 1 to improve hemoglobin levels through increased RBC survival and decrease VOCs through reduced RBC sickling and hemolysis. In some methods, Compound 1 is administered to modify SCD at an early age, potentially preventing end-organ damage, reducing hospitalizations, and improving the patients' overall health and quality of life. In some embodiments, methods of treatment comprise administration of a therapeutically effective amount of Compound 1 to modulate RBC metabolism via a multi-modal approach by decreasing 2,3-DPG and increasing ATP.

Some embodiments provide an oral, once-daily dosage form (e.g., a tablet or capsule) comprising Compound 1 for use in a therapy for increasing hemoglobin oxygen affinity by reducing 2,3-DPG blood concentrations, increasing hemoglobin levels and/or increasing intracellular ATP, without significant effects on sex hormones (e.g., without aromatase inhibition activity) or inducing its own metabolism upon repeat daily administration throughout a course of treatment.

Even a single dose of Compound 1 resulted in favorable biologic effects including: (1) improved oxygen affinity, decreased point of sickling and improving deformability at low oxygen concentration, (2) improved membrane function, demonstrated by an improved response to an osmotic gradient in the presence of a shear stress, and (3) increased hemoglobin and RBCs and decreased reticulocytes when maximum PD effects were observed, indicating a sustained 2,3-DPG reduction and increased ATP production may improve the hemolytic anemia and the frequency of VOCs that characterize SCD. In addition, Compound 1 improves SCD patient RBC deformability, increases oxygen affinity and improves osmolality dependent membrane function. A single dose of Compound 1 has a favorable safety profile in patients with SCD.

BRIEF DESCRIPTION OF THE DRAWINGS

FIG. 12 shows each data point in grayscale, while FIG. 13 shows the same data with stylized lines.

FIG. 24A is a table of data obtained from the single ascending dose (SAD) human clinical study of Compound 1 described in Example 8, showing pharmacokinetic (PK) properties of single doses of Compound 1. Values are presented as geometric mean [CV %] for Cmax, $AUC_{0-24}$, and half-life; and median [CV %] for Tmax.

FIG. 24B is a table of data obtained from the multiple ascending dose (MAD) human clinical study of Compound 1 described in Example 8, showing time-independent pharmacokinetic (PK) properties over 14 days of dosing Compound 1 either QD or BID. Values are presented as geometric mean [CV %] for Cmax, $AUC_{0-tau}$, Ratio Day14/Day1 Cmax, and Ratio Day14/Day1 $AUC_{0-tau}$; and median [CV %] for Tmax.

FIGS. 48A and 48B are scatter plots of 2,3-DPG levels and p50 values observed in healthy volunteers and SCD patients before and after administration of Compound 1.

DETAILED DESCRIPTION

Figure 1:
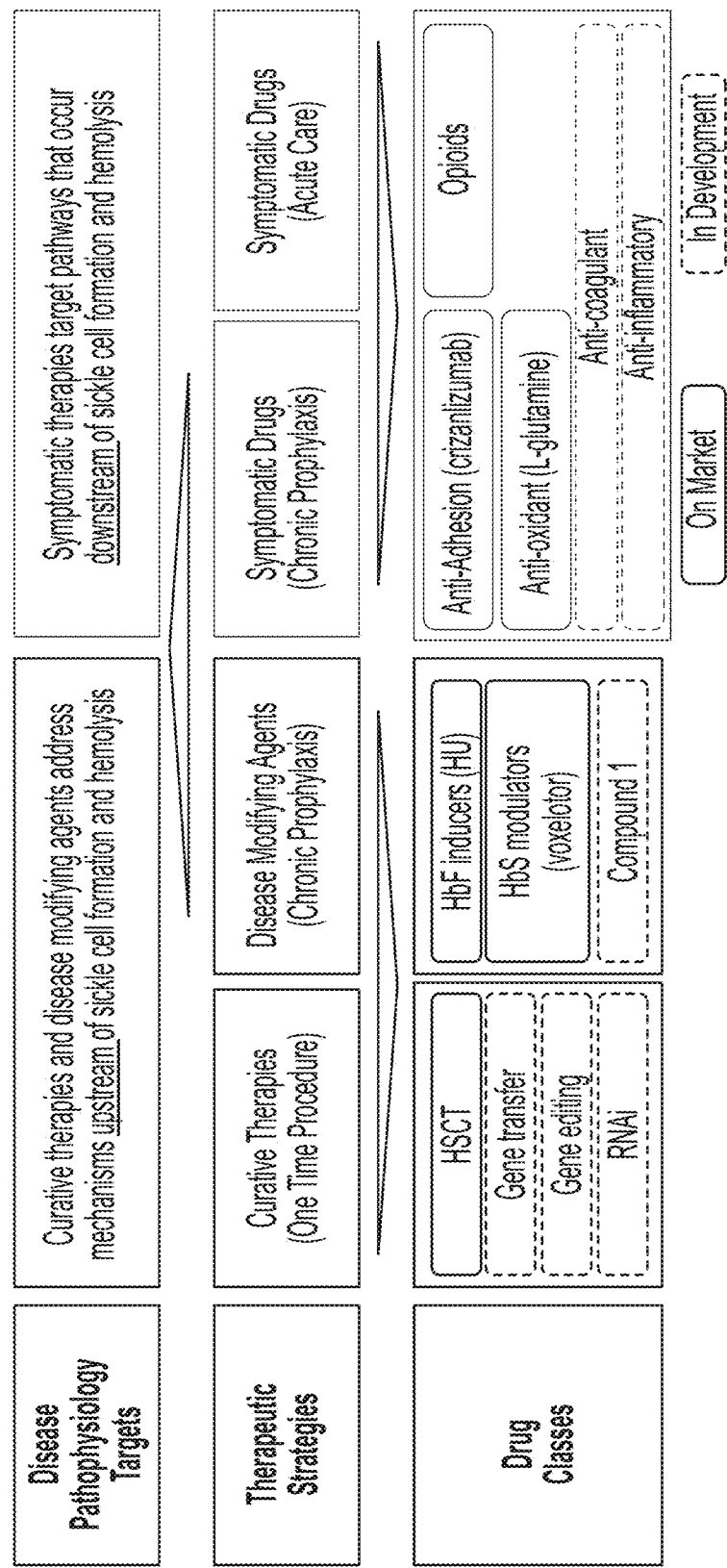
FIG. 1 is a diagram of hemoglobin mutations giving rise to hemoglobinopathies summary of current therapeutic strategies for the treatment of sickle cell disease.

The PKR Activating Compound (5)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one (Compound 1):

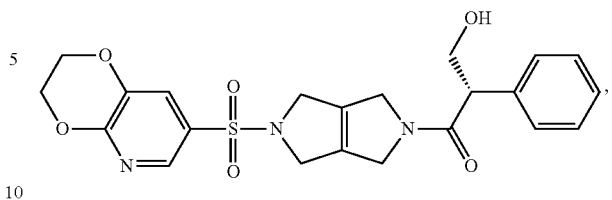

is a selective, orally bioavailable PKR Activating Compound that decreases 2,3-DPG, increases ATP, and has anti-sickling effects in disease models with a wide therapeutic margin relative to preclinical toxicity. Compound 1 is a potent activator of PKR and a multi-modal metabolic modulator of RBCs. Activation of PKR simultaneously reduces 2,3-DPG concentrations, which increases hemoglobin-oxygen affinity and decreases sickling, while also increasing intracellular ATP, which improves RBC health and reduces hemolysis, or RBC death. Compound 1 is a BCS class II compound with poor water solubility and high permeability. Compound 1 has a solubility of about 22-25 μg/mL in water or buffered solutions over the pH range from about 1.07 to about 8.69. Compound 1 has a permeability of $P_{app}$, (A-B), 5.46×10−6 cm/s and a Log $D_{7.4}$ of 1.09.

Compound 1 can be identified as a PKR Activating Compound of Formula I:

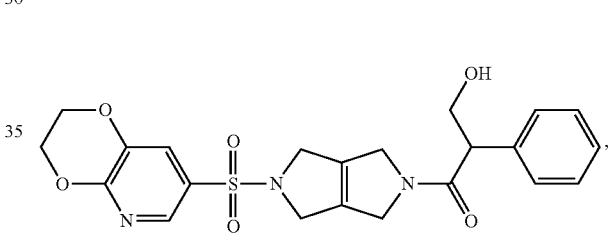

(including, e.g., Compound 1 and mixtures of Compound 1 and Compound 2) having an $AC_{50}$ value of less than 1 μM using the Luminescence Assay described in Example 2.

Compound 1 potentially represents an important advancement for patients living with SCD and other hemoglobinopathies, including beta thalassemia. PKR Activating Compounds, such as 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a pharmaceutically acceptable salt thereof, are useful in pharmaceutical compositions for the treatment of patients diagnosed with hemoglobinopatiies such as SCD. The invention is based in part on the discovery that the activation of PKR can target both sickling, by reducing deoxy-HgbS, and hemolysis. Compound 1 decreases 2,3-DPG, increases ATP in RBCs and increases oxygen affinity of hemoglobin (as measured by a left shift in the partial pressure of oxygen at 50% hemoglobin saturation, or p50) in patients diagnosed with a hemoglobinopathy such as Sickle Cell Disease.

Compound 1 modulates RBC metabolism via a multi-modal approach by decreasing 2,3-DPG and increasing ATP. Decreasing the concentration of 2,3-DPG has been observed to normalize hemoglobin-oxygen affinity and decrease RBC sickling in vitro. Reduced RBC sickling has the potential to improve patients' hemoglobin levels and reduce their VOCs. Compound 1 may also improve RBC membrane health and integrity by increasing ATP, resulting in a more flexible RBC membrane for improved blood flow and potentially lessening the occurrences of VOCs. Improvement of RBC membrane health by increasing ATP is particularly useful in the setting of beta-thalassemia. A rapid onset of activity has been observed within hours in vitro and within 24 hours in healthy volunteers and SCD patients, including improved RBC deformability across an oxygen gradient (oxygen scan) and across an osmolality gradient (osmoscan), indicating an effect on RBC sickling and RBC membrane health, respectively. The relatively rapid onset of Compound 1's impact contrasts with current treatment regimens that applicant believes may take longer to demonstrate anti-sickling effects, improvements in Hb and RBC counts, or decreases in reticulocyte counts.

Applicant has discovered that Compound 1 may be administered orally once daily. A dose-exposure-response analysis utilizing the pharmacokinetics/pharmacodynamics, or PK/PD, of results obtained from healthy volunteers and SCD patients supports once-daily dosing, without the need for extensive monitoring or dose adjustments, potentially improving compliance issues historically seen with SCD patients.

Definitions

As used herein, the following terms shall be understood to have the following meanings:

"Compound 1" refers to (2S)-1-[5-(2,3-dihydro[1,4]dioxino[2,3-b]pyridine-7-sulfonyl)-3,4,5,6-tetrahydropyrrolo[3,4-c]pyrrol-2(1H)-yl]-3-hydroxy-2-phenylpropan-1-one, also known as (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, which has the following structure:

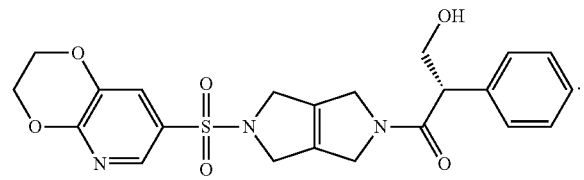 [SMILES: O=C([C@H](CO)c1ccccc1)N1CC2=C(C1)CN(S(=O)(=O)c1cnc3c(c1)OCCO3)C2]

"Amorphous" refers to a solid material having no long-range order in the position of its atoms, i.e., a solid material in non-crystalline form. A compound shall be understood to be amorphous if the compound is in non-crystalline form and is free or substantially free of any crystalline form of the compound. In some embodiments, an amorphous compound contains no more than about 1%, no more than about 2%, no more than about 5%, no more than about 10%, or no more than about 15% of any crystalline form of the compound, based on the total weight of the compound. In other embodiments, an amorphous compound does not show diffraction peaks characteristic of any crystalline form of the compound by XRPD analysis.

"Solid dispersion" refers to a molecular mixture of a compound and one or more denucleating agents, wherein the denucleating agent functions to minimize or eliminate the crystallinity of the compound. The compound may be dispersed as amorphous clusters in the matrix, or the compound may be dispersed at the molecular level throughout the matrix. Solid dispersions generally are prepared by converting a fluid drug-carrier combination into a solid state, typically by a melting or solvent evaporation process as known in the art, or by anti-solvent co-precipitation. Different types of solid dispersions can be distinguished by their molecular arrangement. These different types of solid dispersions include, but are not limited to, (1) eutectic mixtures; (2) amorphous solids with disordered or completely randomized crystal lattice at molecular level; (3) solid solutions, including continuous solid solutions, discontinuous solid solutions, substituted solid solutions, and interstitial solid solutions; (4) a glass suspension, wherein the matrix exhibits an amorphous state and the compound is dispersed as amorphous clusters in the matrix; and (5) a glass solution, wherein the matrix is in an amorphous state and the compound is dispersed at a molecular level throughout the matrix. Dispersion of the compound in the denucleating agent by mechanical mixing is not covered by this definition.

"Denucleating agent" refers to a carrier in a pharmaceutical formulation that reduces or prevents nucleation and crystallization of a compound in the formulation. In some embodiments, a denucleating agent is a water-soluble polymer, such as polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), or a combination thereof.

Denucleating agents suitable for use with Compound 1 can be identified by performing solubility tests with Compound 1 in the presence and absence of a particular denucleating agent, wherein exhibition of prolonged supersaturation of Compound 1 in the presence of the denucleating agent indicates the agent's suitability. The tests can be conducted with a single denucleating agent at a series of concentrations to find a suitable concentration for further testing. The tests can also be conducted with a series of agents, each at the same concentration or series of concentrations, to select one or more agents for further screening via additional in vitro tests and/or in vivo PK studies.

A suitable solubility test for denucleating agents is as follows: An solution of Compound 1 is introduced into a USP II dissolution vessel (i.e., a dissolution vessel equipped with a stirring paddle connected by a stirring shaft to a variable speed motor) containing a simulated intestinal fluid (SIF) medium equilibrated at 37° C. with or without a denucleating agent, wherein the initial total drug concentration in the dissolution vessel is about 5× to 10× the equilibrium solubility of the drug in the medium. The solution is stirred (e.g., 50 rpm). Samples are removed from the medium at periodic time intervals (e.g., 5, 10, 15, 20, 30, 60, 120, 180 and 240 minutes) and filtered (0.2 μm filter). The filtrate is diluted with a suitable solvent in which the solubility of the drug is higher than the initial total drug concentration in the media. The concentration of Compound 1 in the diluted solution sample is then determined. Plots of drug solubility in the medium in the presence and absence of a denucleating agent against time are then used to assess the efficacy of the agent in prolonging drug supersaturation. The same type of test can be used to identify denucleating agents suitable for use with Compound 1.

In some embodiments, the denucleating agent comprises a water-soluble polymer. The term "water-soluble polymer" refers herein to any polymer which is freely soluble in water or which dissolves or solubilizes in water in an amount sufficient to provide denucleating activity in compositions of the present invention (e.g., in an amount of at least about 0.005 mg/ml). Suitable water-soluble polymers include hydroxyalkylcelluloses, alkylcelluloses, polyvinylpyrrolidones, and polyacrylic acids. Suitable hydroxyalkylcelluloses include hydroxypropylmethylcellulose (HPMC), hydroxyethylcellulose, and hydroxypropylcellulose. A suitable alkylcellulose is methylcellulose. The water-soluble polymers can be employed in the present invention singly or in mixtures. It is known in the art to use the water-soluble polymers just described as stabilizing agents in pharmaceutical formulations; e.g., they can be employed to prevent or minimize settling of drug particles in dispersions before their administration (oral or otherwise) to patients. In the present invention, these polymers are employed as denucleating agents; i.e., their primary role is to inhibit and/or delay precipitation of the drug in the subject's stomach and/or intestine after oral administration.

In other embodiments, the denucleating agent comprises a low-viscosity, water-soluble polymer. The term "low viscosity" means that the water-soluble polymer produces a 2 wt. % (i.e., weight of polymer/weight of water) aqueous solution having a viscosity in a range of from about 2 to about 100 centipoise (cps) at 20° C. (1 cps=1 mPa sec). The low-viscosity, water-soluble polymer typically produces a 2 wt. % solution having a viscosity in a range of from about 2 to about 50 cps (e.g., from about 3 to about 20 cps) at 20° C. Suitable low-viscosity, water-soluble polymers include hydroxyalkylcelluloses, alkylcelluloses, polyvinylpyrrolidones, and polyacrylic acids. Suitable hydroxyalkylcelluloses include hydroxypropylmethylcellulose (HPMC), hydroxyethylcellulose, and hydroxypropylcellulose. A suitable alkylcellulose is methylcellulose. The low-viscosity, water-soluble polymers can be used singly or in mixtures of two or more (e.g., two or more HPMC polymers), wherein the polymer mixture produces a 2 wt. % solution with an average viscosity in the low viscosity range. The average viscosity of the polymer mixture typically differs from the viscosity of each component polymer.

In other embodiments, the denucleating agent comprises a hydroxyalkylcellulose. In an aspect of this embodiment, the denucleating agent is HPMC (or a mixture of two or more HPMCs). Suitable HPMCs include those (whether singly or in mixtures) that produce 2 wt. % aqueous solutions of polymer in water with viscosities in a range of from about 3 to about 150,000 cps at 20° C. Suitable HPMCs include those sold under the trademark METHOCEL® (Dow Chemical) (e.g., METHOCEL grades K100LVP, K4M, K15M, and K100M) and METOLOSE® (Shin-Etsu). Suitable HPMCs also include U.S. Pharmacopeia standard substitution types 2208, 2906 and 2910.

In still other embodiments, the denucleating agent comprises a low-viscosity hydroxyalkylcellulose. In an aspect of this embodiment, the denucleating agent is HPMC (or a mixture of two or more HPMCs) that produces a 2 wt. % aqueous solution having a viscosity in a range of from about 2 to about 100 cps at 20° C. In another aspect of this embodiment, the denucleating agent is an HPMC (or a mixture of two or more HPMCs) that produces a 2 wt. % aqueous solution having a viscosity in a range of from about 2 to about 50 cps (e.g., from about 3 to about 20 cps) at 20° C. In still another aspect, the denucleating agent is an HPMC having a hydroxypropyl content of from about 7 to about 12 wt. %, a methoxy content of from about 28 to about 30 wt. %, and a viscosity for 2% w/w aqueous solutions of from about 3 to about 20 cps. In yet another aspect, the HPMC is U.S. Pharmacopeia standard substitution type 2208, 2906 or 2910, such as HPMC 2910 (6 cps) which is available as PHARMACOAT from Shin-Etsu Chemical Co.

Compound 1 Activates PKR

Figure 2:
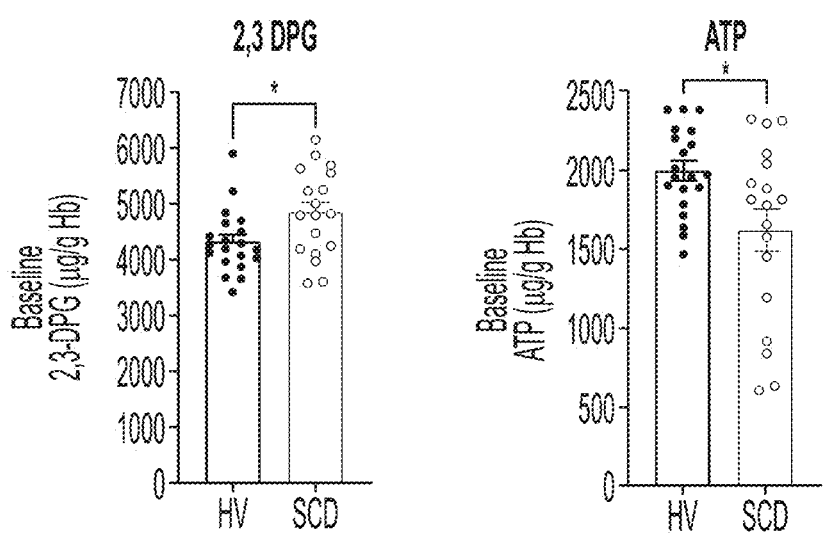
FIG. 2 is a pair of graphs comparing 2,3-DPG and ATP levels in SCD RBCs and healthy RBCs.

Pyruvate kinase R (PKR) is the isoform of pyruvate kinase expressed in RBCs, and is a key enzyme in glycolysis. PKR plays a major role as a regulator of metabolic flux through glycolysis. Activation of PKR offers the potential to decrease 2,3-DPG and increase ATP, which would reduce RBC sickling and cell membrane damage from HbS polymerization. As illustrated in FIG. 2, 2,3-DPG levels are significantly higher and ATP levels significantly lower in SCD RBCs compared with normal healthy RBCs. Through a reduction in 2,3-DPG and an increase in ATP, a PKR activator has the potential to positively impact physiological changes that lead to the clinical pathologies of SCD and yield a broader and more significant impact on SCD disease than other agents that directly modify HbS, which may not otherwise improve RBC health and membrane integrity.

The invention is based in part on the discovery that the activation of PKR can target both sickling, by reducing deoxy-HgbS, and hemolysis. Targeting hemolysis may be achieved by improving RBC membrane integrity. One aspect of the disclosure is the recognition that activation of PKR can reduce 2,3-diphosphoglycerate (2,3-DPG), which leads to decreased deoxy-HgbS (and, therefore, sickling), as well as can increase ATP, which promotes membrane health and reduces hemolysis. Another aspect of the disclosure is the recognition that activation of PKR can reduce 2,3-diphosphoglycerate (2,3-DPG), which inhibits Hgb deoxygenation/increases oxygen affinity of HgbS and leads to decreased deoxy-HgbS (and, therefore, sickling), as well as can increase ATP, which promotes membrane health and reduces hemolysis. ATP also supports elimination of reactive oxygen species (ROS) which damage RBC and impair their functionality, and reduces vascular adhesion associated with membrane injuries. Accordingly, in one embodiment, PKR activation (e.g., by administration of a therapeutically effective amount of a PKR Activating Compound to a patient diagnosed with SCD) reduces RBC sickling via a reduction in levels of 2,3-diphosphoglycerate (2,3-DPG), which in turn reduces the polymerization of sickle Hgb (HgbS) into rigid aggregates that deform the cell. Furthermore, in some embodiments, PKR activation may contribute to overall RBC membrane integrity via increasing levels of adenosine triphosphate (ATP), which is predicted to reduce vaso-occlusive and hemolytic events which cause acute pain crises and anemia in SCD patients.

A PKR Activating Compound, such as Compound 1, is useful to promote activity in the glycolytic pathway. As the rate-limiting enzyme that catalyzes the last step of glycolysis, PKR directly impacts the metabolic health and primary functions of RBCs. PKR Activating Compounds (e.g., Compound 1), are useful to decrease 2,3-DPG and increase ATP. PKR Activating Compounds (e.g., Compound 1) are also useful to increase Hgb oxygen affinity in RBC. The disclosure is based in part on the discovery that PKR activation is a therapeutic modality for SCD, whereby HgbS polymerization and RBC sickling and hemolysis are reduced via decreased 2,3-DPG and increased ATP levels.

Figure 3:
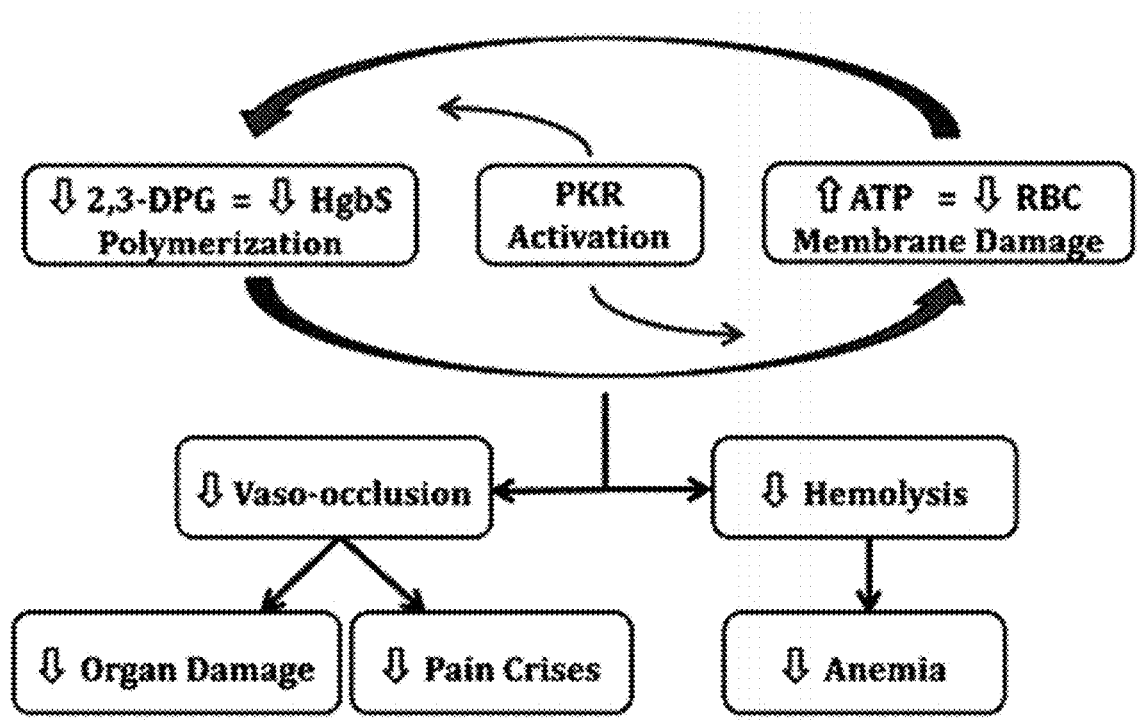
FIG. 3 is a schematic showing the relationship of PKR activation to the reduction of the clinical consequences of sickle cell disease (SCD).

One aspect of this disclosure is targeting PKR activation to reduce 2,3-DPG levels, based on PKR's role in controlling the rate of glycolysis in RBCs. Increased activity of PKR tends to deplete organic phosphate precursors upstream of phosphoenolpyruvate, including 2,3-DPG. A decrease in 2,3-DPG with PKR activation has been demonstrated in preclinical studies and in healthy volunteers. Additionally, PKR activation has been observed to increase ATP in these same studies. NADH, generated along with ATP during glycolysis, is essential to reduce methemoglobin to Hb, thus reducing potential for oxidative stress. Furthermore, ATP plays a role in maintaininig lipid asymmetry and ion gradients across the RBC membrane. Accordingly, elevating ATP levels is likely to have broad beneficial effects. Therefore, activation of PKR offers the potential for a 2,3-DPG effect (i.e., reduced cell membrane damage from HgbS polymerization) that is augmented by ATP support for membrane integrity. It is via these changes that a PKR activator is could positively impact physiological changes that lead to the clinical pathologies of SCD (FIG. 3). In another aspect, the disclosure relates to a method of improving the anemia and the complications associated with anemia in SCD patients (e.g., ≥12 years of age) with Hgb SS or Hgb SB⁰-thalassemia.

Figure 4:
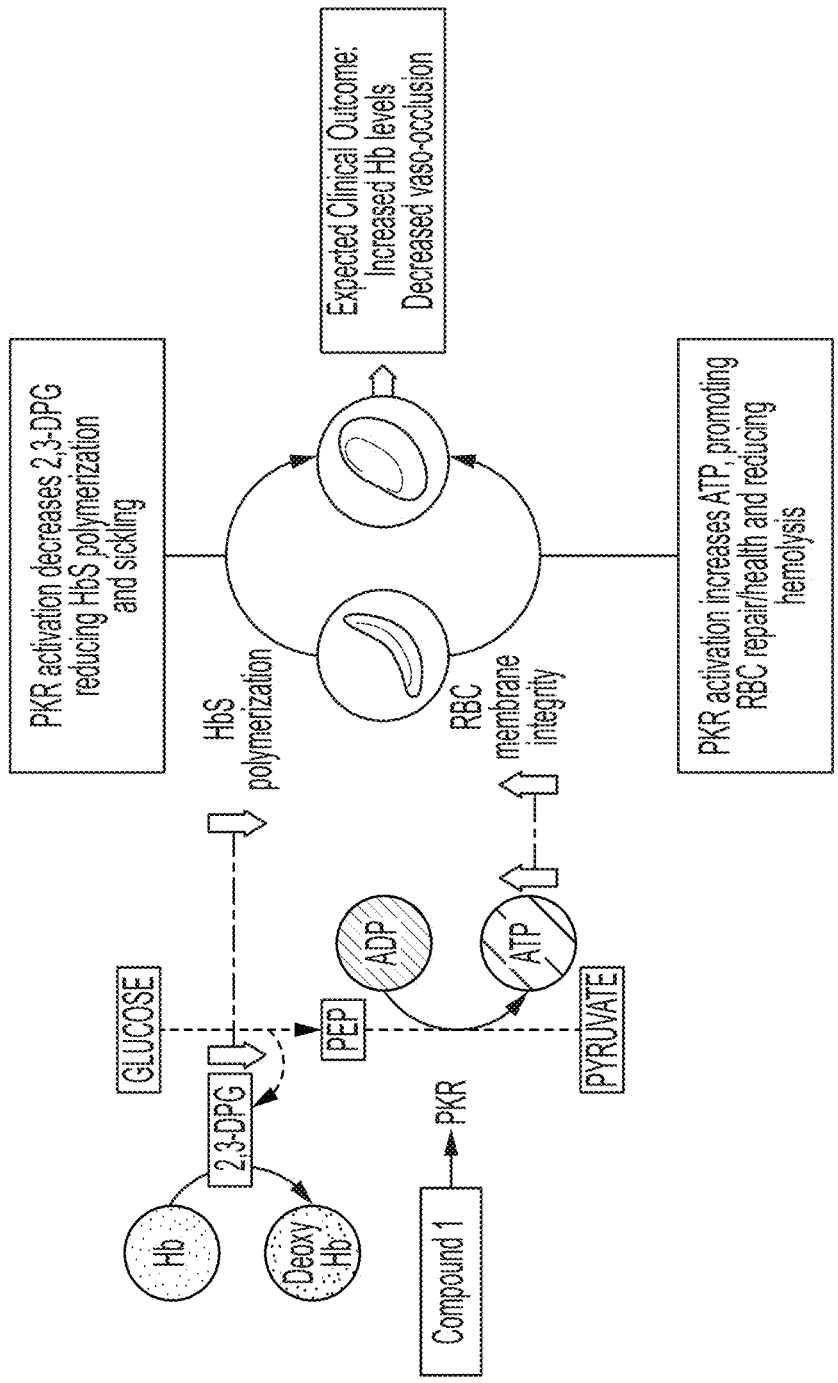
FIG. 4 is a diagram of the proposed mechanism of action of Compound 1.

As illustrated in FIG. 4, RBC metabolism utilizes glycolysis in order to generate ATP. 2,3-DPG is an intermediate in the glycolytic pathway and accumulates in RBCs under certain physiologic conditions. 2,3-DPG plays an important role in the ability of hemoglobin to bind oxygen. 2,3-DPG selectively binds to deoxyhemoglobin, making it harder for oxygen to bind hemoglobin and more likely to be released to adjacent tissues. 2,3-DPG is part of a feedback loop that can help prevent tissue hypoxia in conditions where it is most likely to occur. Under conditions of low tissue oxygen concentration such as high altitude, airway obstruction, or congestive heart failure, RBCs activate the Lubering-Rappoport shunt, a branch of the glycolytic pathway, to generate more 2,3-DPG. The accumulation of 2,3-DPG decreases the affinity of hemoglobin for oxygen eventually releasing it into the tissues that need it most.

PKR activation has potential to reduce both hemoglobin sickling and hemolysis via a reduction in 2,3-DPG and an increase in ATP. PKR activation depletes 2,3-DPG and increases ATP levels, thus increasing the energy supply of cells. Increasing cellular ATP may enhance the RBCs' ability to repair membrane damage and tolerate deformation in capillaries. Combining these two activities, a PKR activator has the potential to reduce the likelihood of sickling and increase the ability of RBCs to transit through small blood vessels without hemolysis. As illustrated in FIG. 4, the multimodal action of a PKR-agonist (e.g., Compound 1) may increase hemoglobin levels and reduce VOCs in SCD patients. The multimodal effects of PKR activation, including the combination of anti-sickling effects, decreased hemolysis, and improved RBC membrane fitness, may also reduce the incidence of VOCs and, in parallel, ameliorate chronic anaemia in SCD. The studies described in the Examples demonstrate the Compound 1 mechanism of action.

Compound 1 Increases Hemoglobin Oxygen Affinity

Applicants have discovered that the compound (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one ("Compound 1") or a pharmaceutically acceptable salt thereof, increases oxygen affinity of hemoglobin as measured by a left shift in the partial pressure of oxygen at 50% hemoglobin saturation (p50). Reduction in p50 indicates an increase in hemoglobin affinity for oxygen.

Applicants have discovered a method of increasing the oxygen affinity of hemoglobin A (HgbA) in red blood cells (RBCs). A method of treatment, can comprise administering to a patient (S)-1-(5-((2,3-dihydro-[1,4]dioxino[2,3-b]pyridin-7-yl)sulfonyl)-3,4,5,6-tetrahydropyrrolo[3,4-c]pyrrol-2 (1H)-yl)-3-hydroxy-2-phenylpropan-1-one or a pharmaceutically acceptable salt thereof, in an amount effective to increase oxygen affinity of HbA. A method of treatment, can comprise administering to a patient (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, in an amount effective to increase oxygen affinity of HgbA.

Applicants have discovered a method of increasing the oxygen affinity of hemoglobin A (HgbA) in red blood cells (RBCs). In human clinical studies, Compound 1 exhibited dose linear and time-independent PK, and the PD activity was observed at all dose levels after 24 h (decreased 2,3-DPG, p<0.0001) and after 14-days (increased ATP, p<0.0001) of dosing. Healthy volunteers who received Compound 1 experienced a decrease in p50 relative to baseline and relative to healthy volunteers who received placebo, reflecting an increase in oxygen affinity, while subjects who received the placebo did not. The biologic consequence of this PD response was an increase in oxygen affinity (decreased p50, p<0.0001) within 24 h of Compound 1 dosing and a decrease in absolute reticulocyte counts (p<0.0001) with a slight increase in hemoglobin levels (ns) by Day 4 of the dosing period in all Compound 1 dose cohorts. The increase in hemoglobin A (HgbA) affinity for oxygen in healthy subjects can be seen by the oxyhemoglobin dissociation curve (p50; partial pressure of 02 at which 50% of hemoglobin is saturated with 02) after a single dose and after 14-day dosing of Compound 1. A mean decrease in 2,3-DPG and p50, and a mean increase in ATP, relative to baseline, was observed in both the single ascending dose (SAD) and multiple ascending dose (MAD) cohorts. Within 24 hr of a single dose of Compound 1, a decrease in 2,3-DPG with a corresponding increase in p50 was observed. Healthy volunteers (having normal hemoglobin, or HgbA) who received Compound 1 experienced a change (decrease) in p50 relative to baseline, while subjects who received the placebo did not. In the SAD cohorts, the subjects' p50 (PO2 at 50% hemoglobin saturation) were determined 24-hours post-dose. The pp50 values measured 24 hours after a single dose of Compound 1 were reduced at all dose levels tested (median reduction ranged from ~3-5 mmHg). In the MAD cohorts, the subjects' p50 (PO2 at 50% hemoglobin saturation) were determined on day 14. p50 values measured after 14 days of once or twice daily dosing were reduced at all dose levels tested (median reduction ranged from ~3-5 mmHg).

In some embodiments, a method of treatment comprises administering Compound 1 to a patient in an amount effective to increase the oxygen affinity of RBC from the patient (e.g., as measured by a reduction in p50 from a blood sample take 24 hours after administration of Compound 1 to the patient). In some embodiments, a method of treatment can comprise administering Compound 1 to a patient in an amount effective to reduce the p50 (pO2 at 50% hemoglobin saturation) measured 24 hours after administration of Compound 1 relative to baseline by more than 0.2 mmHg (mean absolute change), including reducing the effective p50 of a patient by 1, 2, 3, 4, 5, or more mmHg (including reductions of about 2.9, 3.4, 4.9 and 5.1 mmHg) relative to baseline at 24 hours after administration of Compound 1. In some embodiments, a method of treatment comprises administering Compound 1 followed by measuring a decrease in p50 relative to baseline in the patient (e.g., from a blood sample) 24 hours after the administration of Compound 1, reflecting an increase in oxygen affinity. In some embodiments, due to the lack of cytochrome P450 induction and the extended half-life of the pharmacodynamic effect, the compound is taken on a QD regimen.

A method of treating a patient diagnosed with a hemoglobinopathy, can comprise administering Compound 1 (or a pharmaceutically acceptable salt thereof) in an amount effective to increase oxygen affinity of HbS in the patient or to provide a left shift in the point of sickling (PoS) with an increase in the Elmin in the patient, or a combination thereof. For example, the hemoglobinopathy can be Sickle Cell Disease. In another embodiment, a method of treating a patient diagnosed with a hemoglobinopathy can comprise administering Compound 1 (or a pharmaceutically acceptable salt thereof) in an amount effective to increase intracellular ATP levels in the RBC or to improve the membrane function, for example in Sickle Cell Disease or beta-thalassemia.

A method of treatment, can comprise administering to a patient (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, in an amount effective to increase oxygen affinity of HbS. A method for increasing oxygen affinity of sickle hemoglobin (HbS) in vivo in a patient in need thereof can comprise administering to said patient a sufficient amount of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof. In some embodiments, the administration of a single dose of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a salt thereof can increase the oxygen affinity of said HbS in the patient.

A method for increasing oxygen affinity of sickle hemoglobin (HbS) in vivo in a patient in need thereof can comprise administering to said patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, to increase oxygen affinity of the blood of a SCD patient. In some embodiments, the administration of a single dose of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a salt thereof can increase the oxygen affinity of said HbS in the patient.

In some embodiments, methods of increasing the oxygen affinity of hemoglobin in red blood cells (RBCs) can comprise contacting the RBCs with an amount of Compound 1 under conditions and for a time effective to reduce the amount of 2,3-DPG in the RBCs.

In some embodiments, methods of treatment comprise administering a pharmaceutical composition comprising Compound 1 to a patient diagnosed with a hemolytic anemia in an amount effective to increase hemoglobin oxygen affinity in RBC, including a patient diagnosed with Sickle Cell Disease.

In some embodiments, the administration of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods of increasing hemoglobin oxygen affinity described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

Compound 1 Increases ATP and Reduces 2,3-DPG Concentrations in Blood

Another aspect of the disclosure is the recognition that activation of PKR can reduce 2,3-diphosphoglycerate (2,3-DPG), which inhibits Hgb deoxygenation/increases oxygen affinity of HgbS and leads to decreased deoxy-HgbS (and, therefore, sickling), as well as can increase ATP, which promotes membrane health and reduces hemolysis. Accordingly, in one embodiment, PKR activation (e.g., by administration of a therapeutically effective amount of Compound 1 or a pharmaceutically acceptable salt thereof to a patient diagnosed with SCD) reduces RBC sickling via a reduction in levels of 2,3-diphosphoglycerate (2,3-DPG), which in turn reduces the polymerization of sickle Hgb (HgbS) into rigid aggregates that deform the cell. Furthermore, in some embodiments, PKR activation may contribute to overall RBC membrane integrity via increasing levels of adenosine triphosphate (ATP), which is predicted to reduce vaso-occlusive and hemolytic events which cause acute pain crises and anemia in SCD patients.

In some embodiments, Compound 1 is administered in a dose that is pharmacodynamically effective. In some embodiments, Compound 1 is administered in a dose resulting in a reduction in RBC 2,3-DPG in the patient (e.g., measured in the blood of the patient 6 hours after administration of Compound 1). The reduction of 2,3-DPG can be measured in patient blood by a qualified LC-MS/MS method for the quantitation of 2,3-DPG in blood, or using a commercially available kit. In some embodiments, a method of treatment can comprise administering Compound 1 to a patient in an amount effective to reduce 2,3-DPG levels by one or more of the following after administering a dose of Compound 1, relative to patient baseline:

at least 10% after 6 hours (e.g., by more than 7.8% after 6 hours, by at least 18% after 6 hours, or by about 18-29% after 6 hours),
  by at least 10% after 8 hours (e.g., by more than 7.6% after 8 hours, by at least 17% after 8 hours, or by about 17-29% after 8 hours),
  by at least 10% after 12 hours (e.g., by more than 4.0% after 12 hours, by at least 25% after 12 hours, or by about 25-44% after 8 hours),
  by at least 10% after 16 hours (e.g., by more than 6.0% after 16 hours, by at least 33% after 16 hours, or by about 33-50% after 16 hours),
  by at least 10% after 24 hours (e.g., by more than 2.0% after 24 hours, by at least 31% after 24 hours, or by about 31-49% after 24 hours),
  by at least 10% after 36 hours (e.g., by more than 6.9% after 36 hours, by at least 33% after 36 hours, or by about 33-47% after 36 hours),
  by at least 10% after 48 hours (e.g., by more than 15% after 48 hours, by at least 29% after 48 hours, or by about 29-48% after 48 hours), and
  by at least 10% after 72 hours (e.g., by more than 6.9% after 72 hours, by at least 18% after 72 hours, or by about 18-33% after 72 hours).

In some embodiments, Compound 1 is administered in a dose resulting in an increase in RBC ATP in the patient (e.g., measured in the blood of the patient 6 hours after administration of Compound 1). In some embodiments, a method of treatment comprises administering Compound 1 to a patient in an amount effective to elevate ATP levels in the patient, relative to baseline, for one or more consecutive days (e.g., 1-14 days or more), wherein the levels of ATP remain elevated in the patient ATP levels remain elevated, relative to baseline, for 60 hours after the last dose of Compound 1. ATP is measured in RBCs. For example, in some embodiments, a method of treatment comprises administering Compound 1 daily to a patient for 14 consecutive days in an amount to increase ATP levels in the patient by one or more of the following amounts, relative to patient baseline:
- more than 0% within less than 6 hours after administration of Compound 1 on day 14 (e.g., by at least 41% within 6 hours, or by about 41-55% within 6 hours),
- more than 2.8% after 6 hours after administration of Compound 1 on day 14 (e.g., by at least 44% after 6 hours, or by about 44-48% after 6 hours),
- more than 0% after 8 hours after administration of Compound 1 on day 14 (e.g., by at least 47% after 12 hours, or by about 47-58% after 8 hours),
- more than 2.3% after 12 hours after administration of Compound 1 on day 14 (e.g., by at least 45% after 12 hours, or by about 45-56% after 12 hours),
- more than 0% after 16 hours after administration of Compound 1 on day 14 (e.g., by at least 44% after 16 hours, or by about 44-57% after 16 hours),
- more than 2.9% after 24 hours after administration of Compound 1 on day 14 (e.g., by at least 55% after 24 hours, or by about 55-64% after 24 hours),
- more than 4.7% after 48 hours (e.g., by at least 52% after 48 hours, or by about 52-59% after 48 hours), and
- more than 2.2% after 72 hours after administration of Compound 1 on day 14 (e.g., by at least 49% after 72 hours, or by about 49-54% after 72 hours).

In some embodiments, a method of treatment can comprise administering Compound 1 to a patient for multiple consecutive days (e.g., 14 days or more) in an amount and dose interval effective to reduce 2,3-DPG levels, relative to baseline, of at least about 25% when tested 24 hours after administration of the first dose on day 1 and at least about 40% when tested 24 hours after administration of the first dose on day 14. For example, in some embodiments, a method of treatment comprises administering Compound 1 daily to a patient for 14 consecutive days in an amount to reduce 2,3-DPG levels by one or more of the following amounts, relative to patient baseline:
- more than 7.6% within less than 6 hours after administration of Compound 1 on day 14 (e.g., by at least 42% within 6 hours, or by about 42-59% within 6 hours),
- more than 10.9% after 6 hours after administration of Compound 1 on day 14 (e.g., by at least 44% after 6 hours, or by about 44-53% after 6 hours),
- more than 1.6% after 8 hours after administration of Compound 1 on day 14 (e.g., by at least 44% after 12 hours, or by about 44-54% after 8 hours),
- more than 1.6% after 12 hours after administration of Compound 1 on day 14 (e.g., by at least 42% after 12 hours, or by about 42-55% after 12 hours),
- more than 5.3% after 16 hours after administration of Compound 1 on day 14 (e.g., by at least 42% after 16 hours, or by about 42-52% after 16 hours),
- more than 10.7% after 24 hours after administration of Compound 1 on day 14 (e.g., by at least 44% after 24 hours, or by about 44-52% after 24 hours),
- more than 1% after 48 hours (e.g., by at least 34% after 48 hours, or by about 34-44% after 48 hours), and
- more than 7% after 72 hours after administration of Compound 1 on day 14 (e.g., by at least 20% after 72 hours, or by about 20-32% after 72 hours).

In some embodiments, the administration of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods of increasing ATP levels and/or reducing 2,3-DPG levels described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

Compound 1 Reduces Sickling in SCD Patient RBCs

Compound 1 can improve RBC membrane integrity. One aspect of the disclosure is the recognition that activation of PKR can reduce 2,3-diphosphoglycerate (2,3-DPG), which leads to decreased deoxy-HgbS (and, therefore, sickling), as well as can increase ATP, which promotes membrane health and reduces hemolysis.

In some embodiments, the disclosure relates to a method of improving RBC membrane function in a patient diagnosed with sickle cell disease (SCD), comprising administering to the patient a sufficient amount of (S)-1-(5-((2,3-dihydro[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof. In some embodiments, improving RBC membrane function comprises improving RBC membrane response to an osmotic gradient, as evidenced by a shift toward normal in Omin and Ohyper.

A method for inhibiting sickling of HbS in a patient diagnosed with Sickle Cell Disease, (SCD), can comprise administering to said patient a sufficient amount of a composition comprising (S)-1-(5-((2,3-dihydro[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof. A method of treating a patient diagnosed with Sickle Cell Disease (SCD), can comprise administering to said patient a therapeutically effective single dose of (S)-1-(5-((2,3-dihydro[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, such that the patient experiences a left shift in the point of sickling (PoS) with an increase in the Elmin after 24 hours. A method of treatment, can comprise administering to a patient (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, in an amount effective to result in a left shift in the point of sickling (PoS) with an increase in the Elmin in the patient.

A method for inhibiting sickling of HbS in a patient diagnosed with Sickle Cell Disease, (SCD), can comprise administering to said patient a sufficient amount of a composition comprising (S)-(5-((2,3-dihydro[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of treating a patient diagnosed with Sickle Cell Disease (SCD), can comprise administering to said patient a therapeutically effective single dose of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, such that the patient experiences a left shift in the point of sickling (PoS) with an increase in the Elmin after 24 hours.

In some embodiments, the disclosure relates to a method of reducing RBC turnover in a patient diagnosed with sickle cell disease (SCD), comprising administering to the patient a sufficient amount of a PKR Activating Compound, e.g., (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the administration of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods of reducing sickling described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

Treating Pediatric Patients with Compound 1

In some embodiments, methods of treating sickle cell disease or other hemoglobinopathy comprise administering Compound 1 once per day (QD) to adults and pediatric patients 12 years of age and older. In some embodiments, methods of treating sickle cell disease or other hemoglobinopathy comprise administering Compound 1 once per day (QD) to adults and pediatric patients younger than 12 years of age. In some embodiments, methods of treating sickle cell disease or other hemoglobinopathy comprise administering Compound 1 once per day (QD) to pediatric patients 2-12 years of age. In some embodiments, methods of treating sickle cell disease or other hemoglobinopathy comprise administering Compound 1 once per day (QD) to adults and pediatric patients up to age 2 years of age.

Compound 1 has the potential to be a foundational treatment for patients early in life. Patients may benefit from being treated early to potentially lessen the impact of the disease. For example, as further described in Example 8, Compound 1 has not shown evidence of aromatase inhibition, CYP induction or CYP inhibition.

Compound 1 is well-tolerated and has not shown evidence of inhibition of aromatase, an enzyme involved in converting testosterone to estrogen, which may permit dosing in a broad range of patients, including both pediatric and adult populations (e.g., treatment of patients ages 12 and older diagnosed with SCD or other conditions, or treatment of pediatric patients younger than 12 diagnosed with SCD), as it does not lead to alterations in the hormones that affect pediatric growth and development. Aromatase is an enzyme encoded by the CYP19A1 gene. It is located in the endoplasmic reticulum of estrogen-producing cells and catalyzes the rate-limiting step in the conversion of androgens to estrogens in many tissues. Aromatase is a cytochrome P-450 hemoprotein-containing enzyme complex that catalyzes the rate-limiting step in the production of estrogens, i.e. the conversion of androstenedione and testosterone, via three hydroxylation steps, to estrone and estradiol. Aromatase activity is present in many tissues, such as the ovaries, adipose tissue, muscle, liver, breast tissue, and in malignant breast tumors. The main sources of circulating estrogens are the ovaries in premenopausal women and adipose tissue in post-menopausal women. Aromatase catalyzes the conversion of androgens to estrone (E1), which is further converted to the potent estrogen estradiol (E2) by the enzyme 17β-HSD type 1 in the granulosa cell.

Aromatase is a key enzyme in the steroidogenic pathway that catalyzes the conversion of androgens, including testosterone, into estradiol. Inhibition of aromatase increases testosterone and decreases estradiol, both important hormones for human sexual development during childhood. Sickle cell disease is an inherited disorder manifesting as early as 6 months old. Activators of PKR, including Compound 1, are promising investigational therapies being developed for the treatment of Sickle Cell Disease. Aromatase inhibition has been observed with AG-348 (mitapivat) a clinical PKR activator (Yang et al. 2018; Grace et al. 2019). Absence of aromatase inhibition is a desired property for therapies intended to treat children and adolescents, including those with sickle cell disease. Affecting the production of these sex hormones in children and adolescents could have adverse effects on a child/adolescent's sexual maturation/development and growth. Based on the preclinical studies and confirmed by the healthy volunteers receiving Compound 1 continuously for up to 14 days, Compound 1 has no effect on estradiol and testosterone levels.

In some embodiments, the administration of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods of treating pediatric patients described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

Treating Hemaglobinopathies with Compound 1

Hemoglobinopathies are a diverse range of rare inherited genetic disorders in which there is production of an abnormal hemoglobin, dysregulation of the amount of hemoglobin, or the complete absence of one of the hemoglobin subunits. Compound 1's mechanism of action supports its use across a number of adjacent indications. Compound 1 is a potent activator of PKR, designed to improve RBC metabolism, function and survival, by impacting the critical glycolytic pathway. An increase in ATP resulting from the activation of PKR may improve RBC membrane health and integrity. Applicant believes this approach will improve hemoglobin-related diseases through increased RBC survival, reduce the hemolysis associated with beta thalassemia and alleviate the primary symptoms in patients.

One aspect of the disclosure relates to methods of treating a patient comprising the administration of a therapeutically effective amount of a pyruvate kinase R (PKR) activator to a patient in need thereof. Preferably, a patient diagnosed with a hemoglobinopathy is treated with a compound that is a PKR Activating Compound. The PKR activator can be a compound identified as a PKR Activating Compound or a composition identified as a PKR Activating Composition having an $AC_{50}$ value of less than 1 μM using the Luminescence Assay described in Example 2, or a pharmaceutically acceptable salt and/or other solid form thereof. One aspect of the disclosure relates to methods of treating a patient, such as a patient diagnosed with a hemoglobinopathy, comprising the administration of a therapeutically effective amount of Compound 1 or a pharmaceutically acceptable salt thereof. Methods of treating various hemoglobinopathy conditions can comprise the administration of a therapeutically effective amount of a PKR Activating Compound to a patient in need thereof. Various additional methods of administering a PKR Activating Compound to a patient diagnosed with a hemoglobinapthy are provided herein.

As used herein, the term "hemoglobinopathy" means any defect in the structure, function or expression of any hemoglobin of an individual, and includes defects in the primary, secondary, tertiary or quaternary structure of hemoglobin caused by any mutation, such as deletion mutations or substitution mutations in the coding regions of the β-globin gene, or mutations in, or deletions of, the promoters or enhancers of such genes that cause a reduction in the amount of hemoglobin produced as compared to a normal or standard condition. The term "hemoglobinopathy" further includes any decrease in the amount or effectiveness of hemoglobin, whether normal or abnormal, caused by external factors such as disease, chemotherapy, toxins, poisons, or the like, β-hemoglobinopathies contemplated herein include, but are not limited to, sickle cell disease (SCD, also referred to a sickle cell anemia or SCA), sickle cell trait, hemoglobin C disease, hemoglobin C trait, hemoglobin S/C disease, hemoglobin D disease, hemoglobin E disease, thalassemias, hemoglobins with increased oxygen affinity, hemoglobins with decreased oxygen affinity, unstable hemoglobin disease and methemoglobinemia.

In some embodiments, the hemoglobinopathy is a condition that can be therapeutically treated by PKR activation resulting from the administration of a therapeutically effective amount of Compound 1. Enhancement of PKR activity may also increase NADH levels and therefore ability to reduce methemoglobin to hemoglobin. The enzyme methemoglobin reductase utilizes NADH, which like ATP, is generated during glycolysis.

In some embodiments, the disease or disorder is selected from the group consisting of PKD, SCD, sickle cell anemia, thalassemia (e.g., beta-thalassemia or alpha-thalassemia), hereditary non-spherocytic hemolytic anemia, hemolytic anemia (e.g., chronic hemolytic anemia caused by phosphoglycerate kinase deficiency (PKD)), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases.

In some embodiments, the method comprises administering a therapeutically effective amount of a Compound 1 for the treatment of a patient diagnosed with a condition selected from the group consisting of: hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), and anemia of chronic diseases. In some embodiments, the disease or disorder is hereditary non-sperocytic hemolytic anemia. In some embodiments, the disease or disorder is SCD (e.g., sickle cell anemia) or thalassemia (e.g., beta-thalassemia). In some embodiments, the disease or disorder is hemolytic anemia (e.g., in a patient diagnosed with PKD). In some embodiments, the disease or disorder is beta thalassemia. In some embodiments, the disease or disorder is SCD. In some embodiments, the disease or disorder is selected from the group consisting of SCD, sickle cell anemia, thalassemia (e.g., beta-thalassemia), hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), and anemia of chronic diseases.

In another embodiment, the present disclosure relates to a compound of Formula (I) or a pharmaceutical composition comprising a compound of the present disclosure and a pharmaceutically acceptable carrier used for the treatment of SCD, sickle cell anemia, thalassemia (e.g., beta-thalassemia), hereditary non-spherocytic hemolytic anemia, hemolytic anemia (e.g., chronic hemolytic anemia caused by phosphoglycerate kinase deficiency), hereditary spherocytosis, hereditary elliptocytosis, abetalipoproteinemia (or Bassen-Kornzweig syndrome), paroxysmal nocturnal hemoglobinuria, acquired hemolytic anemia (e.g., congenital anemias (e.g., enzymopathies)), or anemia of chronic diseases.

A method of treating a patient diagnosed with a hemoglobinopathy, can comprise administering a PKR Activating Compound in an amount effective to increase oxygen affinity of HbS in the patient or to provide a left shift in the point of sickling (PoS) with an increase in the deformability (Elmin) in the patient, or a combination thereof. For example, the hemoglobinopathy can be Sickle Cell Disease or beta-thalassemia. In some embodiments, a patient diagnosed with a hemoglobinopathy is treated with Compound 1 or a pharmaceutically acceptable salt thereof. In some embodiments, the patient is diagnosed with Sickle Cell Disease or beta-thalassemia.

In some embodiments, the administration of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods of treating hemoglobinopathies described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

Patient Hemoglobin Genotype

Compound 1 can be administered to subjects having various genotypes. In some embodiments, Compound 1 can be administered to red blood cells of a subject having normal hemoglobin (e.g., HbA, HbA1, HbA2, HbE, HbF, HbS, HbC, HbH, and HbM, and HbF <2% of total hemoglobin). In some embodiments, methods of treatment comprise the step of administering a pharmaceutical composition to a patient diagnosed with hemoglobinopathies comprising hemoglobin genotypes other than HbA. In some embodiments, the patient is diagnosed with a condition previously confirmed by hemoglobin electrophoresis or genotyping. In some embodiments, the patient can be diagnosed with a genotype indicating one of the following hemoglobin genotypes: Hgb SS, Hgb Sβ+-thalassemia, Hgb Sβ0-thalassemia, or Hgb SC, which is often determined as part of universal newborn screening available in the majority of U.S. states. In some embodiments, the disclosure relates to a method of improving the anemia and the complications associated with anemia in SCD patients (e.g., ≥12 years of age, and/or <12 years of age) with Hgb SS or Hgb SB0-thalassemia. In some embodiments, Compound 1 is administered to a patient diagnosed with a SCD genotype comprising HbS. In some embodiments, methods of treatment can comprise administering compound 1 to a patient diagnosed with a HbSS disease or sickle cell anemia (i.e., homozygote for the S globin), HbS/b-0 thalassemia (double heterozygote for HbS and b-0 thalassemia), HbS/b+ thalassemia, HbSC disease (i.e., double heterozygote for HbS and HbC), HbS/hereditary persistence of fetal Hb (S/HPHP), HbS/HbE syndrome, or rare combinations of HbS (e.g., HbD Los Angeles, G-Philadelphia, or HbO Arab).

Treating Sickle Cell Disease (SCD) with Compound 1

In some embodiments, methods of treatment comprise the step of administering Compound 1 to a patient diagnosed with SCD, where the patient is further characterized by one or more of the following: (1) previously confirmed hemoglobin genotype selected from the group consisting of Hb SS and Hb SC, (2) age 12 to 65 years, (3) patients having had ≤6 vaso-occlusive crises (VOCs) within the past 12 months prior to receiving Compound 1, (4) no PRBC transfusion within 30 days of first receiving Compound 1; and, optionally, (5) concomitant hydroxyurea use.

Figure 5:
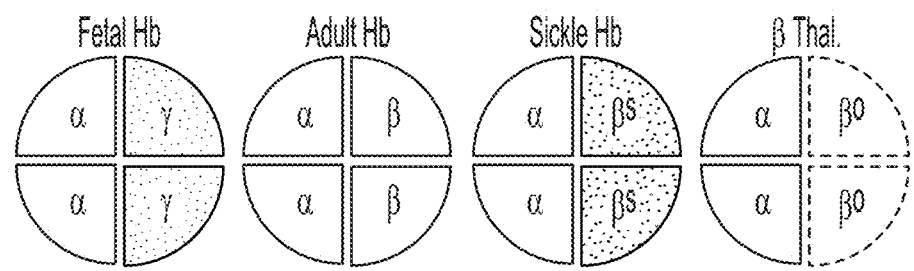
FIG. 5 is a diagram of hemoglobin mutations giving rise to hemoglobinopathies.

Referring to the schematic in FIG. 5, SCD arises from abnormalities in the beta subunit, specifically when a genetic mutation creates the variant form of the beta subunit, called βs. SCD is an autosomal recessive disorder characterized by a point mutation in the beta-globin gene that results in a single amino acid substitution that predisposes polymerization of deoxy hemoglobin. This polymerization results in deformation of RBCs into a less-pliable, sickle shape. The sickle-shaped RBCs also exhibit membrane damage in the form of altered surface lipids and are prone to adhere to vascular endothelium and white blood cells in small blood vessels in peripheral tissues that can block blood flow to organs and cause acute and painful VOC events. As a result of this obstruction, there is destruction of some RBCs, or hemolysis. This destruction of RBCs leads to the intravascular release of hemoglobin which itself can generate highly damaging oxidative chemicals. The release of hemoglobin and other cytoplasmic molecules from RBCs also trigger signaling cascades that lead to platelet activation, increased endothelial adhesion, inflammation in the vasculature and further obstruction of blood vessels. Acute complications of VOC cause tissue damage due to the lack of oxygen delivery to tissues, resulting in severe pain and symptoms, such as acute chest syndrome. Tissues that are deprived of oxygen are subject to ischemia and reperfusion injuries that can cause damage and long-term organ failure.

Sickle cell disease (SCD) is a chronic hemolytic anemia caused by inheritance of a mutated form of hemoglobin (Hgb), sickle Hgb (HgbS). It is the most common inherited hemolytic anemia, affecting 70,000 to 80,000 patients in the United States (US). SCD is characterized by polymerization of HgbS in red blood cells (RBCs) when HgbS is in the deoxygenated state (deoxy-HgbS), resulting in a sickle-shaped deformation. Sickled cells aggregate in capillaries precipitating vaso-occlusive events that generally present as acute and painful crises resulting in tissue ischemia, infarction, and long-term tissue damage. RBCs in patients with SCD tend to be fragile due to repeated cycles of sickling and mechanical deformation, which induce damage including membrane dysfunction. Reactive oxygen species caused by HbS lead to oxidative damage. Together, these sources of damage lead to hemolysis and chronic anemia. Finally, damaged RBCs have abnormal surfaces that adhere to and damage vascular endothelium, provoking a proliferative/inflammatory response that underlies large-vessel stroke and potentially pulmonary-artery hypertension. Collectively, these contribute to the significant morbidity and increased mortality associated with this disease.

The described clinical symptoms of SCD are largely due to perturbations in RBC membrane shape and function resulting from aggregation of HgbS molecules. Unlike normal Hgb, HgbS polymerizes when it is in the deoxygenated state and ultimately causes a deformed, rigid cell that is unable to pass through small blood vessels, thereby blocking normal blood flow through microvasculature. The loss of membrane elasticity also increases hemolysis and clearance by the spleen, reducing RBC longevity. Furthermore, decreased cellular ATP and oxidative damage contribute to a sickle RBC membrane that is stiffer and weaker than that of normal RBCs. The damaged membrane has a greater propensity for adhering to vasculature, leading to hemolysis, increased aggregation of sickled RBCs, and increased coagulation and inflammation associated with vaso-occlusive crises.

The underlying cause of sickling is the formation of rigid deoxy-HgbS aggregates that alter the cell shape and consequently impact cellular physiology and membrane elasticity. These aggregates are highly structured polymers of deoxygenated HgbS; the oxygenated form does not polymerize. Polymerization is promoted by a subtle shift in conformation from the oxygen-bound relaxed (R)-state to the unbound tense (T)-state that exposes the mutant hydrophobic valine residue at position 6 of the β-globin chain. These valine residues within the β-chain of HgbS are able to interact in a specific and repetitive manner, facilitating polymerization.

Figure 6:
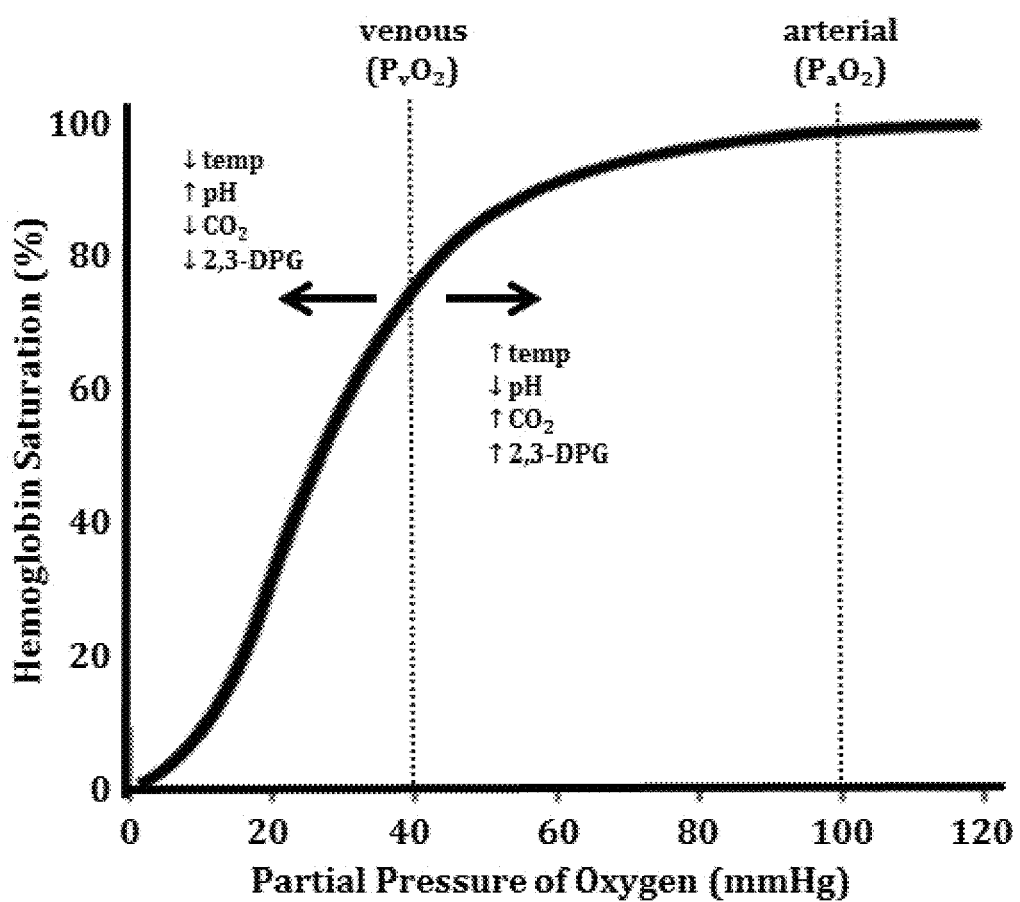
FIG. 6 is a graph showing the oxyhemoglobin dissociation curve and modulating factors by plotting the relationship between hemoglobin saturation (percent) vs. partial pressure of oxygen (mmHg).

The concentration of deoxy-HgbS depends on several factors, but the predominant factor is the partial pressure of oxygen ($PO_2$). Oxygen reversibly binds to the heme portions of the Hgb molecule. As oxygenated blood flows via capillaries to peripheral tissues and organs that are actively consuming oxygen, $PO_2$ drops and Hgb releases oxygen. The binding of oxygen to Hgb is cooperative and the relationship to $PO_2$ levels fits a sigmoidal curve (FIG. 6). This relationship can be impacted by temperature, pH, carbon dioxide, and the glycolytic intermediate 2,3-DPG. 2,3-DPG binds within the central cavity of the Hgb tetramer, causes allosteric changes, and reduces Hgb's affinity for oxygen. 2,3-DPG is normally increased in response to anemia, and is therefore higher in SCD patients. Therapeutic approaches that increase oxygen affinity (i.e., reduce deoxygenation) of HgbS will decrease the rate of polymer formation, changes to the cell membrane, and clinical consequences associated with certain hemoglobinopathy conditions such as SCD. These changes would be observed at the cellular level but also would be reflected in clinical measurements such as Hb, RBC and reticulocyte counts, as well as in measures of hemolysis such as LDH levels in plasma or serum.

SCD is the most common type of hemoglobinopathy, a diverse range of rare inherited genetic disorders that affect hemoglobin, the iron-containing protein in RBCs responsible for transporting oxygen in the blood. In SCD, a structural abnormality in hemoglobin results in RBCs with a sickle-shaped deformation after off-loading oxygen to tissues. These sickle RBCs can aggregate in tissue blood vessels and block blood flow and oxygen delivery to organs, which can lead to acute and painful VOC events that result in tissue ischemia, infarction, and long-term tissue damage. In addition, sickle RBCs tend to be fragile due to sickling and have a half-life of 10 to 20 days versus normal RBCs, which have a half-life of 90 to approximately 120 days. This fragility leads to hemolysis, or the destruction of sickle RBCs, and chronic anemia, or reduced levels of RBCs and total hemoglobin. Additionally, damaged RBCs release factors that are detrimental to the vascular endothelium and can induce an inflammatory response that underlies large-vessel stroke and pulmonary arterial hypertension. On average, adult SCD patients are hospitalized three times per year and have significant morbidity and increased mortality.

The VOC events generally begin early in childhood and may lead to heart and lung complications, renal dysfunction, priapism, spleen enlargement and failure, stroke, retinopathy and mental and physical disabilities. Chronic pain is common, occurring on approximately 55% of days, as self-reported in SCD patients. Acute chest syndrome occurs in approximately half of all patients with SCD and is a leading cause of hospitalization and death among patients with SCD. Stroke occurs in 11% of patients with SCD by the age of 20 and in 24% of patients by the age of 45. Approximately 10% of patients with SCD suffer from pulmonary hypertension. Some patients with SCD experience end-stage renal failure that requires dialysis and portends a one-year mortality of 26%. Adult patients with SCD are hospitalized 1.5 times per year on average, and one-third of patients with SCD are readmitted to the hospital within 30 days of initial hospitalization.

SCD clinically manifests with potentially severe pathological conditions associated with substantial physical, emotional, and economic burden. For instance, acute vaso-occlusive pain crises can be debilitating and necessitate rapid medical response. Chronic hemolytic anemia causes fatigue and often necessitates blood transfusions and supportive care. Over time, impaired oxygen transport through microvasculature precipitates organ and tissue damage. While there are a number of options available for treating symptoms, overall disease management would benefit from therapies that target upstream processes to prevent vaso-occlusion and hemolysis.

As provided herein, certain methods of treating SCD preferably include administration of a therapeutically effective amount of a PKR Activating Compound (e.g., Compound 1) that reduces HgbS polymerization, for example by increasing HgbS affinity for oxygen. Methods of treating SCD also preferably include administration of a therapeutically effective amount of a compound (e.g., Compound 1) that reduces HgbS polymerization, for example by increasing HgbS affinity for oxygen. Methods of lowering 2,3-DPG and/or increasing ATP levels in human RBCs comprise administering a PKR Activating Compound, such as Compound 1. Methods of lowering 2,3-DPG and/or increasing ATP levels in human RBCs also comprise administering a PKR Activating Compound, such as Compound 1. Together these effects are consistent with providing therapies to reduce HgbS sickling and to improve RBC membrane health, presenting a unique disease-modifying mechanism for treating SCD.

A PKR Activator Compound, such as Compound 1, can be administered orally, once-daily, for the treatment of SCD. SCD, one of the most common single-gene disorders in the world, is a chronic hemolytic anemia that affects hemoglobin, the iron-containing protein in red blood cells, or RBCs, that delivers oxygen to cells throughout the body. SCD is often characterized by low hemoglobin levels, painful vaso-occlusive crises, or VOCs, progressive multi-organ damage and early death. Compound 1 is a potent activator of pyruvate kinase-R, or PKR, designed to improve RBC metabolism, function and survival, and potentially resulting in both increased hemoglobin levels and reduced VOCs. Unlike other emerging SCD therapies, Compound 1 modulates RBC metabolism by impacting two critical pathways through PKR activation: a decrease in 2,3 diphosphoglycerate, or 2,3-DPG, which increases oxygen affinity and an increase in adenosine triphosphate, or ATP, which may improve RBC and membrane health and integrity. This multi-modal approach may improve hemoglobin levels through increased RBC survival and decrease VOCs through reduced RBC sickling. Compound 1 has the potential to become the foundational standard of care for SCD patients by modifying the disease at an early stage and potentially preventing end-organ damage, reducing hospitalizations, and improving the patients' overall health and quality of life.

In some embodiments, the disclosure relates to a method of increasing Hb concentration in a patient diagnosed with sickle cell disease (SCD), comprising orally administering to the patient in need thereof a therapeutically effective amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, once per day (QD). In some embodiments, the disclosure relates to a method of increasing Hb concentration in a patient diagnosed with sickle cell disease (SCD), comprising administering to the patient a sufficient amount of a PKR Activating Compound, e.g., (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the disclosure relates to a method of reducing point of sickling (POS) in a patient diagnosed with sickle cell disease (SCD), comprising administering to the patient a sufficient amount of a PKR Activating Compound, e.g., (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the disclosure relates to a method of increasing Elmin in a patient diagnosed with sickle cell disease (SCD), comprising administering to the patient a sufficient amount of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the disclosure relates to a method of improving RBC deformability in a patient diagnosed with sickle cell disease (SCD), comprising administering to the patient a sufficient amount of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the disclosure relates to a method of reducing RBC turnover in a patient diagnosed with sickle cell disease (SCD), comprising administering to the patient a sufficient amount of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the disclosure relates to a method of increasing RBC count in a patient diagnosed with sickle cell disease (SCD), comprising administering to the patient a sufficient amount of a PKR Activating Compound, e.g., (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof. In some embodiments, the disclosure relates to a method of increasing RBC count in a patient diagnosed with sickle cell disease (SCD), comprising administering to the patient a sufficient amount of (S)-1-(5-

((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the disclosure relates to a method of decreasing reticulocyte count in a patient diagnosed with sickle cell disease (SCD), comprising administering to the patient a sufficient amount of a PKR Activating Compound, e.g., (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

In some embodiments, the disclosure relates to a method of decreasing lactate dehydrogenase (LDH) concentration in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

Compound 1 was evaluated in a multi-center, placebo-controlled Phase I trial in healthy volunteers and SCD patients ages 12 years and older. The healthy volunteer portion of the trial has been completed, and data has been presented at the 2019 American Society of Hematology meeting demonstrating the tolerability and proof of mechanism of Compound 1 in healthy volunteers. In RBCs of the healthy volunteers, Compound 1 demonstrated a reduction in 2,3-DPG and an increase in ATP, which provides confirmatory evidence of PKR activation in healthy RBCs. In addition, the reduction of 2,3-DPG correlated with increased oxygen affinity with single and multiple doses of Compound 1. In the single dose cohort in SCD patients, a favorable tolerability profile and favorable biologic effects have been observed with evidence of pharmacodynamic activity translating into increased oxygen affinity and a shift in the Point of Sickling to lower oxygen tensions and improved membrane deformability of sickle RBCs. Furthermore, a second MAD cohort and a three-month open label extension in SCD patients are planned. Based on the results of this trial, global pivotal Phase II/III trial in SCD patients is planned. Clinical development of Compound 1 in pediatric SCD populations and other SCD patient populations in future trials is planned.

Methods of treating SCD also include administration of a therapeutically effective amount of a bioactive compound (e.g., a small molecule, nucleic acid, or antibody or other therapy) that reduces HgbS polymerization, for example by increasing HgbS affinity for oxygen.

In some embodiments, Compound 1 is administered to a patient diagnosed with SCD, prior to, after or in combination with one or more additional SCD treatments administered to the patient. SCD treatments include curative therapies, disease modifying agents, symptomatic therapies administered as chronic prophylaxis or supportive care for acute crises.

The methods of treating SCD provided herein can offer greater protection against vaso-occlusive crises and hemolytic anemia, as compared to other therapies. Therefore, use of a PKR Activating Compound, such as Compound 1, provides a novel and improved therapeutic approach either alone or in combination with drugs that act through alternative mechanisms (e.g., drugs that increase HbF), such as hydroxyurea (HU). In some embodiments, Compound 1 is administered to a SCD patient who has previously received a drug that increases HbF or to a SCD patient undergoing treatment with such a drug, including patients who continue to receive such a drug when treated with Compound 1. In some embodiments, Compound 1 is administered to a SCD patient who has previously received hydroxyurea (HU) or to a SCD patient undergoing HU treatment including patients who continue to receive HU when treated with Compound 1. HU, marketed under trade names including DROXIA by Bristol Myers Squibb Company, as well as in generic form, is approved for the treatment of anemia related to SCD, to reduce the frequency of VOCs and the need for blood transfusions. Hydroxyurea (HU) induces HgbF which interrupts the polymerization of HgbS, and thereby has activity in decreasing the onset of vaso-occlusive crises and pathological sequelae of SCD. While HU is in wide use as a backbone therapy for SCD, it remains only partially effective, and is associated with toxicity, such as myelosuppression and teratogenicity. Patients receiving HU still experience hemolysis, anemia, and vaso-occlusive crises, suggesting a need for more effective therapies, either as a replacement or in combination with HU. Beyond HU, therapeutic intervention is largely supportive care, aimed at managing the symptoms of SCD. For instance, blood transfusions help with the anemia and other SCD complications by increasing the number of normal RBCs and suppressing the synthesis of sickle RBCs. However, repeated transfusions lead to iron overload and the need for chelation therapies to avoid consequent tissue damage. In addition to these approaches, analgesic medications are used to manage pain. Many patients do not respond to HU therapy, and even in responding patients, HU can lose efficacy over time. Although HU is considered to have an acceptable therapeutic index given the consequences of SCD, HU is underutilized due to safety concerns and side effects. HU and opioids are the standard non-curative treatments for chronic and acute care, respectively.

In some embodiments, a method of treating a patient diagnosed with SCD can include the steps of administering Compound 1 to the patient in combination with an antimetabolite such as HU, that is indicated to reduce the frequency of painful crises and to reduce the need for blood transfusions in patients with sickle cell anemia with recurrent moderate to severe painful crises. In some embodiments, the antimetabolite HU is administered with an initial dose of 15 mg/kg once daily, and the patient's blood count is monitored every two weeks. The dose of HU may be increased by 5 mg/kg/day every 12 weeks until a maximum tolerated dose or 35 mg/kg/day is reached if blood counts are in an acceptable range. The dose is not increased if blood counts are between the acceptable range and toxic. HU may be discontinued until hematologic recovery if blood counts are considered toxic. Treatment may then be resumed after reducing the dose by 2.5 mg/kg/day from the dose associated with hematological toxicity. The HU can be administered to the patient in hydroxyurea capsules, available for oral use as capsules containing 200 mg, 300 mg, and 400 mg hydroxyurea. Inactive ingredients with the HU can include citric acid, gelatin, lactose, magnesium stearate, sodium phosphate, titanium dioxide, and capsule colorants. Known pharmacologic effects of DROXIA that may contribute to its beneficial effects include increasing hemoglobin F levels in red blood cells (RBCs), decreasing neutrophils, increasing the water content of RBCs, increasing deformability of sickled cells, and altering the adhesion of RBCs to endothelium.

In some embodiments, Compound 1 is administered to a patient diagnosed with SCD who is also receiving L-glutamine for treatment of complications of SCD, and/or to a patient diagnosed with SCD who is has previously received L-glutamine for treatment of complications of SCD. Endari, marketed by Emmaus Life Sciences, Inc., is an oral powder form of L-glutamine approved to reduce severe complications associated with the disorder. L-glutamine is an amino acid indicated to reduce the acute complications of sickle cell disease in adult and pediatric patients 5 years of age and older. L-glutamine can be administered in an amount of 5 grams to 15 grams orally, twice daily based on body weight. Each dose of L-glutamine should be mixed in 8 oz. (240 mL) of cold or room temperature beverage or 4 oz. to 6 oz. of food before ingestion. L-glutamine is designated chemically as (S)-2-aminoglutaramic acid, L-glutamic acid 5-amide, or (S)-2, Oxidative stress phenomena are involved in the pathophysiology of SCD. Sickle red blood cells (RBCs) are more susceptible to oxidative damage than normal RBCs, which may contribute to the chronic hemolysis and vaso-occlusive events associated with SCD. The pyridine nucleotides, NAD+ and its reduced form NADH, play roles in regulating and preventing oxidative damage in RBCs. L-glutamine may improve the NAD redox potential in sickle RBCs through increasing the availability of reduced glutathione. 5-diamino-5-oxopentanoic acid. Following single-dose oral administration of L-glutamine at 0.1 g/kg, mean peak L-glutamine concentration was 1028 μM (or 150 mcg/mL) occurring approximately 30 minutes after administration. After an intravenous (IV) bolus dose, the volume of distribution was estimated to be approximately 200 mL/kg.

In some embodiments, Compound 1 is administered to a patient receiving supportive care for the management of VOCs. Supportive care for the management of painful VOCs entails the use of opioids or other pain medication.

In some embodiments, Compound 1 is administered to a patient diagnosed with SCD who has received (or is concurrently receiving) one or more therapies selected from the group consisting of voxelotor and crizanlizumab. In November 2019, the FDA approved voxelotor and crizanlizumab for the treatment of SCD.

In some embodiments, a method of treatment comprises administering Compound 1 to a patient diagnosed with SCD who has previously received a therapy for inhibiting polymerization of the HbS molecule. For example, Compound 1 can be administered to a SCD patient who has been treated with voxelotor. In some embodiments, Compound 1 is administered to a SCD patient in combination with voxelotor. FDA granted accelerated approval for voxelotor for the treatment of SCD in adults and children 12 years of age and older. Voxelotor is an oral therapy taken once daily and is the first approved treatment that directly inhibits HbS polymerization. Voxelotor is an oral small molecule therapy, which demonstrated improvement in total hemoglobin levels but failed to significantly decrease VOCs. Voxelotor is designed to reduce HbS polymerization by binding to the HbS molecule and stabilizing its binding to oxygen. Thus, the mechanism of voxelotor is specific for increasing HbS oxygenation to reduce HbS polymerization. While it achieved moderate increases in Hb content and reduction in hemolysis, this mechanism of action by itself is likely to be insufficient to effectively counter the significant anemia and blood vessel damage associated with this disease. Voxelotor is a hemoglobin S polymerization inhibitor indicated for the treatment of sickle cell disease in adults and pediatric patients 12 years of age and older. This indication is approved under accelerated approval based on increase in hemoglobin (Hb). Continued approval for this indication may be contingent upon verification and description of clinical benefit in confirmatory trial(s). The chemical name of voxelotor is: 2-hydroxy-6-((2-(1-isopropyl-1H-pyrazol-5-yl)pyridin-3-yl) methoxy)benzaldehyde. Voxelotor is a hemoglobin S polymerization inhibitor. Voxelotor is a hemoglobin S (HbS) polymerization inhibitor that binds to HbS with a 1:1 stoichiometry and exhibits preferential partitioning to red blood cells (RBCs). By increasing the affinity of Hb for oxygen, voxelotor demonstrates dose-dependent inhibition of HbS polymerization. Nonclinical studies suggest that voxelotor may inhibit RBC sickling, improve RBC deformability, and reduce whole blood viscosity. Voxelotor is absorbed into plasma and is then distributed predominantly into RBCs due to its preferential binding to Hb. The major route of elimination of voxelotor is by metabolism with subsequent excretion of metabolites into urine and feces. The PK are linear and voxelotor exposures increased proportionally with either single or multiple doses in whole blood, plasma, and RBCs. A high-fat, high-calorie meal increased voxelotor AUC by 42% and Cmax by 45% in whole blood relative to AUC and Cmax in the fasted state. Similarly, AUC increased by 42% and Cmax increased by 95% in plasma. In vitro and in vivo studies indicate that voxelotor is extensively metabolized through Phase I (oxidation and reduction), Phase II (glucuronidation) and combinations of Phase I and II metabolism. Oxidation of voxelotor is mediated primarily by CYP3A4, with minor contribution from CYP2C19, CYP2B6, and CYP2C9. The pharmacokinetic parameters of voxelotor were similar in pediatric patients 12 to <17 years and adults. Voxelotor steady state whole blood AUC and Cmax were 50% and 45% higher in HbSC genotype patients (n=11) compared to HbSS genotype (n=220) patients and voxelotor steady state plasma AUC and Cmax were 23% and 15% higher in HbSC genotype patients compared to HbSS genotype patients.

Another approach to treatment is exemplified by the monoclonal antibody crizanlizumab, a P-selectin blocking monoclonal antibody, which reduces VOCs but does not impact HbS polymerization. FDA approved crizanlizumab, to reduce the frequency of VOCs in adult and pediatric patients aged 16 years and older with SCD. Crizanlizumab is administered intravenously and binds to P-selectin, which is a cell adhesion protein that plays a central role in the multicellular interactions that can lead to vaso-occlusion. Crizanlizumab has shown benefit in reducing the number of VOCs but does not treat the underlying cause of SCD and is only administered through intravenous administration.

Blood transfusions are also used to treat SCD and can transiently bolster hemoglobin levels by adding functional RBCs. There are a number of limitations associated with this therapeutic approach, including limited patient access and serious complications such as iron overload.

Hematopoietic stem cell transplantation, or HSCT, is also an option for SCD patients, but this therapy is limited by toxic preconditioning regimens involving chemotherapy ablation, donor availability, and the need for post-transplant immunosuppression. Allogeneic HSCT is an invasive, potentially toxic, high-risk procedure limited by matched donor availability and significant procedure-associated morbidities. This treatment option is not commonly used given the difficulties of finding a suitable matched donor and the risks associated with the treatment, which include an approximately 5% mortality rate. HSCT is more commonly offered to pediatric patients with available sibling-matched donors. HSCT is typically recommended for only the most serious cases, and is largely offered only to children with sibling-matched donors. However, HSCT use can be severely limited by toxic preconditioning regimens, donor availability and the need for post-transplant immunosuppression.

Gene therapy is another SCD therapy also under investigation with promising preliminary results. Gene therapy and gene editing approaches in development provide promise for cures but are invasive, high-risk procedures that require toxic preconditioning regimens to ablate the bone marrow and make room for engineered cells that express either normal beta-globin or elevated levels of HbF. Furthermore, the long-term therapeutic durability of these approaches is unknown. These factors, in addition to the expected relatively high cost for treatment, may limit the use of gene therapy. A number of different therapeutic approaches are in development for patients with SCD. For example, a therapy called LentiGlobin is in clinical trial testing for the treatment of SCD. LentiGlobin is a one-time gene therapy treatment for SCD that aims to treat SCD by inserting a functional human beta-globin gene into the patient's own hematopoietic stem cells ex vivo and then transplanting the modified stem cell into the patient's bloodstream. Another therapy in development for treatment of SCD patients RVT-1801, a gene therapy, being evaluated in human clinical trials. Another therapy in development for treatment of SCD patients is BIVV-003, a gene editing cell therapy that modifies cells to produce functional RBCs using HbF.

The compound designated as IMR-687, a small molecule inhibitor of phosphodiesterase-9, is designed to increase production of HbF for the treatment of SCD. Another compound in development for treatment of SCD patients is EPI01, a small molecule designed to increase production of HbF, in clinical trials.

In some embodiments, the administration of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods of treating SCD described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

In some embodiments, Compound 1 may be given with or without hydroxyurea. Hydroxyurea is indicated to reduce the frequency of painful crises and to reduce the need for blood transfusions in adult patients with sickle cell anemia with recurrent moderate to severe painful crises (generally at least 3 during the preceding 12 months). Dosage of hydroxyurea can be based on the patient's actual or ideal weight, whichever is less. The initial dose of hydroxyurea is 15 mg/kg/day as a single dose. The patient's blood count may be monitored every two weeks. If blood counts are in an acceptable range, the dose may be increased by 5 mg/kg/day every 12 weeks until a maximum tolerated dose (the highest dose that does not produce toxic blood counts over 24 consecutive weeks), or 35 mg/kg/day, is reached. If blood counts are between the acceptable range and toxic, the dose is not increased. If blood counts are considered toxic, hydroxyurea should be discontinued until hematologic recovery. Blood counts may be understood to be acceptable when neutrophils ≥2500 cells/mm$^3$, platelets ≥95,000/mm$^3$, hemoglobin >5.3 g/dL, and reticulocytes ≥95,000/mm$^3$ if the hemoglobin concentration <9 g/dL. Blood counts may be understood to be toxic when neutrophils <2000 cells/mm$^3$, platelets <80,000/mm$^3$, hemoglobin <4.5 g/dL, and reticulocytes <80,000/mm$^3$ if the hemoglobin concentration <9 g/dL.

In the event that hydroxyurea is discontinued, and hematologic recovery occurs, treatment may then be resumed after reducing the dose by 2.5 mg/kg/day from the dose associated with hematologic toxicity. Hydroxyurea may then be titrated up or down, every 12 weeks in 2.5 mg/kg/day increments, until the patient is at a stable dose that does not result in hematologic toxicity for 24 weeks. Any dosage on which a patient develops hematologic toxicity twice should not be tried again.

Hydroxyurea capsules (USP) are available for oral use as capsules providing 200 mg, 300 mg, and 400 mg hydroxyurea. Inactive ingredients: citric acid, gelatin, lactose, magnesium stearate, sodium phosphate, titanium dioxide, and capsule colorants; FD&C Blue No. 1 and FD&C Green No. 3 (200 mg capsules); D&C Red No. 28, D&C Red No. 33, and FD&C Blue No. 1 (300 mg capsules); D&C Red No. 28, D&C Red No. 33, and D&C Yellow No. 10 (400 mg capsules).

The precise mechanism by which hydroxyurea produces its cytotoxic and cytoreductive effects is not known. However, various studies support the hypothesis that hydroxyurea causes an immediate inhibition of DNA synthesis by acting as a ribonucleotide reductase inhibitor, without interfering with the synthesis of ribonucleic acid or of protein. The mechanisms by which hydroxyurea produces its beneficial effects in patients with sickle cell anemia (SCA) are uncertain. Known pharmacologic effects of hydroxyurea that may contribute to its beneficial effects include increasing hemoglobin F levels in RBCs, decreasing neutrophils, increasing the water content of RBCs, increasing deformability of sickled cells, and altering the adhesion of RBCs to endothelium.

In some embodiments, an SCD patient treated in the a method described herein (1) has a previously confirmed hemoglobin genotype selected from the group consisting of Hgb SS, Hgb Sβ$^+$-thalassemia, Hgb Sβ$^0$-thalassemia, and Hgb SC; (2) has had ≥6 vaso-occlusive crises (VOCs) within the 12 months prior to receiving Compound 1; (3) has had no RBC transfusion within 30 days of first receiving Compound 1; (4) has received hydroxyurea treatment for at least 90 days prior to first receiving Compound 1; and/or (5) has a baseline hemoglobin blood level of 7.0-10.5 g/dL.

Treating beta-Thallasemia with Compound 1

The administration of Compound 1 increased ATP in patients during the clinical trial of Example 8. Increasing ATP (and thereby improving membrane function) can benefit patients diagnosed with a thalassemia hemaglobinopathy. In some embodiments, Compound 1 can be administered for the treatment of beta thalassemia, which is a hemoglobinopathy that results from decreased or absent production of hemoglobin, thereby producing RBCs that have less oxygen carrying capacity than normal RBCs. Unlike SCD, beta thalassemia results from decreased or absent production of the beta subunit of hemoglobin, thereby producing RBCs that have less oxygen carrying capacity than normal RBCs. Further, the reduced levels of beta hemoglobin subunits result in an excess of alpha hemoglobin subunits, which form aggregates that can increase membrane damage and cause hemolysis. In some embodiments, Compound 1 can be administered to enhance the energy levels in beta thalassemia affected RBCs and enable the patients to tolerate the increased membrane damage and reduce hemolysis. The reduction in hemolysis can result in an increase in total hemoglobin that can improve symptoms.

Red blood cells (RBCs) in beta thalassemia patients have increased alpha-globin protein aggregates, free heme, and free iron that all cause an increase in the levels of toxic reactive oxygen species, which damage RBC membranes.

Consequently, ATP is consumed more avidly in the RBCs of beta thalassemia patients, and this depletion of ATP stores is believed to be key to the reduced life span of RBCs and increased hemolysis in these patients. By increasing ATP levels in the RBCs of beta thalassemia patients, Compound 1 may reduce hemolysis and increase total body hemoglobin levels.

In some embodiments, Compound 1 can enhance the energy levels in beta thalassemia affected RBCs and enable the patients to tolerate the increased membrane damage and reduce hemolysis. The reduction in hemolysis can result in an increase in total hemoglobin that can improve symptoms.

Methods of treating beta thalassemia also include administration of a therapeutically effective amount of a bioactive compound (e.g., a small molecule, nucleic acid, or antibody or other therapy) that reduces HgbS polymerization, for example by increasing HgbS affinity for oxygen.

In some embodiments, methods of treatment comprise the step of administering Compound 1 to a patient diagnosed with previously confirmed hemoglobin genotype selected from the group consisting of Sβ0-thalassemia, or Sβ+-thalassemia, and wherein the patient is further characterized by one or more of the following: (1) age 12 to 65 years, (2) patients having had ≤6 vaso-occlusive crises (VOCs) within the past 12 months prior to receiving Compound 1, (3) no PRBC transfusion within 30 days of first receiving Compound 1; and (4) concomitant hydroxyurea use.

Patients with beta thalassemia are often classified into one of two groups; (i) transfusion dependent patients, and (ii) non-transfusion dependent patients. Transfusion dependent patients can require frequent blood transfusions, which may result in an overload of iron in tissues that can damage organs such as the liver, heart, and endocrine organs. As a consequence, iron depleting agents are used to minimize the consequences of iron overload. HSCT can be curative for beta thalassemia patients, but procedure related toxicity and donor availability limit this as a therapeutic option.

Until November 2019, there were no approved drug therapies for beta thalassemia in the United States. The standard of care for many patients with beta thalassemia has been frequent blood transfusions to manage anemia. A potentially curative therapy for beta thalassemia is HSCT, which is associated with serious risk and is limited to patients with a suitable donor.

In November 2019, luspatercept-aamt was approved by the FDA for the treatment of anemia in adult patients with beta thalassemia who are transfusion dependent (i.e., require regular RBC transfusions). Luspatercept-aamt, is a modified receptor protein that promotes RBC maturation and increases overall RBC production, but does not address other cell types implicated in beta thalassemia. Luspatercept-aamt is not indicated for use as a substitute for RBC transfusions in patients who require immediate correction of anemia. Luspatercept-aamt is dosed subcutaneously and is administered every three weeks in an outpatient setting. While studies suggest that luspatercept-aamt can reduce the number of transfusions that these patients may require and reduce iron loading, these patients remain transfusion dependent, and significant unmet needs remain for these patients.

Gene therapy approaches to increasing either beta-globin or HbF expression in autologous hematopoietic stem cells for transplantation are also in development but are limited by the need for marrow preconditioning and anticipated high cost. One gene therapy in development is the administration of autologous CD34$^+$ cells encoding $β^{A-T87Q}$-globin gene, a gene therapy developed for the treatment of adult and adolescent patients with transfusion-dependent beta thalassemia and with certain genotypes.

Other therapeutic approaches in development for patients with transfusion-dependent beta thalassemia include Rivocel, a modified donor T cell therapy to be used in conjunction with HSCT; IMR-687, a small molecule inhibitor of phosphodiesterase-9; EPI01, a small molecule designed to increase production of HbF; OTL-300, an autologous ex vivo gene therapy for the treatment of transfusion-dependent beta thalassemia; ST-400, a genome-edited cell therapy approach designed to produce functional RBCs using HbF; CTX001, a gene editing approach to upregulate the expression of HbF, in patients with transfusion-dependent beta thalassemia; and gene control agents to activate gamma globin expression to induce the production of HbF for the treatment of beta thalassemia.

In some embodiments, the administration of (S)-1-(5-((2, 3-dihydro-[1,4]dioxino[2,3-b]pyridin-7-yl) sulfonyl)-3,4,5, 6-tetrahydropyrrolo[3,4-c]pyrrol-2(1H)-yl)-3-hydroxy-2-phenylpropan-1-one (Compound 1), or a pharmaceutically acceptable salt thereof, in any of the methods of treating beta-thalassemia described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

Once-Daily (QD) Dosing of Compound 1

In some embodiments, Compound 1 is administered once-daily (QD) to achieve the therapeutic effects described above (i.e., activating PKR, increasing hemoglobin oxygen affinity, increasing ATP concentrations in blood, reducing 2,3-DPG concentrations in blood, increasing hemoglobin concentrations in blood, reducing sickling in SCD patient RBCs, treating pediatric patients, treating hemoglobinopathies, treating SCD, and treating beta-thallasemia) and other therapeutic effects described herein.

Compound 1 demonstrates pharmacological response in healthy volunteers dosed with a single daily dose of 400 mg that is not directly related to plasma concentrations. Maximal decrease in blood levels of the target engagement biomarker 2,3-DPG occurs ~16 to 24 h post-dose, long after the plasma Cmax, and is sustained up to ~48 h post dose (e.g, FIG. 41). Furthermore, after 14 days of dosing, the downstream effect on hemoglobin oxygen affinity is similar with once daily doses of 400 mg or twice daily dosing of 200 mg (e.g., FIG. 40).

In healthy volunteers receiving a single dose of Compound 1, dose normalized Cmax and AUC increased with increasing doses ≥700 mg suggesting greater than dose proportional increases in exposure at the highest doses tested (FIG. 24A). In healthy volunteers receiving multiple doses of Compound 1, a dose linear exposure was observed across all dose levels tested and PK parameters (Cmax and AUC) remained constant on Day 14 compared to Day 1 indicating Compound 1 demonstrates time-independent pharmacokinetics (FIG. 24B). After multiple-doses (every 12 or 24 hours for 14 consecutive days), dose linear exposure was observed across all dose levels tested and PK parameters (Cmax and AUC) remained similar on Day 14 compared to Day 1, indicating time-independent PK. The underlying properties of Compound 1 driving the observed time-independent PK include a lack of observed CYP inhibition or induction demonstrated by Compound 1 in vitro, thereby reducing the risk of inhibiting or inducing its own clearance as well as reducing the risk for drug-drug interactions.

Compound 1 has not demonstrated any preclinical evidence of arrhythmia risk, mutagenicity, or nonspecific binding activity for panels of receptors, enzymes, ion channels, and kinases in vitro, suggesting a potentially positive tolerability profile.

In some embodiments, the administration of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods of once-daily (QD) dosing described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

In some embodiments, a therapeutically effective amount of Compound 1 can be administered orally once daily with or without food. If a daily dose of Compound 1 is missed, dosing of Compound 1 can be continued on the day following the missed dose.

In some embodiments, a therapeutically effective amount of Compound 1 for once daily (QD) administration is 200 mg (i.e., 200 mg QD). Thus, in some embodiments, this disclosure relates to:

1. A method of treating sickle cell disease in a patient, the method comprising repeatedly administering about 200 mg of Compound 1 at a dosage interval of about 24 hours to the patient.
2. A method of treating sickle cell disease in a patient, the method comprising repeatedly administering about 200 mg of Compound 1 to the patient once per day (QD).
3. A method of treating sickle cell disease in a patient, the method comprising:
   i. administering a first dose of about 200 mg of Compound 1 to the patient; and
   ii. administering a second dose of about 200 mg of Compound 1 to the patient about 20 hours to about 23.5 hours after reaching $C_{max}$ from the first dose.
4. The method of embodiment 3, the method further comprising repeatedly administering about 200 mg of Compound 1 to the patient about 20 hours to about 23.5 hours after reaching $C_{max}$ from the previous dose.
5. A method of treating sickle cell disease, the method comprising repeatedly administering about 200 mg of Compound 1 to a patient in need thereof at a dosage interval of about 20 hours to about 23.5 hours after reaching $C_{max}$ from the previous dose.
6. A method of increasing hemoglobin oxygen affinity in a patient in need thereof, the method comprising repeatedly administering about 200 mg of Compound 1 at a dosage interval of about 24 hours to the patient.
7. A method of increasing hemoglobin oxygen affinity in a patient in need thereof, the method comprising repeatedly administering about 200 mg of Compound 1 to the patient once per day (QD).
8. A method of increasing ATP blood levels in a patient in need thereof, the method comprising repeatedly administering about 200 mg of Compound 1 at a dosage interval of about 24 hours to the patient.
9. A method of increasing ATP blood levels in a patient in need thereof, the method comprising repeatedly administering about 200 mg of Compound 1 to the patient once per day (QD).
10. A method of decreasing 2,3-DPG blood levels in a patient in need thereof, the method comprising repeatedly administering about 200 mg of Compound 1 at a dosage interval of about 24 hours to the patient.
11. A method of decreasing 2,3-DPG blood levels in a patient in need thereof, the method comprising repeatedly administering about 200 mg of Compound 1 to the patient once per day (QD).
12. A method comprising repeatedly administering about 200 mg of Compound 1 at a dosage interval of about 24 hours to a patient in need thereof.
13. A method comprising repeatedly administering about 200 mg of Compound 1 to a patient in need thereof once per day (QD).
14. The method of any one of embodiments 6-13, wherein the patient is diagnosed with a hemoglobinopathy.
15. The method of embodiment 14, wherein the hemoglobinopathy is sickle cell disease.
16. The method of any one of embodiments 1-5 and 15, wherein the patient's ATP blood levels are increased by about 8% to about 18%, relative to baseline, 24 hours after the first administration.
17. The method of any one of embodiments 1-5 and 15-16, wherein the patient's ATP blood levels are increased by about 38% to about 48%, relative to baseline, 24 hours after the fourteenth administration.
18. The method of any one of embodiments 1-5 and 15-17, wherein the patient's 2,3-DPG blood levels are reduced by about 16% to about 26%, relative to baseline, 24 hours after the first administration.
19. The method of any one of embodiments 1-5 and 15-18, wherein the patient's 2,3-DPG blood levels are reduced by about 23% to about 33%, relative to baseline, 24 hours after the fourteenth administration.
20. The method of any one of embodiments 1-5 and 15-19, wherein the patient's p50 value decreases by about 10% to about 20%, relative to baseline, 24 hours after the fourteenth administration.
21. The method of any one of embodiments 1-5 and 15-20, wherein the patient's p50 value is between about 20 mm Hg and about 25 mm Hg 24 hours after the first dose.
22. The method of any one of embodiments 1-5 and 15-21, wherein the patient's p50 value is between about 22.5 mm Hg and about 27.5 mm Hg 24 hours after the fourteenth dose.
23. The method of any one of embodiments 1-5 and 15-22, wherein the patient's p50 value decreases by about 2.5 mm Hg to about 4.5 mm Hg, relative to baseline, 24 hours after the first dose.
24. The method of any one of embodiments 1-5 and 15-23, wherein the patient's p50 value decreases by about 2.5 mm Hg to about 4.5 mm Hg, relative to baseline, 24 hours after the fourteenth dose.
25. The method of any one of embodiments 6-14, wherein the patient has not been diagnosed with sickle cell disease.
26. The method of embodiment 25, wherein the patient's ATP blood levels are increased by about 0% to about 5%, relative to baseline, 24 hours after the first administration.

27. The method of embodiment 25 or 26, wherein the patient's ATP blood levels are increased by about 50% to about 60%, relative to baseline, 24 hours after the fourteenth administration.
28. The method of any one of embodiments 25-27, wherein the patient's 2,3-DPG blood levels are reduced by about 25% to about 45%, relative to baseline, 24 hours after the first administration.
29. The method of any one of embodiments 25-28, wherein the patient's 2,3-DPG blood levels are reduced by about 38% to about 53%, relative to baseline, 24 hours after the fourteenth administration.
30. The method of any one of embodiments 25-29, wherein the patient's p50 value decreases by about 10% to about 20%, relative to baseline, 24 hours after the fourteenth administration.
31. The method of any one of embodiments 25-30, wherein the patient's p50 value is between about 20 mm Hg and about 25 mm Hg 24 hours after the first dose.
32. The method of any one of embodiments 25-31, wherein the patient's p50 value is between about 20 mm Hg and about 25 mm Hg 24 hours after the fourteenth dose.
33. The method of any one of embodiments 25-32, wherein the patient's p50 value decreases by about 2.5 mm Hg to about 3.5 mm Hg, relative to baseline, 24 hours after the first dose.
34. The method of any one of embodiments 25-33, wherein the patient's p50 value decreases by about 2.5 mm Hg to about 4.5 mm Hg, relative to baseline, 24 hours after the fourteenth dose.
35. The method of any one of embodiments 1-34, wherein the Compound 1 is amorphous.
36. The method of embodiment 35, wherein the Compound 1 is administered in a pharmaceutical composition comprising a solid dispersion, the solid dispersion comprising the Compound 1 and a denucleating agent.
37. The method of embodiment 36, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
38. The method of embodiment 37, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
39. The method of any one of embodiments 36-38, wherein the solid dispersion is a spray dried dispersion.
40. The method of any one of embodiments 36-39, wherein the pharmaceutical composition is an oral dosage form.
41. The method of embodiment 40, wherein the pharmaceutical composition is a tablet.
42. The method of embodiment 40, wherein the pharmaceutical composition is a capsule.
43. The method of any one of embodiments 1-42, wherein Compound 1 $C_{max}$ is at least about 300 ng/mL after the first administration.
44. The method of embodiment 43, wherein Compound 1 $C_{max}$ is about 300 ng/mL to about 700 ng/mL after the first administration.
45. The method of any one of embodiments 1-44, wherein Compound 1 $T_{max}$ is about 0.5-4 hours after the first administration.
46. The method of any one of embodiments 1-45, wherein aromatase is not inhibited in the patient.
47. The method of any one of embodiments 1-46, wherein the patient is less than 18 years old.
48. The method of any one of embodiments 1-47, wherein the method comprises increasing hemoglobin blood levels in the patient.
49. The method of any one of embodiments 1-48, wherein the method comprises reducing the point of sickling in the patient.
50. The method of any one of embodiments 1-49, wherein the method comprises decreasing the percent reticulocytes in the patient.

In some embodiments, a therapeutically effective amount of Compound 1 for once daily (QD) administration is 300 mg (i.e., 300 mg QD). Thus, in some embodiments, this disclosure relates to:

1. A method of treating sickle cell disease in a patient, the method comprising repeatedly administering about 300 mg of Compound 1 at a dosage interval of about 24 hours to the patient.
2. A method of treating sickle cell disease in a patient, the method comprising repeatedly administering about 300 mg of Compound 1 to the patient once per day (QD).
3. A method of treating sickle cell disease in a patient, the method comprising:
    i. administering a first dose of about 300 mg of Compound 1 to the patient; and
    ii. administering a second dose of about 300 mg of Compound 1 to the patient about 20 hours to about 23.5 hours after reaching $C_{max}$ from the first dose.
4. The method of embodiment 3, the method further comprising repeatedly administering about 300 mg of Compound 1 to the patient about 20 hours to about 23.5 hours after reaching $C_{max}$ from the previous dose.
5. A method of treating sickle cell disease, the method comprising repeatedly administering about 300 mg of Compound 1 to a patient in need thereof at a dosage interval of about 20 hours to about 23.5 hours after reaching $C_{max}$ from the previous dose.
6. A method of increasing hemoglobin oxygen affinity in a patient in need thereof, the method comprising repeatedly administering about 300 mg of Compound 1 at a dosage interval of about 24 hours to the patient.
7. A method of increasing hemoglobin oxygen affinity in a patient in need thereof, the method comprising repeatedly administering about 300 mg of Compound 1 to the patient once per day (QD).
8. A method of increasing ATP blood levels in a patient in need thereof, the method comprising repeatedly administering about 300 mg of Compound 1 at a dosage interval of about 24 hours to the patient.
9. A method of increasing ATP blood levels in a patient in need thereof, the method comprising repeatedly administering about 300 mg of Compound 1 to the patient once per day (QD).
10. A method of decreasing 2,3-DPG blood levels in a patient in need thereof, the method comprising repeatedly administering about 300 mg of Compound 1 at a dosage interval of about 24 hours to the patient.

11. A method of decreasing 2,3-DPG blood levels in a patient in need thereof, the method comprising repeatedly administering about 300 mg of Compound 1 to the patient once per day (QD).

12. A method comprising repeatedly administering about 300 mg of Compound 1 at a dosage interval of about 24 hours to a patient in need thereof.

13. A method comprising repeatedly administering about 300 mg of Compound 1 to a patient in need thereof once per day (QD).

14. The method of any one of embodiments 6-13, wherein the patient is diagnosed with a hemoglobinopathy.

15. The method of embodiment 14, wherein the hemoglobinopathy is sickle cell disease.

16. The method of any one of embodiments 1-5 and 15, wherein the patient's ATP blood levels are increased by about 10% to about 20%, relative to baseline, 24 hours after the first administration.

17. The method of any one of embodiments 1-5 and 15-16, wherein the patient's ATP blood levels are increased by about 40% to about 50%, relative to baseline, 24 hours after the fourteenth administration.

18. The method of any one of embodiments 1-5 and 15-17, wherein the patient's 2,3-DPG blood levels are reduced by about 18% to about 28%, relative to baseline, 24 hours after the first administration.

19. The method of any one of embodiments 1-5 and 15-18, wherein the patient's 2,3-DPG blood levels are reduced by about 25% to about 35%, relative to baseline, 24 hours after the fourteenth administration.

20. The method of any one of embodiments 1-5 and 15-19, wherein the patient's p50 value decreases by about 10% to about 20%, relative to baseline, 24 hours after the fourteenth administration.

21. The method of any one of embodiments 1-5 and 15-20, wherein the patient's p50 value is between about 22.5 mm Hg and about 27.5 mm Hg 24 hours after the first dose.

22. The method of any one of embodiments 1-5 and 15-21, wherein the patient's p50 value is between about 22.5 mm Hg and about 27.5 mm Hg 24 hours after the fourteenth dose.

23. The method of any one of embodiments 1-5 and 15-22, wherein the patient's p50 value decreases by about 3.0 mm Hg to about 5.0 mm Hg, relative to baseline, 24 hours after the first dose.

24. The method of any one of embodiments 1-5 and 15-23, wherein the patient's p50 value decreases by about 3.0 mm Hg to about 5.0 mm Hg, relative to baseline, 24 hours after the fourteenth dose.

25. The method of any one of embodiments 6-14, wherein the patient has not been diagnosed with sickle cell disease.

26. The method of embodiment 25, wherein the patient's ATP blood levels are increased by about 0% to about 5%, relative to baseline, 24 hours after the first administration.

27. The method of embodiment 25 or 26, wherein the patient's ATP blood levels are increased by about 52% to about 62%, relative to baseline, 24 hours after the fourteenth administration.

28. The method of any one of embodiments 25-27, wherein the patient's 2,3-DPG blood levels are reduced by about 30% to about 45%, relative to baseline, 24 hours after the first administration.

29. The method of any one of embodiments 25-28, wherein the patient's 2,3-DPG blood levels are reduced by about 43% to about 53%, relative to baseline, 24 hours after the fourteenth administration.

30. The method of any one of embodiments 25-29, wherein the patient's p50 value decreases by about 10% to about 20%, relative to baseline, 24 hours after the fourteenth administration.

31. The method of any one of embodiments 25-30, wherein the patient's p50 value is between about 20 mm Hg and about 25 mm Hg 24 hours after the first dose.

32. The method of any one of embodiments 25-31, wherein the patient's p50 value is between about 20 mm Hg and about 25 mm Hg 24 hours after the fourteenth dose.

33. The method of any one of embodiments 25-32, wherein the patient's p50 value decreases by about 2.5 mm Hg to about 3.5 mm Hg, relative to baseline, 24 hours after the first dose.

34. The method of any one of embodiments 25-33, wherein the patient's p50 value decreases by about 3.0 mm Hg to about 5.0 mm Hg, relative to baseline, 24 hours after the fourteenth dose.

35. The method of any one of embodiments 1-34, wherein the Compound 1 is amorphous.

36. The method of embodiment 35, wherein the Compound 1 is administered in a pharmaceutical composition comprising a solid dispersion, the solid dispersion comprising the Compound 1 and a denucleating agent.

37. The method of embodiment 36, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.

38. The method of embodiment 37, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.

39. The method of any one of embodiments 36-38, wherein the solid dispersion is a spray dried dispersion.

40. The method of any one of embodiments 36-39, wherein the pharmaceutical composition is an oral dosage form.

41. The method of embodiment 40, wherein the pharmaceutical composition is a tablet. 42. The method of embodiment 40, wherein the pharmaceutical composition is a capsule. 43. The method of any one of embodiments 1-42, wherein Compound 1 $C_{max}$ is at least about 500 ng/mL after the first administration.

44. The method of embodiment 43, wherein Compound 1 $C_{max}$ is about 500 ng/mL to about 2000 ng/mL after the first administration.

45. The method of any one of embodiments 1-44, wherein Compound 1 $T_{max}$ is about 0.5-4 hours after the first administration.

46. The method of any one of embodiments 1-45, wherein aromatase is not inhibited in the patient.
47. The method of any one of embodiments 1-46, wherein the patient is less than 18 years old.
48. The method of any one of embodiments 1-47, wherein the method comprises increasing hemoglobin blood levels in the patient.
49. The method of any one of embodiments 1-48, wherein the method comprises reducing the point of sickling in the patient.
50. The method of any one of embodiments 1-49, wherein the method comprises decreasing the percent reticulocytes in the patient.

In some embodiments, a therapeutically effective amount of Compound 1 for once daily (QD) administration is 400 mg (i.e., 400 mg QD). Thus, in some embodiments, this disclosure relates to:

1. A method of treating sickle cell disease in a patient, the method comprising repeatedly administering about 400 mg of Compound 1 at a dosage interval of about 24 hours to the patient.
2. A method of treating sickle cell disease in a patient, the method comprising repeatedly administering about 400 mg of Compound 1 to the patient once per day (QD).
3. A method of treating sickle cell disease in a patient, the method comprising:
   i. administering a first dose of about 400 mg of Compound 1 to the patient; and
   ii. administering a second dose of about 400 mg of Compound 1 to the patient about 20 hours to about 23.5 hours after reaching $C_{max}$ from the first dose.
4. The method of embodiment 3, the method further comprising repeatedly administering about 400 mg of Compound 1 to the patient about 20 hours to about 23.5 hours after reaching $C_{max}$ from the previous dose.
5. A method of treating sickle cell disease, the method comprising repeatedly administering about 400 mg of Compound 1 to a patient in need thereof at a dosage interval of about 20 hours to about 23.5 hours after reaching $C_{max}$ from the previous dose.
6. A method of increasing hemoglobin oxygen affinity in a patient in need thereof, the method comprising repeatedly administering about 400 mg of Compound 1 at a dosage interval of about 24 hours to the patient.
7. A method of increasing hemoglobin oxygen affinity in a patient in need thereof, the method comprising repeatedly administering about 400 mg of Compound 1 to the patient once per day (QD).
8. A method of increasing ATP blood levels in a patient in need thereof, the method comprising repeatedly administering about 400 mg of Compound 1 at a dosage interval of about 24 hours to the patient.
9. A method of increasing ATP blood levels in a patient in need thereof, the method comprising repeatedly administering about 400 mg of Compound 1 to the patient once per day (QD).
10. A method of decreasing 2,3-DPG blood levels in a patient in need thereof, the method comprising repeatedly administering about 400 mg of Compound 1 at a dosage interval of about 24 hours to the patient.
11. A method of decreasing 2,3-DPG blood levels in a patient in need thereof, the method comprising repeatedly administering about 400 mg of Compound 1 to the patient once per day (QD).
12. A method comprising repeatedly administering about 400 mg of Compound 1 at a dosage interval of about 24 hours to a patient in need thereof.
13. A method comprising repeatedly administering about 400 mg of Compound 1 to a patient in need thereof once per day (QD).
14. The method of any one of embodiments 6-13, wherein the patient is diagnosed with a hemoglobinopathy.
15. The method of embodiment 14, wherein the hemoglobinopathy is sickle cell disease.
16. The method of any one of embodiments 1-5 and 15, wherein the patient's ATP blood levels are increased by about 14% to about 30%, relative to baseline, 24 hours after the first administration.
17. The method of any one of embodiments 1-5 and 15-16, wherein the patient's ATP blood levels are increased by about 40% to about 50%, relative to baseline, 24 hours after the fourteenth administration.
18. The method of any one of embodiments 1-5 and 15-17, wherein the patient's 2,3-DPG blood levels are reduced by about 23% to about 31%, relative to baseline, 24 hours after the first administration.
19. The method of any one of embodiments 1-5 and 15-18, wherein the patient's 2,3-DPG blood levels are reduced by about 25% to about 35%, relative to baseline, 24 hours after the fourteenth administration.
20. The method of any one of embodiments 1-5 and 15-19, wherein the patient's p50 value decreases by about 10% to about 20%, relative to baseline, 24 hours after the fourteenth administration.
21. The method of any one of embodiments 1-5 and 15-20, wherein the patient's p50 value is between about 22.5 mm Hg and about 27.5 mm Hg 24 hours after the first dose.
22. The method of any one of embodiments 1-5 and 15-21, wherein the patient's p50 value is between about 22.5 mm Hg and about 27.5 mm Hg 24 hours after the fourteenth dose.
23. The method of any one of embodiments 1-5 and 15-22, wherein the patient's p50 value decreases by about 3.0 mm Hg to about 5.0 mm Hg, relative to baseline, 24 hours after the first dose.
24. The method of any one of embodiments 1-5 and 15-23, wherein the patient's p50 value decreases by about 3.0 mm Hg to about 5.0 mm Hg, relative to baseline, 24 hours after the fourteenth dose.
25. The method of any one of embodiments 6-14, wherein the patient has not been diagnosed with sickle cell disease.
26. The method of embodiment 25, wherein the patient's ATP blood levels are increased by about 0% to about 5%, relative to baseline, 24 hours after the first administration.
27. The method of embodiment 25 or 26, wherein the patient's ATP blood levels are increased by about 52% to about 62%, relative to baseline, 24 hours after the fourteenth administration.
28. The method of any one of embodiments 25-27, wherein the patient's 2,3-DPG blood levels are reduced by about 43% to about 53%, relative to baseline, 24 hours after the first administration.
29. The method of any one of embodiments 25-28, wherein the patient's 2,3-DPG blood levels are reduced by about 48% to about 58%, relative to baseline, 24 hours after the fourteenth administration.
30. The method of any one of embodiments 25-29, wherein the patient's p50 value decreases by about 10% to about 20%, relative to baseline, 24 hours after the fourteenth administration.

31. The method of any one of embodiments 25-30, wherein the patient's p50 value is between about 20 mm Hg and about 25 mm Hg 24 hours after the first dose.
32. The method of any one of embodiments 25-31, wherein the patient's p50 value is between about 20 mm Hg and about 25 mm Hg 24 hours after the fourteenth dose.
33. The method of any one of embodiments 25-32, wherein the patient's p50 value decreases by about 3.0 mm Hg to about 4.0 mm Hg, relative to baseline, 24 hours after the first dose.
34. The method of any one of embodiments 25-33, wherein the patient's p50 value decreases by about 3.0 mm Hg to about 5.0 mm Hg, relative to baseline, 24 hours after the fourteenth dose.
35. The method of any one of embodiments 1-34, wherein the Compound 1 is amorphous.
36. The method of embodiment 35, wherein the Compound 1 is administered in a pharmaceutical composition comprising a solid dispersion, the solid dispersion comprising the Compound 1 and a denucleating agent.
37. The method of embodiment 36, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
38. The method of embodiment 37, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
39. The method of any one of embodiments 36-38, wherein the solid dispersion is a spray dried dispersion.
40. The method of any one of embodiments 36-39, wherein the pharmaceutical composition is an oral dosage form.
41. The method of embodiment 40, wherein the pharmaceutical composition is a tablet.
42. The method of embodiment 40, wherein the pharmaceutical composition is a capsule.
43. The method of any one of embodiments 1-42, wherein Compound 1 $C_{max}$ is at least about 1500 ng/mL after the first administration.
44. The method of embodiment 43, wherein Compound 1 $C_{max}$ is about 1500 ng/mL to about 3000 ng/mL after the first administration.
45. The method of any one of embodiments 1-44, wherein Compound 1 $T_{max}$ is about 0.5-4 hours after the first administration.
46. The method of any one of embodiments 1-45, wherein aromatase is not inhibited in the patient.
47. The method of any one of embodiments 1-46, wherein the patient is less than 18 years old.
48. The method of any one of embodiments 1-47, wherein the method comprises increasing hemoglobin blood levels in the patient.
49. The method of any one of embodiments 1-48, wherein the method comprises reducing the point of sickling in the patient.
50. The method of any one of embodiments 1-49, wherein the method comprises decreasing the percent reticulocytes in the patient.

In some embodiments, a therapeutically effective amount of Compound 1 for once daily (QD) administration is 600 mg (i.e., 600 mg QD). Thus, in some embodiments, this disclosure relates to:

1. A method of treating sickle cell disease in a patient, the method comprising repeatedly administering about 600 mg of Compound 1 at a dosage interval of about 24 hours to the patient.
2. A method of treating sickle cell disease in a patient, the method comprising repeatedly administering about 600 mg of Compound 1 to the patient once per day (QD).
3. A method of treating sickle cell disease in a patient, the method comprising:
    i. administering a first dose of about 600 mg of Compound 1 to the patient; and
    ii. administering a second dose of about 600 mg of Compound 1 to the patient about 20 hours to about 23.5 hours after reaching $C_{max}$ from the first dose.
4. The method of embodiment 3, the method further comprising repeatedly administering about 600 mg of Compound 1 to the patient about 20 hours to about 23.5 hours after reaching $C_{max}$ from the previous dose.
5. A method of treating sickle cell disease, the method comprising repeatedly administering about 600 mg of Compound 1 to a patient in need thereof at a dosage interval of about 20 hours to about 23.5 hours after reaching $C_{max}$ from the previous dose.
6. A method of increasing hemoglobin oxygen affinity in a patient in need thereof, the method comprising repeatedly administering about 600 mg of Compound 1 at a dosage interval of about 24 hours to the patient.
7. A method of increasing hemoglobin oxygen affinity in a patient in need thereof, the method comprising repeatedly administering about 600 mg of Compound 1 to the patient once per day (QD).
8. A method of increasing ATP blood levels in a patient in need thereof, the method comprising repeatedly administering about 600 mg of Compound 1 at a dosage interval of about 24 hours to the patient.
9. A method of increasing ATP blood levels in a patient in need thereof, the method comprising repeatedly administering about 600 mg of Compound 1 to the patient once per day (QD).
10. A method of decreasing 2,3-DPG blood levels in a patient in need thereof, the method comprising repeatedly administering about 600 mg of Compound 1 at a dosage interval of about 24 hours to the patient.
11. A method of decreasing 2,3-DPG blood levels in a patient in need thereof, the method comprising repeatedly administering about 600 mg of Compound 1 to the patient once per day (QD).
12. A method comprising repeatedly administering about 600 mg of Compound 1 at a dosage interval of about 24 hours to a patient in need thereof.
13. A method comprising repeatedly administering about 600 mg of Compound 1 to a patient in need thereof once per day (QD).
14. The method of any one of embodiments 6-13, wherein the patient is diagnosed with a hemoglobinopathy.
15. The method of embodiment 14, wherein the hemoglobinopathy is sickle cell disease.

16. The method of any one of embodiments 1-5 and 15, wherein the patient's ATP blood levels are increased by about 14% to about 30%, relative to baseline, 24 hours after the first administration.
17. The method of any one of embodiments 1-5 and 15-16, wherein the patient's ATP blood levels are increased by about 40% to about 55%, relative to baseline, 24 hours after the fourteenth administration.
18. The method of any one of embodiments 1-5 and 15-17, wherein the patient's 2,3-DPG blood levels are reduced by about 23% to about 31%, relative to baseline, 24 hours after the first administration.
19. The method of any one of embodiments 1-5 and 15-18, wherein the patient's 2,3-DPG blood levels are reduced by about 25% to about 40%, relative to baseline, 24 hours after the fourteenth administration.
20. The method of any one of embodiments 1-5 and 15-19, wherein the patient's p50 value decreases by about 10% to about 20%, relative to baseline, 24 hours after the fourteenth administration.
21. The method of any one of embodiments 1-5 and 15-20, wherein the patient's p50 value is between about 22.5 mm Hg and about 27.5 mm Hg 24 hours after the first dose.
22. The method of any one of embodiments 1-5 and 15-21, wherein the patient's p50 value is between about 22.5 mm Hg and about 27.5 mm Hg 24 hours after the fourteenth dose.
23. The method of any one of embodiments 1-5 and 15-22, wherein the patient's p50 value decreases by about 3.0 mm Hg to about 5.0 mm Hg, relative to baseline, 24 hours after the first dose.
24. The method of any one of embodiments 1-5 and 15-23, wherein the patient's p50 value decreases by about 3.0 mm Hg to about 5.0 mm Hg, relative to baseline, 24 hours after the fourteenth dose.
25. The method of any one of embodiments 6-14, wherein the patient has not been diagnosed with sickle cell disease.
26. The method of embodiment 25, wherein the patient's ATP blood levels are increased by about 0% to about 15%, relative to baseline, 24 hours after the first administration.
27. The method of embodiment 25 or 26, wherein the patient's ATP blood levels are increased by about 55% to about 65%, relative to baseline, 24 hours after the fourteenth administration.
28. The method of any one of embodiments 25-27, wherein the patient's 2,3-DPG blood levels are reduced by about 43% to about 53%, relative to baseline, 24 hours after the first administration.
29. The method of any one of embodiments 25-28, wherein the patient's 2,3-DPG blood levels are reduced by about 50% to about 60%, relative to baseline, 24 hours after the fourteenth administration.
30. The method of any one of embodiments 25-29, wherein the patient's p50 value decreases by about 10% to about 20%, relative to baseline, 24 hours after the fourteenth administration.
31. The method of any one of embodiments 25-30, wherein the patient's p50 value is between about 20 mm Hg and about 25 mm Hg 24 hours after the first dose.
32. The method of any one of embodiments 25-31, wherein the patient's p50 value is between about 20 mm Hg and about 25 mm Hg 24 hours after the fourteenth dose.
33. The method of any one of embodiments 25-32, wherein the patient's p50 value decreases by about 3.0 mm Hg to about 4.0 mm Hg, relative to baseline, 24 hours after the first dose.
34. The method of any one of embodiments 25-33, wherein the patient's p50 value decreases by about 3.0 mm Hg to about 5.0 mm Hg, relative to baseline, 24 hours after the fourteenth dose.
35. The method of any one of embodiments 1-34, wherein the Compound 1 is amorphous.
36. The method of embodiment 35, wherein the Compound 1 is administered in a pharmaceutical composition comprising a solid dispersion, the solid dispersion comprising the Compound 1 and a denucleating agent.
37. The method of embodiment 36, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
38. The method of embodiment 37, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
39. The method of any one of embodiments 36-38, wherein the solid dispersion is a spray dried dispersion.
40. The method of any one of embodiments 36-39, wherein the pharmaceutical composition is an oral dosage form.
41. The method of embodiment 40, wherein the pharmaceutical composition is a tablet.
42. The method of embodiment 40, wherein the pharmaceutical composition is a capsule.
43. The method of any one of embodiments 1-42, wherein Compound 1 $C_{max}$ is at least about 2000 ng/mL after the first administration.
44. The method of embodiment 43, wherein Compound 1 $C_{max}$ is about 2000 ng/mL to about 3000 ng/mL after the first administration.
45. The method of any one of embodiments 1-44, wherein Compound 1 $T_{max}$ is about 0.5-4 hours after the first administration.
46. The method of any one of embodiments 1-45, wherein aromatase is not inhibited in the patient.
47. The method of any one of embodiments 1-46, wherein the patient is less than 18 years old.
48. The method of any one of embodiments 1-47, wherein the method comprises increasing hemoglobin blood levels in the patient.
49. The method of any one of embodiments 1-48, wherein the method comprises reducing the point of sickling in the patient.
50. The method of any one of embodiments 1-49, wherein the method comprises decreasing the percent reticulocytes in the patient.

In some embodiments, the disclosure relates to a method of treating sickle cell disease in adult patients 18 years of age, pediatric patients ages 12 to less than 18 years of age, pediatric patients ages 2 to less than 12 years of age, or patients 18 to 21 years of age, comprising administering to the patient in need thereof a therapeutically effective amount of Compound 1 once daily with or without food. In some embodiments, the disclosure also relates to a method of treating a hemaglobinopathy in a patient having a hemoglobin genotype selected from the group consisting of Hgb SS, Hgb Sβ+-thalassemia, Hgb Sβ0-thalassemia, or Hgb SC, a hemaglobinopathy in a patient having a HbSC hemoglobin genotype, a hemaglobinopathy in a patient having a HbSS hemoglobin genotype, or a hemaglobinopathy in a patient having a HbS/beta0-thalassemia hemoglobin genotype, comprising administering to the patient in need thereof a therapeutically effective amount of Compound 1 once daily with or without food. In some embodiments, the disclosure also relates to a method of increasing hemoglobin oxygen affinity in a patient having a HbA hemoglobin genotype, the method comprising the step of administering to the patient in need thereof a therapeutically effective amount of Compound 1 once daily with or without food. In some embodiments, the therapeutically effective amount of Compound 1 is selected from the group consisting of 200 mg, 300 mg, 400 mg, and 600 mg. In some embodiments, the Compound 1 is administered as a non-crystalline solid form in a pharmaceutical composition in an oral unit dosage form. In some embodiments, the oral unit dosage form comprises an active pharmaceutical ingredient consisting of a total of 100 mg or 200 mg of Compound 1. In some embodiments, the oral unit dosage form further comprises a denucleating agent and the active pharmaceutical ingredient. In some embodiments, the oral unit dosage form has a total weight of less than 1,000 mg or less than 800 mg. In some embodiments, the total weight of API in the oral unit dosage form is 200 mg. In some embodiments, the oral unit dosage form comprises up to about 15% by weight of Compound 1. In some embodiments, the non-crystalline solid form comprises no more than 10% crystalline form detectable by XRPD. In some embodiments, the oral unit dosage form is a tablet or a capsule.

In some embodiments, including any of the foregoing embodiments involving once-daily administration of Compound 1 to a patient who has been diagnosed with sickle cell disease, the patient's ATP blood levels are increased by about 5% to about 40%, about 8% to about 30%, about 10% to about 30%, about 15% to about 25%, about 17% to about 23%, about 5% to about 20%, about 10% to about 20%, about 12% to about 18%, about 20% to about 35%, about 25% to about 35%, or about 20% to about 40%, relative to baseline, 24 hours after the first administration.

In some embodiments, including any of the foregoing embodiments involving once-daily administration of Compound 1 to a patient who has been diagnosed with sickle cell disease, the patient's ATP blood levels are increased by about 30% to about 70%, about 38% to about 55%, about 40% to about 50%, about 43% to about 47%, about 30% to about 50%, about 40% to about 50%, about 43% to about 47%, about 50% to about 60%, about 53% to about 57%, or about 50% to about 70%, relative to baseline, 24 hours after the fourteenth administration.

In some embodiments, including any of the foregoing embodiments involving once-daily administration of Compound 1 to a patient who has been diagnosed with sickle cell disease, the patient's 2,3-DPG blood levels are reduced by about 10% to about 40%, about 16% to about 31%, about 20% to about 30%, about 23% to about 27%, about 10% to about 25%, about 15% to about 25%, about 18% to about 22%, about 25% to about 35%, about 28% to about 32%, or about 25% to about 40%, relative to baseline, 24 hours after the first administration.

In some embodiments, including any of the foregoing embodiments involving once-daily administration of Compound 1 to a patient who has been diagnosed with sickle cell disease, the patient's 2,3-DPG blood levels are reduced by about 15% to about 50%, about 23% to about 40%, about 25% to about 35%, about 27% to about 33%, about 15% to about 30%, about 23% to about 30%, about 25% to about 28%, about 30% to about 40%, about 33% to about 37%, or about 30% to about 50%, relative to baseline, 24 hours after the fourteenth administration.

In some embodiments, including any of the foregoing embodiments involving once-daily administration of Compound 1 to a patient who has been diagnosed with sickle cell disease, the patient's p50 value decreases by about 5% to about 25%, about 10% to about 20%, about 12% to about 18%, about 13% to about 17%, about 5% to about 15%, about 10% to about 15%, about 11% to about 14%, about 15% to about 20%, about 16% to about 19%, or about 15% to about 25%, relative to baseline, 24 hours after the fourteenth administration.

In some embodiments, including any of the foregoing embodiments involving once-daily administration of Compound 1 to a patient who has been diagnosed with sickle cell disease, the patient's p50 value is between about 15 mm Hg and about 30 mm Hg, about 20 mm Hg and about 27.5 mm Hg, about 21 mm Hg and about 26 mm Hg, about 22 mm Hg and about 25 mm Hg, about 23 mm Hg and about 24 mm Hg, about 15 mm Hg and about 22.5 mm Hg, about 20 mm Hg and about 22.5 mm Hg, about 22.5 mm Hg and about 27.5 mm Hg, or about 22.5 mm Hg and about 30 mm Hg, 24 hours after the first dose.

In some embodiments, including any of the foregoing embodiments involving once-daily administration of Compound 1 to a patient who has been diagnosed with sickle cell disease, the patient's p50 value is between about 15 mm Hg and about 30 mm Hg, about 20 mm Hg and about 27.5 mm Hg, about 21 mm Hg and about 26 mm Hg, about 22 mm Hg and about 25 mm Hg, about 23 mm Hg and about 24 mm Hg, about 15 mm Hg and about 22.5 mm Hg, about 20 mm Hg and about 22.5 mm Hg, about 22.5 mm Hg and about 27.5 mm Hg, or about 22.5 mm Hg and about 30 mm Hg, 24 hours after the fourteenth dose.

In some embodiments, including any of the foregoing embodiments involving once-daily administration of Compound 1 to a patient who has been diagnosed with sickle cell disease, the patient's p50 value decreases by about 2.0 mm Hg to about 6.0 mm Hg, about 2.5 mm Hg to about 5.0 mm Hg, about 3.0 mm Hg to about 4.5 mm Hg, about 3.5 mm Hg to about 4.0 mm Hg, about 2.0 mm Hg to about 4.0 mm Hg, about 2.5 mm Hg to about 4.0 mm Hg, about 3.0 mm Hg to about 3.5 mm Hg, about 4.0 mm Hg to about 5.0 mm Hg, about 4.2 mm Hg to about 4.8 mm Hg, or about 4.0 mm Hg to about 6.0 mm Hg, relative to baseline, 24 hours after the first dose.

In some embodiments, including any of the foregoing embodiments involving once-daily administration of Compound 1 to a patient who has been diagnosed with sickle cell disease, the patient's p50 value decreases by about 2.0 mm Hg to about 6.0 mm Hg, about 2.5 mm Hg to about 5.0 mm Hg, about 3.0 mm Hg to about 4.5 mm Hg, about 3.5 mm Hg to about 4.0 mm Hg, about 2.0 mm Hg to about 4.0 mm Hg, about 2.5 mm Hg to about 4.0 mm Hg, about 3.0 mm Hg to about 3.5 mm Hg, about 4.0 mm Hg to about 5.0 mm Hg, about 4.2 mm Hg to about 4.8 mm Hg, or about 4.0 mm Hg to about 6.0 mm Hg, relative to baseline, 24 hours after the fourteenth dose.

In some embodiments, including any of the foregoing embodiments involving once-daily administration of Compound 1 to a patient who has been diagnosed with sickle cell disease, the patient's hemoglobin blood levels are increased by at least 1 g/dL, by at 1.0 to 1.5 g/dL, or by 1.0 to 1.2 g/dL.

In some embodiments, including any of the foregoing embodiments involving once-daily administration of Compound 1 to a patient who has not been diagnosed with sickle cell disease, the patient's ATP blood levels are increased by about 0% to about 20%, about 0% to about 15%, about 5% to about 10%, about 0% to about 10%, or about 10% to about 20%, relative to baseline, 24 hours after the first administration.

In some embodiments, including any of the foregoing embodiments involving once-daily administration of Compound 1 to a patient who has not been diagnosed with sickle cell disease, the patient's ATP blood levels are increased by about 45% to about 75%, about 50% to about 65%, about 55% to about 60%, about 45% to about 60%, or about 60% to about 75%, relative to baseline, 24 hours after the fourteenth administration.

In some embodiments, including any of the foregoing embodiments involving once-daily administration of Compound 1 to a patient who has not been diagnosed with sickle cell disease, the patient's 2,3-DPG blood levels are reduced by about 20% to about 60%, about 25% to about 53%, about 30% to about 50%, about 35% to about 45%, about 20% to about 40%, or about 40% to about 60%, relative to baseline, 24 hours after the first administration.

In some embodiments, including any of the foregoing embodiments involving once-daily administration of Compound 1 to a patient who has not been diagnosed with sickle cell disease, the patient's 2,3-DPG blood levels are reduced by about 30% to about 70%, about 38% to about 60%, about 45% to about 55%, about 30% to about 50%, or about 50% to about 70%, relative to baseline, 24 hours after the fourteenth administration.

In some embodiments, including any of the foregoing embodiments involving once-daily administration of Compound 1 to a patient who has not been diagnosed with sickle cell disease, the patient's p50 value decreases by about 5% to about 25%, about 10% to about 20%, about 13% to about 17%, about 5% to about 15%, or about 15% to about 25%, relative to baseline, 24 hours after the fourteenth administration.

In some embodiments, including any of the foregoing embodiments involving once-daily administration of Compound 1 to a patient who has not been diagnosed with sickle cell disease, the patient's p50 value is between about 17.5 mm Hg and about 27.5 mm Hg, about 20 mm Hg and about 25 mm Hg, about 21 mm Hg and about 24 mm Hg, about 17.5 mm Hg and about 22.5 mm Hg, or about 22.5 mm Hg and about 27.5 mm Hg, 24 hours after the first dose.

In some embodiments, including any of the foregoing embodiments involving once-daily administration of Compound 1 to a patient who has not been diagnosed with sickle cell disease, the patient's p50 value is between about 17.5 mm Hg and about 27.5 mm Hg, about 20 mm Hg and about 25 mm Hg, about 21 mm Hg and about 24 mm Hg, about 17.5 mm Hg and about 22.5 mm Hg, or about 22.5 mm Hg and about 27.5 mm Hg, 24 hours after the fourteenth dose.

In some embodiments, including any of the foregoing embodiments involving once-daily administration of Compound 1 to a patient who has not been diagnosed with sickle cell disease, the patient's p50 value decreases by about 2.0 mm Hg to about 5.0 mm Hg, about 2.5 mm Hg to about 4.0 mm Hg, about 3.0 mm Hg to about 3.5 mm Hg, about 2.0 mm Hg to about 3.5 mm Hg, or about 3.5 mm Hg to about 5.0 mm Hg, relative to baseline, 24 hours after the first dose.

In some embodiments, including any of the foregoing embodiments involving once-daily administration of Compound 1 to a patient who has not been diagnosed with sickle cell disease, the patient's p50 value decreases by about 2.0 mm Hg to about 6.0 mm Hg, about 2.5 mm Hg to about 5.0 mm Hg, about 3.0 mm Hg to about 4.5 mm Hg, about 2.0 mm Hg to about 4.0 mm Hg, or about 4.0 mm Hg to about 6.0 mm Hg, relative to baseline, 24 hours after the fourteenth dose.

In some embodiments, including any of the foregoing embodiments involving once-daily administration of Compound 1 to a patient who has not been diagnosed with sickle cell disease, the patient's hemoglobin blood levels are increased by at least 1 g/dL, by at 1.0 to 1.5 g/dL, or by 1.0 to 1.2 g/dL.

Other Dosing Regimens

In some embodiments, Compound 1 may be administered in other doses. For example, Compound 1 may be administered in a dose of 200 mg, which may be a single (one-time) dose or the first dose in a repeated administration regimen (e.g., QD, BID, etc.). Thus, in some embodiments, this disclosure relates to:

1. A method of treating sickle cell disease in a patient, the method comprising administering about 200 mg of Compound 1 to the patient.
2. A method of increasing hemoglobin oxygen affinity in a patient in need thereof, the method comprising administering about 200 mg of Compound 1 to the patient.
3. A method of increasing ATP blood levels in a patient in need thereof, the method comprising administering about 200 mg of Compound 1 to the patient.
4. A method of decreasing 2,3-DPG blood levels in a patient in need thereof, the method comprising administering about 200 mg of Compound 1 to the patient.
5. A method comprising administering about 200 mg of Compound 1 to a patient in need thereof.
6. The method of any one of embodiments 2-5, wherein the patient is diagnosed with a hemoglobinopathy.
7. The method of embodiment 6, wherein the hemoglobinopathy is sickle cell disease.
8. The method of embodiment 1 or 7, wherein the patient's ATP blood levels are increased by about 10% to about 20%, relative to baseline, 24 hours after administration.
9. The method of any one of embodiments 1 and 7-8, wherein the patient's 2,3-DPG blood levels are reduced by about 15% to about 30%, relative to baseline, 24 hours after administration.
10. The method of any one of embodiments 1 and 7-9, wherein the patient's p50 value decreases by about 2.5 mm Hg to about 4.5 mm Hg, relative to baseline, 24 hours after administration.
11. The method of any one of embodiments 2-6, wherein the patient has not been diagnosed with sickle cell disease.
12. The method of embodiment 11, wherein the patient's ATP blood levels are increased by about 0% to about 5%, relative to baseline, 24 hours after administration.

13. The method of embodiment 11 or 12, wherein the patient's 2,3-DPG blood levels are reduced by about 25% to about 35%, relative to baseline, 24 hours after administration.
14. The method of any one of embodiments 11-13, wherein the patient's p50 value decreases by about 2.5 mm Hg to about 3.5 mm Hg, relative to baseline, 24 hours after administration.
15. The method of any one of embodiments 1-14, wherein the Compound 1 is amorphous.
16. The method of embodiment 15, wherein the Compound 1 is administered in a pharmaceutical composition comprising a solid dispersion, the solid dispersion comprising the Compound 1 and a denucleating agent.
17. The method of embodiment 16, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
18. The method of embodiment 17, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
19. The method of any one of embodiments 16-18, wherein the solid dispersion is a spray dried dispersion.
20. The method of any one of embodiments 16-19, wherein the pharmaceutical composition is an oral dosage form.
21. The method of embodiment 20, wherein the pharmaceutical composition is a tablet.
22. The method of embodiment 20, wherein the pharmaceutical composition is a capsule.
23. The method of any one of embodiments 1-22, wherein Compound 1 $C_{max}$ is at least about 300 ng/mL.
24. The method of embodiment 23, wherein Compound 1 $C_{max}$ is about 300 ng/mL to about 500 ng/mL.
25. The method of any one of embodiments 1-24, wherein Compound 1 $T_{max}$ is about 0.5-4 hours after administration.
26. The method of any one of embodiments 1-25, wherein aromatase is not inhibited in the patient.
27. The method of any one of embodiments 1-26, wherein the patient is less than 18 years old.
28. The method of any one of embodiments 1-27, wherein the method comprises increasing hemoglobin blood levels in the patient.
29. The method of any one of embodiments 1-28, wherein the method comprises reducing the point of sickling in the patient.
30. The method of any one of embodiments 1-29, wherein the method comprises decreasing the percent reticulocytes in the patient.

In other embodiments, Compound 1 may be administered in a dose of 400 mg, which may be a single (one-time) dose or the first dose in a repeated administration regimen (e.g., QD, BID, etc.). Thus, in some embodiments, this disclosure relates to:

1. A method of treating sickle cell disease in a patient, the method comprising administering about 400 mg of Compound 1 to the patient.
2. A method of increasing hemoglobin oxygen affinity in a patient in need thereof, the method comprising administering about 400 mg of Compound 1 to the patient.
3. A method of increasing ATP blood levels in a patient in need thereof, the method comprising administering about 400 mg of Compound 1 to the patient.
4. A method of decreasing 2,3-DPG blood levels in a patient in need thereof, the method comprising administering about 400 mg of Compound 1 to the patient.
5. A method comprising administering about 400 mg of Compound 1 to a patient in need thereof.
6. The method of any one of embodiments 2-5, wherein the patient is diagnosed with a hemoglobinopathy.
7. The method of embodiment 6, wherein the hemoglobinopathy is sickle cell disease.
8. The method of embodiment 1 or 7, wherein the patient's ATP blood levels are increased by about 14% to about 30%, relative to baseline, 24 hours after administration.
9. The method of any one of embodiments 1 and 7-8, wherein the patient's 2,3-DPG blood levels are reduced by about 23% to about 31%, relative to baseline, 24 hours after administration.
10. The method of any one of embodiments 1 and 7-9, wherein the patient's p50 value decreases by about 2.5 mm Hg to about 4.5 mm Hg, relative to baseline, 24 hours after administration.
11. The method of any one of embodiments 2-6, wherein the patient has not been diagnosed with sickle cell disease.
12. The method of embodiment 11, wherein the patient's ATP blood levels are increased by about 10% to about 20%, relative to baseline, 24 hours after administration.
13. The method of embodiment 11 or 12, wherein the patient's 2,3-DPG blood levels are reduced by about 35% to about 45%, relative to baseline, 24 hours after administration.
14. The method of any one of embodiments 11-13, wherein the patient's p50 value decreases by about 3.0 mm Hg to about 4.0 mm Hg, relative to baseline, 24 hours after administration.
15. The method of any one of embodiments 1-14, wherein the Compound 1 is administered in a pharmaceutical composition comprising a solid dispersion, the solid dispersion comprising the Compound 1 and a denucleating agent.
16. The method of embodiment 15, wherein the Compound 1 is amorphous.
17. The method of embodiment 16, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.

18. The method of embodiment 17, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
19. The method of any one of embodiments 16-18, wherein the solid dispersion is a spray dried dispersion.
20. The method of any one of embodiments 16-19, wherein the pharmaceutical composition is an oral dosage form.
21. The method of embodiment 20, wherein the pharmaceutical composition is a tablet.
22. The method of embodiment 20, wherein the pharmaceutical composition is a capsule.
23. The method of any one of embodiments 1-22, wherein Compound 1 $C_{max}$ is at least about 500 ng/mL.
24. The method of embodiment 23, wherein Compound 1 $C_{max}$ is about 500 ng/mL to about 1000 ng/mL.
25. The method of any one of embodiments 1-24, wherein Compound 1 $T_{max}$ is about 0.5-4 hours after administration.
26. The method of any one of embodiments 1-25, wherein aromatase is not inhibited in the patient.
27. The method of any one of embodiments 1-26, wherein the patient is less than 18 years old.
28. The method of any one of embodiments 1-27, wherein the method comprises increasing hemoglobin blood levels in the patient.
29. The method of any one of embodiments 1-28, wherein the method comprises reducing the point of sickling in the patient.
30. The method of any one of embodiments 1-29, wherein the method comprises decreasing the percent reticulocytes in the patient.

In other embodiments, Compound 1 may be administered in a dose of 700 mg, which may be a single (one-time) dose or the first dose in a repeated administration regimen (e.g., QD, BID, etc.). Thus, in some embodiments, this disclosure relates to:

1. A method of treating sickle cell disease in a patient, the method comprising administering about 700 mg of Compound 1 to the patient.
2. A method of increasing hemoglobin oxygen affinity in a patient in need thereof, the method comprising administering about 700 mg of Compound 1 to the patient.
3. A method of increasing ATP blood levels in a patient in need thereof, the method comprising administering about 700 mg of Compound 1 to the patient.
4. A method of decreasing 2,3-DPG blood levels in a patient in need thereof, the method comprising administering about 700 mg of Compound 1 to the patient.
5. A method comprising administering about 700 mg of Compound 1 to a patient in need thereof.
6. The method of any one of embodiments 2-5, wherein the patient is diagnosed with a hemoglobinopathy.
7. The method of embodiment 6, wherein the hemoglobinopathy is sickle cell disease.
8. The method of embodiment 1 or 7, wherein the patient's ATP blood levels are increased by about 25% to about 35%, relative to baseline, 24 hours after administration.
9. The method of any one of embodiments 1 and 7-8, wherein the patient's 2,3-DPG blood levels are reduced by about 26% to about 36%, relative to baseline, 24 hours after administration.
10. The method of any one of embodiments 1 and 7-9, wherein the patient's p50 value decreases by about 3 mm Hg to about 5 mm Hg, relative to baseline, 24 hours after administration.
11. The method of any one of embodiments 2-6, wherein the patient has not been diagnosed with sickle cell disease.
12. The method of embodiment 11, wherein the patient's ATP blood levels are increased by about 10% to about 20%, relative to baseline, 24 hours after administration.
13. The method of embodiment 11 or 12, wherein the patient's 2,3-DPG blood levels are reduced by about 40% to about 55%, relative to baseline, 24 hours after administration.
14. The method of any one of embodiments 11-13, wherein the patient's p50 value decreases by about 4.5 mm Hg to about 5.5 mm Hg, relative to baseline, 24 hours after administration.
15. The method of any one of embodiments 1-14, wherein the Compound 1 is amorphous.
16. The method of embodiment 15, wherein the Compound 1 is administered in a pharmaceutical composition comprising a solid dispersion, the solid dispersion comprising the Compound 1 and a denucleating agent.
17. The method of embodiment 16, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
18. The method of embodiment 17, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
19. The method of any one of embodiments 16-18, wherein the solid dispersion is a spray dried dispersion.
20. The method of any one of embodiments 16-19, wherein the pharmaceutical composition is an oral dosage form.
21. The method of embodiment 20, wherein the pharmaceutical composition is a tablet.
22. The method of embodiment 20, wherein the pharmaceutical composition is a capsule.
23. The method of any one of embodiments 1-22, wherein Compound 1 $C_{max}$ is at least about 2000 ng/mL.
24. The method of embodiment 23, wherein Compound 1 $C_{max}$ is about 2000 ng/mL to about 3000 ng/mL.
25. The method of any one of embodiments 1-24, wherein Compound 1 Tmax is about 0.5-4 hours after administration.
26. The method of any one of embodiments 1-25, wherein aromatase is not inhibited in the patient.

27. The method of any one of embodiments 1-26, wherein the patient is less than 18 years old.
28. The method of any one of embodiments 1-27, wherein the method comprises increasing hemoglobin blood levels in the patient.
29. The method of any one of embodiments 1-28, wherein the method comprises reducing the point of sickling in the patient.
30. The method of any one of embodiments 1-29, wherein the method comprises decreasing the percent reticulocytes in the patient.

In other embodiments, Compound 1 may be administered in a dose of 1000 mg, which may be a single (one-time) dose or the first dose in a repeated administration regimen (e.g., QD, BID, etc.). Thus, in some embodiments, this disclosure relates to:

1. A method of treating sickle cell disease in a patient, the method comprising administering about 1000 mg of Compound 1 to the patient.
2. A method of increasing hemoglobin oxygen affinity in a patient in need thereof, the method comprising administering about 1000 mg of Compound 1 to the patient.
3. A method of increasing ATP blood levels in a patient in need thereof, the method comprising administering about 1000 mg of Compound 1 to the patient.
4. A method of decreasing 2,3-DPG blood levels in a patient in need thereof, the method comprising administering about 1000 mg of Compound 1 to the patient.
5. A method comprising administering about 1000 mg of Compound 1 to a patient in need thereof.
6. The method of any one of embodiments 2-5, wherein the patient is diagnosed with a hemoglobinopathy.
7. The method of embodiment 6, wherein the hemoglobinopathy is sickle cell disease.
8. The method of embodiment 1 or 7, wherein the patient's ATP blood levels are increased by about 25% to about 35%, relative to baseline, 24 hours after administration.
9. The method of any one of embodiments 1 and 7-8, wherein the patient's 2,3-DPG blood levels are reduced by about 26% to about 36%, relative to baseline, 24 hours after administration.
10. The method of any one of embodiments 1 and 7-9, wherein the patient's p50 value decreases by about 3 mm Hg to about 5 mm Hg, relative to baseline, 24 hours after administration.
11. The method of any one of embodiments 2-6, wherein the patient has not been diagnosed with sickle cell disease.
12. The method of embodiment 11, wherein the patient's ATP blood levels are increased by about 10% to about 20%, relative to baseline, 24 hours after administration.
13. The method of embodiment 11 or 12, wherein the patient's 2,3-DPG blood levels are reduced by about 40% to about 55%, relative to baseline, 24 hours after administration.
14. The method of any one of embodiments 11-13, wherein the patient's p50 value decreases by about 4.5 mm Hg to about 5.5 mm Hg, relative to baseline, 24 hours after administration.
15. The method of any one of embodiments 1-14, wherein the Compound 1 is amorphous.
16. The method of embodiment 15, wherein the Compound 1 is administered in a pharmaceutical composition comprising a solid dispersion, the solid dispersion comprising the Compound 1 and a denucleating agent.
17. The method of embodiment 16, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly(methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
18. The method of embodiment 17, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
19. The method of any one of embodiments 16-18, wherein the solid dispersion is a spray dried dispersion.
20. The method of any one of embodiments 16-19, wherein the pharmaceutical composition is an oral dosage form.
21. The method of embodiment 20, wherein the pharmaceutical composition is a tablet.
22. The method of embodiment 20, wherein the pharmaceutical composition is a capsule.
23. The method of any one of embodiments 1-22, wherein Compound 1 $C_{max}$ is at least about 2000 ng/mL.
24. The method of embodiment 23, wherein Compound 1 $C_{max}$ is about 2000 ng/mL to about 3000 ng/mL.
25. The method of any one of embodiments 1-24, wherein Compound 1 $T_{max}$ is about 0.5-4 hours after administration.
26. The method of any one of embodiments 1-25, wherein aromatase is not inhibited in the patient.
27. The method of any one of embodiments 1-26, wherein the patient is less than 18 years old.
28. The method of any one of embodiments 1-27, wherein the method comprises increasing hemoglobin blood levels in the patient.
29. The method of any one of embodiments 1-28, wherein the method comprises reducing the point of sickling in the patient.
30. The method of any one of embodiments 1-29, wherein the method comprises decreasing the percent reticulocytes in the patient.

In other embodiments, the disclosure relates to a method of inducing a durable increase in hemoglobin oxygen affinity, a durable increase in ATP blood levels, and/or a durable decrease in 2,3-DPG blood levels in a patient diagnosed with sickle cell disease by administering a therapeutically effective amount of amorphous Compound 1 to the patient. A used herein, such an increase/decrease is understood to be "durable" if the effect lasts at least 24 hours after administration of amorphous Compound 1, 24-144 hours after administration of amorphous Compound 1, 24-72 hours after administration of amorphous Compound 1, at least 20 hours after Compound 1 $T_{max}$, 20-140 hours after Compound 1 $T_{max}$, 20-68 hours after Compound 1 $T_{max}$, at least 24 hours after Compound 1 plasma levels reach zero, 24-144 hours after Compound 1 plasma levels reach zero, and/or 24-48 hours after Compound 1 plasma levels reach zero. Thus, in some embodiments, the disclosure relates to:

1. A method of inducing a durable increase in hemoglobin oxygen affinity in a patient diagnosed with sickle cell disease, the method comprising administering a therapeutically effective amount of Compound 1 to the patient.
2. A method of inducing a durable increase in ATP blood levels in a patient diagnosed with sickle cell disease, the method comprising administering a therapeutically effective amount of Compound 1 to the patient.
3. A method of inducing a durable decrease in 2,3-DPG blood levels in a patient diagnosed with sickle cell disease, the method comprising administering a therapeutically effective amount of Compound 1 to the patient.
4. The method of any one of embodiments 1-3, wherein the Compound 1 is amorphous.
5. The method of embodiment 4, wherein the Compound 1 is administered in a pharmaceutical composition comprising a solid dispersion, the solid dispersion comprising the Compound 1 and a denucleating agent.
6. The method of embodiment 5, wherein the denucleating agent is selected from the group consisting of polyvinylpyrrolidone (PVP), hydroxypropylmethyl cellulose (HPMC), hydroxypropylcellulose (HPC), hydroxypropylmethyl cellulose acetate succinate (HPMC AS), hydroxyethylcellulose (HEC), poly (methacrylic acid-co-methyl methacrylates) (e.g., Eudragit® L100-55), macrogol 15 hydroxystearate (e.g., Solutol® HS15), polyvinyl caprolactam-polyvinyl acetate-polyethylene glycol graft copolymer (e.g., Soluplus®), polyethylene glycol (PEG), and a combination thereof.
7. The method of embodiment 6, wherein the denucleating agent is selected from the group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof.
8. The method of any one of embodiments 5-7, wherein the solid dispersion is a spray dried dispersion. 9. The method of any one of embodiments 5-8, wherein the pharmaceutical composition is an oral dosage form.
10. The method of embodiment 9, wherein the pharmaceutical composition is a tablet.
11. The method of embodiment 9, wherein the pharmaceutical composition is a capsule.
12. The method of any one of embodiments 1-11, wherein Compound 1 $T_{max}$ is about 0.5-4 hours after the first administration.
13. The method of any one of embodiments 1-12, wherein aromatase is not inhibited in the patient.
14. The method of any one of embodiments 1-13, wherein the patient is less than 18 years old.
15. The method of any one of embodiments 1-14, wherein the therapeutically effective amount of amorphous Compound 1 is selected from the group consisting of 200 mg, 300 mg, 400 mg, 600 mg, 700 mg, and 1000 mg, which may be a single (one-time) dose or the first dose in a repeated administration regimen (e.g., QD, BID, etc.).
16. The method of any one of embodiments 1-15, wherein the patient's ATP blood levels are increased by any of the amounts disclosed herein, relative to baseline, 24 hours after administration.
17. The method of any one of embodiments 1-16, wherein the patient's 2,3-DPG blood levels are reduced by any of the amounts disclosed herein, relative to baseline, 24 hours after administration.
18. The method of any one of embodiments 1-17, wherein the patient's p50 value decreases by any of the amounts disclosed herein, relative to baseline, 24 hours after administration.

In some embodiments, including any of the foregoing embodiments involving administration of a 200 mg, 300 mg, 400 mg, 600 mg, 700 mg, or 1000 mg dose of Compound 1 to a patient who has been diagnosed with sickle cell disease, the patient's ATP blood levels are increased by about 5% to about 45%, about 10% to about 35%, about 15% to about 30%, about 20% to about 25%, about 5% to about 25%, about 10% to about 25%, about 25% to about 35%, or about 25% to about 45%, relative to baseline, 24 hours after administration.

In some embodiments, including any of the foregoing embodiments involving administration of a 200 mg, 300 mg, 400 mg, 600 mg, 700 mg, or 1000 mg dose of Compound 1 to a patient who has been diagnosed with sickle cell disease, the patient's 2,3-DPG blood levels are reduced by about 10% to about 40%, about 15% to about 36%, about 20% to about 30%, about 22% to about 28%, about 10% to about 25%, about 15% to about 25%, about 25% to about 35%, or about 25% to about 40%, relative to baseline, 24 hours after administration.

In some embodiments, including any of the foregoing embodiments involving administration of a 200 mg, 300 mg, 400 mg, 600 mg, 700 mg, or 1000 mg dose of Compound 1 to a patient who has been diagnosed with sickle cell disease, the patient's p50 value decreases by about 2.0 mm Hg to about 6.0 mm Hg, about 2.5 mm Hg to about 5.0 mm Hg, about 3.0 mm Hg to about 4.5 mm Hg, about 3.5 mm Hg to about 4.0 mm Hg, about 2.0 mm Hg to about 4.0 mm Hg, about 2.5 mm Hg to about 4.0 mm Hg, about 4.0 mm Hg to about 5.0 mm Hg, or about 4.0 mm Hg to about 6.0 mm Hg, relative to baseline, 24 hours after administration.

In some embodiments, including any of the foregoing embodiments involving administration of a 200 mg, 300 mg, 400 mg, 600 mg, 700 mg, or 1000 mg dose of Compound 1 to a patient who has been diagnosed with sickle cell disease, the patient's hemoglobin blood levels are increased by at least 1 g/dL, by at 1.0 to 1.5 g/dL, or by 1.0 to 1.2 g/dL.

In some embodiments, including any of the foregoing embodiments involving administration of a 200 mg, 300 mg, 400 mg, 600 mg, 700 mg, or 1000 mg dose of Compound 1 to a patient who has not been diagnosed with sickle cell disease, the patient's ATP blood levels are increased by about 0% to about 30%, about 0% to about 20%, about 5% to about 15%, about 0% to about 15%, or about 15% to about 30%, relative to baseline, 24 hours after administration.

In some embodiments, including any of the foregoing embodiments involving administration of a 200 mg, 300 mg, 400 mg, 600 mg, 700 mg, or 1000 mg dose of Compound 1 to a patient who has not been diagnosed with sickle cell disease, the patient's 2,3-DPG blood levels are reduced by about 20% to about 60%, about 25% to about 55%, about 30% to about 50%, about 35% to about 45%, about 20% to about 40%, about 25% to about 60%, about 40% to about 55%, or about 40% to about 60%, relative to baseline, 24 hours after administration.

In some embodiments, including any of the foregoing embodiments involving administration of a 200 mg, 300 mg, 400 mg, 600 mg, 700 mg, or 1000 mg dose of Compound 1 to a patient who has not been diagnosed with sickle cell disease, the patient's p50 value decreases by about 2.0 mm Hg to about 6.0 mm Hg, about 2.5 mm Hg to about 5.5 mm Hg, about 3.0 mm Hg to about 5.0 mm Hg, about 3.5 mm Hg to about 4.5 mm Hg, about 2.0 mm Hg to about 4.0 mm Hg, about 2.5 mm Hg to about 4.0 mm Hg, about 4.0 mm Hg to about 5.5 mm Hg, or about 4.0 mm Hg to about 6.0 mm Hg, relative to baseline, 24 hours after administration.

In some embodiments, including any of the foregoing embodiments involving administration of a 200 mg, 300 mg, 400 mg, 600 mg, 700 mg, or 1000 mg dose of Compound 1 to a patient who has not been diagnosed with sickle cell disease, the patient's hemoglobin blood levels are increased by at least 1 g/dL, by at 1.0 to 1.5 g/dL, or by 1.0 to 1.2 g/dL.

Avoidance of Drug-Drug Interactions (DDIs)

Underlying the observed constant exposure over time is the lack of CYP inhibition or induction demonstrated by Compound 1 in vitro, thereby reducing risk of inhibiting or inducing its own metabolism as well as reducing the risk for drug-drug interactions due to CYP's effects on pharmacokinetics of other drugs through changes in plasma concentration. SCD patients typically take numerous concurrent medications to address their disease. The body will naturally break down many of these medications through CYP. When the expression of these enzymes is inhibited or induced by another medication, it can impact the efficacy of concurrent medications. Limiting the potential for drug-drug interactions is imperative to effectively treat this patient population. Compound 1 has been observed preclinically to have no significant impact on CYP enzyme inhibition or induction. Some compounds according to the present invention, including the physiologically acceptable salts, exhibit favourable, that is low Cytochrome P450 (CYP) induction potential. CYP induction can affect the pharmacokinetics of a drug molecule upon multiple dosing, which can result in pharmacokinetic drug-drug interactions with coadministered drugs (e.g., by increasing the metabolic clearance of co-administered CYP3A4 substrates), or can cause loss of drug exposure due to autoinduction. CYP induction can lead to decreased exposure of the inducing drug (e.g. autoinduction) or decreased exposure of a coadministered drug metabolized by the induced enzyme. CYP induction can also lead to an increase in the metabolism of a drug causing changes in pharmacological (active metabolite) and toxicological (toxic metabolite) outcomes. Characterizing the induction potential of discovery or development drug candidates has become an important screen throughout the pharmaceutical industry. A PXR transactivation assay is used to assess the induction potential of CYP3A4. Reduced inhibition of CYP isozymes may translate into a reduced risk for undesirable drug-drug interactions which is the interference of one drug with the normal metabolic or pharmacokinetic behavior of a co-administered drug. Thus, in some embodiments, Compound 1 is administered to a patient that is concurrently being treated with a CYP substrate, e.g., a sensitive CYP substrate.

Methods of Preparing Compound 1 and Pharmaceutical Compositions

PKR Activating Compounds, such as 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a pharmaceutically acceptable salt thereof, are useful in pharmaceutical compositions for the treatment of patients. PKR Activating Compounds, such as Compound 1, or a pharmaceutically acceptable salt thereof, are useful in pharmaceutical compositions for the treatment of patients. The compositions comprising Compound 1, or a pharmaceutically acceptable salt thereof, can be obtained by certain processes also provided herein. The compositions comprising Compound 1, or a pharmaceutically acceptable salt thereof, can be obtained by certain processes also provided herein, such as the process provided in Example 1.

Pharmaceutical compositions can comprise Compound 1 and a pharmaceutically acceptable carrier. In some embodiments, a pharmaceutical composition comprises Compound 1 and Compound 2. In some embodiments, a provided pharmaceutical composition contains Compound 1 and Compound 2:

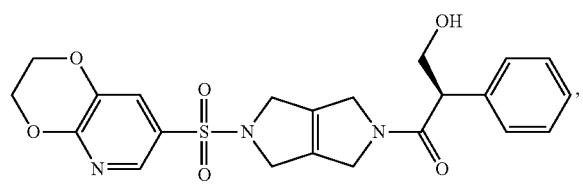

or a pharmaceutically acceptable salt thereof.

Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

In some embodiments, pharmaceutical compositions reported herein can be provided in a unit dosage form (e.g., capsule, tablet or the like).

Pharmaceutical compositions comprising a PKR Activating Composition containing a compound of Formula (I) can be formulated for oral administration (e.g., as a capsule or tablet). For example, Compound 1 can be combined with suitable compendial excipients to form an oral unit dosage form, such as a capsule or tablet, containing a target dose of Compound 1. The drug product can be prepared by first manufacturing Compound 1 as an active pharmaceutical ingredient (API), followed by spray drying with suitable polymer to obtain spray dried intermediate (SDD). SDD is then further processed by roller compaction/milling with intragranular excipients and blending with extra granular excipients. A Drug Product can contain the Compound 1 API and excipient components in Table 1A or 1B in a tablet in a desired dosage strength of Compound 1 (e.g., a 25 mg or 100 mg tablet formed from a Pharmaceutical Composition in Table 1A or a 100 or 200 mg tablet formed from a pharmaceutical composition in Table 1B). The blended material can be compressed to form tablets and then film coated.

In some embodiments, the API is an amorphous solid dispersion comprising Compound 1 and a polymer. In some embodiments, the polymer is selected from a group consisting of hydroxypropylmethyl cellulose (HPMC), hydroxypropylmethyl cellulose acetate succinate (HPMC AS), hydroxypropyl methyl cellulose phthalate (HPMCP), hydroxypropyl cellulose (HPC), ethylcellulose, cellulose acetate phthalate, polyvinylpyrrolidone (PVP), and a combination thereof. In some embodiments, the polymer is hydroxypropylmethyl cellulose (HPMC) or hydroxypropylmethyl cellulose acetate succinate (HPMC AS). In some embodiments, the weight ratio of Compound 1 to the polymer in the amorphous solid dispersion is about 1:3. In other embodiments, the weight ratio of Compound 1 to the polymer in the amorphous solid dispersion is about 1:1.

In some embodiments, a Compound 1 pharmaceutical composition is a tablet comprising 100 mg of Compound 1 in a tablet weighing no more than about 800 mg. Table 1A provides an example of a tablet comprising a SDD obtained by the method of Example 1, Step 6, and other components. In some examples, a tablet can weigh less than about 800 mg. In some examples, a tablet contains an amorphous Compound 1 API material in an amount providing about 10-40% by weight in the tablet of Compound 1 in addition to other ingredients such as a filler, dry binder, glidant and lubricant. In one example, a tablet contains 100 mg of Compound 1 in a tablet weight that is less than about 800 mg.

In other embodiments, a Compound 1 pharmaceutical composition is a tablet comprising 200 mg of Compound 1 in a tablet weighing no more than about 800 mg. Table 1B provides an example of a tablet comprising a SDD obtained by the method of Example 1, Step 8, and other components.

TABLE 1A

Exemplary Pharmaceutical Compositions of Compound 1 for Oral Administration

| | % Formulation (weight) | Exemplary Component |
|---|---|---|
| Intra-Granular | 50% | 1:3 SDD of Compound 1: HPMC AS-MG |
| | 30% | Microcrystalline cellulose (Avicel PH 102) |
| | 5% | Crospovidone (Kollidon CL-F) |
| | <5% | Colloidal silicon dioxide (Aerosil 200) |
| | <1% | Magnesium Stearate (Hyqual) |
| Extra-Granular | 11% | Microcrystalline cellulose (Avicel PH 200) |
| | <5% | Croscarmellose sodium (Ac-Di-Sol) |
| | <1% | Magnesium Stearate (Hyqual) |

TABLE 1B

Exemplary Pharmaceutical Compositions of Compound 1 for Oral Administration

| % Formulation (weight) | Exemplary Component |
|---|---|
| 50-75% | 1:3 SDD of Compound 1: HPMC AS-MG |
| 15-30% | Microcrystalline Cellulose |
| 0-20% | Lactose Monohydrate |
| 2-10% | Crosslinked polyvinylpyrrolidone |
| <2% | Colloidal Silicon Dioxide |
| 2-10% | Croscarmellose Sodium |
| <2% | Magnesium Stearate |

In some embodiments, a provided composition containing a compound of Formula I comprises a mixture of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one and (R)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one. In some embodiments, a provided composition containing a compound of Formula I is a mixture of Compound 1 and Compound 2 as part of a PKR Activating Composition. In some embodiments, a compound of Formula I is racemic. In some embodiments, a compound of Formula I consists of about 50% of Compound 1 and about 50% of Compound 2. In some embodiments, a compound of Formula I is not racemic. In some embodiments, a compound of Formula I does not consist of about 50% of Compound 1 and about 50% of Compound 2. In some embodiments, a compound of Formula I comprises about 99-95%, about 95-90%, about 90-80%, about 80-70%, or about 70-60% of Compound 1. In some embodiments, a compound of Formula I comprises about 99%, 98%, 95%, 90%, 80%, 70%, or 60% of Compound 1.

In some embodiments, a PKR Activating Composition comprises a mixture of Compound 1 and Compound 2. In some embodiments, a PKR Activating Composition comprises a mixture of Compound 1 and Compound 2, wherein the PKR Activating Composition comprises a therapeutically effective amount of Compound 1.

Compounds of Formula I, including Compound 1, can be obtained from a series of four reaction steps from commercially available starting materials, as outlined in Example 1. Commercially available 7-bromo-2H,3H-[1,4]dioxino[2,3-b]pyridine was treated with a mixture of n-butyl lithium and dibutylmagnesium followed by sulfuryl chloride to give sulfonyl chloride 3. Treatment of 3 with tert-butyl 1H,2H,3H,4H,5H,6H-pyrrolo[3,4-c]pyrrole-2-carboxylate in the presence of triethylamine (TEA) afforded Boc-protected monosulfonamide 4. Compound 4 was then de-protected in the presence of trifluoroacetic acid (TFA) to give 5, the free base of the monosulfonamide. The last step to generate Compound 1 (Example 1, Step 5) or Compound 1 and Compound 2 (Example 1, Step 4) was an amide coupling of 5 and tropic acid in the presence of 1-[bis(dimethylamino)methylene]-1H-1,2,3-triazolo [4,5-b]pyridinium 3-oxide hexafluorophosphate (HATU).

In some embodiments, pharmaceutical compositions reported herein can be provided in an oral dosage form. In some embodiments, the pharmaceutical composition is orally administered in any orally acceptable dosage form. In some embodiments, an oral dosage form of a PKR Activating Compound be a capsule. In some embodiments, an oral dosage form of a PKR Activating Compound is a tablet. In some embodiments, an oral dosage form comprises one or more fillers, disintegrants, lubricants, glidants, anti-adherents and/or anti-statics. In some embodiments, an oral dosage form is prepared via dry blending. In some embodiments, an oral dosage form is a tablet and is prepared via dry granulation.

ADDITIONAL EMBODIMENTS

Methods of treatment (e.g., by activating PKR) can comprise administering to a subject in need thereof a therapeutically effective amount of (i) a compound disclosed herein, or a pharmaceutically acceptable salt thereof or (ii) a pharmaceutical composition comprising a compound disclosed herein, or a pharmaceutically acceptable salt thereof, and a pharmaceutically acceptable carrier. The PKR Activating Compound can be administered orally, for the treatment of diseases or conditions that therapeutically benefit from the administration of a compound that activates PKR, including hemoglobinopathies such as SCD or beta-thalassemia. In some embodiments, Compound 1 can be administered orally, for the treatment of diseases or conditions that therapeutically benefit from the administration of a compound that activates PKR, such as SCD or beta-thalassemia. Compound 1 is a potent activator of PKR and may improve RBC metabolism, function and survival. Compound 1 may also be useful for improving both hemoglobin levels and decreasing the rate of VOCs.

In some embodiments, a method of treating a disease associated with modulation of PKR comprises administering a therapeutically effective amount of a compound disclosed herein. In some embodiments, a method of treating pyruvate kinase deficiency (PKD) comprises administering a therapeutically effective amount of a compound disclosed herein. In some embodiments, a method of treating PKD-associated hemolytic anemia comprises administering a therapeutically effective amount of a compound disclosed herein.

Methods of treatment can comprise administering to a subject in need thereof a therapeutically effective amount of (i) a PKR Activating Compound (e.g., a compound disclosed herein), or a pharmaceutically acceptable salt thereof; or (ii) a PKR Activating Composition (e.g., a pharmaceutical composition comprising a compound disclosed herein, or a pharmaceutically acceptable salt thereof, and a pharmaceutically acceptable carrier). The pharmaceutical composition may be orally administered in any orally acceptable dosage form.

One aspect of the disclosure relates to methods of treating a patient comprising the administration of a therapeutically effective amount of Compound 1 or a pharmaceutically acceptable salt thereof, such as a patient diagnosed with a hemoglobinopathy. In some embodiments, the patient is diagnosed with a hemoglobinopathy, such as Sickle Cell Disease or beta-thalassemia.

In some embodiments, Compound 1 can be administered orally, once-daily, for the treatment of a hemoglobinopathy, such as or beta-thalassemia or SCD. In some embodiments, Compound 1 can be administered orally, once-daily, for the treatment of SCD. In some embodiments, Compound 1 can be administered orally, once-daily, for the treatment of beta-thalassemia. Compound 1 is a potent activator of PKR and may improve RBC metabolism, function and survival. Compound 1 may also be useful for improving both hemoglobin levels and decreasing the rate of VOCs. Methods of treating a patient diagnosed with SCD can include administering to the patient in need thereof a therapeutic compound targeting reduction of deoxy-HgbS, which may or may not directly improve RBC membrane integrity. Compound 1 has been shown to decrease 2,3-DPG and increase ATP, and reduced cell sickling has been demonstrated in disease models. Accordingly, in some embodiments, the methods of treatment can address not only sickling, but also hemolysis and anemia.

In some embodiments, Compound 1 can be administered orally, once-daily, for the treatment of beta-thalassemia. Compound 1 is a potent activator of PKR and may improve RBC metabolism, function and survival. Compound 1 may also be useful for improving both hemoglobin levels. Methods of treating a patient diagnosed with beta-thalassemia can include administering to the patient in need thereof a therapeutic compound targeting reduction of deoxy-HgbS, which may or may not directly improve RBC membrane integrity. Compound 1 has been shown to decrease 2,3-DPG and increase ATP, and reduced cell sickling has been demonstrated in disease models. Accordingly, in some embodiments, the methods of treatment can address not only sickling, but also hemolysis and anemia.

Methods of treating a patient diagnosed with sickle cell disease, and PKR Activating Compounds for use in such methods, can include administering to the patient the PKR Activating Compound (e.g., a composition comprising one or more compounds of Formula I, such as Compound 1 or a mixture of Compound 1 and Compound 2) in an amount sufficient to reduce 2,3-DPG levels in the patient's red blood cells. Methods of treating a patient diagnosed with beta thalassemia, and PKR Activating Compounds for use in such methods, can include administering to the patient the PKR Activating Compound (e.g., a composition comprising one or more compounds of Formula I, such as Compound 1 or a mixture of Compound 1 and Compound 2) in an amount sufficient to reduce 2,3-DPG levels in the patient's red blood cells. In some embodiments, the amount is sufficient to reduce 2,3-DPG levels by at least 30% after 24 hours, or greater (e.g., reducing 2,3-DPG levels in the patient's red blood cells by at least 40% after 24 hours). In some embodiments, the amount is sufficient to reduce 2,3-DPG levels by 30-50% after 24 hours. In some embodiments, the amount is sufficient to reduce 2,3-DPG levels by 40-50% after 24 hours. In some embodiments, the amount is sufficient to reduce 2,3-DPG levels by at least 25% after 12 hours. In some embodiments, the amount is sufficient to reduce 2,3-DPG levels by 25-45% after 12 hours. In some embodiments, the amount is sufficient to reduce 2,3-DPG levels by at least 15% after 6 hours. In some embodiments, the amount is sufficient to reduce 2,3-DPG levels by 15-30% after 6 hours. In some embodiments, the amount is sufficient to reduce 2,3-DPG levels by at least 40% on day 14 of treatment. In some embodiments, the amount is sufficient to reduce 2,3-DPG levels by 40-60% on day 14 of treatment. In some embodiments, the amount is sufficient to reduce 2,3-DPG levels by at least 50% on day 14 of treatment. In some embodiments, the amount is sufficient to reduce 2,3-DPG levels by 50-60% on day 14 of treatment.

Methods of treating a patient diagnosed with sickle cell disease, and PKR Activating Compounds for use in such methods, can also include administering to the patient the PKR Activating Compound (e.g., a composition comprising one or more compounds of Formula I, such as Compound 1 or a mixture of Compound 1 and Compound 2) in a daily amount sufficient to increase the patient's ATP blood levels. Methods of treating a patient diagnosed with beta thalassemia, and PKR Activating Compounds for use in such methods, can also include administering to the patient the PKR Activating Compound (e.g., a composition comprising one or more compounds of Formula I, such as Compound 1 or a mixture of Compound 1 and Compound 2) in a daily amount sufficient to increase the patient's ATP blood levels. In some embodiments, the amount is sufficient to increase ATP blood levels by at least 40% on day 14 of treatment, or greater (e.g., at least 50% on day 14 of treatment). In some embodiments, the amount is sufficient to increase ATP blood levels by 40-65% on day 14 of treatment. In some embodiments, the amount is sufficient to increase ATP blood levels by at least 50% on day 14 of treatment, or greater (e.g., at least 50% on day 14 of treatment). In some embodiments, the amount is sufficient to increase ATP blood levels by 50-65% on day 14 of treatment.

A therapeutically effective amount of a Compound 1 can be administered to a patient in need thereof in a pharmaceutical composition. For example, administration of a therapeutically effective amount of a PKR Activating Compound can include administration of a total of about 25 mg-1,500 mg of Compound 1 each day, in single or divided doses. In some embodiments, Compound 1 is administered to patients diagnosed with SCD in total once daily (QD) doses of 25 mg, 50 mg, 75 mg, 100 mg, 125 mg, 150 mg, and/or higher if tolerated (e.g., 250 mg, 300 mg, 500 mg, 600 mg, 1000 mg, and/or 1500 mg). In some embodiments, a human dose of 80 to 130 mg of Compound 1 is administered once daily (QD) to a patient in need thereof (e.g., a patient diagnosed with SCD). In some embodiments, a PKR Activating Compound is administered in an amount of 400 mg per day (e.g., 400 mg QD or 200 mg BID). In some embodiments, Compound 1 or a pharmaceutically acceptable salt thereof is administered in an amount of 400 mg per day (e.g., 400 mg QD or 200 mg BID). In some embodiments, Compound 1 or a pharmaceutically acceptable salt thereof is administered in an amount of 400 mg per day (e.g., 400 mg QD or 200 mg BID). In some embodiments, a PKR Activating Compound is administered in an amount of 700 mg per day (e.g., 700 mg QD or 350 mg BID). In some embodiments, Compound 1 or a pharmaceutically acceptable salt thereof is administered in an amount of 700 mg per day (e.g., 700 mg QD or 350 mg BID). In some embodiments, Compound 1 or a pharmaceutically acceptable salt thereof is administered in an amount of 700 mg per day (e.g., 700 mg QD or 350 mg BID). In some embodiments, a PKR Activating Compound is administered in an amount of 100 mg, 200 mg, 400 mg, 600 mg, 700 mg, 1100 mg, or 1500 mg per day, in single or divided doses. In some embodiments, Compound 1 or a pharmaceutically acceptable salt thereof is administered in an amount of 100 mg, 200 mg, 400 mg, 600 mg, 700 mg, 1100 mg, or 1500 mg per day, in single or divided doses. In some embodiments, Compound 1 or a pharmaceutically acceptable salt thereof is administered in an amount of 100 mg, 200 mg, 400 mg, 600 mg, 700 mg, 1100 mg, or 1500 mg per day, in single or divided doses.). In some embodiments, Compound 1 or a pharmaceutically acceptable salt thereof is administered in an amount of 200 mg per day (QD).

In some embodiments, a daily dose of between 100 mg to 1500 mg of a PKR Activating Compound is administered to humans. In some embodiments, a daily dose of between 100 mg to 1500 mg of Compound 1 is administered to humans. In some embodiments, a daily dose of between 100 mg to 1500 mg of Compound 1 is administered to humans. In particular, a total daily dose of 100 mg-600 mg of a PKR Activating Compound can be administered to humans (including, e.g., a dose of 100 mg, 200 mg, 300 mg, 400 mg, 500 mg, or 600 mg, per day, in single or divided doses). In particular, a total daily dose of 100 mg-600 mg of Compound 1 can be administered to humans (including, e.g., a dose of 100 mg, 200 mg, 300 mg, 400 mg, 500 mg, or 600 mg, per day, in single or divided doses). In particular, a total daily dose of 100 mg-600 mg of Compound 1 can be administered to humans (including, e.g., a dose of 100 mg, 200 mg, 300 mg, 400 mg, 500 mg, or 600 mg, per day, in single or divided doses). In some embodiments, a daily dose of 400 mg (e.g., 400 mg QD or 200 mg BID) of a PKR Activating Compound is administered to humans. In some embodiments, a daily dose of 400 mg (e.g., 400 mg QD or 200 mg BID) of Compound 1, or a pharmaceutically acceptable salt thereof, is administered to humans. In some embodiments, a daily dose of 400 mg (e.g., 400 mg QD or 200 mg BID) Compound 1 is administered to humans.

In some embodiments, a total daily dose of 100 mg-600 mg of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered to the patient per day. In some embodiments, the method can comprise administering (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one to the patient in a total dose and dose interval selected from the group consisting of 100 mg BID, 200 mg BID, 300 mg BID and 400 mg QD. In some embodiments, a total of 300 mg QD of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is administered to a patient diagnosed with SCD. In some embodiments, a total of 300 mg QD of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered to a patient diagnosed with beta-thalassemia. A method of treating a patient diagnosed with Sickle Cell Disease (SCD) can comprise repeatedly administering to the patient in need thereof a total of 300 mg QD of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

In some examples, a pharmaceutical composition comprising Compound 1 can be used in a method of treating a patient diagnosed with sickle cell disease, the method comprising administering to the patient 400 mg of Compound 1 or a pharmaceutically acceptable salt thereof, once per day (QD)

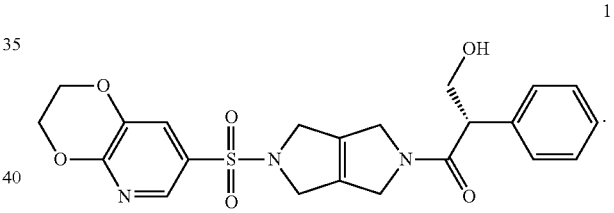

In some examples, a pharmaceutical composition comprising Compound 1 can be used in a method of treating a patient diagnosed with sickle cell disease, the method comprising administering to the patient 300 mg of Compound 1 or a pharmaceutically acceptable salt thereof once per day (QD)

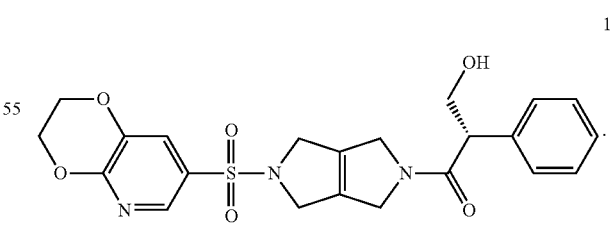

In some examples, a pharmaceutical composition comprising Compound 1 can be used in a method of treating a patient diagnosed with sickle cell disease, the method comprising administering to the patient 200 mg of Compound 1 or a pharmaceutically acceptable salt thereof, once per day (QD)

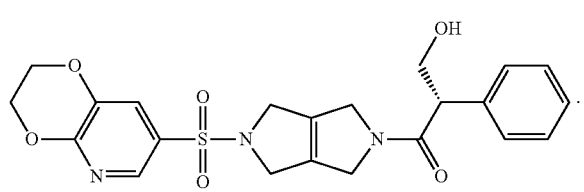

1

In some embodiments, the present disclosure provides PKR Activating Compounds of Formula I:

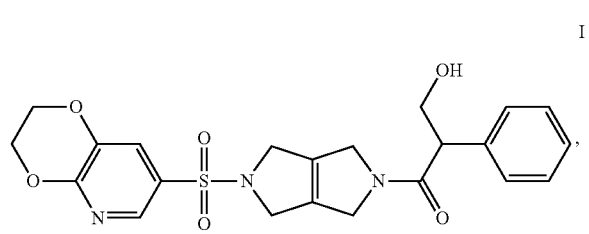 [SMILES: O=C(C(CO)c1ccccc1)N1CC2=C(C1)CN(S(=O)(=O)c1cnc3c(c1)OCCO3)C2]

I or a pharmaceutically acceptable salt thereof. In some embodiments, a PKR Activating Compound is 1-(5-((2,3-dihydro-[ 1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

The compound of Formula I is preferably Compound 1:

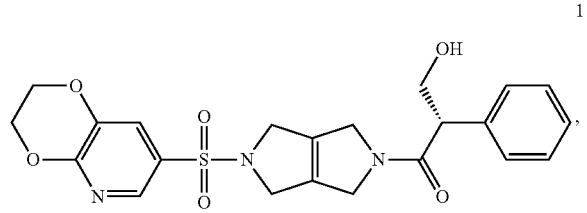 [SMILES: O=C([C@H](CO)c1ccccc1)N1CC2=C(C1)CN(S(=O)(=O)c1cnc3c(c1)OCCO3)C2]

1 or a pharmaceutically acceptable salt thereof. In some embodiments, a compound of Formula I is (S)-1-(5-(2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one. In some examples, Compound 1 is a stable, crystalline substance. In some examples, Compound 1 is an amorphous substance.

The pharmaceutical composition comprising Compound 1 can be administered to the patient throughout a medically appropriate course of treatment, which can be a series of consecutive days for multiple consecutive weeks. In some embodiments, (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered to the patient over multiple consecutive days.

Some embodiments provide an oral, once-daily dosage form (e.g., a tablet or capsule) comprising Compound 1 for use in a therapy for increasing hemoglobin oxygen affinity by reducing 2,3-DPG blood concentrations, increasing hemoglobin levels and/or increasing intracellular ATP, without significant effects affecting sex hormones (e.g., without aromatase inhibition activity) or inducing its own metabolism upon repeat daily administration throughout a course of treatment.

Some embodiments provide an oral, once-daily dosage form (e.g., a tablet or capsule) comprising Compound 1 for use in a therapy for increasing hemoglobin oxygen affinity without significant effects affecting sex hormones (e.g., without aromatase inhibition activity) or inducing its own metabolism upon repeat daily administration throughout a course of treatment.

Some embodiments provide an oral, once-daily dosage form (e.g., a tablet or capsule) comprising Compound 1 for use in a therapy for reducing 2,3-DPG blood concentrations, without significant effects affecting sex hormones (e.g., without aromatase inhibition activity) or inducing its own metabolism upon repeat daily administration throughout a course of treatment.

Some embodiments provide an oral, once-daily dosage form (e.g., a tablet or capsule) comprising Compound 1 for use in a therapy for increasing hemoglobin levels, without significant effects affecting sex hormones (e.g., without aromatase inhibition activity) or inducing its own metabolism upon repeat daily administration throughout a course of treatment.

Some embodiments provide an oral, once-daily dosage form (e.g., a tablet or capsule) comprising Compound 1 for use in a therapy for increasing intracellular ATP, without significant effects affecting sex hormones (e.g., without aromatase inhibition activity) or inducing its own metabolism upon repeat daily administration throughout a course of treatment.

Some embodiments provide an oral, once-daily dosage form (e.g., a tablet or capsule) comprising Compound 1 for use in a therapy without significant effects affecting sex hormones (e.g., without aromatase inhibition activity) or inducing its own metabolism upon repeat daily administration throughout a course of treatment.

In some embodiments, the administration of (S)-1-(5-((2,3-dihydro-[1,4]dioxino [2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

In other embodiments, the disclosure relates to each of the following numbered embodiments:

1. A composition comprising a PKR Activating Compound of Formula I, or a pharmaceutically acceptable salt thereof:

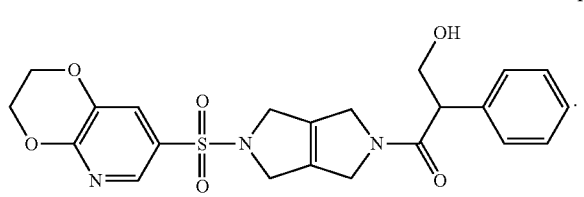

I

2. The composition of embodiment 1, wherein the compound of Formula I is Compound 1, or a pharmaceutically acceptable salt thereof:

1

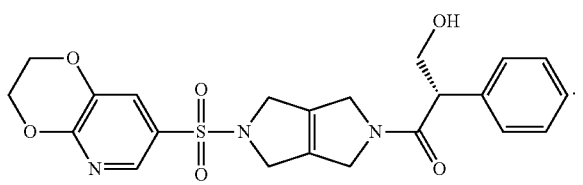

3. The composition of embodiment 2, wherein the composition comprises a mixture of Compound 1 and Compound 2, or a pharmaceutically acceptable salt thereof:

2

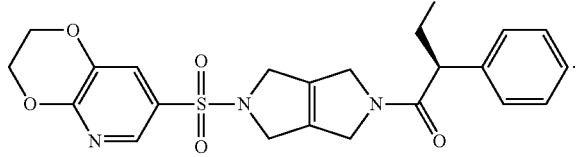

4. The composition of embodiment 1, comprising the compound: 1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.
5. The composition of any one of embodiments 1-4, formulated as an oral unit dosage form.
6. A method of treating a patient diagnosed with a sickle cell disease (SCD), the method comprising administering to the patient in need thereof a therapeutically effective amount of a pharmaceutical composition comprising (S)-1-(5-(2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, or a pharmaceutically acceptable salt thereof.
7. The method of embodiment 6, wherein the method comprises oral administration of the pharmaceutical composition comprising (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, as the only PKR Activating Compound in the pharmaceutical composition.
8. A method of treating a patient diagnosed with a sickle cell disease (SCD), the method comprising administering to the patient in need thereof a therapeutically effective amount of a pharmaceutical composition comprising Compound 1:

1

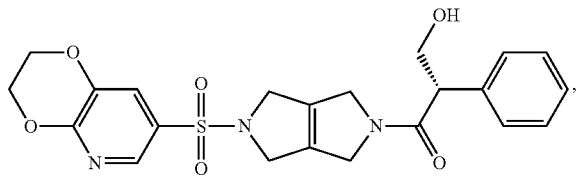

or a pharmaceutically acceptable salt thereof.
9. A composition comprising a compound of Formula I obtainable by a process comprising the step of converting compound 5 into a compound of Formula I in a reaction described as Step 4:

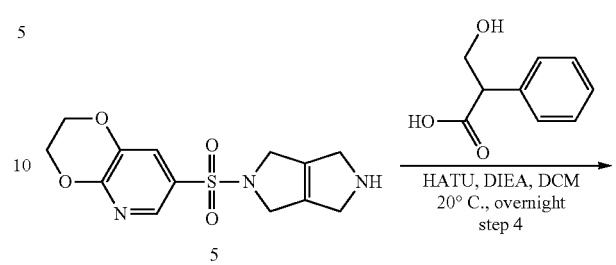

10. The composition of embodiment 9, wherein the process further comprises first obtaining the compound 5 from a compound 4 by a process comprising Step 3:

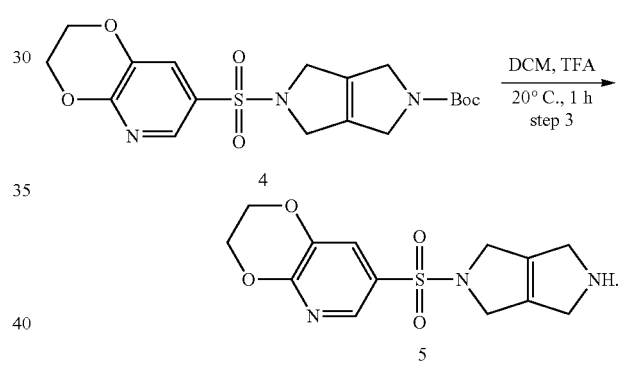

11. The composition of embodiment 10, wherein the process further comprises first obtaining the compound 4 from a compound 3 by a process comprising Step 2:

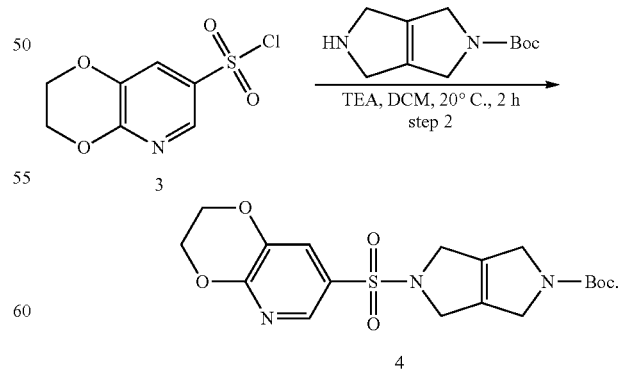

12. The composition of embodiment 11, wherein the process further comprises first obtaining the compound 3 from a process comprising Step 1:

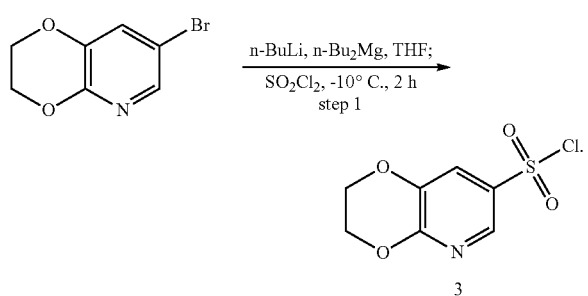

13. A method of treating a patient diagnosed with sickle cell disease (SCD), the method comprising administering to the patient in need thereof a therapeutically effective amount of a PKR Activating Compound having an AC$_{50}$ value of less than 1 μM using the Luminescence Assay described in Example 2.
14. The method of embodiment 13, wherein the PKR Activating Compound is Compound 1.
15. The method of any one of embodiments 13-14, wherein the PKR Activating Compound is orally administered to the patient in need thereof.
16. The use of Compound 1:

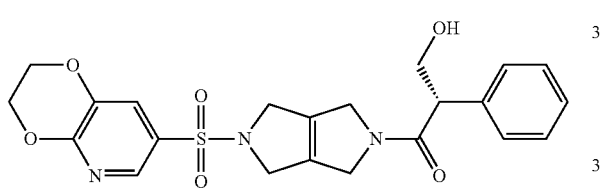

or a pharmaceutically acceptable salt thereof, for the treatment of patients diagnosed with sickle cell disease (SCD).

17. The use of a PKR Activating Compound having an AC$_{50}$ value of less than 1 μM using the Luminescence Assay described in Example 2, in the treatment of patients diagnosed with sickle cell disease.
18. The method of any one of embodiments 6-8 or 13-15, comprising the administration of Compound 1 once per day.
19. The method of any one of embodiments 6-8 or 13-15, comprising the administration of a total of 25 mg-1,500 mg of Compound 1 each day.
20. The method of any one of embodiments 18-19, comprising the administration of a total of 25 mg-130 mg of Compound 1 each day.
21. A method of treating a patient diagnosed with SCD, comprising the administration to the patient of a therapeutically effective amount of a PKR Activating Compound, wherein the PKR Activating Compound exhibits one or more of the following characteristics: (a) increases oxygen affinity to Hgb in hypoxic conditions; (b) decreases p50 in hypoxic conditions; (c) decreases the percentage of RBC that sickle at low oxygen pressures; (d) increases the time of a cell to sickle; and/or (e) increases Hgb by at least approximately 1 g/dL.
22. The method of embodiment 21, wherein the PKR Activating Compound is an antibody.
23. The method of embodiment 21, wherein the PKR Activating Compound is a protein.
24. The method of embodiment 21, wherein the PKR Activating Compound is a nucleic acid.
25. The method of embodiment 21, wherein the PKR Activating Compound is a DNA nucleic acid.
26. The method of embodiment 21, wherein the PKR Activating Compound is a RNA nucleic acid.

In other embodiments, the disclosure relates to each of the following numbered embodiments:
1. A PKR Activating Compound for use in a method of treating a patient diagnosed with sickle cell disease (SCD), comprising administering to the patient the PKR Activating Compound in a therapeutically effective amount, wherein the PKR Activating Compound is a compound of Formula I:

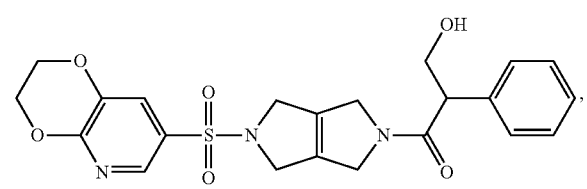

or a pharmaceutically acceptable salt thereof, having an AC$_{50}$ value of less than 1 μM using the Luminescence Assay described in Example 2.

2. The PKR Activating Compound of embodiment 1, wherein the PKR Activating Compound is Compound 1:

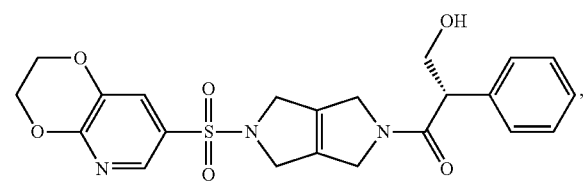

or a pharmaceutically acceptable salt thereof.

3. The PKR Activating Compound of embodiment 1, wherein the PKR Activating Compound is Compound 1:

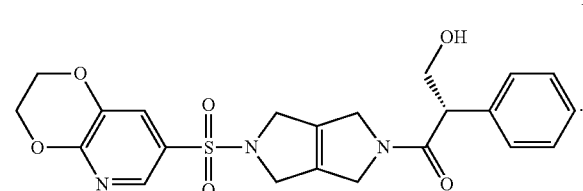

4. The PKR Activating Compound of embodiment 3, wherein the PKR Activating Compound is administered in an amount of 25-1500 mg per day.
5. The PKR Activating Compound of embodiment 3, wherein the PKR Activating Compound is administered once daily in an amount of 250 mg, 300 mg, 500 mg, 600 mg, 1000 mg, or 1500 mg per day.

6. The PKR Activating Compound of embodiment 3, wherein the PKR Activating Compound is administered once daily in an amount of 100 mg per day.
7. The PKR Activating Compound of embodiment 3, wherein the PKR Activating Compound is administered once daily in an amount of 600 mg per day.
8. The PKR Activating Compound of embodiment 3, wherein the PKR Activating Compound is administered once per day.
9. The PKR Activating Compound of embodiment 3, wherein the PKR Activating Compound is orally administered to the patient.
10. The PKR Activating Compound of embodiment 3, wherein Compound 1 is the only PKR Activating Compound administered to the patient.
11. A PKR Activating Compound for use in a method of treating a patient diagnosed with sickle cell disease, comprising administering to the patient the PKR Activating Compound in an amount sufficient to reduce 2,3-DPG levels in the patient's red blood cells by at least 30% after 24 hours, wherein the PKR Activating Compound is a compound of Formula I:

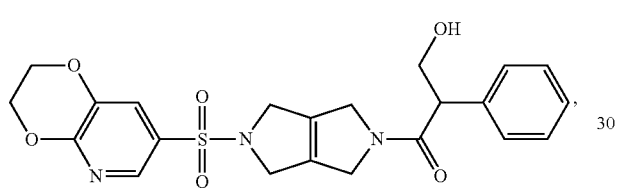

or a pharmaceutically acceptable salt thereof, having an $AC_{50}$ value of less than 1 μM using the Luminescence Assay described in Example 2.
12. The PKR Activating Compound of embodiment 11, wherein the PKR Activating Compound is Compound 1:

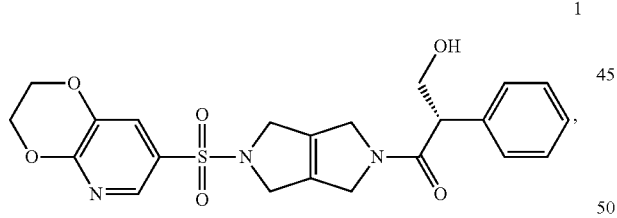

or a pharmaceutically acceptable salt thereof.
13. The PKR Activating Compound of embodiment 1, wherein the PKR Activating Compound is Compound 1:

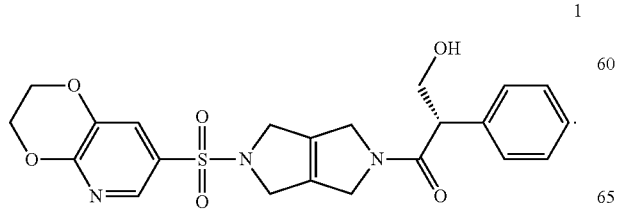

14. The PKR Activating Compound of embodiment 13, wherein Compound 1 is the only PKR Activating Compound administered to the patient.
15. The PKR Activating Compound of any one of embodiments 11-14, wherein the PKR Activating Compound is orally administered to the patient.
16. The PKR Activating Compound of any one of embodiments 11-15, wherein the PKR Activating Compound is administered once per day.
17. The PKR Activating Compound of any one of embodiments 11-16, wherein the PKR Activating Compound is administered in an amount sufficient to reduce 2,3-DPG levels in the patient's red blood cells by at least 40% after 24 hours.
18. The PKR Activating Compound of any one of embodiments 11-17, wherein the PKR Activating Compound is administered in a daily amount sufficient to increase the patient's ATP blood levels by at least 40% on day 14 of treatment.
19. The PKR Activating Compound of any one of embodiments 11-15, wherein the PKR Activating Compound is administered in an amount of 100 mg, 200 mg, 400 mg, 600 mg, 700 mg, 1100 mg, or 1500 mg per day.
20. The PKR Activating Compound of any one of embodiments 11-15, wherein the PKR Activating Compound is administered in an amount of 200 mg per day.
21. The PKR Activating Compound of embodiment 20, wherein the PKR Activating Compound is administered in an amount of 200 mg per day once per day (QD).
22. The PKR Activating Compound of embodiment 20, wherein the PKR Activating Compound is administered in an amount of 100 mg per day twice per day (BID).
23. The PKR Activating Compound of any one of embodiments 11-15, wherein the PKR Activating Compound is administered in an amount of 400 mg per day.
24. The PKR Activating Compound of embodiment 23, wherein the PKR Activating Compound is administered in an amount of 400 mg once per day (QD).
25. The PKR Activating Compound of embodiment 23, wherein the PKR Activating Compound is administered in an amount of 200 mg twice per day (BID).
26. The PKR Activating Compound of any one of embodiments 11-15, wherein the PKR Activating Compound is administered in an amount of 600 mg per day.
27. The PKR Activating Compound of embodiment 26, wherein the PKR Activating Compound is administered in an amount of 300 mg twice per day (BID).
28. The PKR Activating Compound of any one of embodiments 11-15, wherein the PKR Activating Compound is administered in an amount of 700 mg per day.
29. The PKR Activating Compound of embodiment 28, wherein the PKR Activating Compound is administered in an amount of 700 mg once per day (QD).
30. The PKR Activating Compound of embodiment 28, wherein the PKR Activating Compound is administered in an amount of 350 mg twice per day (BID).

In other embodiments, the disclosure relates to each of the following numbered embodiments:
31. A pharmaceutical composition comprising Compound 1 and a pharmaceutically acceptable carrier:

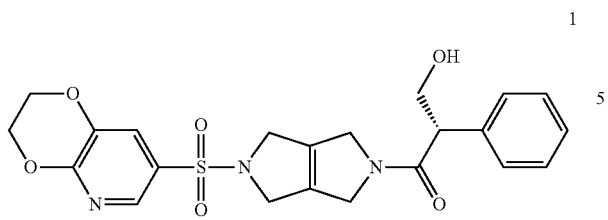

for use in a method of treating a patient diagnosed with a sickle cell disease (SCD), the method comprising administering to the patient in need thereof a total of 25 mg-1,500 mg of Compound 1 per day.

32. The composition of embodiment 31, wherein the method comprises the administration of Compound 1 in a single dose once per day.
33. The composition of embodiment 31, wherein the method comprises the administration of Compound 1 in a divided dose each day.
34. The composition of any one of embodiments 31-33, wherein the composition is orally administered to the patient.
35. The composition of any one of embodiments 31-34, wherein the composition is formulated as an oral unit dosage form.
36. A method of treating a patient diagnosed with a sickle cell disease (SCD), the method comprising orally administering to the patient in need thereof a total of 25 mg-1,500 mg per day of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one in a pharmaceutical composition.
37. A method of treating a patient diagnosed with a sickle cell disease (SCD), the method comprising orally administering to the patient in need thereof a total of 25 mg-1,500 mg of Compound 1 per day:

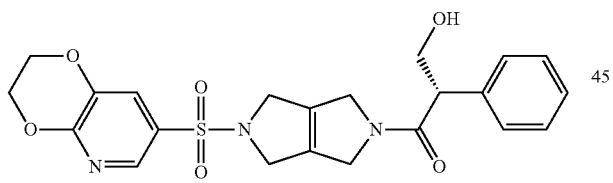

in a pharmaceutical composition comprising Compound 1 and a pharmaceutically acceptable carrier.

38. The method of any one of embodiments 36-37, wherein (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is the only PKR Activating Compound in the pharmaceutical composition.
39. The method of any one of embodiments 36-38, comprising the administration of Compound 1 in a single dose once per day.
40. The method of any one of embodiments 36-38, comprising the administration of Compound 1 in a divided dose each day.
41. A pharmaceutical composition comprising a PKR Activating Compound for use in a method of treating a patient diagnosed with sickle cell disease, comprising administering to the patient the PKR Activating Compound in an amount sufficient to reduce 2,3-DPG levels in the patient's red blood cells by at least 30% after 24 hours, wherein the PKR Activating Compound is a compound of Formula I:

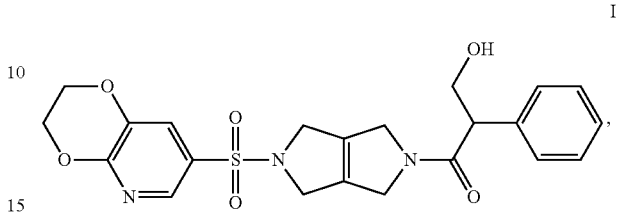

or a pharmaceutically acceptable salt thereof, having an AC50 value of less than 1 μM using the Luminescence Assay described in Example 2.

42. The composition of embodiment 41, wherein the PKR Activating Compound is Compound 1:

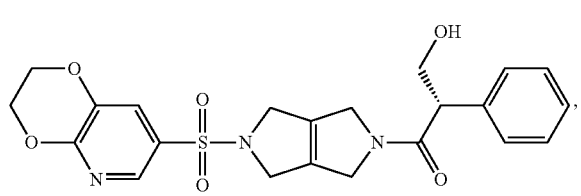

or a pharmaceutically acceptable salt thereof.

43. The composition of embodiment 42, wherein Compound 1 is the only PKR Activating Compound administered to the patient.
44. The composition of any one of embodiments 41-43, wherein the PKR Activating Compound is orally administered to the patient.
45. The composition of any one of embodiments 41-44, wherein the PKR Activating Compound is administered once per day.
46. The composition of any one of embodiments 41-45, wherein the PKR Activating Compound is administered in an amount sufficient to reduce 2,3-DPG levels in the patient's red blood cells by at least 40% after 24 hours.
47. The composition of any one of embodiments 41-46, wherein the PKR Activating Compound is administered in a daily amount sufficient to increase the patient's ATP blood levels by at least 40% on day 14 of treatment.
48. The composition of any one of embodiments 41-45, wherein the PKR Activating Compound is administered in an amount of 100 mg, 200 mg, 400 mg, 600 mg, 700 mg, 1100 mg, or 1500 mg per day.
49. The composition of any one of embodiments 41-44, wherein the PKR Activating Compound is administered in an amount of 200 mg per day.
50. The composition of any one of embodiments 41-44, wherein the PKR Activating Compound is orally administered in an amount of 200 mg per day once per day (QD).
51. The composition of any one of embodiments 41-44, wherein the PKR Activating Compound is orally administered in an amount of 100 mg per day twice per day (BID).

52. The composition of any one of embodiments 41-44, wherein the PKR Activating Compound is administered in an amount of 400 mg per day in a single or divided dose.
53. The composition of embodiment 41, wherein the PKR Activating Compound is orally administered in an amount of 400 mg once per day (QD).
54. The composition of any one of embodiments 41-44, wherein the PKR Activating Compound is orally administered in an amount of 200 mg twice per day (BID).
55. The composition of any one of embodiments 41-44, wherein the PKR Activating Compound is administered in an amount of 700 mg per day in a single or divided dose.
56. The composition of any one of embodiments 41-44, wherein the PKR Activating Compound is administered in an amount of 700 mg once per day (QD).
57. The composition of any one of embodiments 41-44, wherein the PKR Activating Compound is orally administered in an amount of 350 mg twice per day (BID).

In other embodiments, the disclosure relates to each of the following embodiments:

A method for increasing oxygen affinity of sickle hemoglobin (HbS) in vivo in a patient in need thereof which method comprises administering to said patient a sufficient amount of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof. In some embodiments, the administration of a single dose of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a salt thereof increases the oxygen affinity of said HbS in the patient.

A method for inhibiting sickling of HbS in a patient diagnosed with Sickle Cell Disease, (SCD), which method comprises administering to said patient a sufficient amount of a composition comprising (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of treating a patient diagnosed with Sickle Cell Disease (SCD), comprising administering to said patient a therapeutically effective single dose of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, such that the patient experiences a left shift in the point of sickling (PoS) with an increase in the Elmin after 24 hours.

A method of treating a patient diagnosed with Sickle Cell Disease (SCD), comprising administering to a patient (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof, in an amount effective to increase oxygen affinity of HbS.

A method of treatment, comprising administering to a patient (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, in an amount effective to increase oxygen affinity of HbA.

A method of treatment, comprising administering to a patient (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, in an amount effective to increase oxygen affinity of HbS. In some embodiments, the patient is diagnosed with Sickle Cell Disease or beta-thalassemia.

A method of treatment, comprising administering to a patient (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof, in an amount effective to result in a left shift in the point of sickling (PoS) with an increase in the Elmin in the patient. In some embodiments, the patient is diagnosed with Sickle Cell Disease or beta-thalassemia.

A method of increasing Hb concentration in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of reducing RBC turnover in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of decreasing lactate dehydrogenase (LDH) concentration in a patient diagnosed with sickle cell disease (SCD), comprising administering to the patient a sufficient amount of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of increasing RBC count in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of decreasing reticulocyte count in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of reducing point of sickling (POS) in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of increasing Elmin in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of improving RBC deformability in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof.

A method of improving RBC membrane function in a patient diagnosed with sickle cell disease (SCD), comprising administering to the patient a sufficient amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof. In some embodiments, said improving RBC membrane function comprises improving RBC membrane response to an osmotic gradient, as evidenced by a shift toward normal in Omin and Ohyper.

In some or any of the above embodiments, a total daily dose of 100 mg-600 mg of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is administered to the patient per day.

In some or any of the above embodiments, the (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered to the patient over multiple consecutive days.

In some or any of the above embodiments, administering (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one to the patient in a total dose and dose interval selected from the group consisting of 100 mg BID, 200 mg BID, 300 mg BID and 400 mg QD.

In some or any of the above embodiments, a total of 300 mg QD of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered to the patient, wherein the patient is diagnosed with SCD.

In some or any of the above embodiments, a total of 300 mg QD of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered to the patient, wherein the patient is diagnosed with beta-thalassemia.

A method of treating a patient diagnosed with Sickle Cell Disease (SCD) comprising repeatedly administering to the patient in need thereof a total of 300 mg QD of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

A method of treating a patient diagnosed with a hemoglobinopathy, the method comprising administering a PKR Activating Compound in an amount effective to increase oxygen affinity of HbS in the patient or to provide a left shift in the point of sickling (PoS) with an increase in the Elmin in the patient, or a combination thereof.

In some or any of the above embodiments, the hemoglobinopathy is Sickle Cell Disease or beta-thalassemia.

A method of treating a patient diagnosed with Sickle Cell Disease (SCD) comprising repeatedly administering to the patient in need thereof a dose of 400 mg QD of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

A method of treating a patient diagnosed with Sickle Cell Disease (SCD) comprising repeatedly administering to the patient in need thereof a dose of 300 mg QD of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

In some or any of the above embodiments, the (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is administered to the patient each day for at least 7 days.

In some or any of the above embodiments, the (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is administered to the patient each day for at least 14 days.

In some or any of the above embodiments, the (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is administered to the patient each day for at least 28 days.

In some or any of the above embodiments, the (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is administered to the patient each day for at least 60 days.

In some or any of the above embodiments, the (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one is administered to the patient each day for at least 120 days.

In some or any of the above embodiments, the patient had from 1 to 10 vasoocclusive crisis (VOC) events within 12 months prior to enrollment and baseline hemoglobin (Hb) ≥5.5 to ≤10.5 g/dL prior to treatment with (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one.

In some or any of the above embodiments, the patient has not received red blood cell (RBC) transfusions within 60 days or erythropoietin within 28 days, does not have renal insufficiency, does not have uncontrolled liver disease, is not pregnant, and is not lactating, at the time of treatment with (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or the PKR Activating Compound.

In some or any of the above embodiments, the patient is treated with the (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one until the patient has a Hb response rate defined as a Hb increase of >1 g/dL from baseline compared to a patient treated with placebo.

In some or any of the above embodiments, the patient is treated with the (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one once daily for at least 24 consecutive weeks.

In some or any of the above embodiments, the patient is treated with the (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one twice daily for at least 24 consecutive weeks.

A method comprising administering to a patient diagnosed with a hemoglobinopathy a therapeutically effective amount of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one, the therapeutically effective amount being effective to provide one or more effects in the patient in need thereof, selected from the group consisting of: increase oxygen affinity of sickle hemoglobin (HbS) in the patient; and inhibit the sickling of HbS in the patient.

A method of increasing oxygen affinity of sickle hemoglobin (HbS) or inhibiting the sickling of HbS in a patient diagnosed with Sickle Cell Disease, the method comprising administering to the patient in need thereof a therapeutically effective amount of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one.

In some or any of the above embodiments, the (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is orally administered.

In some or any of the above embodiments, the (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered once daily.

In some or any of the above embodiments, the (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered for at least 24 consecutive weeks.

In some or any of the above embodiments, a total of 300 mg per day of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one is administered to the patient each day.

A method of treatment comprising the step of administering to a patient diagnosed with a hemoglobinopathy a therapeutically effective amount of (R)-2-Hydroxy-2-phenyl-1-(5-(pyridin-2-ylsulfonyl)-3,4,5,6-tetrahydropyrrolo[3,4-c]pyrrol-2(1H)-yl)ethan-1-one, or a pharmaceutically acceptable salt thereof.

In some or any of the above embodiments, the hemoglobinopathy is Sickle Cell Disease, PKD or beta-thalassemia.

In some or any of the above embodiments, the patient has a hemoglobin genotype selected from the group consisting of Hgb SS, Hgb Sβ+-thalassemia, Hgb Sβ0-thalassemia, and Hgb SC.

In some or any of the above embodiments, the hemoglobin genotype is Hgb SS.

In some or any of the above embodiments, the hemoglobin genotype was confirmed by hemoglobin electrophoresis or genotyping.

In some or any of the above embodiments, the patient has not started hydroxyurea (HU) therapy within 90 days prior to said administering.

The method of any one of embodiments 1-55, wherein the patient has not received crizanlizumab within 14 days prior to said administering.

In some or any of the above embodiments, the patient has not received voxelotor within 7 days prior to said administering.

In some or any of the above embodiments, the patient has not received a red blood cell transfusion within 30 days prior to said administering.

In some or any of the above embodiments, the patient has a hemoglobin level of about 7.0 g/dL to about 10.5 g/dL.

In some or any of the above embodiments, the patient is ≥12 years of age.

In some or any of the above embodiments, the patient is <18 years of age.

In some or any of the above embodiments, the patient is <12 years of age.

In some or any of the above embodiments, the patient is <6 years of age.

In some or any of the above embodiments, the patient is <3 years of age.

In some or any of the above embodiments, the method comprises improving anemia or complications associated with anemia in a patient with Hgb SS or Hgb SB0-thalassemia.

In some or any of the above embodiments, the patient is being treated with a concurrent medication that is a CYP substrate.

In some or any of the above embodiments, the concurrent medication is a sensitive CYP substrate.

A pharmaceutical composition comprising the compound (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof for use in increasing the oxygen affinity of HgbA in a patient, by administering to the patient the pharmaceutical composition in an amount effective to increase the oxygen affinity of the HgbA as measured by a decrease in the p50 measured 24 hours after the administration of the pharmaceutical composition to the patient.

A pharmaceutical composition comprising the compound (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof for use in increasing the oxygen affinity of HgbS in a patient diagnosed with Sickle Cell Disease (SCD), by administering to the patient the pharmaceutical composition in an amount effective to increase the oxygen affinity of the HgbS as measured by a decrease in the p50 measured 24 hours after the administration of the pharmaceutical composition to the patient.

A pharmaceutical composition comprising the compound (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof for use in increasing the oxygen affinity of HgbS in a patient diagnosed with Sickle Cell Disease (SCD), by administering to the patient the pharmaceutical composition in an amount effective to reduce 2,3-diphosphoglycerate (2,3-DPG) in the blood of the patient measured 24 hours after the administration of the pharmaceutical composition to the patient.

A pharmaceutical composition comprising the compound (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one or a pharmaceutically acceptable salt thereof for use in treating a patient diagnosed with a hemolytic anemia, wherein the patient's hemolytic anemia was previously confirmed by hemoglobin electrophoresis or genotyping indicating one of the following hemoglobin genotypes: Hgb SS, Hgb Sβ+-thalassemia, Hgb Sβ0-thalassemia, or Hgb SC.

In some embodiments, the disclosure relates to:
1. The compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one for use in a single daily (QD) administration of 200 mg to 1,000 mg of (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one a human subject.
2. The compound of embodiment 1, for use in reducing the 2,3-DPG concentration in the blood of the human subject for 24-72 hours after administering the compound once daily to the subject for 14 consecutive days.
3. The compound of embodiment 1, for use in increasing the ATP concentration in the blood of the human subject for 24-72 hours after administering the compound once daily to the subject for 14 consecutive days.
4. The compound of embodiment 1, for use in decreasing the LDH concentration in the blood of the human subject for 24-72 hours after administering the compound once daily to the subject for 14 consecutive days.
5. The compound of embodiment 1, for use in increasing the oxygen affinity (p50) of RBCs in the blood of the human subject for 24 hours after administering the compound once to the subject.
6. The compound of embodiment 1, for use in activating PKR without inhibiting aromatase.
7. The compound of embodiment 1, for use in activating PKR without CYP inhibition or induction.
8. The compound of embodiment 1, for use in simultaneously activating PKR, increasing ATP, decreasing 2,3-DPG and increasing oxygen affinity (p50) in the blood of the subject for 72 hours after administering the compound to the subject.
9. The compound of any one of embodiments 1-8, wherein the subject is diagnosed with Sickle Cell Disease (SCD).
10. The compound of embodiment 9, for use in the treatment of a pediatric patient diagnosed with Sickle Cell Disease (SCD).
11. The compound of embodiment 10, wherein the pediatric SCD patient is younger than age 12.
12. The compound of embodiment 10, wherein the pediatric SCD patient is between the ages of 12 and 18.
13. The compound of embodiment 10, wherein the pediatric SCD patient is younger than age 2.
14. The compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one for use in the treatment of Sickle Cell Disease in a subject having a Hgb SS or Hgb SC hemoglobin genotypes.
15. The compound (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one for use in increasing the oxygen affinity of red blood cells of a subject having a normal hemoglobin genotype selected from the group consisting of HbA, HbA1, HbA2, HbE, HbF, HbS, HbC, HbH, and HbM, and having HbF <2% of total hemoglobin.

In some embodiments, the administration of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

In some embodiments, the administration of (S)-1-(5-((2,3-dihydro-[1,4]dioxino[2,3-b]pyridin-7-yl)sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, in any of the methods described herein comprises a taper in dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof.

In some embodiments, the disclosure relates to a method of administering (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, comprising tapering the dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof, in patients who have demonstrated an increase in hemoglobin over baseline (e.g., a >5.0, 3.0, 2.0, or 1.0 g/dL increase).

In some embodiments, the disclosure relates to a method of administering (S)-1-(5-((2,3-dihydro-[1,4]dioxino[2,3-b]pyridin-7-yl) sulfonyl)-3,4,5,6-tetrahydropyrrolo[3,4-c]pyrrol-2(1H)-yl)-3-hydroxy-2-phenylpropan-1-one (Compound 1), or a pharmaceutically acceptable salt thereof, comprising tapering the dose of Compound 1 (e.g., a 7-day, 5-day, 3-day, or 2-day taper, e.g., with a ~25% or 50% reduction in dose each day), or the pharmaceutically acceptable salt thereof, prior to discontinuing administration of Compound 1, or the pharmaceutically acceptable salt thereof.

The present disclosure enables one of skill in the relevant art to make and use the inventions provided herein in accordance with multiple and varied embodiments. Various alterations, modifications, and improvements of the present disclosure that readily occur to those skilled in the art, including certain alterations, modifications, substitutions, and improvements are also part of this disclosure. Accordingly, the foregoing description and drawings are by way of example to illustrate the discoveries provided herein.

EXAMPLES

As the enzyme that catalyzes the last step of glycolysis, PKR underlies reactions that directly impact the metabolic health and primary functions of RBCs. The following Examples demonstrate how PKR activation by Compound 1 impacts RBCs. The primary effect of Compound 1 on RBCs is a decrease in 2,3-DPG that is proposed to reduce Hgb sickling and its consequences on RBCs and oxygen delivery to tissues. Compound 1 also increases ATP, which may provide metabolic resources to support cell membrane integrity and protect against loss of deformability and increased levels of hemolysis in SCD. With the combination of effects Compound 1 has on RBCs, it is likely to reduce the clinical sequelae of sickle Hgb and provide therapeutic benefits for patients with SCD.

The PKR Activating Compound designated Compound 1 was prepared as described in Example 1, and tested for PKR activating activity in the biochemical assay of Example 2.

The biological enzymatic activity of PKR (i.e., formation of ATP and/or pyruvate) was evaluated in enzyme and cell assays with Compound 1, as described in Example 3 and Example 4, respectively. Results from enzyme assays show that Compound 1 is an activator of recombinant wt-PKR and mutant PKR, (e.g., R510Q), which is one of the most prevalent PKR mutations in North America. PKR exists in both a dimeric and tetrameric state, but functions most efficiently as a tetramer. Compound 1 is an allosteric activator of PKR and is shown to stabilize the tetrameric form of PKR, thereby lowering the $K_m$ (the Michaelis-Menten constant) for PEP.

Similarly, results from assays with RBCs from human patients with SCD showed that treatment with Compound 1 caused a shift in p50 ($PO_2$ at 50% hemoglobin saturation) and that this shift was related to increased oxygen affinity in the presence of Compound 1 (Example 5). Furthermore, Compound 1 decreased sickling under severe hypoxic conditions. Taken together the data suggest that Compound 1 can reduce the clinical consequences of sickled cells by decreasing cell sickling through an increase in oxygen affinity that comes from PKR activation.

Compound 1 activates wild type as well as G332S and R510Q variants of pyruvate kinase R with an AC50 of less than 1 micromolar in the Luminescence Assay of Example 2. Compound 1 activates wild type and R510Q pyruvate kinase with an AC50 value of less than 0.1 micromolar in the Enzyme Assay of Example 3. Compound 1 activates wt-PKR in mature human erythrocytes in a concentration dependent manner with an EC50 of less than 0.5 micromolar in the Cell Assay of Example 4.

Compound 1 increases the oxygen affinity of Hgb in red blood cells (RBCs) from both healthy subjects (HgbA) and in patients diagnosed with Sickle Cell Disease (HgbS), as measured by a reduction in p50, the oxygen level at which 50% of the hemoglobin is oxygenated. Reduction in p50 represents an increase in oxygen affinity. A shift in p50 representing increased oxygen affinity is observed in RBCs after 1 hour and maintained for at least 3 hours from blood obtained from patients diagnosed with SCD (Example 5). Mixing Compound 1 with RBCs from both healthy volunteers and patients diagnosed with SCD results in increased oxygen affinity measured by a reduction in the p50 values measured for both types of RBCs (Example 6).

Compound 1 reduces cell sickling under severe hypoxic conditions of 2% oxygen, providing up to about 16% percent protection defined as the level of activity in treated cells, normalized to the level of activity in untreated cells after exposure to the severe hypoxic conditions as measured in Example 5. Compound 1 reduces the point of sickling (PoS) in RBCs from patients diagnosed with SCD, when measured by improved RBC deformability and a decrease in elongation index (EI) in the presence of Compound 1 as described in Example 7.

General Methods

XRPD Analysis

Method A. XRPD analysis was performed with a Panalytical X'Pert3 Powder XRPD on a Si zero-background holder. The 2θ position was calibrated against Panalytical 640 Si powder standard. Details of the XRPD method used in the experiments are listed in the Table below.

|  | Parameters for Reflection Mode |
| --- | --- |
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2 TH) | 3°-40° |
| Step size (°2 TH) | 0.0262606 |
| Scan speed (°/s) | 0.066482 |

Method B. XRPD analysis was performed with a Rigaku X-Ray Powder Diffractomer MiniFlex 600 with the following parameters:

| Parameter | Setting |
| --- | --- |
| Soller (inc.) | 5.0 deg |
| IHS | 10.0 mm |
| SS | 1.250 deg |
| DS | 1.250 deg |
| Soller (rec) | 5.0 deg |
| RS | 0.3 mm |
| Scan Axis | Theta/2-Theta |
| Mode | Continuous |
| Start (deg) | 2.0000 |
| Stop (deg) | 40.0000 |
| Step (deg) | 0.020 |
| Speed (deg/min) | 2.5 |
| Spin | Yes |
| Voltage (kV) | 40 |
| Current (mA) | 15 |

Method C. XRPD analysis was performed with the following parameters:

|  | Parameters |
| --- | --- |
| Start position (°2 TH) | 2.00 |
| Stop position (°2 TH) | 40.00 |
| DS (°) | 1.250 |
| RS (mm) | 0.3 |
| SS (°) | 1.250 |
| Step size (°) | 0.02 |
| Rate (°/minute) | 0.50 |

Example 1: Synthesis of Compounds of Formula I

The PKR Activating Compound 1 was obtained by the method described herein. Compound 1 has a molecular weight of 457.50 Da.

Step 1. 2H,3H-[1,4]dioxino[2,3-b]pyridine-7-sulfonyl chloride (3)

Into a 100 mL round-bottom flask purged and maintained with an inert atmosphere of nitrogen was placed a solution of n-BuLi in hexane (2.5 M, 2 mL, 5.0 mmol, 0.54 equiv) and a solution of n-Bu2Mg in heptanes (1.0 M, 4.8 mL, 4.8 mmol, 0.53 equiv). The resulting solution was stirred for 10 min at RT (20° C.). This was followed by the dropwise addition of a solution of 7-bromo-2H,3H-[1,4]dioxino[2,3-b]pyridine (2 g, 9.26 mmol, 1.00 equiv) in tetrahydrofuran (16 mL) with stirring at −10° C. in 10 min. The resulting mixture was stirred for 1 h at −10° C. The reaction mixture was slowly added to a solution of sulfuryl chloride (16 mL) at −10° C. The resulting mixture was stirred for 0.5 h at −10° C. The reaction was then quenched by the careful addition of 30 mL of saturated ammonium chloride solution at 0° C. The resulting mixture was extracted with 3×50 mL of dichloromethane. The organic layers were combined, dried over anhydrous sodium sulfate, filtered and concentrated under vacuum. The residue was purified by silica gel column chromatography, eluting with ethyl acetate/petroleum ether (1:3). This provided 1.3 g (60%) of 2H,3H-[1,4]dioxino[2,3-b]pyridine-7-sulfonyl chloride as a white solid. LCMS m/z: calculated for $C_7H_6ClNO_4S$: 235.64; found: 236 [M+H]$^+$.

Step 2. tert-Butyl 5-[2H,3H-[1,4]dioxino[2,3-b]pyridine-7-sulfonyl]-1H,2H,3H,4H,5H,6H-pyrrolo[3,4-c]pyrrole-2-carboxylate (4)

Into a 100-mL round-bottom flask was placed 2H,3H-[1,4]dioxino[2,3-b]pyridine-7-sulfonyl chloride (1.3 g, 5.52 mmol, 1.00 equiv), tert-butyl 1H,2H,3H,4H,5H,6H-pyrrolo[3,4-c]pyrrole-2-carboxylate (1.16 g, 5.52 mmol), dichloromethane (40 mL), and triethylamine (1.39 g, 13.74 mmol, 2.49 equiv). The solution was stirred for 2 h at 20° C., then diluted with 40 mL of water. The resulting mixture was extracted with 3×30 mL of dichloromethane. The organic layers were combined, dried over anhydrous sodium sulfate, filtered and concentrated under vacuum. The residue was purified by silica gel column chromatography, eluting with dichloromethane/methanol (10:1). This provided 1.2 g (53%) of tert-butyl 5-[2H,3H-[1,4]dioxino[2,3-b]pyridine-7-sulfonyl]-1H,2H,3H,4H,5H,6H-pyrrolo[3,4-c]pyrrole-2-carboxylate as a yellow solid. LCMS m/z: calculated for $C_{18}H_{23}N_3O_6S$: 409.46; found: 410 [M+H]$^+$.

Step 3. 2-[2H,3H-[1,4]dioxino[2,3-b]pyridine-7-sulfonyl]-1H,2H,3H,4H,5H,6H-pyrrolo[3,4-c]pyrrole (5)

Into a 100-mL round-bottom flask was placed tert-butyl 5-[2H,3H-[1,4]dioxino[2,3-b]pyridine-7-sulfonyl]-1H,2H,3H,4H,5H,6H-pyrrolo[3,4-c]pyrrole-2-carboxylate (1.2 g, 2.93 mmol, 1.00 equiv), dichloromethane (30 mL), and trifluoroacetic acid (6 mL). The solution was stirred for 1 h at 20° C. The resulting mixture was concentrated under vacuum. The residue was dissolved in 10 mL of methanol and the pH was adjusted to 8 with sodium bicarbonate (2 mol/L). The resulting solution was extracted with 3×10 mL of dichloromethane. The organic layers were combined, dried over anhydrous sodium sulfate, filtered and concentrated under vacuum. The crude product was purified by silica gel column chromatography, eluting with dichloromethane/methanol (10:1). This provided 650 mg (72%) of 2-2H,3H[1,4]dioxino[2,3-b]pyridine-7-sulfonyl-1H,2H,3H,4H,5H,6H-pyrrolo[3,4-c]pyrrole as a yellow solid. LCMS m/z: calculated for $C_{13}H_{15}N_3O_4S$: 309.34; found: 310 [M+H]$^+$.

Step 4. (S)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (1) and (R)-1-(5-2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (2)

Into a 100 mL round-bottom flask was placed 2-[2H,3H-[1,4]dioxino[2,3-b]pyridine-7-sulfonyl]-1H,2H,3H,4H,5H,6H-pyrrolo[3,4-c]pyrrole (150 mg, 0.48 mmol, 1.00 equiv), 3-hydroxy-2-phenylpropanoic acid (97 mg, 0.58 mmol, 1.20 equiv), dichloromethane (10 mL), HATU (369 mg, 0.97 mmol, 2.00 equiv) and DIEA (188 mg, 1.46 mmol, 3.00 equiv). The resulting solution was stirred overnight at 20° C. The reaction mixture was diluted with 20 mL of water and was then extracted with 3×20 mL of dichloromethane. The organic layers were combined, dried over anhydrous sodium sulfate, filtered and concentrated under vacuum. The residue was purified by prep-TLC eluted with dichloromethane/methanol (20:1) and further purified by prep-HPLC (Column: XBridge C18 OBD Prep Column, 100 Å, 5 μm, 19 mm×250 mm; Mobile Phase A: water (10 mmol/L NH$_4$HCO$_3$), Mobile Phase B: MeCN; Gradient: 15% B to 45% B over 8 min; Flow rate: 20 mL/min; UV Detector: 254 nm). The two enantiomers were separated by prep-Chiral HPLC (Column, Daicel CHIRALPAK® IF, 2.0 cm×25 cm, 5 μm; mobile phase A: DCM, phase B: MeOH (hold 60% MeOH over 15 min); Flow rate: 16 mL/min; Detector, UV 254 & 220 nm). This resulted in peak 1 (2, Rt: 8.47 min) 9.0 mg (4%) of (R)-1-(5-[2H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as a yellow solid; and peak 2 (1, Rt: 11.83 min) 10.6 mg (5%) of (S)-1-(542H,3H-[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one as a yellow solid.

(1): $^1$H NMR (400 MHz, DMSO-d$_6$) δ 8.13 (d, J=2.0 Hz, 1H), 7.61 (d, J=2.0 Hz, 1H), 7.31-7.20 (m, 5H), 4.75 (t, J=5.2 Hz, 1H), 4.50-4.47 (m, 2H), 4.40-4.36 (m, 1H), 4.32-4.29 (m, 2H), 4.11-3.87 (m, 8H), 3.80-3.77 (m, 1H), 3.44-3.41 (m, 1H). LC-MS (ESI) m/z: calculated for $C_{22}H_{23}N_3O_6S$: 457.13; found: 458.0 [M+H]$^+$.

(2): $^1$H NMR (400 MHz, DMSO-d$_6$) δ 8.13 (d, J=2.0 Hz, 1H), 7.60 (d, J=2.0 Hz, 1H), 7.31-7.18 (m, 5H), 4.75 (t, J=5.2 Hz, 1H), 4.52-4.45 (m, 2H), 4.40-4.36 (m, 1H), 4.34-4.26 (m, 2H), 4.11-3.87 (m, 8H), 3.80-3.78 (m, 1H), 3.44-3.43 (m, 1H). LC-MS (ESI) m/z: calculated for $C_{22}H_{23}N_3O_6S$: 457.13; found: 458.0 [M+H]$^+$.

Step 5. (S)-1-(5-[2H,3H-[1,4]dioxino[2,3-b]pyridine-7-sulfonyl]-1H,2H, 3H,4H, 5H,6H-pyrrolo[3,4-c]pyrrol-2-yl)-3-hydroxy-2-phenylpropan-1-one (1)

Alternatively, Compound 1 can be synthesized using the procedure described here as Step 5. A solution of 7-(3,4,5,6-tetrahydropyrrolo[3,4-c]pyrrol-2(1H)-yl)sulfonyl)-2,3-dihydro[1,4]dioxino[2,3-b]pyridine (130.9 mg, 0.423 mmol) in DMF (2.5 ml) was cooled on an ice bath, then treated with (S)-3-hydroxy-2-phenylpropanoic acid (84.8 mg, 0.510 mmol), HATU (195.5 mg, 0.514 mmol), and DIEA (0.30 mL, 1.718 mmol) and stirred at ambient temperature overnight. The solution was diluted with EtOAc (20 mL), washed sequentially with water (20 mL) and brine (2×20 mL), dried (MgSO$_4$), filtered, treated with silica gel, and evaporated under reduced pressure. The material was chromatographed by Biotage MPLC (10 g silica gel column, 0 to 5% MeOH in DCM) to provide a white, slightly sticky solid. The sample was readsorbed onto silica gel and chromatographed (10 g silica gel column, 0 to 100% EtOAc in hexanes) to provide (2S)-1-(5-[2H,3H[1,4]dioxino[2,3-b]pyridine-7-sulfonyl]-1H,2H,3H,4H,5H,6H-pyrrolo[3,4-c]pyrrol-2-yl)-3-hydroxy-2-phenylpropan-1-one (106.5 mg, 0.233 mmol, 55% yield) as a white solid.

Step 6. Preparing a Spray Dried Dispersion of Compound 1 (1:3 Compound 1:Polymer)

A Spray Dried Dispersion (SDD) of Compound 1 was prepared. The SDD was made up of Compound 1 and a polymer (Hydroxypropylmethyl Cellulose AS-MG) at a 1:3 ratio. Compound 1 and the polymer were dissolved in organic solvents (Dichloromethane and Methanol) and spray dried to obtain amorphous an amorphous drug substance.

A spray solution was prepared at 7.8% solids content (1:3 Compound 1:HPMC AS-MG) in 80:20 DCM:Methanol per Table A. An API correction factor of 0.966 was used to prepare the spray solution. The spray solution was prepped by adding DCM and Methanol to a 36L stainless steel mixing vessel. HPMC AS-MG was added to the solvent system while mixing with a top down mixer at a medium vortex. Compound 1 was then added to the solution. The solution had a yellow/brown clear appearance.

TABLE A

| Component | Formulation % | Weight, g |
|---|---|---|
| Compound 1 | 2.00% | 595.0 |
| HPMC AS-MG | 5.81% | 1724.3 |
| DCM | 73.75% | 21896.0 |
| Methanol | 18.44% | 5474.0 |
| Total | 100.0% | 29689.3 |

Correction Factor: 0.9660

A Mobile Minor spray-drying apparatus was setup per Table B and warmed up for approximately one hour prior to spraying. Wash solution (80:20 DCM:Methanol) was sprayed prior to the active solution to allow the nozzle to equilibrate. The Compound 1 active solution was sprayed per the settings in Table B. The spray-dried dispersion was dried overnight (~20 hours) in a Shel Vacuum Oven at 50° C. and −25 in Hg vacuum under a nitrogen purge at 15 scfh. The resulting spray-dried dispersion was confirmed to be dry by GC analysis. This run generated approximately 2.1 kg of spray-dried dispersion.

TABLE B

| Parameter | Set Point |
|---|---|
| Inline Filter | Swagelok 140 μm Stainless Steel |
| Nozzle | 0.3 mm, 60° Angle |
| Inlet Air Flow | 80 kg/hr |
| Inlet Air Temperature | 104° C. |
| Pump Stroke Length | 5.70 mm |
| Nozzle Pressure | 600 psi |
| Feed Rate (g/min) | 184 g/min |
| Outlet Temp (° C.) | 36 |
| Set Condenser Air Temp (° C.) | −10 |
| Actual Condenser Air Temp (° C.) | −3 |
| Chiller Temp (° C.) | 20 |
| Parameter | Set Point |
| Feed Temp | Ambient |

Figure 7:
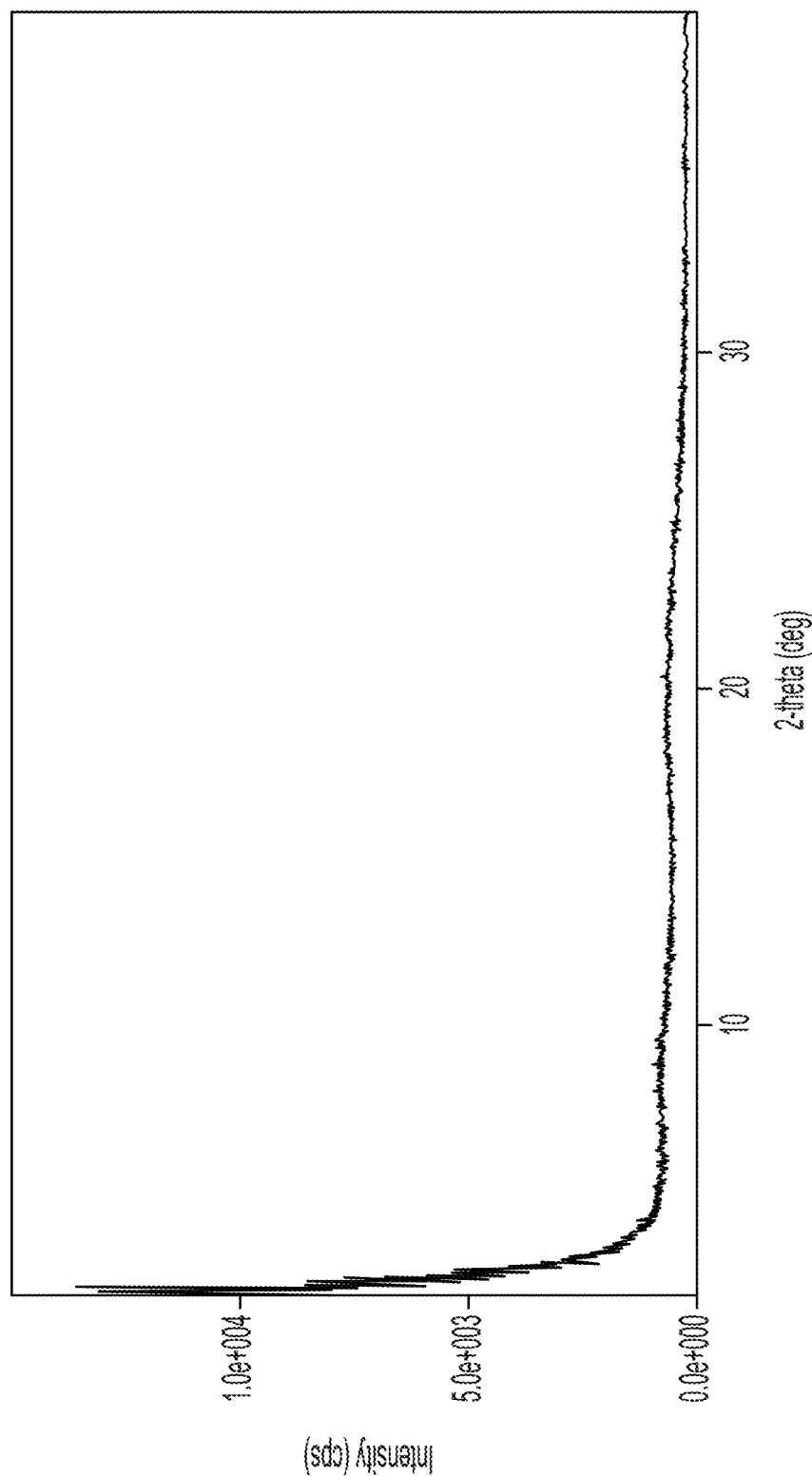
FIG. 7 depicts an XRPD pattern of a spray-dried dispersion (SDD) of Compound 1.
Figure 8:
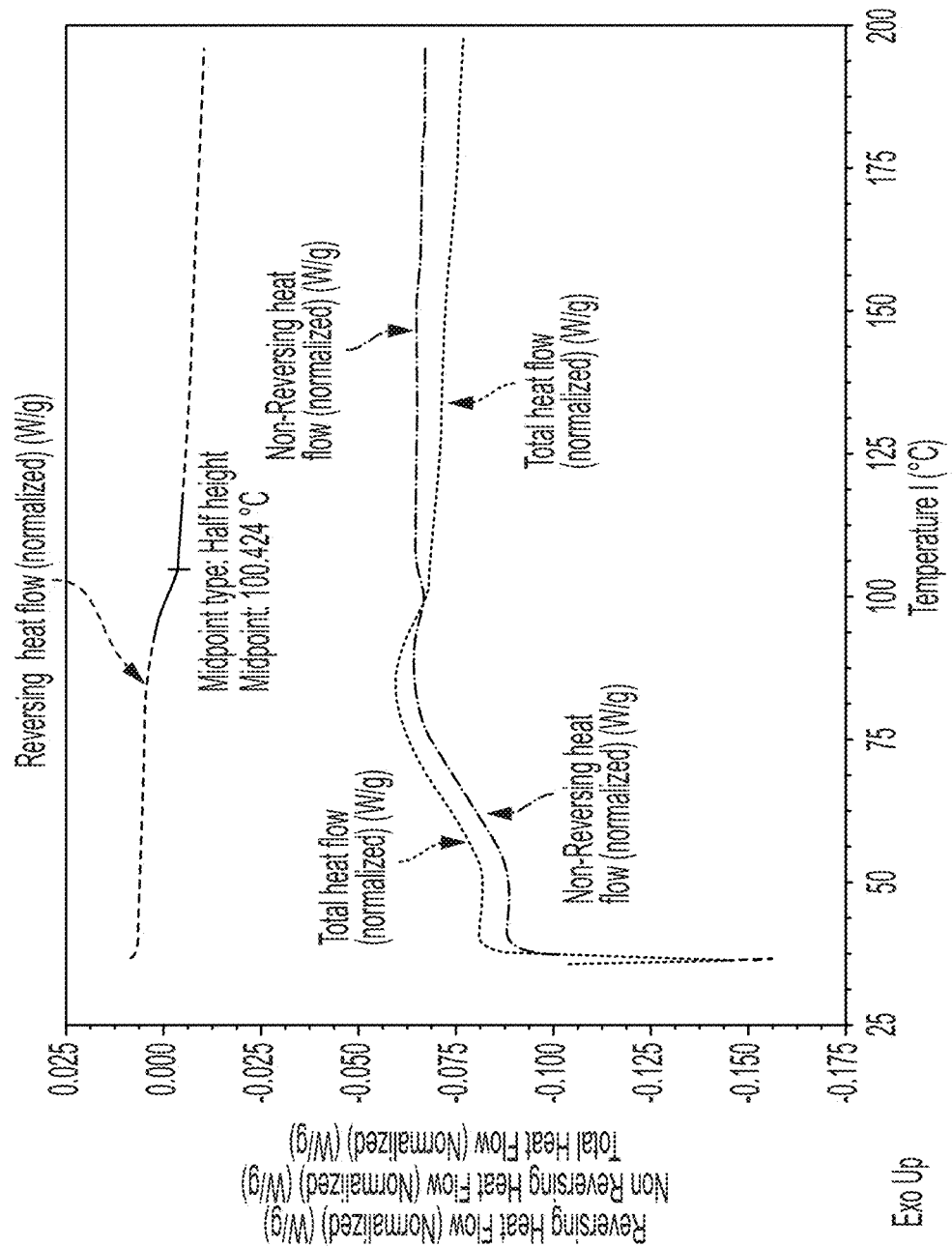
FIG. 8 depicts a differential scanning calorimetry (DSC) thermogram for a spray-dried dispersion (SDD) of Compound 1.

The SDD was characterized by XRPD (Method B) and DSC (ambient to 200° C., 2° C./minute ramp) analysis, as shown in FIGS. 7 and 8, respectively. The SDD was determined to be homogeneous and amorphous, as evidenced by the amorphous diffractogram, lack of a crystalline melt, and single Tg (100° C.).

Step 7. Preparing a Tablet Dosage Form of Compound 1

A tablet dosage form of Compound 1 having the following composition was prepared:

| | Component | % Formulation | Function |
|---|---|---|---|
| Intra Granular Components | Compound 1 Spray Dried Dispersion (Compound 1:LHPMC AS-MG(1:3)) | 50.00% | Drug Product Intermediate |
| | Microcrystalline Cellulose | 30.00% | Filler |
| | Crospovidone | 5.00% | Dry binder |
| | Colloidal Silicon Dioxide | 1.00% | Glidant |
| | Magnesium Stearate | 0.25% | Lubricant |

-continued

| | Component | % Formulation | Function |
|---|---|---|---|
| Extra Granular Components | Microcrystalline Cellulose | 11.00% | Filler |
| | Croscarmellose Sodium | 2.50% | Disintegrant |
| | Magnesium Stearate | 0.25% | Lubricant |
| | Total Common Formulation Blend per Tablet | 100% | — |
| Coating Components | Sterile Water for Injection (SWFI) | Removed through processing | Processing aid |
| | Opadry amb II White | 6.00 | Film Coating Agent |

The tablet formulation manufacturing process consisted of four steps: 1) spray dry dispersion (as described above), 2) intragranular granulation, roller compaction/milling/blending, 3) extragranular granulation/blending, and 4) tableting and coating. The SDD is blended with intra granular excipients followed by roller compaction/milling and blending. The resulting granulation is then mixed with the extra-granular components to create the final common granulation blend. The final blend is pressed into tablets equivalent to either 25 mg or 100 mg active followed by coating.

Step 8. Preparing a Spray Dried Dispersion of Compound 1 (1:1 Compound 1:Polymer)

A spray solution having a 1:1 ratio of Compound 1 to polymer (Hydroxypropylmethyl Cellulose AS-MG) was prepared at 12% solids content in 80:20 DCM:MeOH. The spray solution was sprayed on a GEA Mobile Minor spray dryer, and the SDD was collected and dried at 50° C. and −25 in Hg under a $N_2$ purge. A sample was analyzed by XRPD (Method C) and DSC (modulated 1.00° C. for 60 seconds with a ramp rate of 2° C./min to 250° C.; standby temperature range of 20° to 25° C.) analysis. No crystalline diffraction peaks were observed by XRPD analysis. Moreover, a single TG and no melt endotherm was seen by DSC analysis.

Step 9. Preparing a Tablet Dosage Form of Compound 1

Tablets comprising a spray dried dispersion (SDD) of Compound 1 and compendial excipients are prepared at 100 mg and 200 mg dosage strengths with the following composition:

| Component | Function | Range |
|---|---|---|
| SDD (1:1) | Active | 30-75% |
| Microcrystalline Cellulose | Filler | 15-60% |
| Lactose Monohydrate | Filler | 0-20% |
| Crosslinked polyvinylpyrrolidone | Dry Binder | 2-10% |
| Colloidal Silicon Dioxide | Glidant | <2% |
| Croscarmellose Sodium | Disintegrant | 2-10% |
| Magnesium Stearate | Lubricant | <2% |
| Opadry amb II Brown | Coating | <10% |

The tablets are prepared by first manufacturing the SDD (spray drying an organic solution of Compound 1 and HPMC-AS (1:1 w/w)), followed by roller compaction/milling with intragranular excipients and blending with extragranular excipients. The final blend is pressed into tablets and then film coated.

Example 2: Biochemical Assay for Identification of PKR Activating Activity

PKR Activating Compounds can be identified with the biochemical Luminescence Assay of Example 2. The PKR activating activity of a series of chemical compounds was evaluated using the Luminescence Assay below, including compounds designated Compound 1, and Compound 2, or mixtures thereof.

For each tested compound, the ability to activate PKR was determined using the following Luminescence Assay. The effect of phosphorylation of adenosine-5'-diphosphate (ADP) by PKR is determined by the Kinase Glo Plus Assay (Promega) in the presence or absence of FBP (D-fructose-1,6-diphosphate; BOC Sciences, CAS: 81028-91-3) as follows. Unless otherwise indicated, all reagents are purchased from Sigma-Aldrich. All reagents are prepared in buffer containing 50 mM Tris-HCl, 100 mM KCl, 5 mM $MgCl_2$, and 0.01% Triton X100, 0.03% BSA, and 1 mM DTT. Enzyme and PEP (phosphoenolpyruvate) are added at 2× to all wells of an assay-ready plate containing serial dilutions of test compounds or DMSO vehicle. Final enzyme concentrations for PKR (wt), PKR(R510Q), and PKR (G332S) are 0.8 nM, 0.8 nM, and 10 nM respectively. Final PEP concentration is 100 µM. The Enzyme/PEP mixture is incubated with compounds for 30 minutes at RT before the assay is initiated with the addition of 2×ADP and KinaseGloPlus. Final concentration of ADP is 100 µM. Final concentration of KinaseGloPlus is 12.5%. For assays containing FBP, that reagent is added at 30 µM upon reaction initiation. Reactions are allowed to progress for 45 minutes at RT until luminescence is recorded by the BMG PHERAstar FS Multilabel Reader. The compound is tested in triplicate at concentrations ranging from 42.5 µM to 2.2 nM in 0.83% DMSO. $AC_{50}$ measurements were obtained by the standard four parameter fit algorithm of ActivityBase XE Runner (max, min, slope and $AC_{50}$). The $AC_{50}$ value for a compound is the concentration (µM) at which the activity along the four parameter logistic curve fit is halfway between minimum and maximum activity.

As set forth in Table 2 below, $AC_{50}$ values are defined as follows: ≤0.1 µM (+++); >0.1 µM and ≤1.0 µM (++); >1.0 µM and ≤40 µM (+); >40 µM (0).

TABLE 2

Luminescence Assay Data

| Compound | $AC_{50}$ (PKRG332S) | $AC_{50}$ (PKRR510Q) | $AC_{50}$ (WT) |
|---|---|---|---|
| 1 | ++ | +++ | +++ |
| 2 | + | + | + |

Compounds and compositions described herein are activators of wild type PKR and certain PKR mutants having lower activities compared to the wild type. Such mutations in PKR can affect enzyme activity (catalytic efficiency), regulatory properties, and/or thermostability of the enzyme. One example of a PKR mutation is G332S. Another example of a PKR mutation is R510Q.

Example 3: Enzyme Assays of a PKR Activating Compound

Figure 9:
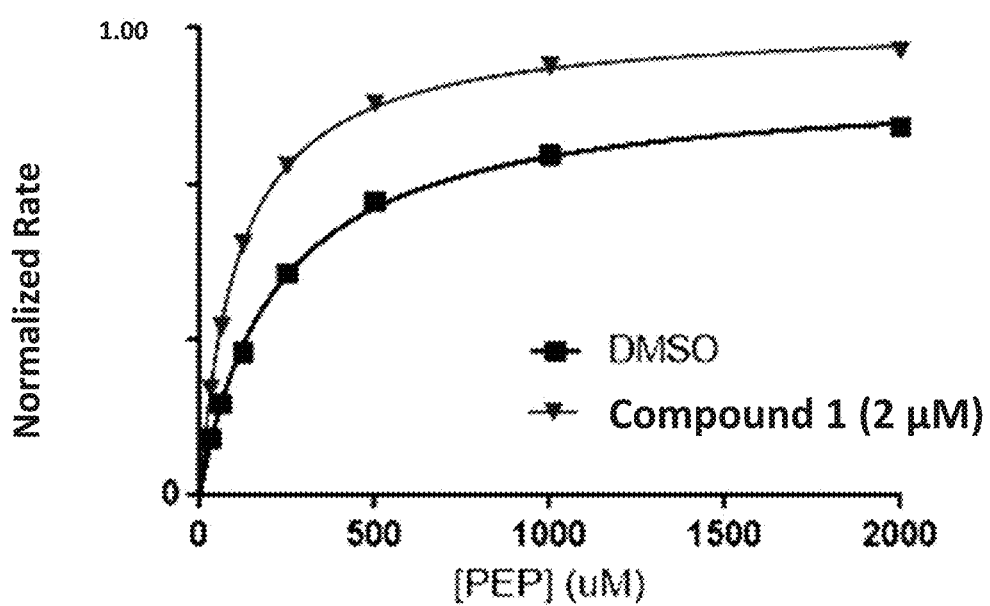
FIG. 9 is a graph showing activation of recombinant PKR-R510Q with Compound 1, plotting the normalized rate vs. concentration of phosphoenolpyruvate (PEP) (Example 3).

The ability of Compound 1 to activate PKR in enzyme-based assays was measured. Significant increases in PKR activity as measured by Vmax, a biochemical measure of the maximal rate of enzyme activity, of up to 1.8-fold were observed under certain physiologic conditions as shown in FIG. 9. In particular, activation of PKR by different concentrations of Compound 1 was evaluated for phosphoenolpyruvate, or PEP, concentrations at or below the Km.

The effect of 2 µM Compound 1 on maximum velocity ($V_{max}$) and PEP $K_m$ (Michaelis-Menten constant, i.e., the concentration of PEP at which $v=\frac{1}{2}v_{max}$) was evaluated for wt-PKR and PKR-R510Q. Tests were conducted in the presence and absence of fructose-1,6-bisphosphate (FBP), a known allosteric activator of PKR. Assessments were made up to 60 min at RT, and $V_{max}$ and PEP $K_m$ were calculated. The effect of Compound 1 on $V_{max}$ ranged from no effect to a modest increase (see FIG. 9 for a representative curve). Compound 1 consistently reduced the PEP $K_m$, typically by ~2 fold, for wt-PKR and PKR-R510Q in the presence or absence of FBP (Table 3), demonstrating that Compound 1 can enhance the rate of PKR at physiological concentrations of PEP.

TABLE 3

Effect of Compound 1 on PKR Enzyme Kinetic Parameters

| | | No FBP | | 30 µM FBP | |
|---|---|---|---|---|---|
| Enzyme | Kinetic Parameter[a] | DMSO | 2 µM Compound 1 | DMSO | 2 µM Compound 1 |
| WT-PKR | $V_{max}$ | 1.00 | 1.14 | 1.19 | 1.16 |
| WT-PKR | PEP $K_m$ | 4.84 | 2.44 | 1.98 | 1.00 |
| PKR R510Q | $V_{max}$ | 1.54 | 1.56 | 1.00 | 1.29 |
| PKR R510Q | PEP $K_m$ | 6.20 | 1.70 | 2.01 | 1.00 |

[a]All values in Table 3 are normalized to 1.00, relative to the other values in the same row.

Compound 1

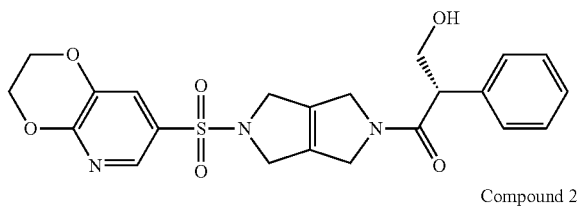

Compound 2

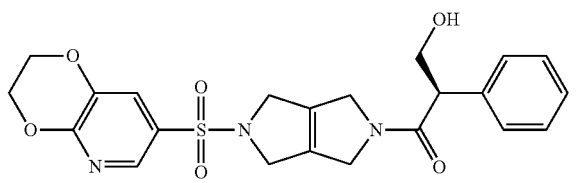

Figure 10:
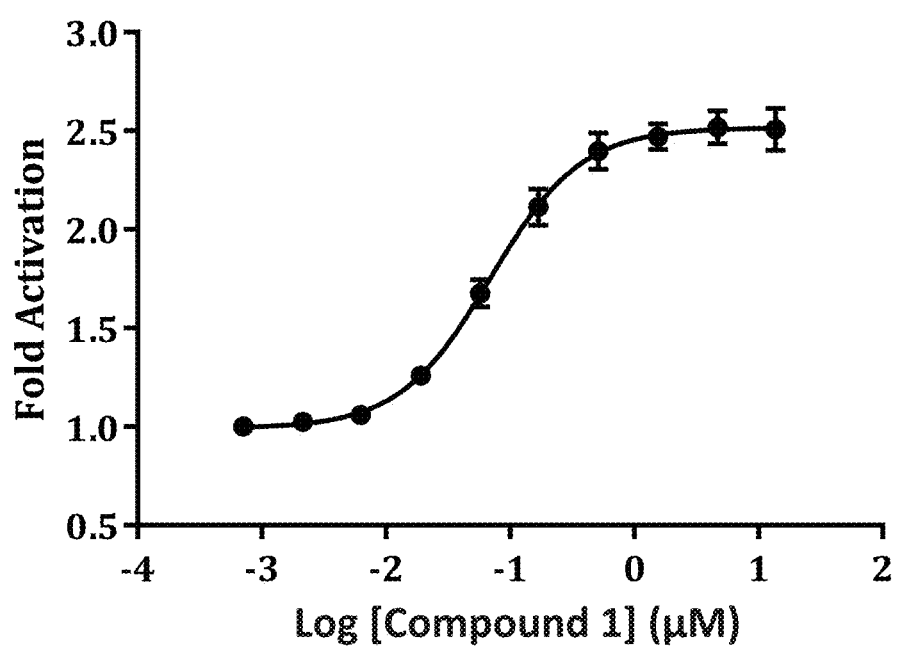
FIG. 10 is a graph of data showing activation of recombinant PKR-R510Q by Compound 1 in the enzyme assay of Example 3.

Activation of wt-PKR and PKR-R510Q by different concentrations of Compound 1 was evaluated for PEP concentrations at or below $K_m$. Compound 1 increased the rate of ATP formation, with $AC_{50}$ values ranging from <0.05 to <0.10 µM and a range of <2.0 to <3.0 maximum-fold activation (ie, <200% to <300%) (Table 4). Representative data from PKR-R510Q showed that the effect was concentration dependent (FIG. 10).

TABLE 4

Activation of PKR Wild and Mutant Types by Compound 1

| PK Enzyme | Maximum-fold Activation | $AC_{50}$ (µM) |
|---|---|---|
| WT-PKR | <2.0 | <0.05 |
| PKR R510Q | <3.0 | <0.10 |

Example 4: Cell Assays of a PKR Activating Compound

Figure 11:
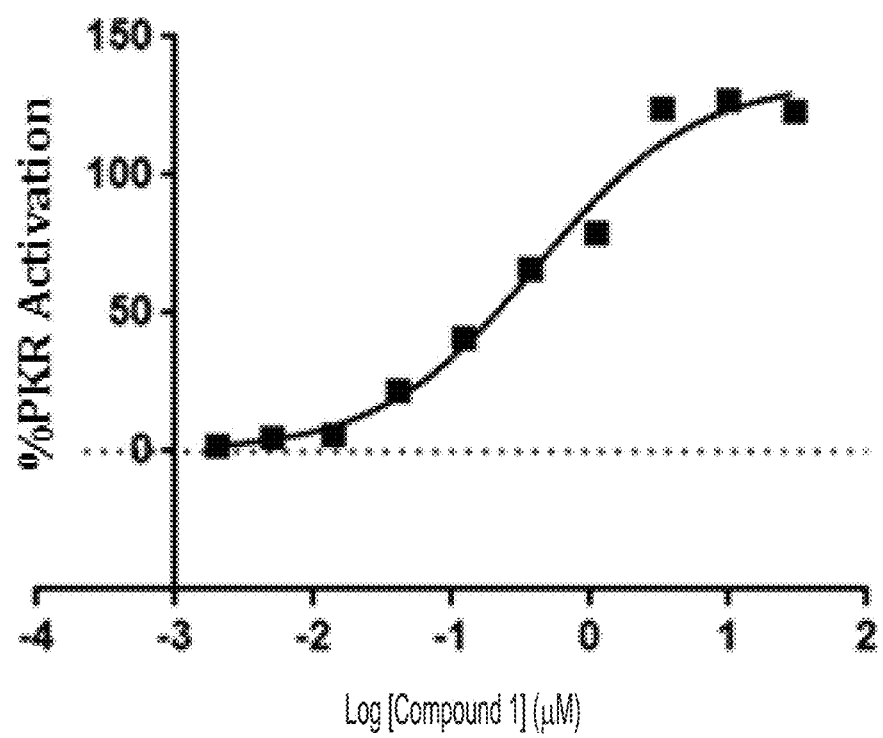
FIG. 11 is a graph of data showing PKR activation in human red blood cells treated with Compound 1 (Example 4).

The activation of wt-PKR by Compound 1 in mature human erythrocytes ex vivo was evaluated in purified RBCs purchased from Research Blood Components. Cells treated with Compound 1 for 3 hr in glucose-containing media were washed, lysed, and assayed using a Biovision Pyruvate Kinase Assay (K709-100). The assay was repeated multiple times to account for donor-to-donor variability and the relatively narrow dynamic range. Mean maximum activation increase (Max-Min) was <100% and mean 50% effective concentration ($EC_{50}$) was <125 nM (Table 5). wt-PKR was activated in a concentration-dependent manner (FIG. 11).

TABLE 5

Wild Type PKR Activation in Human Red Blood Cells Treated with Compound 1

| Replicate | Max − Min (%) | $EC_{50}$ (nM) |
|---|---|---|
| 1 | <125 | <250 |
| 2 | <150 | <150 |
| 3 | <100 | <50 |
| 4 | <50 | <50 |
| Mean | <100 | <125 |

Mouse RBCs were isolated fresh from whole blood using a Ficoll gradient and assayed with methods similar to those used in the human RBCs assays. Maximum activation increase, and EC50 values were comparable to the effects in human RBCs (Table 6).

TABLE 6

Effect of Compound 1 on PKR Activation in Mouse Red Blood Cells

| Replicate | Max − Min (%) | $EC_{50}$ (nM) |
|---|---|---|
| 1 | <50 | <125 |
| 2 | <100 | <125 |
| Mean | <100 | <125 |

Example 5: Ex Vivo Pharmacology of a PKR Activating Compound

Red blood cells from SCD patients were used to evaluate the effects of Compound 1 on Hgb affinity for oxygen (i.e., oxygen affinity) and sickling under hypoxic conditions. Cells were incubated at 37° C. for 1, 2, and 3 hr with HEPES buffered saline (HBS) (untreated), HBS+dimethyl sulfoxide (DMSO) (vehicle), or 10 µM Compound 1. To assess oxygen dissociation, Hgb oxygen equilibrium curves were collected during deoxygenation.

Figure 12:
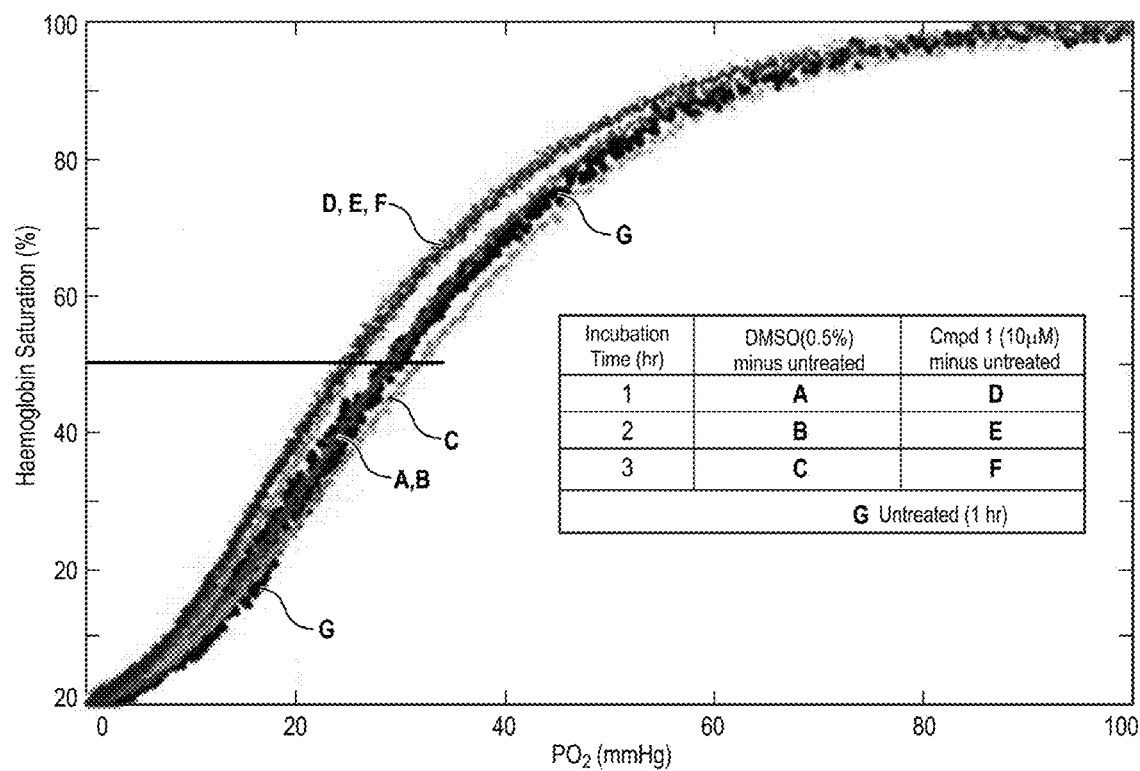
FIGS. 12 and 13 are graphs of data showing the effect of treatment with Compound 1 on oxyhemoglobin dissociation in RBCs from SCD patients (Example 5).
Figure 13:
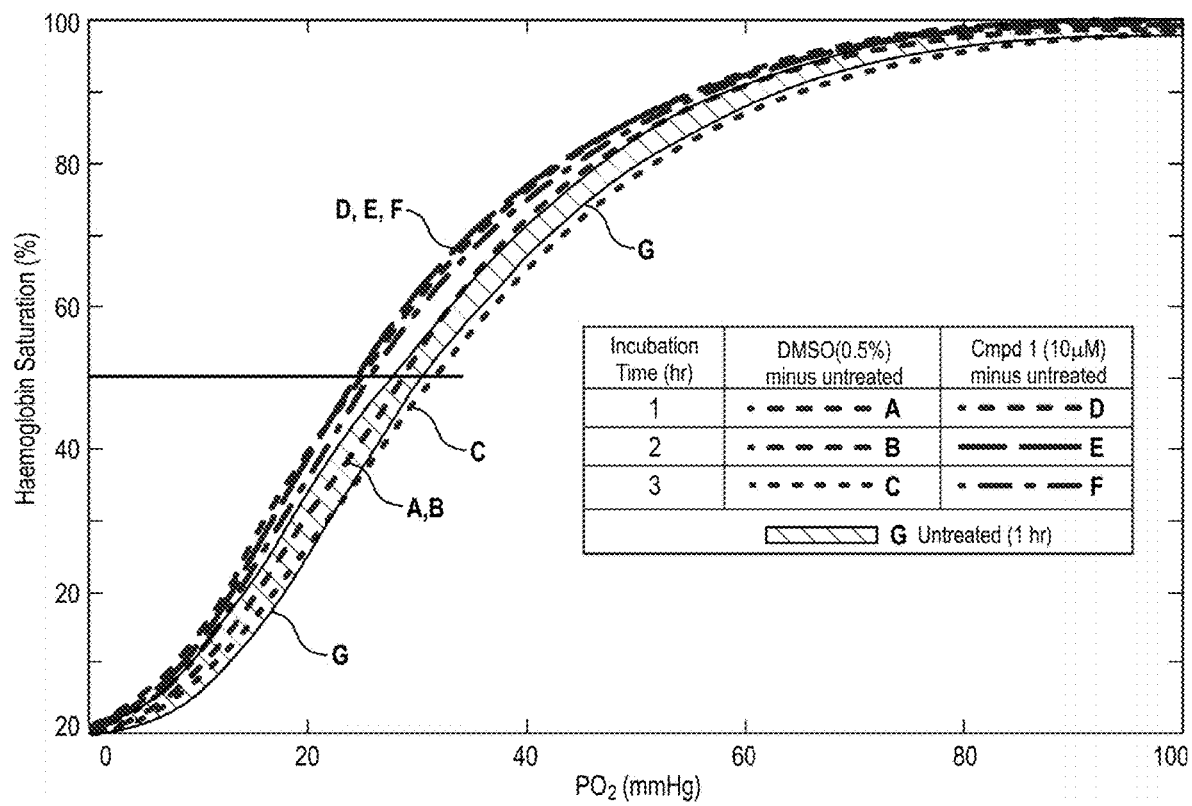

Hemoglobin saturation was shifted to the left in cells treated with Compound 1 and not in untreated or 0.5% DMSO-treated cells (FIGS. 12 and 13). The increased oxygen affinity corresponded to a significant (but limited) shift in p50 from 29 to 25 mmHg after 1 hr that was maintained until at least 3 hr, the last time point evaluated (Table 7). Notably, oxygen affinity in the first 2 hr of incubation was not affected by DMSO.

TABLE 7

Effect of Compound 1 on Hemoglobin Saturation[a]

| | Hemoglobin Saturation | | |
|---|---|---|---|
| Incubation Time (hr) | Untreated[b] | DMSO (0.5%) | Compound 1 (10 µM) |
| 1 | 1.18 | 1.18 | 1.05 |
| 2 | | 1.18 | 1.00 |
| 3 | | 1.30 | 1.02 |

[a]All values in Table 7 are normalized to 1.00, relative to the other values.
[b]Untreated cells are washed RBCs at 40% hematocrit in media without incubation.

Figure 14:
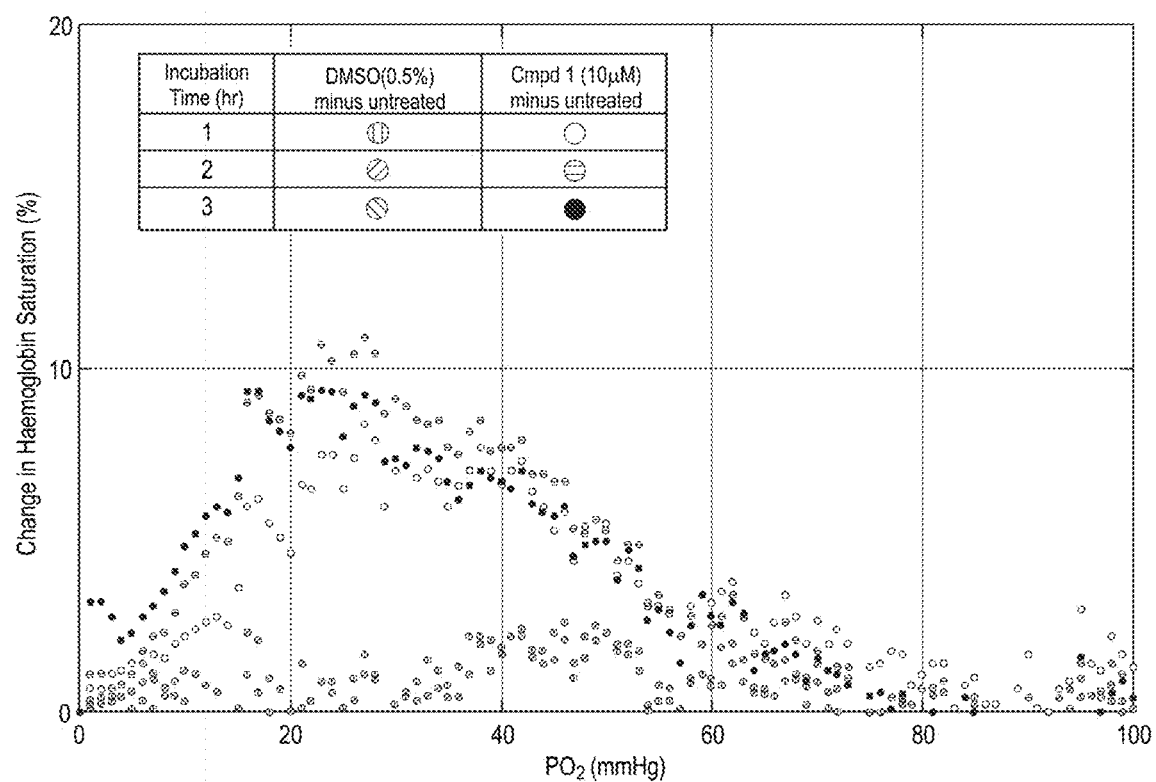
FIG. 14 is a graph of data showing delta curves of hemoglobin saturation at different oxygen tensions for red blood cells from SCD patients (Example 5). The measurement intervals are 1 mmHg.

At each $PO_2$, the average shift in Hgb saturation in the cells treated with Compound 1 was most pronounced around 25 mmHg, compared to a normal $PO_2$ of 26.7 mmHg (FIG. 14). Therefore, the shift in oxygen affinity occurred at oxygen tensions that are relevant for sickling. At 2 hr, Hgb saturation is approximately 10% higher compared to DMSO-treated cells. There is a clear difference between the cells treated with Compound 1 and those treated with DMSO at lower $PO_2$ (approximately 10 mmHg at 1% to 2% oxygen) even at 1 hr.

Figure 15:
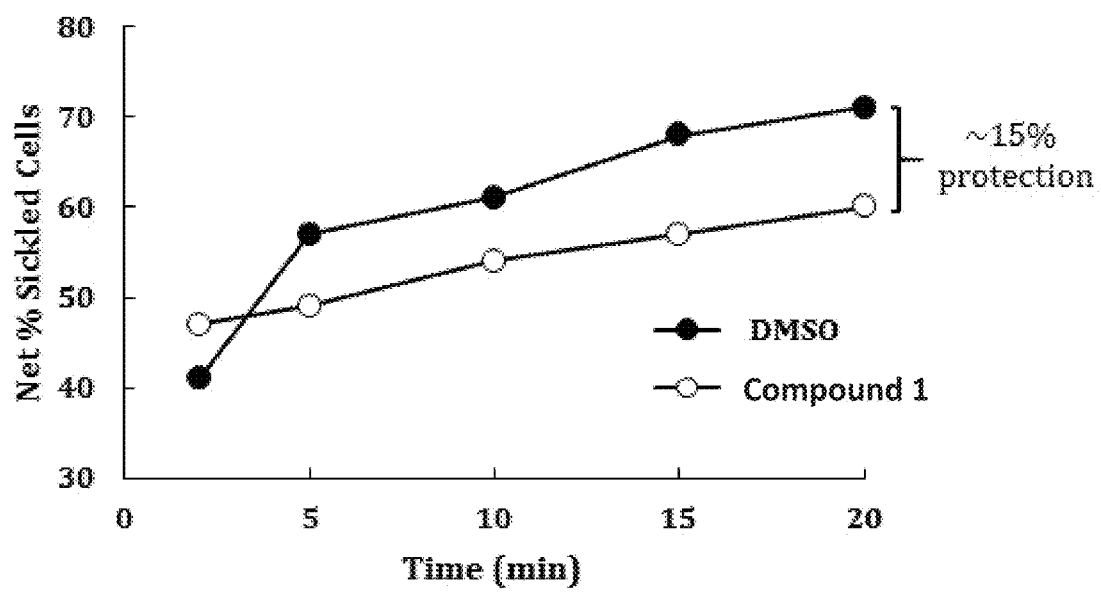
FIG. 15 is a graph of data showing an effect of Compound 1 on sickling of human SCD cells under hypoxic conditions (Example 5).

Compound 1 (10 µM) reduced cell sickling under severe hypoxic conditions of 2% oxygen ($PO_2$ of <20 mmHg) for up to 20 min (Table 8). The percent protection (i.e., the level of activity in treated cells, normalized to the level of activity in untreated cells after exposure to severe hypoxic conditions) reached a maximum of 16% at 15 min under hypoxic conditions (FIG. 15) and remained at 15% at the last time point measured.

TABLE 8

Effect of Compound 1 on Sickling of Human SCD Cells in Hypoxic Conditions

| Time in Hypoxic Conditions (min) | Net % of Sickled Cells | | % Protection |
|---|---|---|---|
| | DMSO (0.5%) | Compound 1 (10 µM) | |
| 0 | 7 | 10 | |
| 2 | 41 | 47 | −15 |
| 5 | 57 | 49 | 14 |
| 10 | 61 | 54 | 11 |
| 15 | 68 | 57 | 16 |
| 20 | 71 | 60 | 15 |

Figure 16:
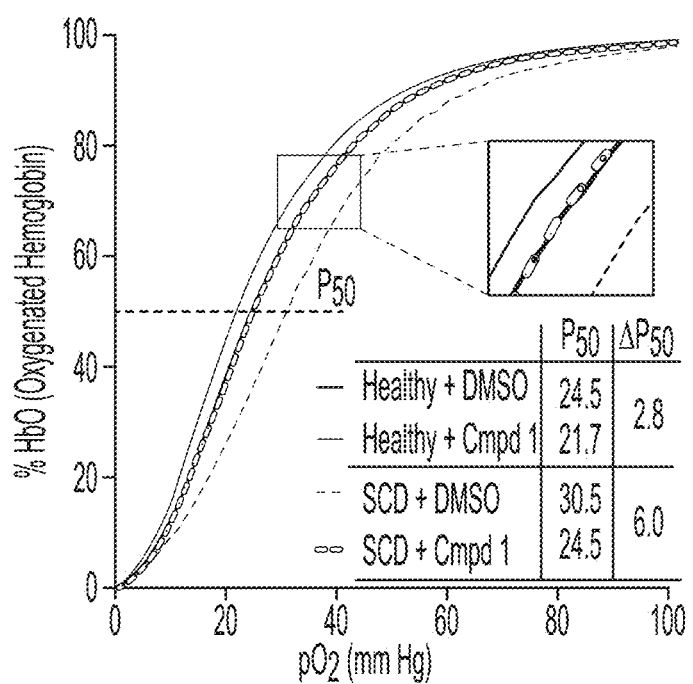
FIG. 16 is a graph showing the effect of Compound 1 on the oxygen affinity on RBCs from healthy donors and SCD donors.

Example 6: Increases in Hemoglobin Oxygen Affinity (p50) in Mixing Compound 1 in In Vitro Studies with RBCs From Healthy and SCD Donors As illustrated in FIG. 16, mixing Compound 1 with RBCs from healthy donors and SCD donors increases RBC oxygen affinity in HbA and HbS RBCs, respectively, as reflected by the leftward shift in the curves, which can be characterized by the oxygen level at which 50% of hemoglobin is oxygenated, or p50. In vitro incubation with Compound 1 increases oxygen affinity in HbA RBCs, consistent with clinical results in studies with healthy volunteers, and increases oxygen affinity in HbS RBCs, indicating that the PKR enzyme in sickle RBCs is also responsive to a PKR activator, and the resulting decrease in 2,3-DPG increases HbS-O2 affinity. The black and green curves represent healthy donors and the blue and dashed-red curves represent SCD donors. Reduction in p50 indicates an increase in hemoglobin affinity for oxygen. As illustrated in FIG. 16, Compound 1 normalizes the SCD oxygen affinity, resulting in overlap of the dashed-red Compound 1-treated SCD donor curve with the black, untreated healthy donor curve.

Example 7: Reduction of the Point of Sickling in SCD RBCs

Figure 17:
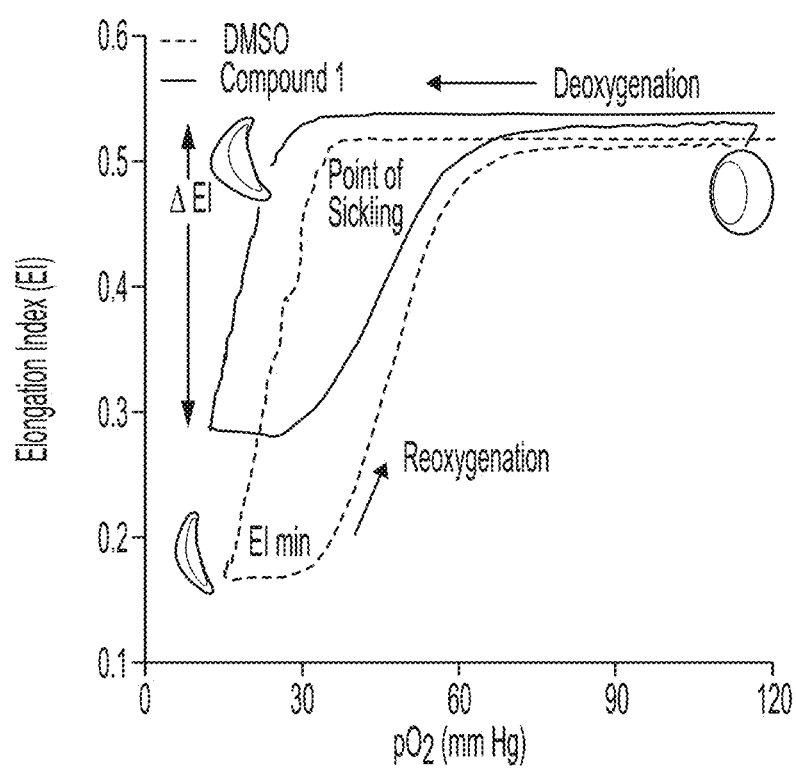
FIG. 17 is a graph showing the effect of Compound 1 on SCD RBC sickling.

The biologic consequences of increased PKR activation by Compound 1 in sickle RBCs is demonstrated in FIG. 17. We observed an effect of Compound 1 on SCD RBC sickling was measured by the deformability or elongation index, or EI, of the sickle RBC under decreasing (and then increasing) levels of oxygen and the Point of Sickling, or POS, defined as the pO2 concentration where a decrease in EI is observed. As shown in FIG. 17, comparison of the solid and dashed curves measuring pO2 concentration in the presence and absence of Compound 1, respectively, demonstrates that Compound 1 treatment improves RBC deformability at a lower oxygen tension suggesting that the Compound 1 treated sickle RBC can maintain a higher level of deformability as the RBCs transverse the microvasculature at lower oxygen levels.

Figure 18:
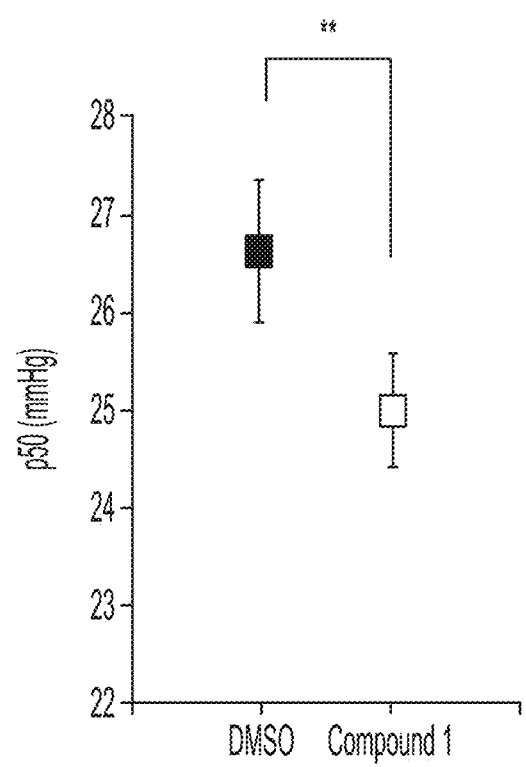
FIG. 18 is a graph showing the effect of Compound 1 on P50 in HbS RBCs.
Figure 19:
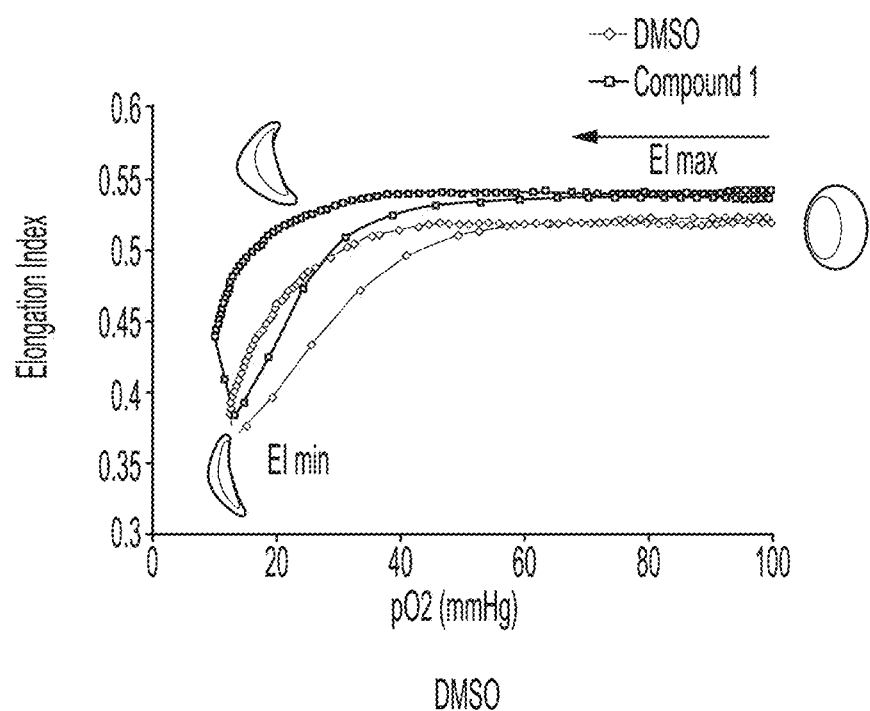
FIG. 19 is a graph showing the effect of Compound 1 on elongation index in HbS RBCs, as measured by oxygenscan.

FIGS. 18 and 19 provide further data demonstrating that Compound 1 improves deformability under de-oxygenation in vitro in HbS RBCs. As shown in FIG. 18, HbS RBCs treated with Compound 1 in vitro had a lower P50 than HbS RBCs treated with DMSO. As shown in FIG. 19, HbS RBCs treated with Compound 1 (20 µM) had a greater elongation index than HbS RBCs treated with DMSO, as measured by oxygenscan (oxygen gradient ektacytometry).

Example 8: A SAD/MAD Study to Assess the Safety, Pharmacokinetics, and Pharmacodynamics of Compound 1 in Healthy Volunteers and Sickle Cell Disease Patients Compound 1 is evaluated in a randomized, placebo-controlled, double blind, single ascending and multiple ascending dose study to assess the safety, pharmacokinetics, and pharmacodynamics of Compound 1 in healthy volunteers and sickle cell disease patients. The use of Compound 1 is disclosed herein for treatment of sickle cell disease in humans.

Figure 20:
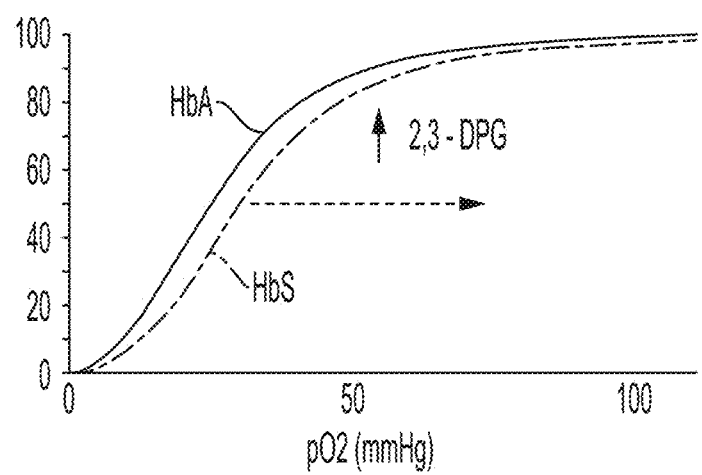
FIG. 20 is a graph demonstrating the 2,3-DPG and oxygen affinity of Hgb S RBCs in comparison to Hgb A RBCs.

The hallmark of sickle cell disease (SCD) is hemoglobin S (HbS) polymerization upon deoxygenation, resulting in red blood cell (RBC) sickling and subsequent oxidative/membrane damage, hemolysis, inflammation, cell adhesion, and vasoocclusions. Exacerbating the pathogenesis of SCD, the HbS RBC has 1) increased 2,3-DPG with decreased oxygen affinity (increased p50) (see FIG. 20); and 2) decreased RBC ATP. Indeed, sickle RBCs contain more 2,3-DPG than healthy RBCs, resulting in decreased hemoglobin $O_2$ affinity (i.e., increased p50) and early release of O2 (leading to deoxygenation of HbS, polymerization, and sickling). Sickle RBCs also have insufficient energy (i.e., less ATP than normal RBCs) for membrane maintenance and repair, contributing to hemolysis and reduced RBC lifespan. Compound 1 is a novel, small molecule allosteric activator of erythrocyte pyruvate kinase (PKR) and functions as an RBC metabolic modulator causing decreased 2,3-DPG and increased ATP levels in RBC. Compound 1 is an oral activator of the Pyruvate Kinase R (PKR) that decreases 2,3-DPG and increases ATP in erythrocytes. As shown in FIG. 4, (1) the reduction in 2,3-DPG may result in an increase in O2 affinity of HbS, thereby reducing HbS polymerization and RBC sickling; and (2) the increase in ATP production may improve sickle RBC repair and membrane health, reducing hemolysis. Thus, the multimodal action of Compound 1 may improve hemoglobin levels and reduce the rate of vaso-occlusion in patients with SCD. In preclinical safety studies, Compound 1 had no effect on steroidogenesis, demonstrated low risk of drug-to-drug interactions, and was well tolerated in vivo at the maximum doses administered. A first-in-human Phase 1 study evaluating Compound 1 in healthy subjects (HS) and subjects with SCD has been initiated. The aims of this study are to evaluate the safety and PK/PD of Compound 1 in HS and subjects with SCD.

Figure 21:
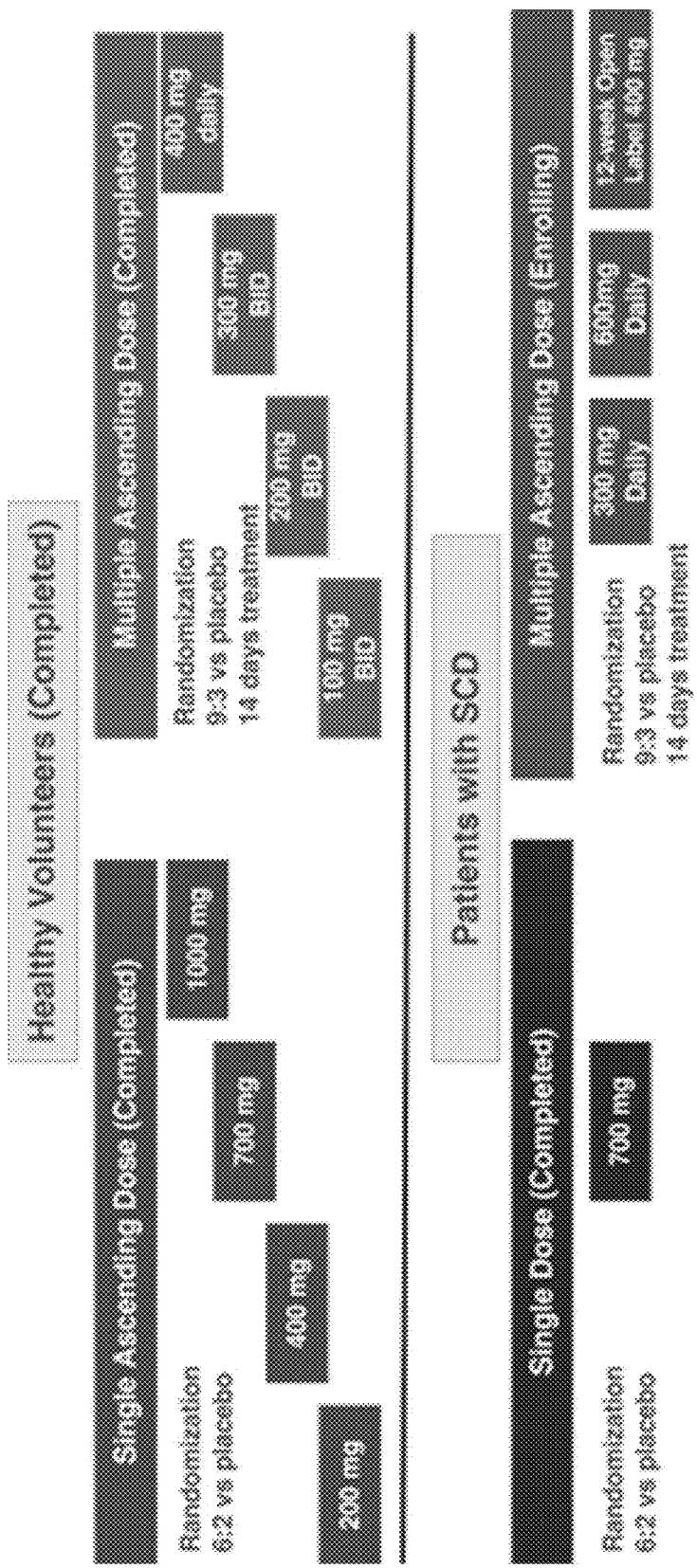
FIG. 21 is a summary of a SAD/MAD trial to assess the safety and PK/PD of Compound 1.

As illustrated in FIG. 21, the trial to assess the safety and PK/PD of Compound 1 is a randomized, placebo-controlled, double blind, single dose and MAD trial in healthy adult volunteers and a single dose and MAD trial in adolescent or adult patients with SCD. The trial also includes a 12-week dosing cohort in which up to 20 SCD patients will each receive up to 84 consecutive daily doses of Compound 1.

Compound 1 is an oral small-molecule agonist of pyruvate kinase red blood cell isozyme (PKR) being developed for the treatment of hemolytic anemias. This human clinical trial study will characterize the safety, tolerability and the pharmacokinetics/pharmacodynamics (PK/PD) of a single ascending dose and multiple ascending doses of Compound 1 in the context of phase 1 studies in healthy volunteers and sickle cell disease patients. The effects of food on the absorption of Compound 1 will also be evaluated, in healthy volunteers.

The objectives of the study include the following:
1. To evaluate the safety and tolerability of a single ascending dose and multiple ascending doses of Compound 1 in healthy volunteers and sickle cell disease (SCD) patients.
2. To characterize the pharmacokinetics (PK) of Compound 1.
3. To evaluate the levels of 2,3-diphosphoglycerate (DPG) and adenosine triphosphate (ATP) in the red blood cells (RBCs) of healthy volunteers and SCD patients after single and multiple doses of Compound 1.
4. To evaluate the relationship between Compound 1 plasma concentration and potential effects on the QT interval in healthy volunteers.
5. To evaluate the effect of single ascending doses of Compound 1 on other electrocardiogram (ECG) parameters (heart rate, PR and QRS interval and T-wave morphology) in healthy volunteers.
6. To explore food effects on the PK of Compound 1 in healthy volunteers.
7. To explore the association of Compound 1 exposure and response variables (such as safety, pharmacodynamics (PD), hematologic parameters as appropriate).
8. To explore effects of Compound 1 after single and multiple doses on RBC function.
9. To explore effects of Compound 1 after multiple doses in SCD patients on RBC metabolism, inflammation and coagulation.
10. To explore effects of Compound 1 on RBC hemoglobin-$O_2$ affinity and membrane mechanics.

This is a first-in-human (FIH), Phase 1 study of Compound 1 that will characterize the safety, PK, and PD of Compound 1 after a single dose and after repeated dosing first in healthy adult volunteers and then in adolescents or adults with sickle cell disease. The study arms and assigned interventions to be employed in the study are summarized in Table 9. Initially, a dose range of Compound 1 in single ascending dose (SAD) escalation cohorts will be explored in healthy subjects. Enrollment of healthy subjects into 2-week multiple ascending dose (MAD) escalation cohorts will be initiated once the safety and PK from at least two SAD cohorts is available to inform the doses for the 2-week MAD portion of the study. The MAD cohorts will then run in parallel to the single dose cohorts. A single dose cohort is planned to understand food effects (FE) on the PK of Compound 1. After the SAD and FE studies in healthy subjects are completed, the safety, PK and PD of a single dose of Compound 1 that was found to be safe in healthy subjects will then be evaluated in sickle cell disease (SCD) subjects. Multiple dose studies in SCD subjects will then be initiated upon completion of MAD studies in healthy volunteers. Compound 1 will be administered in 25 mg and 100 mg tablets delivered orally, prepared as described in Example 1, Step 7.

In this study, SAD/MAD cohorts are randomized (3 to 1) to receive Compound 1 or placebo (P). Compound 1 was evaluated first in 4 healthy SAD cohorts and 4 healthy MAD (14-day dosing period) cohorts. Based on the safety, and PK/PD profile from HS, Compound 1 is then evaluated in 1 SCD SAD cohort and 2 SCD MAD cohorts. Specifically, based on the safety and pharmacokinetic/pharmacodynamics (PK/PD) profile in healthy volunteer studies, Compound 1 is evaluated in patients (pts) with SCD, first in a single dose (SD or SAD) cohort and then in multiple-dose (MD or MAD) cohorts (14-day and 12-week). Safety assessments include AEs, vital signs, ECGs and laboratory parameters. PK/PD blood sampling was performed on Day 1 (SAD/MAD) and Day 14 (MAD) and up to 72 h after the last dose and at the end-of-study visit. PD parameters included 2,3-DPG, ATP, and p50 in all cohorts with additional PD studies (including oxygen scan) performed only in the SCD cohorts. PD parameters included 2,3-DPG, ATP, p50, RBC deformability with controlled deoxygenation and reoxygenation (Lorrca® oxygen scan) and varying osmolality (Lorrca® osmoscan)). To maintain study blind, pt identifiers were removed when needed.

TABLE 9

| Arms | Assigned Interventions |
|---|---|
| Experimental: Single ascending dose cohorts in healthy subjects Healthy volunteer subject cohorts randomized 6:2 receiving a single dose of Compound 1 or placebo. After an overnight fast (minimum of 8 hours), Compound 1/placebo will be administered orally (Day 1) with nothing to eat for at least 4 hr post Compound 1/placebo. The first cohort will receive 200 mg of Compound 1 or placebo. Dose escalation will occur if Compound 1 or placebo is tolerated. The maximum dose of Compound 1 or placebo will be 1500 mg. Planned doses for the SAD cohorts are listed in Table 10. | Drug: Compound 1/Placebo Healthy volunteer subjects will receive Compound 1/placebo and be monitored for side effects while undergoing pharmacokinetics and pharmacodynamic studies |
| Experimental: Multiple ascending dose cohorts in healthy subjects Healthy volunteer subject cohorts randomized 9:3 to receive Compound 1 or placebo for 14 days continuous dosing. The first cohort will receive 100 mg of Compound 1 or placebo daily × 14 days. Alternatively, the first cohort will receive 200 mg (e.g., 100 mg BID or 200 mg QD) of Compound 1 or placebo daily × 14 days. Subjects will be required to fast for a minimum of 1 hour prior to and a minimum of 2 hours after morning (and evening on a BID schedule) dosing of Compound 1/placebo. The maximum dose of Compound 1/placebo will be 600 mg Compound 1/placebo daily for 14 days. Planned doses for the MAD cohorts are listed in Table 11. | Drug: Compound 1/Placebo Healthy volunteer subjects will receive Compound 1/placebo and be monitored for side effects while undergoing pharmacokinetics and pharmacodynamic studies |
| Experimental: Food Effect Cohort in healthy subjects Healthy Volunteer subject cohort of 10 subjects who will receive a single dose of Compound 1 with food and without food, e.g., after an overnight fast of at least 8 hours, Compound 1 will be administered following a high-fat meal (fed conditions, n = 5) or with no food or drink before or within 4 hours after dose administration (fasting conditions, n = 5), followed by crossover Compound 1 dosing after a sufficient washout period (at least 8 days). Dose will be administered per the protocol defined dose. Healthy Volunteer subject cohort of 10 subjects who will receive a | Drug: Compound 1 Healthy subjects will receive Compound 1 with or without food and undergo pharmacokinetic studies |

TABLE 9-continued

| Arms | Assigned Interventions |
|---|---|
| single dose of Compound 1 with food and without food. Dose will be 400 mg or 500 mg of Compound 1, but is subject to change based on the pharmacokinetic profile of Compound 1 observed in the initial SAD cohorts and the safety profile of Compound 1 observed in prior SAD and MAD cohorts. | |
| Experimental: Single ascending dose cohorts in SCD subjects<br>Sickle cell disease subject cohort randomized 5:2 or 6:2 receiving a single dose of Compound 1 or placebo. Subjects will be asked to forego a meal or will need to wait a minimum of 1 hour after completion of their meal before Compound 1/placebo is administered orally, and will be directed to not eat for at least 2 hours post Compound 1/placebo. The dose of Compound 1/placebo administered will be a dose that was found to be safe in healthy subjects. The dose of Compound 1/placebo administered also will be a dose that was found to be pharmacodynamically active (e.g., results in a reduction in 2,3-DPG) in healthy subjects.<br>One single dose cohort in SCD patients is planned to evaluate the safety and PK/PD of Compound 1 within the dose range of Compound 1 previously demonstrated to be tolerable in the healthy subject SAD cohorts, with a minimum of eight SCD patients to be randomly assigned to receive one dose of Compound 1 700 mg (n = 6) or 1 dose of placebo (n = 2). | Drug: Compound 1/Placebo<br>SCD subjects will receive Compound 1/placebo and be monitored for side effects while undergoing pharmacokinetic and pharmacodynamics studies |
| Experimental: Multiple ascending dose cohorts in SCD subjects<br>Sickle cell disease subject cohorts block randomized 7:2 or 9:3 to receive Compound 1 or placebo for 14 days continuous dosing. The dose of Compound 1/placebo administered will be a dose less than maximum tolerable dose evaluated in MAD healthy volunteers. The dose of Compound 1/placebo also will be a dose that was found to be pharmacodynamically active (e.g., results in a reduction in RBC 2,3-DPG and increase in RBC ATP) in MAD healthy volunteers.<br>Up to two MAD cohorts in SCD patients are planned, with 12 patients per cohort to be screened, enrolled and randomly assigned to receive 14 consecutive daily doses of Compound 1 (n = 9) or placebo (n = 3). Alternatively, the up to two MAD cohorts in SCD patients may have 9-12 patients per cohort to be screened, enrolled and randomly assigned to receive 14 consecutive daily doses of Compound 1 (7:2 or 9:3 vs. placebo). The initial daily dose of Compound 1 300 mg for 14 days to be evaluated in SCD patients was selected from the daily dose range of Compound 1 evaluated in the healthy adult volunteers that was found to be tolerable and pharmacodynamically active. If the safety results of the first MAD dose are acceptable and the PK/PD data are supportive, patients may be dosed with an additional daily dose of Compound 1 for 14 days. The additional daily dose may be 600 mg daily (n = 9-12, block randomized 7:2 or 9:3 vs. placebo). The duration of Compound 1/placebo dosing may increase up to 48 hours longer (e.g., through Day 16) to enable a 2-day | Drug: Compound 1/Placebo<br>SCD subjects will receive Compound 1/placebo and be monitored for side effects while undergoing pharmacokinetic and pharmacodynamics studies |

TABLE 9-continued

| Arms | Assigned Interventions |
|---|---|
| taper (~50% reduction in Compound 1 each day) of Compound 1/placebo in subjects who have demonstrated >2.0 g/dL increase in hemoglobin over baseline. | |
| Experimental: 12-week dosing cohort in SCD subjects<br>Sickle cell disease subjects cohort (n = up to 20, e.g., n = 12-20) to receive up to 84 consecutive daily doses of open-label Compound 1. The dose of Compound 1 administered will not exceed the highest dose evaluated in the MAD SCD subject cohorts. The dose of Compound 1 may be 400 mg daily.<br>The duration of Compound 1 dosing may increase up to 48 hours longer (e.g., through Day 86) to enable a 2-day taper (~50% reduction in Compound 1 each day) of Compound 1 in subjects who have demonstrated >2.0 g/dL increase in hemoglobin over baseline. | Drug: Compound 1<br>SCD subjects will receive Compound 1 and be monitored for side effects while undergoing pharmacokinetics and pharmacodynamics studies |

TABLE 10

| Dose Level/Cohort | Dose | Tablet Strength (#/day) |
|---|---|---|
| SAD 1 | 200 mg | 100 mg (2/day) |
| SAD 2 | 400 mg | 100 mg (4/day) |
| SAD 3 | 700 mg | 100 mg (7/day) |
| SAD 4 | 1100 mg | 100 mg (11/day) |
| SAD 5 | 1500 mg | 100 mg (15/day) |

TABLE 11

| Dose Level/Cohort | Dose | Tablet Strength (#/day) |
|---|---|---|
| MAD 1 | 100 mg | 100 mg (1/day) or 25 mg (4/day) |
| MAD 2 | 200 mg | 100 mg (2/day) |
| MAD 3 | 400 mg | 100 mg (4/day) |
| MAD 4 | 600 mg | 100 mg (6/day) |

Outcome Measures
Primary Outcome Measures:
1. Incidence, frequency, and severity of adverse events (AEs) per CTCAE v5.0 of a single ascending dose and multiple ascending doses of Compound 1 in adult healthy volunteers and SCD patients. Incidence of abnormal laboratory test results (clinical chemistry, endocrine hematology, urinalysis). Change from baseline in vital signs (blood pressure, respiratory rate, heart rate, and oral temperature). Incidence of treatment-emergent clinically significant abnormal findings in ECGs.
[Time Frame: Up to 3 weeks of monitoring]
2. Maximum observed plasma concentration (Cmax)
[Time Frame: Up to 3 weeks of testing]
3. Time to maximum observed plasma concentration (Tmax)
[Time Frame: Up to 3 weeks of testing]
4. Area under the plasma concentration-time curve from time zero until the 24-hour time point (AUC0-24)
[Time Frame: Up to 3 weeks of testing]
5. Area under the plasma concentration-time curve from time zero until last quantifiable time point (AUC0-last)
[Time Frame: Up to 3 weeks of testing]
6. Area under the plasma concentration-time curve from time zero to infinity (AUC0-inf)
[Time Frame: Up to 3 weeks of testing]
7. Terminal elimination half-life (t1/2)
[Time Frame: Up to 3 weeks of testing]
8. Apparent clearance (CL/F)
[Time Frame: Up to 3 weeks of testing]
9. Apparent volume of distribution (Vd/F)
[Time Frame: Up to 3 weeks of testing]
10. Terminal disposition rate constant (Lz)
[Time Frame: Up to 3 weeks of testing]
11. Renal clearance (CIR)
[Time Frame: Up to 3 weeks of testing]
Secondary Outcome Measures:
12. Change from baseline in the levels of 2,3-diphosphoglycerate (DPG) and adenosine triphosphate (ATP) in the red blood cells (RBCs) of healthy volunteers and SCD patients after single and multiple doses of Compound 1.
[Time Frame: Up to 3 weeks of testing]
13. Model-based estimate of change from baseline QT interval corrected using Fridericia's correction formula (QTcF) and 90% confidence interval at the estimated Cmax after a single dose of Compound 1 in healthy volunteers and/or SCD subjects.
[Time Frame: up to 7 days]
14. Change from baseline heart rate after a single dose of Compound 1 in healthy volunteers and/or SCD subjects
[Time Frame: up to 7 days]
15. Change from baseline PR after a single dose of Compound 1 in healthy volunteers and/or SCD subjects
[Time Frame: up to 7 days]
16. Change from baseline QRS (AHR, APR, and AQRS) after a single dose of Compound 1 in healthy volunteers and/or SCD subjects
[Time Frame: up to 7 days]
17. Change from baseline T-wave morphology after a single dose of Compound 1 in healthy volunteers and/or SCD subjects
[Time Frame: up to 7 days]

Exploratory Outcome Measures:
18. Effect of food on $C_{max}$, $AUC_{0-24}/AUC_{last}$
19. Effect of $AUC_{last}/AUC_{0-24}$, $C_{max}$, minimum plasma concentration ($C_{min}$), peak-to trough ratio, dose linearity, accumulation ratio on safety, PD, and hematologic parameters of interest, as assessed by exposure-response analyses
20. Effect of 2,3-DPG reduction in RBCs on the oxyhemoglobin dissociation curve (p50; partial pressure of $O_2$ at which 50% of hemoglobin is saturated with $O_2$) after a single dose and after chronic dosing of Compound 1
21. Effect of chronic Compound 1 dosing on normal and SCD RBC deformability by osmotic gradient ektacytometry and oxygen gradient ektacytometry
22. Effect of chronic Compound 1 dosing on SCD RBC response to oxidative stress in SCD Patients (including evaluation of glutathione, glutathione peroxidase and superoxide dismutase levels)
23. Effect of chronic Compound 1 dosing on measurable markers of inflammation in SCD Patients (C-reactive protein, ferritin, interleukin [IL]-β, IL-6, IL-8, and tumor necrosis factor-α)
24. Effects of chronic Compound 1 dosing on measurable markers of hypercoagulation in SCD patients (D-dimer, prothrombin 1.2, and thrombin-antithrombin [TAT] complexes)

Red Blood Cell Function

Functional evaluation of RBCs was performed using Laser-Optical Rotational Red Cell Analyzer (Lorrca®) technology (RR Mechatronics, Zwaag, The Netherlands). Osmoscan was performed for healthy subjects, and both Oxygenscan and Osmoscan analyses were undertaken for the patients with SCD. In brief, the Oxygenscan allows for the measurement and visualisation of RBC elongation in shear stress in an oxygen gradient, during deoxygenation and re-oxygenation, expressed as the elongation index (EI). The Oxygenscan measures (i) the RBC deformability when RBCs are fully oxygenated (maximum elongation index, $EI_{max}$), (ii) the point of sickling (PoS), which is defined as the oxygen pressure at which a 5% decrease in $EI_{max}$ is noted as the RBCs start to sickle and become rigid during deoxygenation, and (iii) the minimum RBC deformability achieved during deoxygenation ($EI_{min}$). These parameters provide an objective biomarker of disease severity and response to treatment. The Osmoscan measures RBC deformability under an osmotic gradient, providing information about the cells' deformability, osmotic fragility, and intracellular viscosity, depending on both the shape of the ektacytometry curve and the position on the osmolality axis. Evaluated Osmoscan parameters included: $EI_{max}$; $O_{min}$ (osmolality at $EL_{max}$; hypotonic region), which corresponds to the value of the hypotonic osmolality at which 50% of the cells hemolyse in an osmotic fragility assay and provides information on the initial surface-to-volume ratio of the RBCs; and $O_{hyper}$ (osmolality corresponding to 50% of the $EI_{max}$; hypertonic region), which correlates with the initial intracellular viscosity of the cell sample. A shift to the left reflects increased intracellular viscosity of the erythrocyte caused by increased intracellular concentration of Hb, typically due to dehydration of the cell.

Eligibility
    Minimum age: 18 Years (healthy volunteers); 12 Years (SCD subjects)
    Maximum age: 60 or 65 Years
    Sex: All
    Gender Based: No
    Accepts Healthy Volunteers: Yes Inclusion Criteria:
    Healthy volunteer: subjects must be between 18 and 60 years of age; SCD: subjects must be between 12 and 50 or 65 years of age
    Subjects must have the ability to understand and sign written informed consent, which must be obtained prior to any study-related procedures being completed.
    Subjects must have no active infection with hepatitis B (HBV, e.g., demonstrated by a negative test result for hepatitis B surface antigen (HBsAg)), hepatitis C (HCV, e.g., demonstrated by a negative test for either hepatitis C virus antibody (HCVAb) or hepatitis C viral load testing (e.g., <100 IU/mL)), and human immunodeficiency virus (HIV, e.g., demonstrated by a negative test for HIV antibody).
    Healthy volunteer: Subjects must be in general good health, based upon the results of medical history, a physical examination, vital signs, laboratory profile, and a 12-lead ECG; SCD: Previously diagnosed sickle cell disease (hemoglobin electrophoresis or genotype).
    Subjects must have a body mass index (BMI) within the range of 18 kg/m2 to 33 kg/m$^2$ (inclusive) and a minimum body weight of 50 kg (healthy volunteer subjects) or 40 kg (SCD subjects)
    For SCD subjects, sickle cell disease previously confirmed by hemoglobin electrophoresis or genotyping indicating one of the following hemoglobin genotypes: Hgb SS, Hgb Sβ$^+$-thalassemia, Hgb Sβ$^0$-thalassemia, or Hgb SC
    All males and females of child bearing potential must agree to use medically accepted contraceptive regimen during study participation and for 90 days after last study drug administration.
    Subjects must be willing to abide by all study requirements and restrictions.

Exclusion Criteria (Healthy Volunteers):
    Evidence of clinically significant medical condition or other condition that might significantly interfere with the absorption, distribution, metabolism, or excretion of study drug, or place the subject at an unacceptable risk as a participant in this study
    History of clinically significant cardiac diseases including condition disturbances
    Abnormal hematologic, renal and liver function studies
    History of drug or alcohol abuse
    History of gastrointestinal (GI) surgery or resection that would potentially alter absorption and/or excretion of orally administered drugs, with the exception of appendectomy
    History of malignancy within previous 5 years (other than successfully treated basal cell or squamous cell skin cancer, or carcinoma-in-situ of the cervix)
    History of clinically significant arrhythmia, left or right bundle branch block, 2nd or 3rd degree atrioventricular (AV) block, pacemaker or implantable cardioverter-defibrillator
    Abnormal and clinically significant 12-lead ECG, including QT interval corrected for heart rate according to Fridericia's formula (QTcF) >450 ms, QRS interval≥120 ms, PR interval >220 ms, based on average of triplicated ECG
    Systolic blood pressure <90 or >150 mmHg (or >95$^{th}$ percentile for age) or diastolic blood pressure <50 or >95 mmHg (or >95$^{th}$ percentile for age)
    A family history of QT prolongation or sudden cardiac death History of severe allergic reaction (including anaphylaxis) to any substance, or previous status asthmaticus Has had an acute illness considered clinically significant within 14 days prior to the study drug administration;

History of alcohol abuse or dependence within one year prior or regular use of alcohol within 6 months prior (more than 14 units of alcohol per week; one unit =150 mL wine, 360 mL beer or 45 mL of 40% alcohol)

Has used any product containing nicotine within 90 days prior or intends to use any product containing nicotine during the course of the study Use of a prohibited prescription or non-prescription drugs and dietary supplements (including herbal and alternative medications)

Has received an investigational drug (including vaccines) within five times the elimination half-life (if known) or within 30 days (if the elimination half-life is unknown) prior to first drug administration or is concurrently enrolled in any research judged not to be scientifically or medically compatible with this study History of allergy or hypersensitivity to Compound 1 or excipients Subject has a history of chronic skin conditions including psoriasis, eczema or any recurring rash/dermatitis requiring oral or topical corticosteroids or chronic skin softeners within 12 months prior Is not willing to avoid extensive sun exposure, phototherapy or use of tanning beds during the study until at least 3 weeks after last study drug administration Difficulty with venous access or unsuitable or unwilling to undergo intravenous catheter insertion Has lost or donated >450 mL (or >10 mL/kg if <18 yrs) of whole blood or blood products within 30 days prior to study drug administration Investigator has reason to believe that the subject may be unable to fulfill the protocol visit schedule or requirements Has any finding that, in the view of the Investigator, would compromise the subject's safety requirements Evidence of clinically significant (or undergoing active medical treatment) hematologic, renal, endocrine, pulmonary, cardiac, GI, hepatic, psychiatric, neurologic, immunologic, allergic disease (including multiple or clinically significant drug allergies), or any other condition that, in the opinion of the Investigator, might significantly interfere with the absorption, distribution, metabolism, or excretion of study drug, or place the subject at an unacceptable risk as a participant in this study Laboratory results (serum chemistry, hematology, coagulation, and urinalysis) outside the normal range at the Screening Visit and first period Check-in that are considered clinically significant in the opinion of the Investigator Any elevation of aspartate aminotransferase and alanine aminotransferase >1.5× the upper limit of normal (ULN), and bilirubin greater than ULN at the Screening Visit and first period check-in is exclusionary Platelet count, absolute neutrophil count, absolute lymphocyte count, and hemoglobin level above or below the limit of normal, at Screening or first Check-in Exclusion Criteria (SCD Subjects):

Had more than 6 episodes of vaso-occlusive crisis (VOC) within the past 12 months that required a hospital, emergency room, or clinic visit Had at least one episode of acute chest syndrome in the last 6 months Received any of the following approved therapies for use in SCD:
Hydroxyurea (HU): excluded if started HU <90 days prior to Day 1 of study treatment
crizanlizumab: excluded if received an infusion within 14 days prior to Day 1 of study treatment
voxelotor: excluded if received a dose within 7 days prior to start of Day 1 of study treatment Received a red blood cell transfusion within 30 days of starting the study drug Hemoglobin <7.0 g/dL or >10.5 g/dL Unable to take and absorb oral medications History of gastrointestinal (GI) surgery or resection that would potentially alter absorption and/or excretion of orally administered drugs, with the exception of appendectomy History of malignancy within previous 5 years (other than successfully treated basal cell or squamous cell skin cancer, or carcinoma-in-situ of the cervix)

History of clinically significant arrhythmia, left or right bundle branch block, 2nd or 3rd degree atrioventricular (AV) block, pacemaker or implantable cardioverter-defibrillator Abnormal and clinically significant 12-lead ECG, including QT interval corrected for heart rate according to Fridericia's formula (QTcF) >450 ms, QRS interval ≥120 ms, PR interval >220 ms, based on average of triplicated ECG Systolic blood pressure <90 or >150 mmHg (or >95$^{th}$ percentile for age) or diastolic blood pressure <50 or >95 mmHg (or >95$^{th}$ percentile for age)

A family history of QT prolongation or sudden cardiac death

History of severe allergic reaction (including anaphylaxis) to any substance, or previous status asthmaticus Has had an acute illness considered clinically significant within 14 days prior to the study drug administration History of alcohol abuse or dependence within one year prior or regular use of alcohol within 6 months prior (more than 14 units of alcohol per week; one unit =150 mL wine, 360 mL beer or 45 mL of 40% alcohol)

Use of a prohibited prescription or non-prescription drugs and dietary supplements (including herbal and alternative medications)

Has received an investigational drug (including vaccines) within five times the elimination half-life (if known) or within 30 days (if the elimination half-life is unknown) prior to first drug administration or is concurrently enrolled in any research judged not to be scientifically or medically compatible with this study History of allergy or hypersensitivity to Compound 1 or excipients Subject has a history of chronic skin conditions including psoriasis, eczema or any recurring rash/dermatitis requiring oral or topical corticosteroids or chronic skin softeners within 12 months prior Difficulty with venous access or unsuitable or unwilling to undergo intravenous catheter insertion Has lost or donated >450 mL (or >10 mL/kg if <18 yrs) of whole blood or blood products within 30 days prior to study drug administration Investigator has reason to believe that the subject may be unable to fulfill the protocol visit schedule or requirements;

Has any finding that, in the view of the Investigator, would compromise the subject's safety requirements Evidence of clinically significant endocrine, hepatic, psychiatric, neurologic, immunologic, allergic disease (including multiple or clinically significant drug allergies), or any other condition that, in the opinion of the Investigator, might significantly interfere with the absorption, distribution, metabolism, or excretion of study drug, or place the subject at an unacceptable risk as a participant in this study Have had >6 episodes of vaso-occlusive crisis (VOC) within the past 12 months that required a hospital, emergency room or clinic visit Hospitalized for sickle cell crisis or other vaso-occlusive event within 14 days of signing the ICF or within 28 days prior to Day 1 of study treatment (i.e., subjects with a vaso-occlusive event must wait at least 14 days before signing an ICF and screening period must be at least 14 days before Day 1 of study treatment)

History of at least one episode of acute chest syndrome that required hospitalization, intubation and mechanical support within 6 months prior History of documented pulmonary arterial hypertension Has received any of the following approved therapies for use in sickle cell disease:

Hydroxurea (HU): subjects are excluded if started HU<90 days prior to Day 1 of study treatment crizanlizumab: subjects are excluded if received an infusion within 14 days prior to Day 1 of study treatment (subjects are allowed to participate if receiving infusion therapy ≥every 4 weeks while on study treatment)

voxelotor: subjects are excluded if received a dose within 7 days prior to start of Day 1 of study treatment (subjects are NOT allowed to continue to participate if receiving this therapy while on study treatment)

Note: No restrictions are in place for SCD subjects receiving L-glutamine (e.g., Endari®) prior to or during study participation Receiving or use of concomitant medications that are moderate or strong inducers or inhibitors of CYP 3A4/5 within 2 weeks of starting study treatment Received a red blood cell transfusion (simple or exchange) within 30 days of Day 1 of study drug administration Hemoglobin (Hgb) <7.0 g/dL or >10.5 g/dL during screening Hepatic dysfunction characterized by alanine aminotransferase (ALT) >3×ULN Severe renal dysfunction (estimated glomerular filtration rate at the Screening visit; calculated by laboratory results) <30 mL/min/1.73 m◯2 or on chronic dialysis Results (Healthy Subjects)

At least 90 healthy volunteers have received Compound 1 (n=70) or placebo (n=20) in the Phase 1 trial, comprising 32 subjects in the SAD cohorts (Compound 1, n=24; placebo, n=8), 48 in the MAD cohorts (Compound 1, n=36; placebo, n=12), and ten in the food-effect cohort. Eight SCD patients have received blinded trial drug or placebo as part of the single dose trial cohort (n=7) or as part of the first 14-day dose MAD 1) cohort (n=1). To date, Compound 1 has demonstrated a promising tolerability profile and time independent PK profile.

Compound 1 has been evaluated in the HS SAD/MAD/Food Effect cohorts (n=90) and in the SCD SAD cohort (n=6). In HS studies, Compound 1 was well tolerated and exhibited a favorable safety profile, with Grade 1 headache as the most common AE reported in HS receiving a single dose (4%) or 14 days (28%) of Compound 1 and in 1/6 SCD subjects receiving Compound 1/P (blinded). The PK profile of Compound 1 was similar in HS and SCD subjects. Compound 1 was rapidly absorbed with a median Tmax of 1 h postdose, a T1/2 of ~10-13 h, and an AUC0-24 ~7000 h·ng/mL. No effect on testosterone or estradiol levels was observed in healthy subjects.

In the HS studies, Compound 1 exhibited linear and time-independent PK, and the PD activity of Compound 1 was observed at all dose levels after 24 h (decreased 2,3-DPG, $p<0.0001$) and after 14-days (increased ATP, $p<0.0001$) of dosing. The biologic consequence of this PD response was an increase in oxygen affinity (decreased p50, $p<0.0001$) within 24 h of Compound 1 dosing and a decrease in absolute reticulocyte counts ($p<0.0001$) with a slight increase in hemoglobin levels (ns) by Day 4 of the dosing period in all Compound 1 dose cohorts.

Four healthy SAD cohorts were evaluated at doses of 200, 400, 700, and 1000 mg, and four healthy MAD cohorts received 200 to 600 mg total daily doses for 14 days at QD or BID dosing (100 mg BID, 200 mg BID, 300 mg BID, and 400 mg QD). In the food effect (FE) cohort, 10 healthy subjects received 400 mg of Compound 1 QD with and without food.

Demographics and baseline characteristics of the healthy volunteers in the SAD and MAD cohorts are provided in Table 12.

TABLE 12

Demographics and Baseline Characteristics

| Characteristic | SAD Placebo N = 8 | SAD Compound 1 N = 24 | MAD Placebo N = 12 | MAD Compound 1 N = 36 |
|---|---|---|---|---|
| Age, years, (mean, SD) | 41 (6) | 45 (11) | 45 (12) | 45 (11) |
| Male, n (%) | 6 (75) | 14 (58) | 6 (50) | 22 (61) |
| Race, n (%) | | | | |
| White | 6 (75) | 10 (42) | 5 (42) | 20 (56) |
| Black | 2 (25) | 14 (58) | 4 (33) | 13 (36) |
| Other/Multiple | 0 | 0 | 3 (25) | 3 (8) |
| Weight, kg, mean (SD) | 79 (15) | 81 (14) | 73 (13) | 80 (9) |
| Height, cm, mean (SD) | 171 (8) | 173 (9) | 170 (10) | 173 (9) |
| BMI, kg/m$^2$, mean (SD) | 27 (3) | 27 (4) | 25 (4) | 27 (3) |

No serious adverse events (SAEs) or AEs leading to withdrawal were reported in the SAD and MAD cohorts of healthy volunteers. The treatment emergent adverse events recorded in the healthy volunteer cohorts are provided in Table 13. Among the TEAEs reported in Table 13, TEAEs of grade 2 or less related to Compound 1 in the SAD cohorts included headache (n=1) and transient ventricular tachycardia (n=1), each in a different subject. TEAEs of grade 2 or less related to Compound 1 in the MAD cohorts included headache (n=4), palpitations (n=1) and somnolence (n=1), each in a different subject. TEAEs of grade 2 or less in the placebo cohorts included headache in one subject. One grade 3 TEAE unrelated to Compound 1. Transient asymptomatic lipase elevation was noted in one subject at the 1000 mg dose. The subject's back-up sample was re-assessed independently, and no lipase elevation was detected.

TABLE 13

Healthy Volunteers: Treatment Emergent Adverse Events

| Characteristic | SAD Placebo N = 8 | SAD Compound 1 N = 24 | MAD Placebo N = 12 | MAD Compound 1 N = 36 |
|---|---|---|---|---|
| Any TEAE, n (%) | 1 (13) | 5 (21) | 3 (25) | 15 (42) |
| Any grade 3 or greater TEAE, n (%) | 0 | 1 (4) | 0 | 0 |
| Drug interruption, reduction, or discontinuation due to TEAE, n (%) | 0 | 0 | 0 | 0 |

Figure 22:
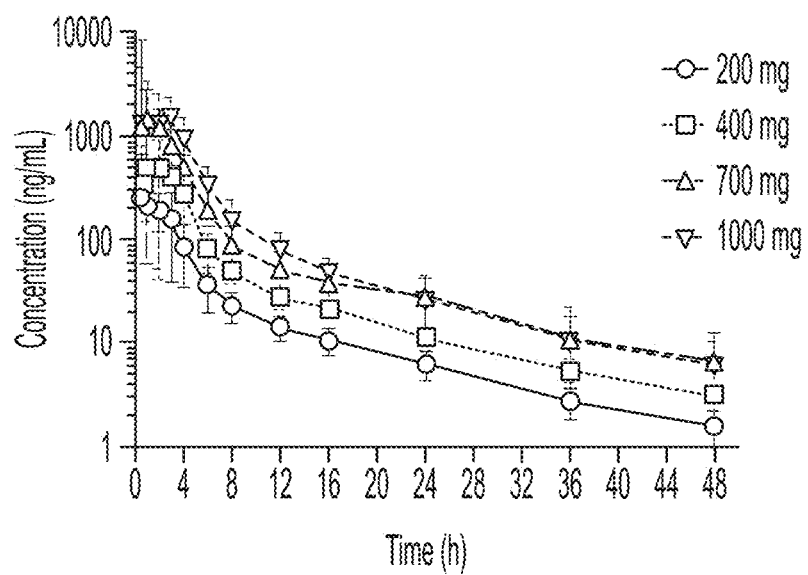
FIG. 22 is a graph depicting Compound 1 plasma concentrations following a single dose of Compound 1 in healthy volunteers.

In PK assessments, Compound 1 was rapidly absorbed with a median $T_{max}$ of 1 hr postdose. FIG. 22 illustrates plasma Compound 1 pharmacokinetics in healthy volunteers following a single dose. Linear pharmacokinetics was observed from single doses up to 700 mg, with a $T_{1/2}$ of 11-15 hrs. Single dose exposure increased in greater than dose-proportional manner at doses ≥700 mg, as evidenced in dose-normalized $C_{max}$ and AUC data. In multiple-doses delivered BID or QD, linear PK was observed across all dose levels (100-300 mg BID, 400 mg QD), and exposure remained steady up to day 14, without cumulative effect. No significant changes in exposure were observed after 14 days of dosing. Compound 1 exposure under fed/fasted conditions was similar.

FIG. 24A is a table of pharmacokinetic data obtained from the healthy subjects in a single ascending dose (SAD) clinical study of Compound 1 described in Example 8. As shown in FIG. 24A, dose normalized Cmax and AUC increased with increasing doses ≥700 mg suggesting greater than dose proportional increases in exposure at the highest doses tested. FIG. 24B is a table of pharmacokinetic data obtained from the healthy subjects in a multiple ascending dose (MAD) human clinical study of Compound 1 described in Example 8, showing time-independent pharmacokinetic (PK) properties over 14 days of dosing Compound 1 either QD or BID. In the tables of FIGS. 24A and 24B, AUC refers to the area under the concentration-time curve; BID refers to twice daily administration of Compound 1; $C_{max}$ refers to the maximum concentration; QD refers to once daily administration of Compound 1; $T_{max}$ refers to the time to maximum concentration of Compound 1. Values in FIG. 24A are presented as geometric mean for $C_{max}$ and $AUC_{0-24}$; $T_{max}$ is presented as median. Values in FIG. 24B are presented as geometric mean [CV %] for $C_{max}$, $AUC_{0-tau}$, R $C_{max}$, and R $AUC_{0-tau}$; $T_{max}$ presented as median [CV %].

PD activity was demonstrated at all dose levels evaluated in Compound 1-treated subjects (Table 14). Table 14 reports the mean maximum percentage change in 2,3-DPG, ATP, and p50 across all doses and timepoints in the SAD and MAD cohorts. As shown in Table 14, a mean decrease in 2,3-DPG and p50, and a mean increase in ATP, relative to baseline, was observed in both the SAD and MAD cohorts. Within 24 hr of a single dose of Compound 1, a decrease in 2,3-DPG with a corresponding increase in p50 was observed. After 14 days of Compound 1 dosing these PD effects were maintained along with an increase in ATP over baseline. Accordingly, the mean maximum reduction in the concentration of 2,3-DPG was at least about 40% in patients receiving Compound 1 in the SAD study (range 35.4-56.1%) and at least about 50% in patients receiving Compound 1 in the MAD study (range 46.1-63.6%).

TABLE 14

Summary of Mean Maximum Percent Change in Key PD Measures from Baseline

| PD Marker | Statistics | SAD Placebo (N = 8) | SAD Compound 1 (N = 24) | MAD Placebo (N = 12) | MAD Compound 1 (N = 36) |
|---|---|---|---|---|---|
| 2,3-DPG | Mean | −19.5 | −46.8 | −17.0 | −56.3 |
|  | (95% CI) | (−25.0, −14.0) | (−50.3, −43.2) | (−22.9, −11.1) | (−58.9, −53.7) |
|  | P-value |  | <0.0001 |  | <0.0001 |
| ATP | Mean | 9.2 | 24.4 | 7.2 | 68.5 |
|  | (95% CI) | (0.5, 18.0) | (18.4, 30.3) | (−0.3, 14.7) | (63.6, 73.3) |
|  | P-value |  | 0.0094 |  | <0.0001 |
| p50 | Mean | 0.9 | −15.6 | −0.8 | −15.9 |
|  | (95% CI) | (−1.2, 2.9) | (−17.5, −13.8) | (−3.0, 1.4) | (−17.2, −14.5) |
|  | P-value |  | <0.0001 |  | <0.0001 |

Single Ascending Doses (SAD) in Healthy Volunteers (HVs)

In the SAD cohorts, the subjects' blood 2,3-DPG levels were measured periodically after dosing by a qualified LC-MS/MS method for the quantitation of 2,3-DPG in blood. Decreased 2,3-DPG blood levels were observed 6 hours following a single dose of Compound 1 at all dose levels (earlier timepoints were not collected). Maximum decreases in 2,3-DPG levels generally occurred ~24 hours after the first dose with the reduction sustained ~48-72 hr postdose. Table 15 reports the median percentage change in 2,3-DPG blood levels, relative to baseline, measured over time in healthy volunteers after a single dose of Compound 1 (200 mg, 400 mg, 700 mg, or 1000 mg) or placebo. Table 16 reports the mean percentage change in 2,3-DPG blood levels, relative to baseline, measured over time in healthy volunteers after a single dose of Compound 1 (200 mg, 400 mg, 700 mg, or 1000 mg). Accordingly, the median and mean reduction in the concentration of 2,3-DPG, relative to baseline, was at least about 30% at all dose levels tested 24 hours after administration of the single dose.

TABLE 15

Median Percentage Change in 2,3-DPG Levels

| Time After Dose | Dose |  |  |  |  |
|---|---|---|---|---|---|
|  | Placebo | 200 mg | 400 mg | 700 mg | 1000 mg |
| 0 | 0.0 | 0.0 | 0.0 | 0.0 | 0.0 |
| 6 | −7.8 | −18 | −23 | −29 | −21 |
| 8 | −7.6 | −17 | −29 | −28 | −33 |

TABLE 15-continued

Median Percentage Change in 2,3-DPG Levels

| Time After Dose | | | | |
|---|---|---|---|---|
| Dose | Placebo | 200 mg | 400 mg | 700 mg | 1000 mg |
| 12 | −4.0 | −25 | −40 | −41 | −38 |
| 16 | −6.0 | −33 | −35 | −46 | −40 |
| 24 | −2.0 | −31 | −39 | −49 | −48 |
| 36 | −6.9 | −33 | −38 | −46 | −47 |
| 48 | −15 | −29 | −31 | −48 | −44 |
| 72 | −6.9 | −18 | −30 | −33 | −24 |

TABLE 16

Mean Percentage Change in 2,3-DPG Levels

| Time After Dose | | | | |
|---|---|---|---|---|
| Dose | Placebo | 200 mg | 400 mg | 700 mg | 1000 mg |
| 0 | 0 | 0 | 0 | 0 | 0 |
| 6 | −5.6 | −17 | −24 | −30 | −18 |
| 8 | −6.4 | −21 | −29 | −29 | −31 |
| 12 | −5.9 | −26 | −35 | −41 | −35 |
| 16 | −3.2 | −28 | −38 | −46 | −40 |
| 24 | −1.1 | −30 | −41 | −49 | −44 |
| 36 | −5.6 | −31 | −37 | −47 | −46 |
| 48 | −11 | −33 | −34 | −48 | −43 |
| 72 | −9.8 | −14 | −30 | −32 | −27 |

Figure 23:
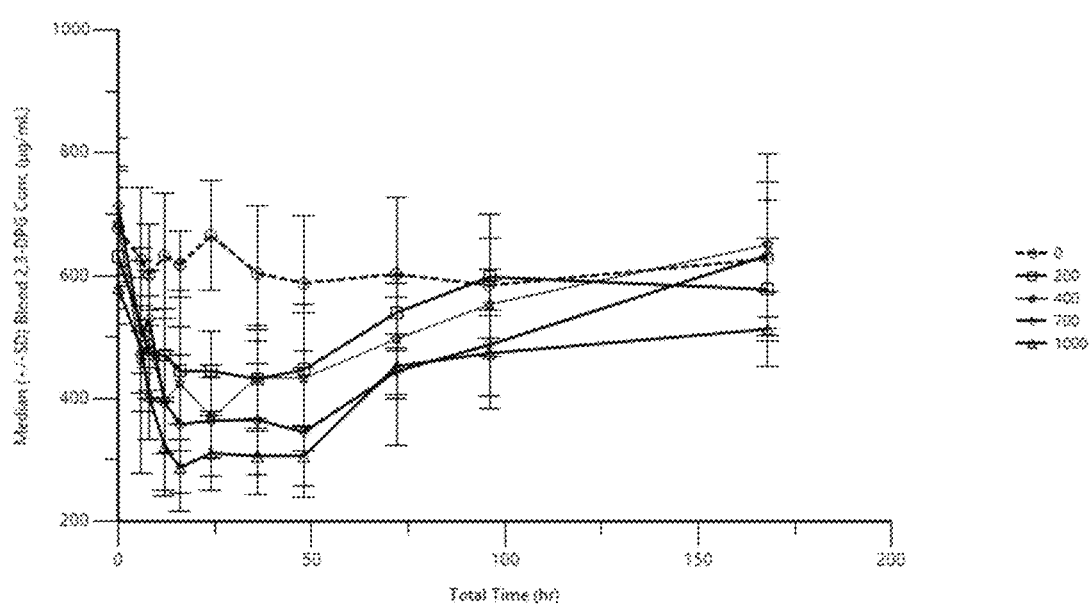
FIG. 23 is a graph of the blood 2,3-DPG levels measured over time in healthy volunteers who received a single dose of Compound 1 or placebo.

FIG. 23 is a graph of the blood 2,3-DPG levels measured over time in healthy volunteers who received a single dose of Compound 1 (200 mg, 400 mg, 700 mg, or 1000 mg) or placebo. As shown in FIG. 23, healthy volunteers who received Compound 1 experienced a decrease in blood 2,3-DPG levels, relative subjects who received the placebo.

Figure 25:
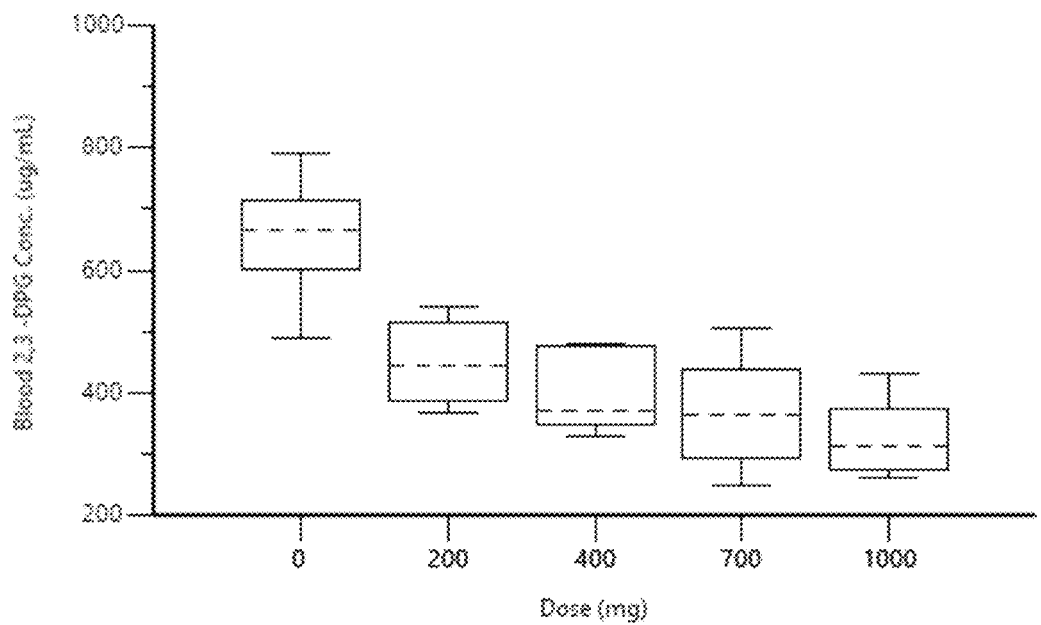
FIG. 25 is a graph of the blood 2,3-DPG levels measured 24 hours post-dose in healthy volunteers who received a single dose of Compound 1 or placebo.

FIG. 25 is a graph of the blood 2,3-DPG levels measured 24 hours post-dose in healthy volunteers who received a single dose of Compound 1 (200 mg, 400 mg, 700 mg, or 1000 mg) or placebo. As shown in FIG. 25, healthy volunteers who received Compound 1 experienced a decrease in blood 2,3-DPG levels at 24 hours post-dose, relative to subjects who received the placebo.

Increased ATP blood levels were observed following a single dose of Compound 1 at all dose levels in healthy volunteers.

The following table reports the median percentage change in ATP blood levels, relative to baseline, measured over time in healthy volunteers after a single dose of Compound 1 (200 mg, 400 mg, 700 mg, or 1000 mg):

| Time After Dose | | | | |
|---|---|---|---|---|
| Dose | Placebo | 200 mg | 400 mg | 700 mg | 1000 mg |
| 0 | 0 | 0 | 0 | 0 | 0 |
| 6 | −2.6 | −4.5 | 4.1 | −2.6 | 5.1 |
| 8 | −8.0 | −1.7 | −8.8 | −1.6 | 3.1 |
| 12 | −7.1 | 1.7 | 7.2 | −5.4 | 7.3 |
| 16 | −6.3 | −6.6 | 4.5 | −2.4 | 2.4 |
| 24 | −7.2 | 4.7 | 13 | 12 | 14 |
| 36 | −9.3 | 4.1 | 16 | 3.6 | 16 |
| 48 | −11 | −2.4 | 14 | 0 | 10 |
| 72 | −11 | 11 | 18 | 5.1 | 20 |

The following table reports the mean percentage change in ATP blood levels, relative to baseline, measured over time in healthy volunteers after a single dose of Compound 1 (200 mg, 400 mg, 700 mg, or 1000 mg):

| Time After Dose | | | | |
|---|---|---|---|---|
| Dose | Placebo | 200 mg | 400 mg | 700 mg | 1000 mg |
| 0 | 0 | 0 | 0 | 0 | 0 |
| 6 | 1.4 | 0.7 | 2.2 | −2.8 | −1.7 |
| 8 | −7.5 | −2.1 | −2.5 | −2.9 | 4.0 |
| 12 | −8.0 | 2.0 | 5.6 | −5.5 | 2.9 |
| 16 | −5.8 | −6.9 | 5.6 | −1.3 | 6.9 |
| 24 | −2.8 | 3.4 | 15 | 13 | 12 |
| 36 | −9.7 | 6.2 | 18 | 4.5 | 13 |
| 48 | −9.2 | 2.0 | 14 | 2.5 | 14 |
| 72 | −11 | 12 | 14 | 10 | 22 |

Figure 26A:
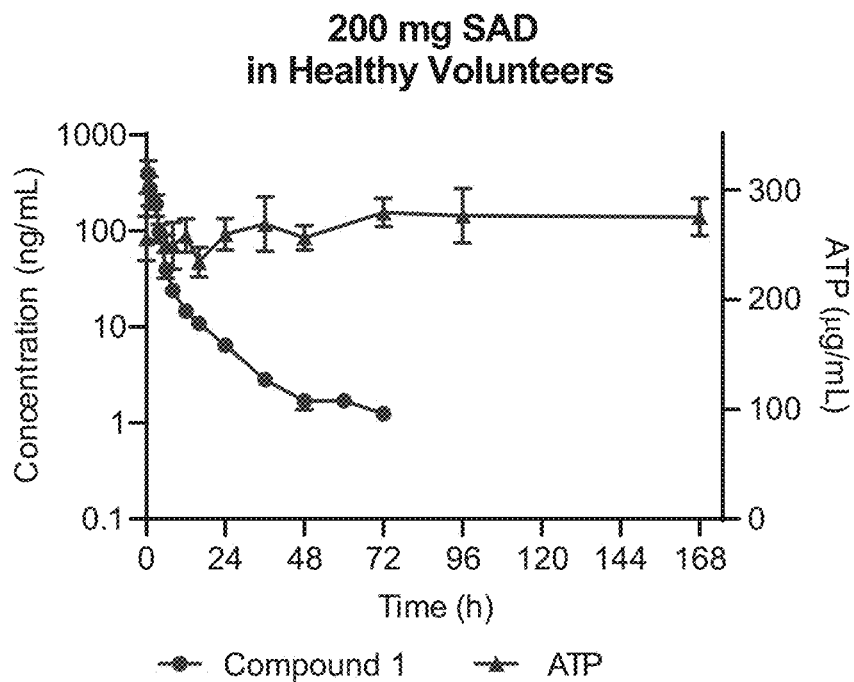
FIG. 26A and FIG. 26B are graphs of ATP blood levels and 2,3-DPG blood levels, respectively, and Compound 1 plasma concentrations, over time, following a single 200 mg dose of Compound 1 in healthy volunteers.
Figure 26B:
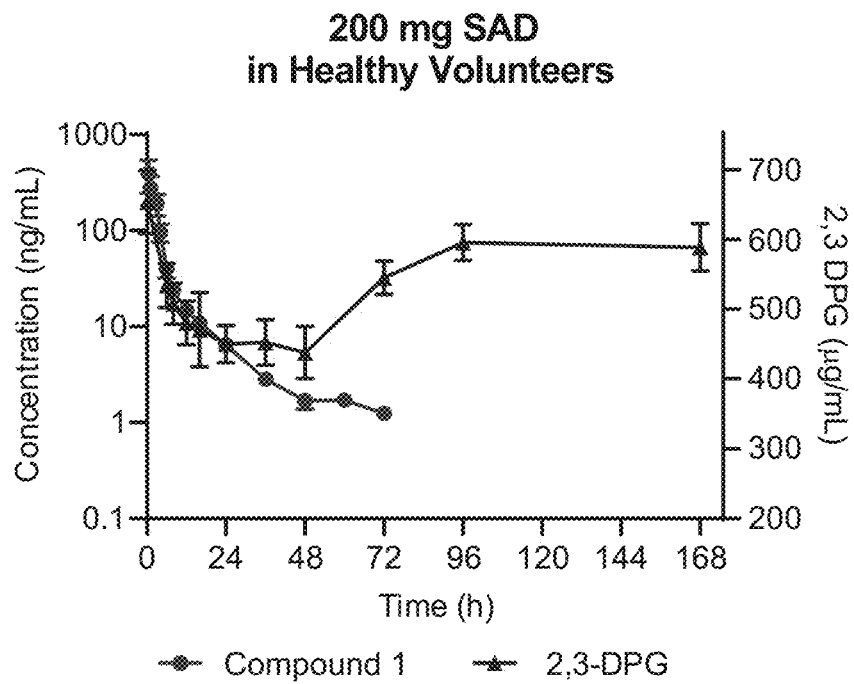
Figure 27A:
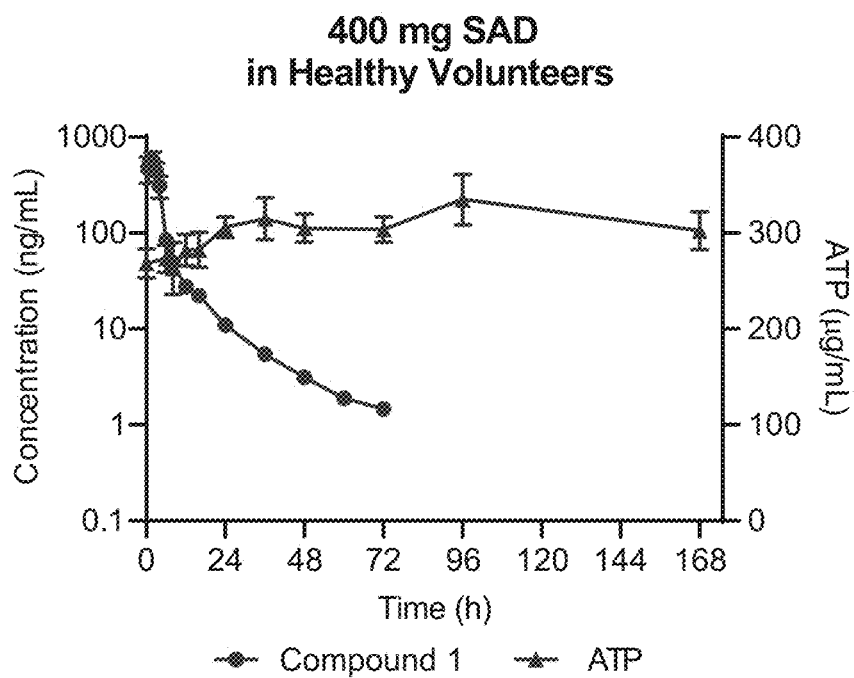
FIG. 27A and FIG. 27B are graphs of ATP blood levels and 2,3-DPG blood levels, respectively, and Compound 1 plasma concentrations, over time, following a single 400 mg dose of Compound 1 in healthy volunteers.
Figure 27B:
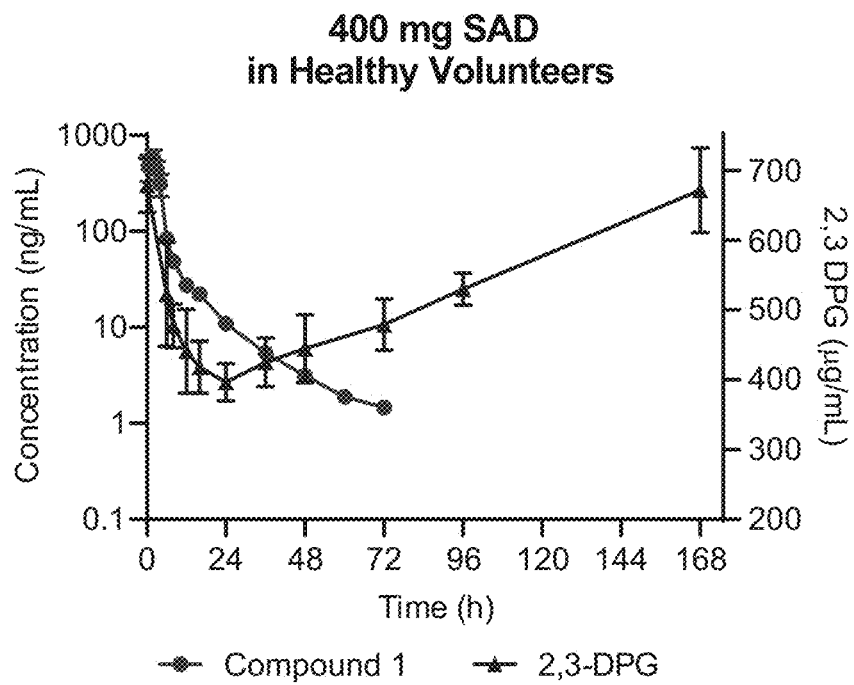
Figure 28A:
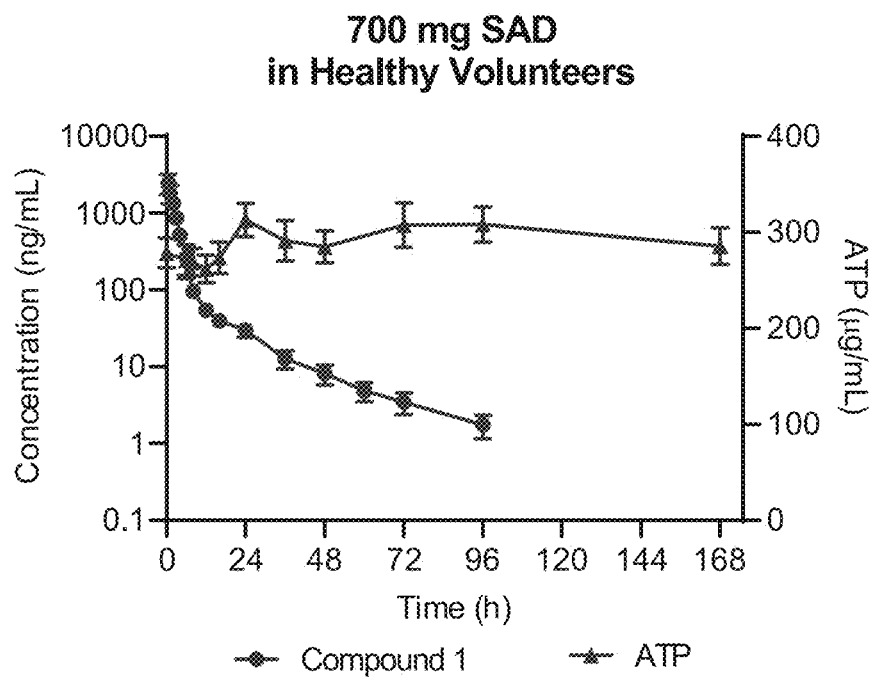
FIG. 28A and FIG. 28B are graphs of ATP blood levels and 2,3-DPG blood levels, respectively, and Compound 1 plasma concentrations, over time, following a single 700 mg dose of Compound 1 in healthy volunteers.
Figure 28B:
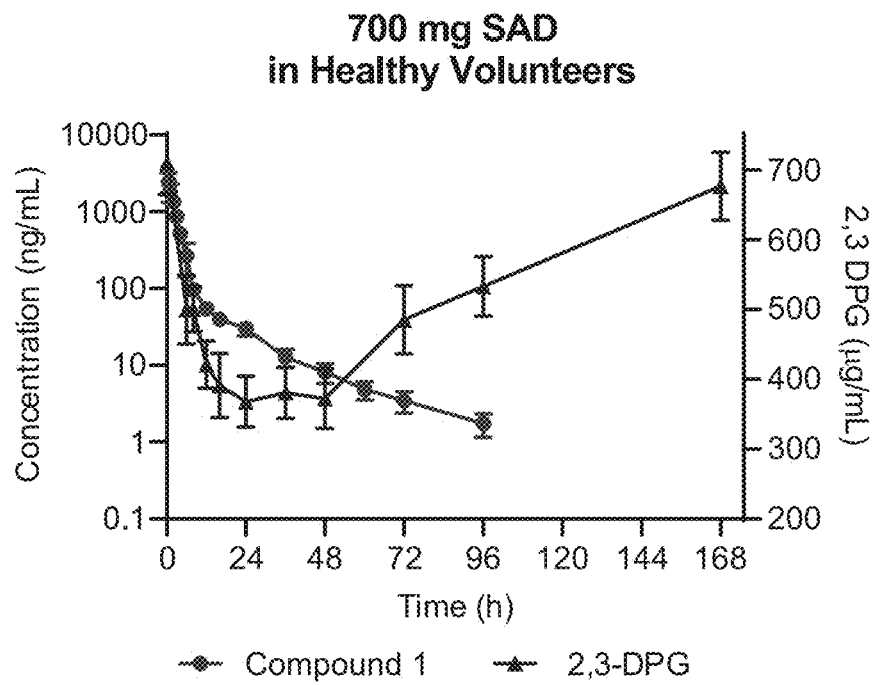
Figure 29A:
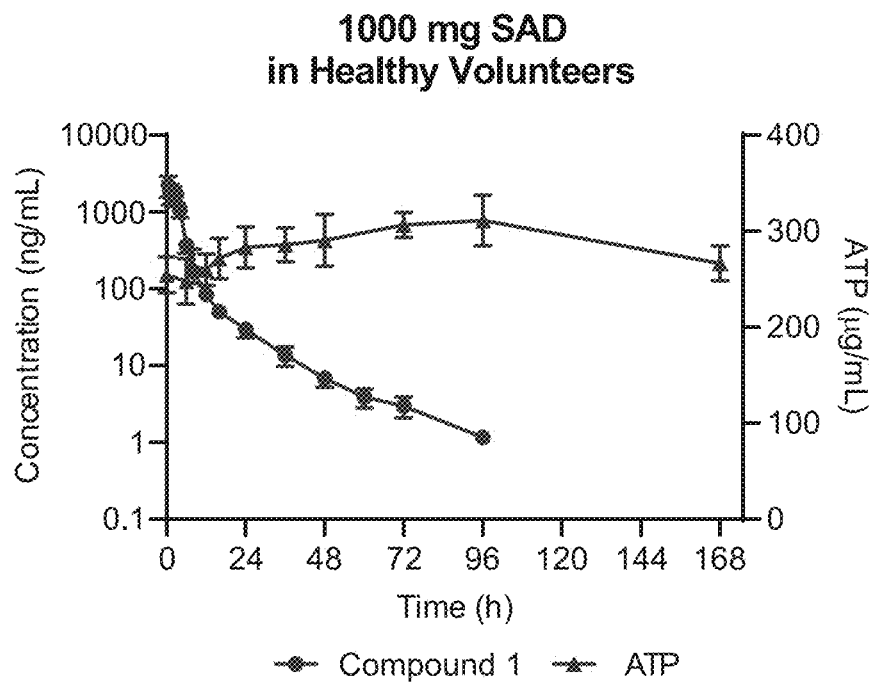
FIG. 29A and FIG. 29B are graphs of ATP blood levels and 2,3-DPG blood levels, respectively, and Compound 1 plasma concentrations, over time, following a single 1000 mg dose of Compound 1 in healthy volunteers.
Figure 29B:
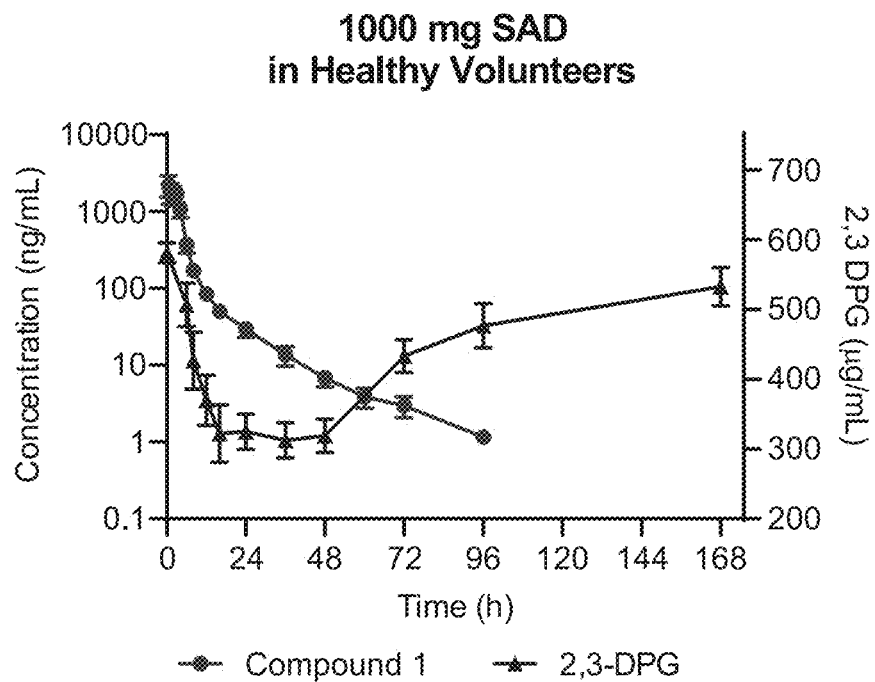

The pharmacodynamic maximum effects on blood ATP and 2,3-DPG concentrations lagged behind the pharmacokinetic maximum plasma concentration of Compound 1 after a single dose of Compound 1 (200 mg, 400 mg, 700 mg, or 1000 mg) in healthy volunteers. Specifically, the pharmacodynamic maximum increase in blood ATP concentration lagged at least about 24 hours behind the pharmakinetic maximum plasma concentration of Compound 1 after a single 200 mg dose (FIG. 26A), 400 mg dose (FIG. 27A), 700 mg dose (FIG. 28A), or 1000 mg dose (FIG. 29A) of Compound 1. Likewise, the pharmacodynamic maximum decrease in blood 2,3-DPG concentration lagged about 24 hours behind the pharmakinetic maximum plasma concentration of Compound 1 after a single 200 mg dose (FIG. 26B), 400 mg dose (FIG. 27B), 700 mg dose (FIG. 28B), or 1000 mg dose (FIG. 29B) of Compound 1.

In the SAD cohorts, the subjects' p50 (PO2 at 50% hemoglobin saturation) were determined 24-hours post-dose. p50 measured 24 hours after a single dose of Compound 1 were reduced at all dose levels tested (median reduction ranged from ~3-5 mmHg). Table 17 reports the mean absolute change in p50, relative to baseline, measured 24 hours after a single dose of Compound 1 (200 mg, 400 mg, 700 mg, or 1000 mg) or placebo in healthy volunteers.

TABLE 17

Mean Absolute Change in p50 (mmHg)

| Dose | Mean Absolute Change |
|---|---|
| Placebo | 0.20 |
| 200 mg | −2.91 |
| 400 mg | −3.41 |
| 700 mg | −4.85 |
| 1000 mg | −5.05 |

Figure 30:
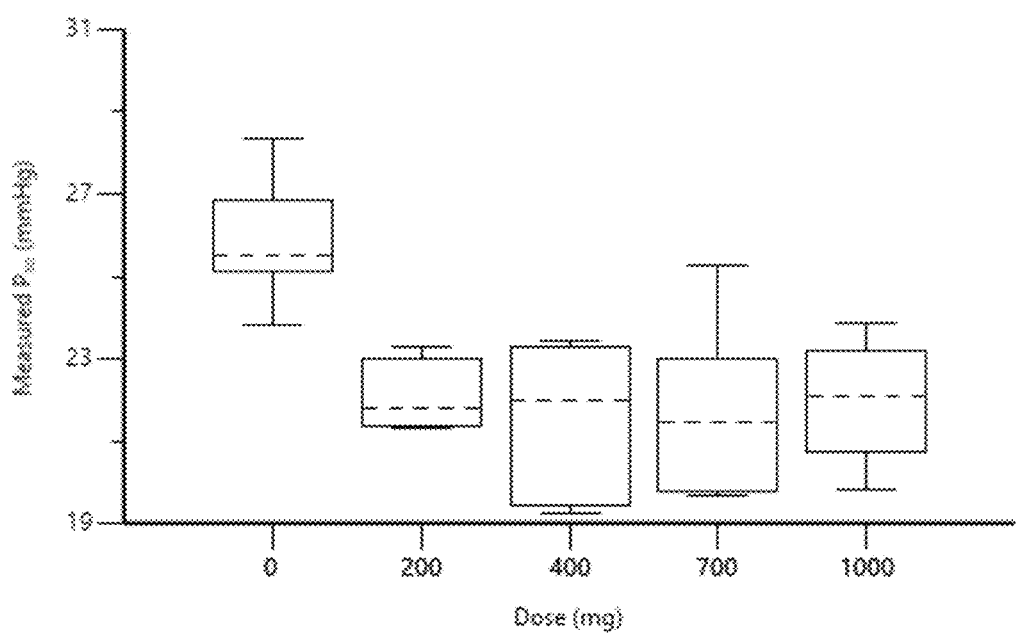
FIG. 30 is a graph of the p50 values measured 24 hours post-dose in healthy volunteers who received a single dose of Compound 1 or placebo.
Figure 31:
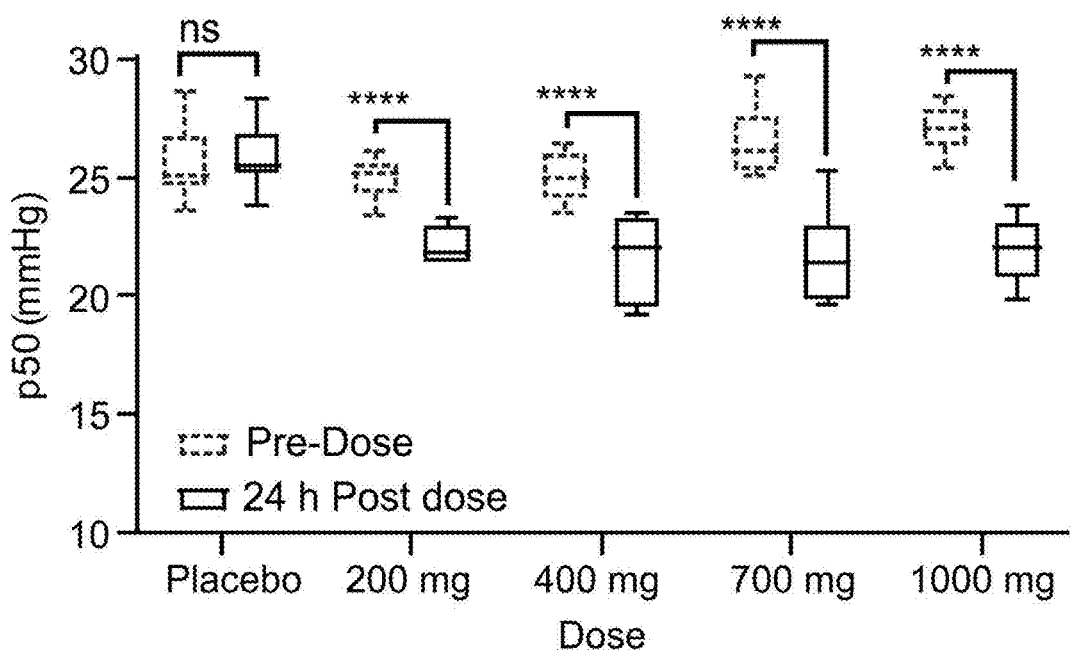
FIG. 31 is a graph of the p50 values measured pre-dose and 24-hours post-dose in healthy volunteers who received a single dose of Compound 1 or placebo.

Following single doses, all HVs receiving Compound 1 exhibited a PD response associated with decreased p50 (increased Hb oxygen affinity). FIG. 30 is a graph of the p50 values measured 24 hours post-dose in healthy volunteers who received a single dose of Compound 1 (200 mg, 400 mg, 700 mg, or 1000 mg) or placebo. As shown in FIG. 30, healthy volunteers who received Compound 1 experienced a decrease in p50, relative to subjects who received the placebo. FIG. 31 is a graph of the p50 values measured pre-dose and 24-hours post-dose in healthy volunteers who received a single dose of Compound 1 (200 mg, 400 mg, 700 mg, or 1000 mg) or placebo. As shown in FIG. 31, healthy volunteers who received Compound 1 experienced a decrease in p50 relative to baseline, reflecting an increase in oxygen affinity, while subjects who received the placebo did not.

Multiple Ascending Doses (MAD) in Healthy Volunteers (HVs)

In the MAD cohorts, the subjects' blood 2,3-DPG levels were measured periodically after dosing by a qualified LC-MS/MS method for the quantitation of 2,3-DPG in blood. The maximum decrease in 2,3-DPG on Day 14 was 55% from baseline (median). 2,3-DPG levels reached a nadir and plateaued on Day 1 and had not returned to baseline levels 72 hours after the final dose on Day 14. Table 18A reports the median percentage change in 2,3-DPG blood levels, relative to baseline, measured over time after the first dose on days 1 and 14 in healthy volunteers who received daily doses of Compound 1 (100 mg BID, 200 mg BID, or 300 mg BID) or placebo for 14 days. Table 18B reports the mean percentage change in 2,3-DPG blood levels, relative to baseline, measured over time after the first dose on days 1 and 14 in healthy volunteers who received daily doses of Compound 1 (100 mg BID, 200 mg BID, 300 mg BID, or 400 mg QD) for 14 days. Accordingly, the median and mean reduction in the concentration of 2,3-DPG, relative to baseline, was at least about 25% at all dose levels tested 24 hours after administration of the first dose on day 1 and at least about 40% at all dose levels tested 24 hours after administration of the first dose on day 14.

TABLE 18A

Median Percentage Change in 2,3-DPG Levels (Days 1 and 14)

| Time After First Daily Dose | 100 mg BID Day 1 | 100 mg BID Day 14 | 200 mg BID Day 1 | 200 mg BID Day 14 | 300 mg BID Day 1 | 300 mg BID Day 14 | 400 mg QD Day 1 | 400 mg QD Day 14 |
|---|---|---|---|---|---|---|---|---|
| 0  | 0.0  | -42.0 | 0.0  | -49 | 0.0 | -59   | 0.0 | -51 |
| 6  | -16  | -44   | -13  | -49 | -19 | -53.0 | -22 | -53 |
| 8  | -12  | -45   | -22  | -44 | -24 | -55   | -27 | -56 |
| 12 | -18  | -44   | -23  | -42 | -32 | -55   | -38 | -49 |
| 16 | -18  | -44   | -34  | -43 | -41 | -52   | -41 | -52 |
| 24 | -28  | -44   | -48  | -48 | -51 | -53   | -48 | -53 |
| 48 |      | -35   |      | -39 |     | -45   |     | -40 |
| 72 |      | -20   |      | -20 |     | -33   |     | -25 |

TABLE 18B

Mean Percentage Change in 2,3-DPG Levels (Days 1 and 14)

| Time After First Daily Dose | 100 mg BID Day 1 | 100 mg BID Day 14 | 200 mg BID Day 1 | 200 mg BID Day 14 | 300 mg BID Day 1 | 300 mg BID Day 14 | 400 mg QD Day 1 | 400 mg QD Day 14 |
|---|---|---|---|---|---|---|---|---|
| 0  | 0   | -43 | 0   | -49 | 0   | -57 | 0   | -52 |
| 6  | -15 | -44 | -16 | -49 | -20 | -56 | -26 | -54 |
| 8  | -13 | -45 | -19 | -47 | -22 | -55 | -29 | -55 |
| 12 | -18 | -44 | -22 | -43 | -31 | -54 | -38 | -50 |
| 16 | -20 | -42 | -33 | -49 | -39 | -53 | -42 | -51 |
| 24 | -29 | -43 | -45 | -47 | -47 | -52 | -48 | -53 |
| 48 |     | -32 |     | -40 |     | -43 |     | -38 |
| 72 |     | -22 |     | -23 |     | -34 |     | -28 |

Figure 32:
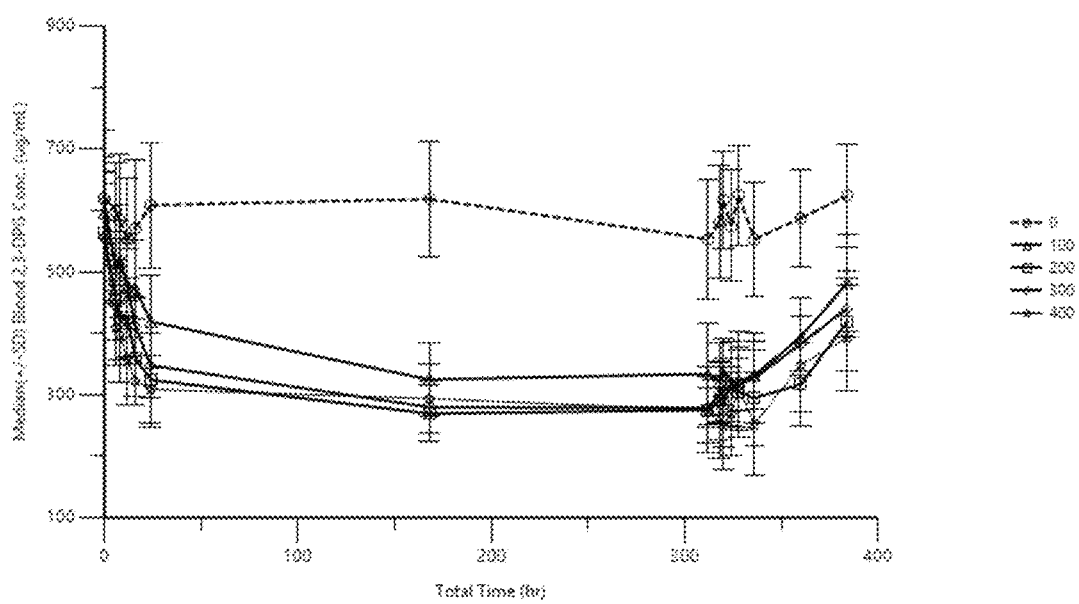
FIGS. 32 and 33 are graphs of the blood 2,3-DPG levels measured over time in healthy volunteers who received daily doses of Compound 1 or placebo for 14 days.
Figure 33:
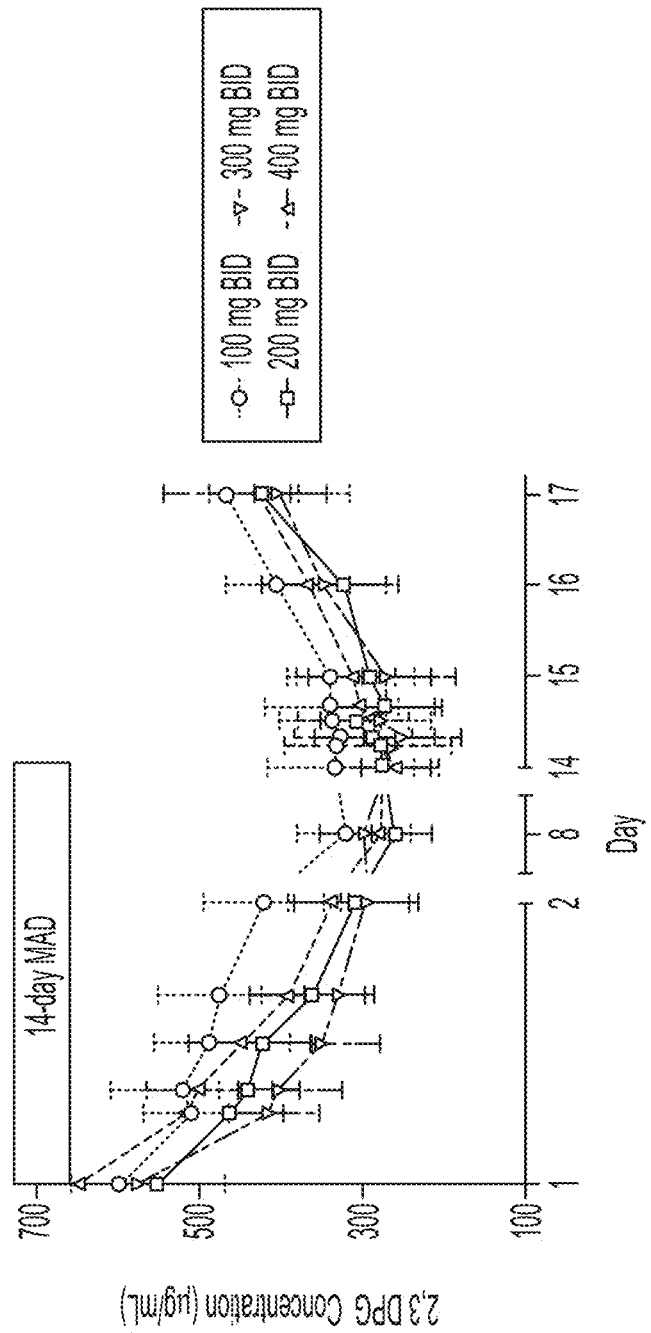
Figure 34:
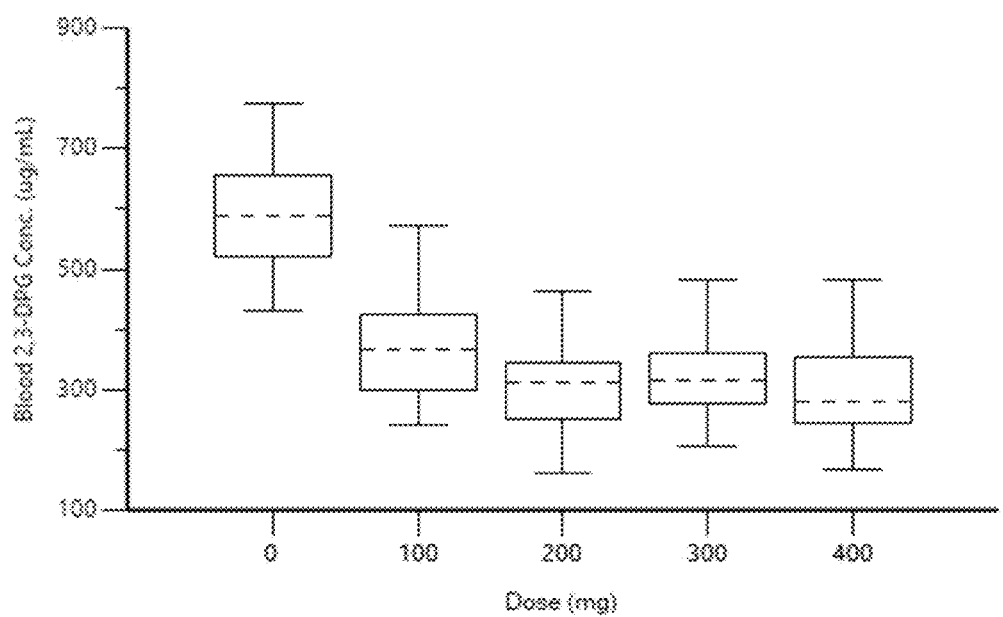
FIG. 34 is a graph of the blood 2,3-DPG levels measured on day 14 in healthy volunteers who received daily doses of Compound 1 or placebo for 14 days.

FIGS. 32 and 33 are graphs of the blood 2,3-DPG levels measured over time in healthy volunteers who received daily doses of Compound 1 (100 mg BID, 200 mg BID, 300 mg BID, or 400 mg QD) or placebo for 14 days. As shown in FIG. 32, healthy volunteers who received Compound 1 experienced a decrease in blood 2,3-DPG levels, relative subjects who received the placebo. As illustrated in FIG. 33, in RBCs of healthy volunteers, Compound 1 has demonstrated a reduction in 2,3-DPG, thus providing support for PKR activation in healthy RBCs. Notably, these effects were maintained for more than one day after Compound 1 dosing was stopped at day 14. PK/PD modelling predicts maximal 2,3-DPG response at doses ≥150 mg BID or ≥400 mg QD in HV RBCs. FIG. 34 is a graph of the blood 2,3-DPG levels measured on day 14 in healthy volunteers who received daily doses of Compound 1 (100 mg BID, 200 mg BID, 300 mg BID, or 400 mg QD) or placebo for 14 days. As shown in FIG. 34, healthy volunteers who received Compound 1 experienced a decrease in blood 2,3-DPG levels, relative to subjects who received the placebo.

In the MAD cohorts, the subjects' p50 (PO2 at 50% hemoglobin saturation) were determined on day 14. p50 values measured after 14 days of twice daily dosing were reduced at all dose levels tested (median reduction ranged from ~3-5 mmHg). Table 19 reports the mean p50 value and the mean absolute change and percentage change in p50, relative to baseline, measured 24 hours after the first dose given on day 14 in healthy volunteers who received daily doses of Compound 1 (100 mg BID, 200 mg BID, 300 mg BID, or 400 mg QD) or placebo for 14 days.

TABLE 19

Mean p50 and Change in p50 (mmHg) (Day 14)

| Dose | Mean p50 Value | Mean Absolute Change | Mean Percentage Change |
|---|---|---|---|
| Placebo    | 26.22 | -0.24 | -0.82  |
| 100 mg BID | 22.96 | -3.26 | -12.42 |
| 200 mg BID | 22.33 | -5.34 | -19.33 |
| 300 mg BID | 21.69 | -4.24 | -16.05 |
| 400 mg QD  | 21.75 | -4.09 | -15.76 |

Figure 35:
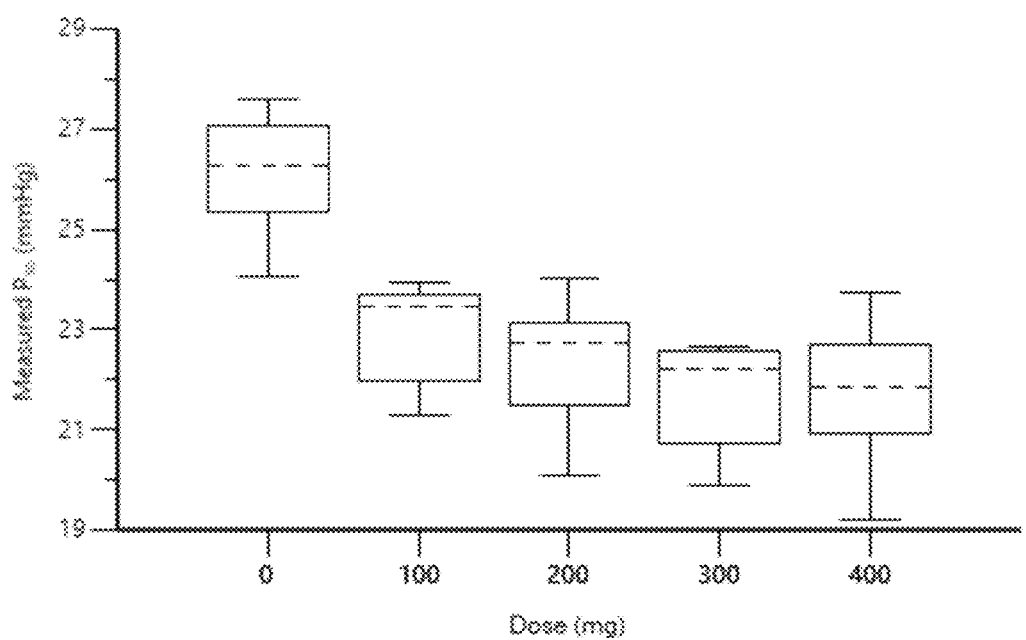
FIG. 35 is a graph of the p50 values measured on day 14 in healthy volunteers who received daily doses of Compound 1 or placebo for 14 days.
Figure 36:
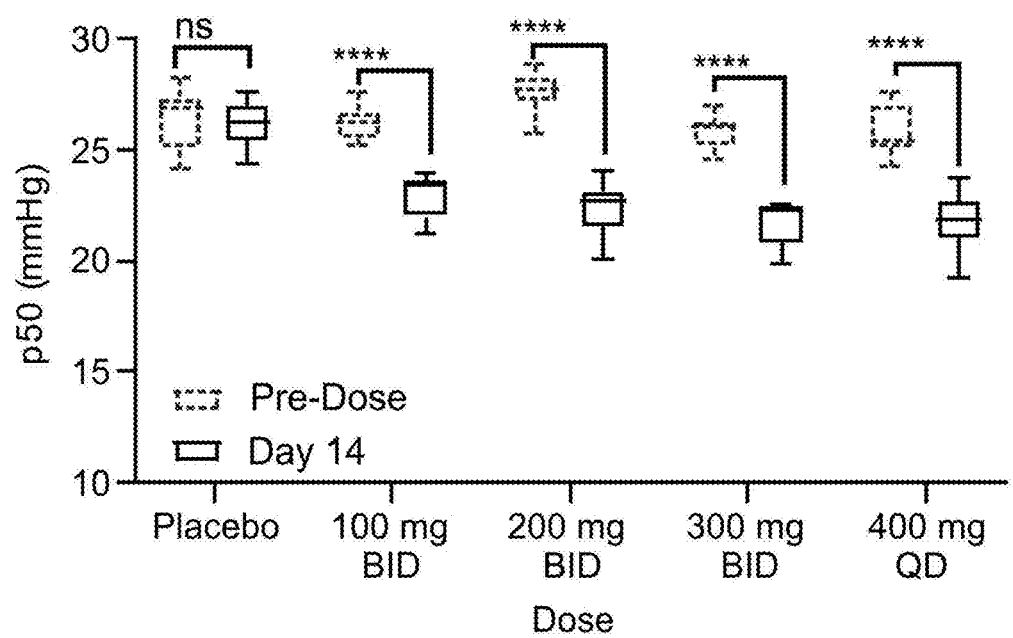
FIG. 36 is a graph of the p50 values measured pre-dose and on day 14 in healthy volunteers who received daily doses of Compound 1 or placebo for 14 days.

Following multiple doses, all HVs receiving Compound 1 exhibited a PD response associated with decreased p50 (increased Hb oxygen affinity). FIG. 35 is a graph of the p50 values measured on day 14 in healthy volunteers who received daily doses of Compound 1 (100 mg BID, 200 mg BID, 300 mg BID, or 400 mg QD) or placebo for 14 days. As shown in FIG. 35, healthy volunteers who received Compound 1 experienced a decrease in p50, relative to subjects who received the placebo. FIG. 36 is a graph of the p50 values measured pre-dose and on day 14 in healthy volunteers who received daily doses of Compound 1 (100 mg BID, 200 mg BID, 300 mg BID, or 400 mg QD) or placebo for 14 days. As shown in FIG. 36, healthy volunteers who received Compound 1 experienced a decrease in p50 relative to baseline, reflecting an increase in oxygen affinity, while subjects who received the placebo did not.

In the MAD cohorts, the subjects' blood ATP levels were measured on day 14 by a qualified LC-MS/MS method for the quantitation of ATP in blood. ATP levels were elevated, relative to baseline, on day 14, and remained elevated 60 hours after the last dose. Table 20A reports the median percentage change in blood ATP levels, relative to baseline, measured over time after the first dose on days 1 and 14 in healthy volunteers who received daily doses of Compound 1 (100 mg BID, 200 mg BID, 300 mg BID, or 400 mg QD) or placebo for 14 days. Table 20B reports the mean percentage change in ATP blood levels, relative to baseline, measured over time after the first dose on days 1 and 14 in healthy volunteers who received daily doses of Compound 1 (100 mg BID, 200 mg BID, 300 mg BID, or 400 mg QD) for 14 days.

TABLE 20A

Median Percentage Change in ATP Levels (Day 14)

| Time After First Daily Dose | 100 mg BID Day | | 200 mg BID Day | | 300 mg BID Day | | 400 mg QD Day | |
|---|---|---|---|---|---|---|---|---|
| | 1 | 14 | 1 | 14 | 1 | 14 | 1 | 14 |
| 0 | 0 | 42 | 0 | 62 | 0 | 46 | 0 | 52 |
| 6 | −5.7 | 44 | −4.3 | 48 | −7.6 | 51 | −1.7 | 52 |
| 8 | 0.0 | 48 | 5.4 | 58 | −2.4 | 50 | −4.5 | 52 |
| 12 | −1.2 | 45 | 4.3 | 56 | 0.9 | 51 | 3.5 | 56 |
| 16 | 3.3 | 45 | 6.0 | 57 | −1.1 | 53 | −1.8 | 51 |
| 24 | 5.7 | 55 | 1.1 | 65 | 1.8 | 52 | 0.0 | 52 |
| 48 | | 52 | | 70 | | 58 | | 61 |
| 72 | | 49 | | 54 | | 49 | | 54 |

TABLE 20B

Mean Percentage Change in ATP Levels (Days 1 and 14)

| Time After First Daily Dose | 100 mg BID Day | | 200 mg BID Day | | 300 mg BID Day | | 400 mg QD Day | |
|---|---|---|---|---|---|---|---|---|
| | 1 | 14 | 1 | 14 | 1 | 14 | 1 | 14 |
| 0 | 0 | 49 | 0 | 59 | 0 | 46 | 0 | 54 |
| 6 | −5.6 | 45 | 1.7 | 50 | −4.5 | 51 | −1.2 | 48 |
| 8 | −2.0 | 49 | 4.7 | 56 | −2.0 | 52 | −2.9 | 51 |
| 12 | −0.6 | 45 | 6.7 | 56 | −0.6 | 49 | 2.4 | 50 |
| 16 | 1.9 | 47 | 5.6 | 53 | −0.5 | 52 | −2.2 | 51 |
| 24 | 4.4 | 55 | −0.2 | 66 | 2.2 | 56 | 1.9 | 57 |
| 48 | | 51 | | 62 | | 57 | | 60 |
| 72 | | 47 | | 57 | | 48 | | 51 |

Figure 37:
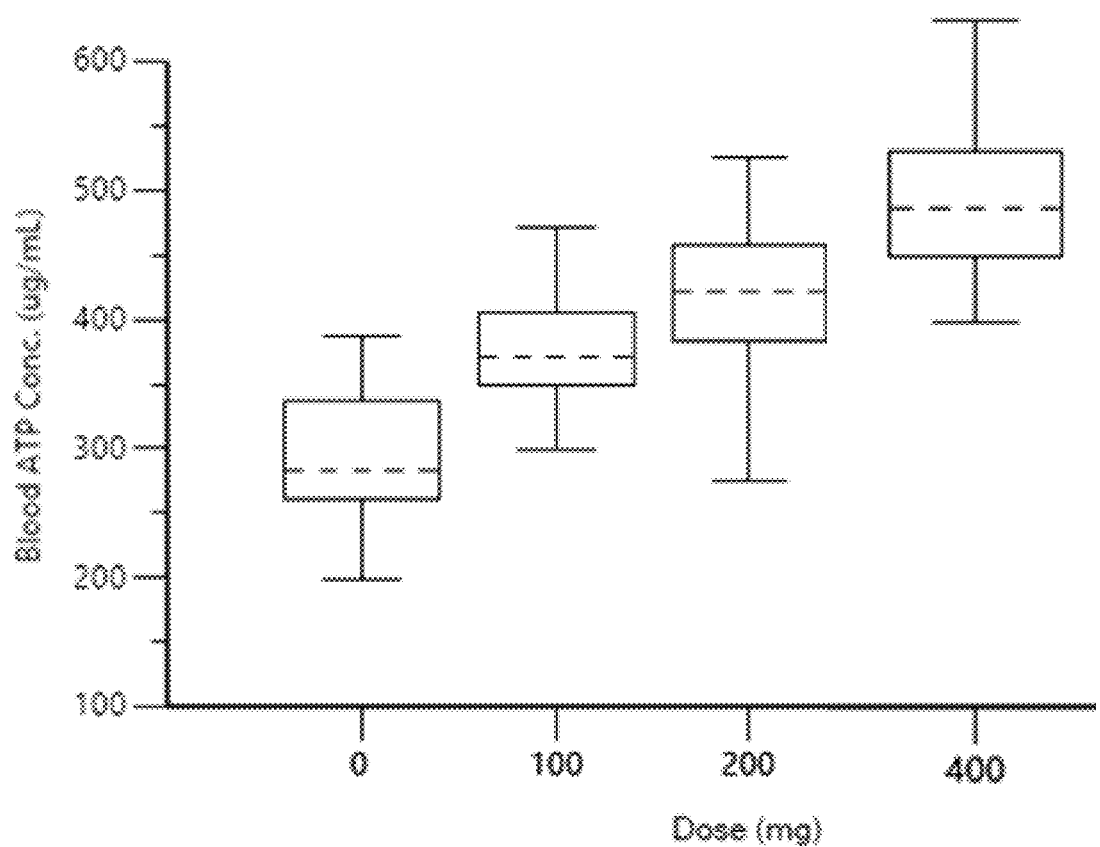
FIG. 37 is a graph of the blood ATP levels measured on day 14 in healthy volunteers who received daily doses of Compound 1 or placebo for 14 days.

FIG. 37 is a graph of the blood ATP levels measured on day 14 in healthy volunteers who received daily doses of Compound 1 (100 mg BID, 200 mg BID, 300 mg BID, or 400 mg QD) or placebo for 14 days. As shown in FIG. 37, healthy volunteers who received Compound 1 experienced an increase in blood ATP levels, relative to subjects who received the placebo.

Figure 38:
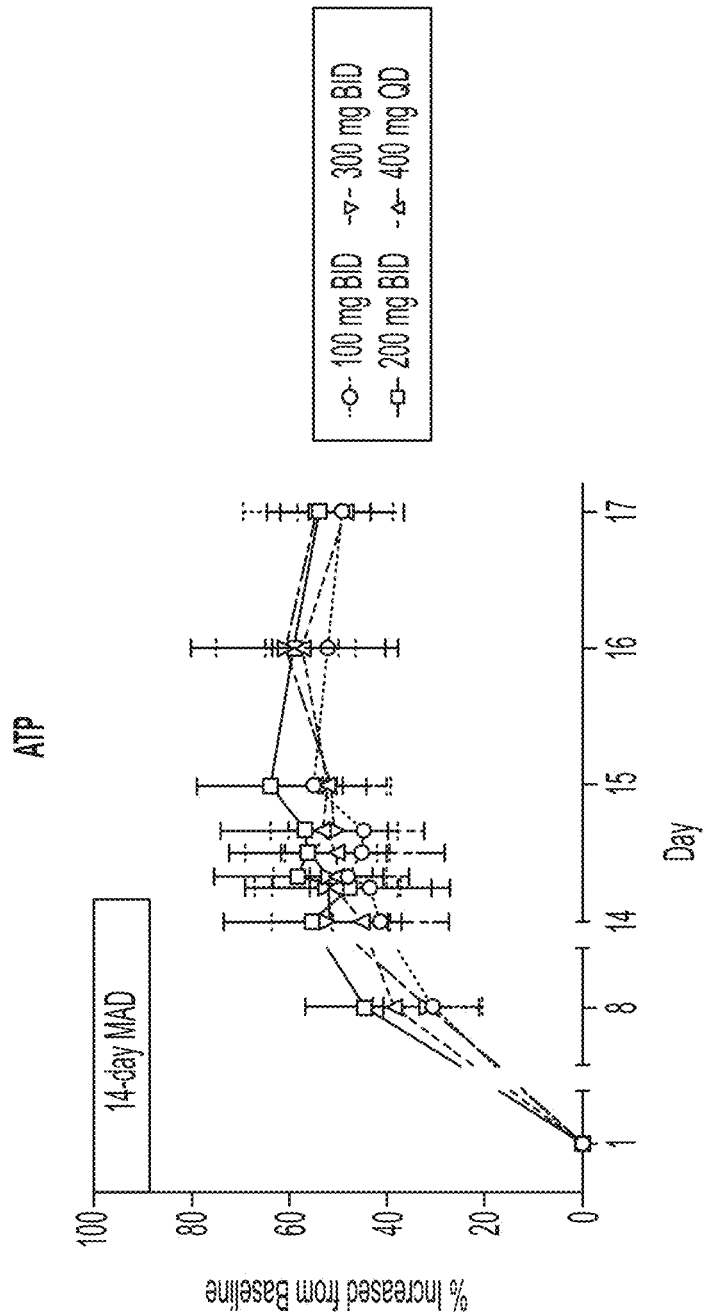
FIG. 38 is a graph showing the effect of Compound 1 on ATP levels in RBCs of healthy volunteers.

As illustrated in FIG. 38, in RBCs of healthy volunteers, Compound 1 has demonstrated an increase in ATP, thus providing support for PKR activation in healthy RBCs. Notably, these effects were maintained for more than three days after Compound 1 dosing was stopped at day 14. PK/PD modelling predicts maximal ATP response at doses ≥50 mg BID or ≥150 mg QD in HV RBCs.

Figure 39A:
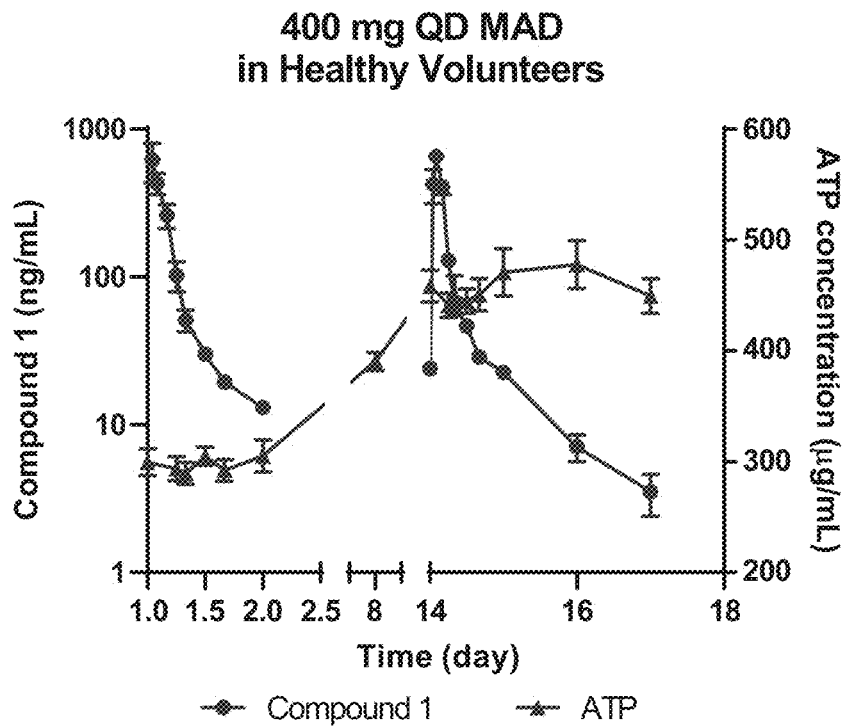
FIG. 39A and FIG. 39B are graphs of ATP blood levels and 2,3-DPG blood levels, respectively, and Compound 1 plasma concentrations, over time, during and after 400 mg QD administration of Compound 1 in healthy volunteers for 14 days.
Figure 39B:
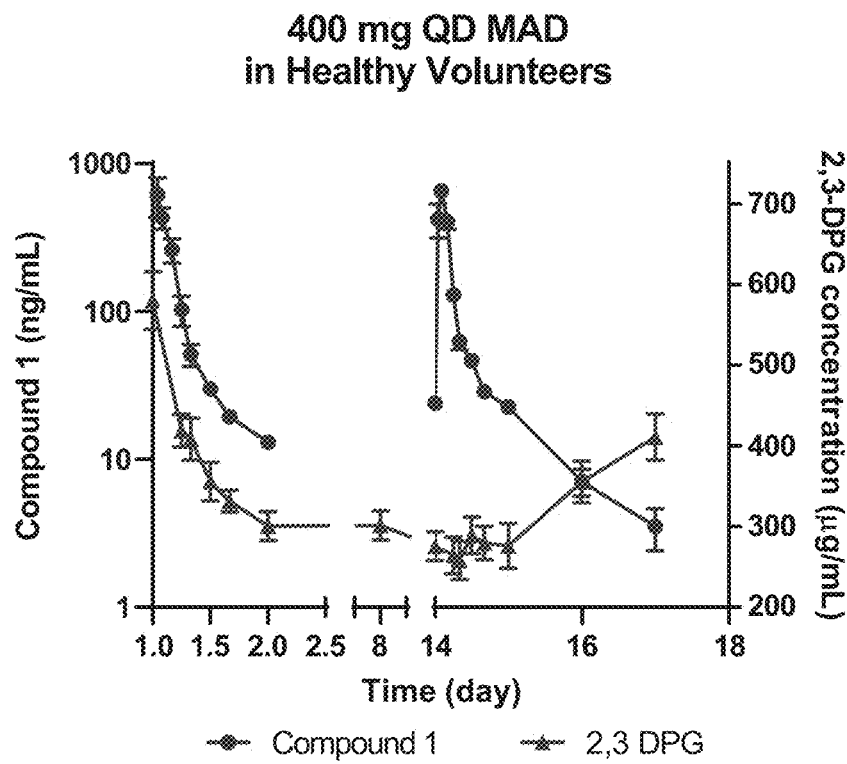

As shown in FIGS. 39A and 39B, stable pharmacodynamic effects on blood ATP and 2,3-DPG concentrations were observed despite fluctuactions the pharmacokinetic plasma concentration of Compound 1 during 400 mg QD dosing in healthy volunteers. Specifically, a stable increase in blood ATP concentration (FIG. 39A) and a stable decrease in blood 2,3-DPG concentration (FIG. 39B) were observed.

Figure 40:
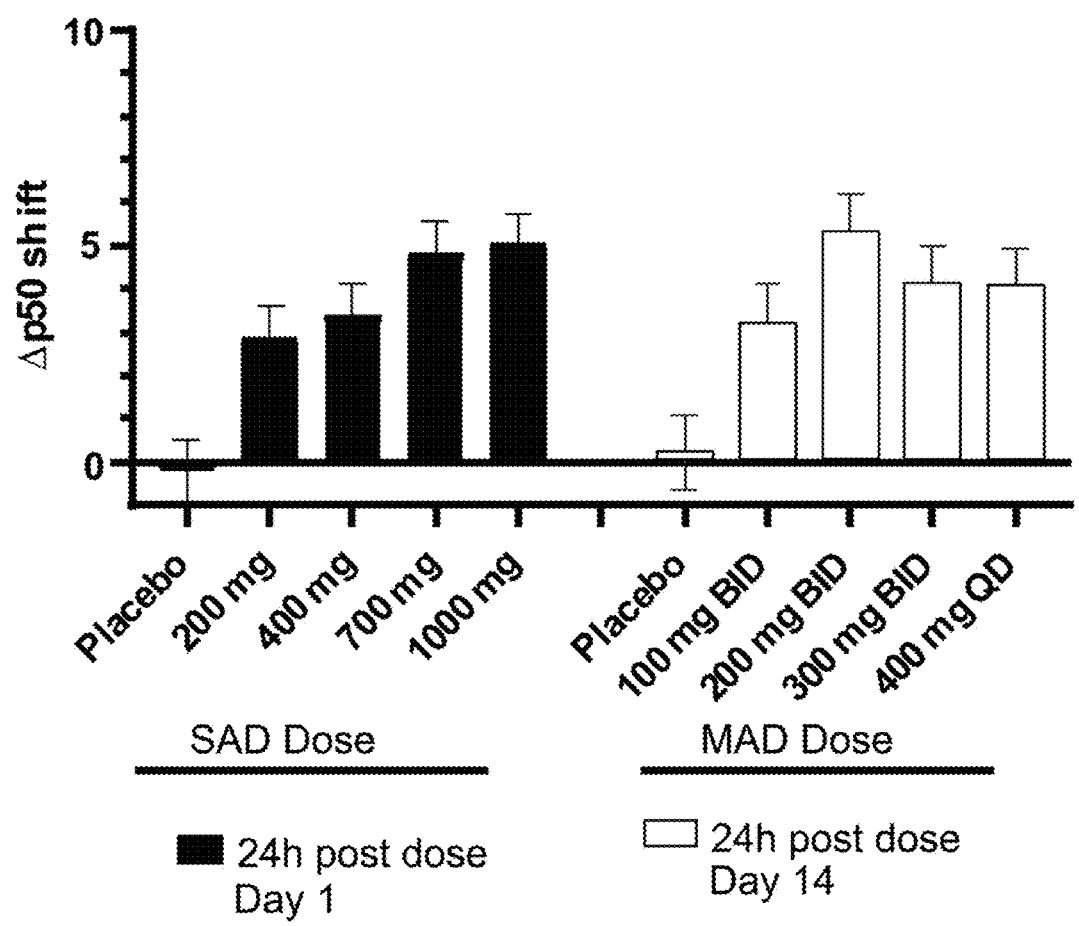
FIG. 40 is a graph showing the difference in the p50 values determined pre-dose and 24 hours post-dose (SAD cohorts) and 24 hours post-dose on day 14 (MAD cohorts) in healthy volunteers who received Compound 1 or placebo.

FIG. 40 is a graph showing the difference in the p50 values determined pre-dose and 24 hours post-dose (SAD cohorts) and 24 hours post-dose on day 14 (MAD cohorts) in healthy volunteers who received Compound 1 or placebo. As shown in FIG. 40, healthy volunteers who received Compound 1 experienced a change (decrease) in p50 relative to baseline, while subjects who received the placebo did not.

Figure 41:
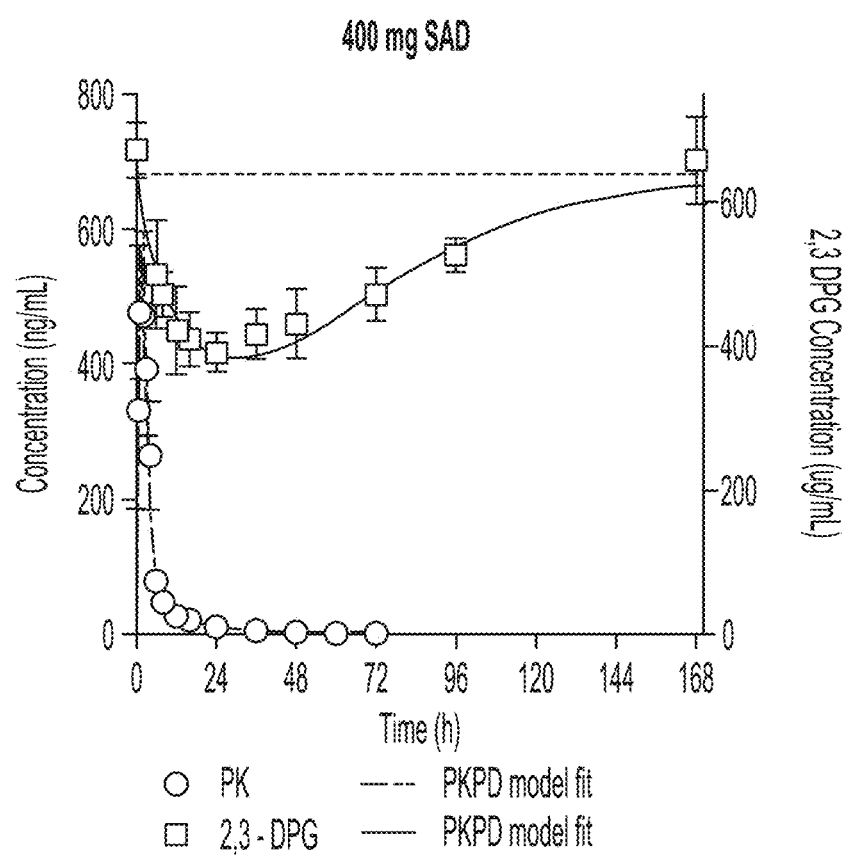
FIG. 41 is a graph plotting the blood concentration of Compound 1 (ng/mL) measured in healthy volunteer (HV) patients on a first (left) axis and the concentration of 2,3-DPG (micrograms/mL) measured in these HV patients on a second (right) axis after administration of a single dose of Compound 1 (400 mg).

FIG. 41 is a graph plotting the blood concentration of Compound 1 (ng/mL) measured in healthy volunteer (HV) patients on a first (left) axis and the concentration of 2,3-DPG (micrograms/mL) measured in these HV patients on a second (right) axis after administration of a single dose of Compound 1 (400 mg). Solid symbols represent geometric means and Standard errors of the observed Compound 1 plasma and 2,3 DPG concentrations. As shown in the figure, the observed 2,3 DPG modulation does not track directly plasma pharmacokinetics (blood concentration of Compound 1) where the pharmacodynamic maximum (i.e., the minimum of the 2,3-DPG concentration, at time ~24 h) occurred nearly 24 h after the pharmacokinetic maximum (i.e., maximum of the PK curve, at time ~1-2 h). The observed pharmacodynamic response in HVs was durable, where 2,3-DPG depression was observed long after plasma Cmax. Taken together, this suggests that identifying the pharmacologically active dose cannot be adequately performed using pharmacokinetic parameters ($C_{max}/C_{min}/AUC$) in isolation, but rather support an approach that includes integrating the temporal pharmacokinetic/pharmacodynamic relationship to provide the platform of evidence that QD dosing may be feasible in sickle cell disease patients.

Figure 42:
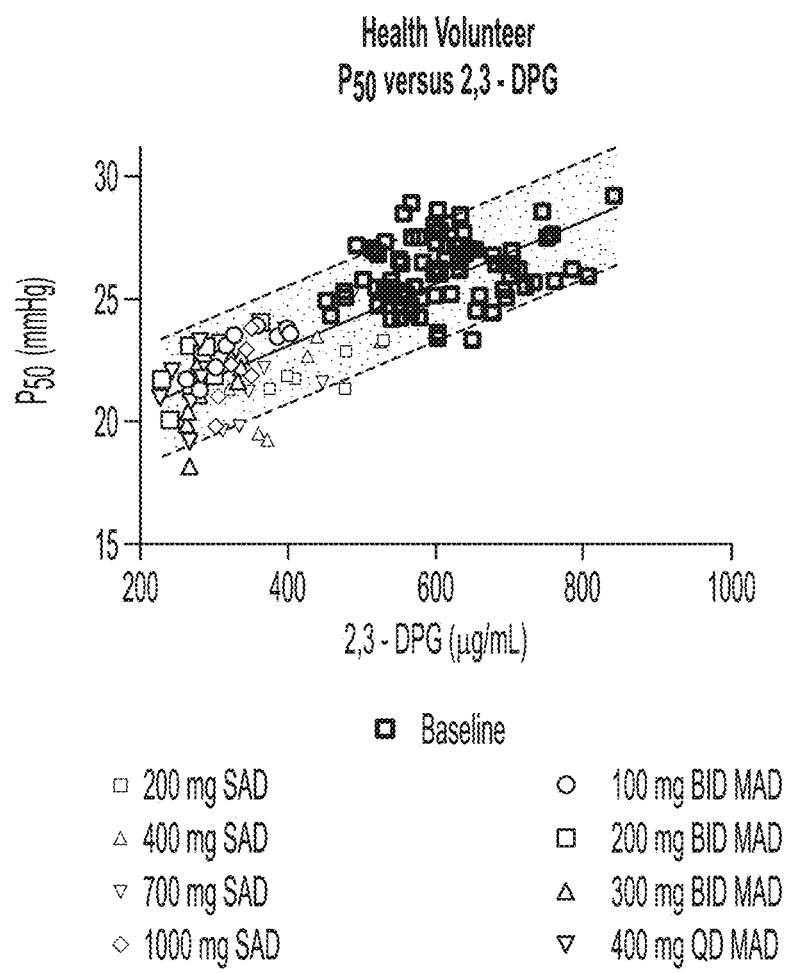
FIG. 42 is a scatter plot of 2,3-DPG levels and p50 values observed in healthy volunteers in the SAD and MAD cohorts.
Figure 43:
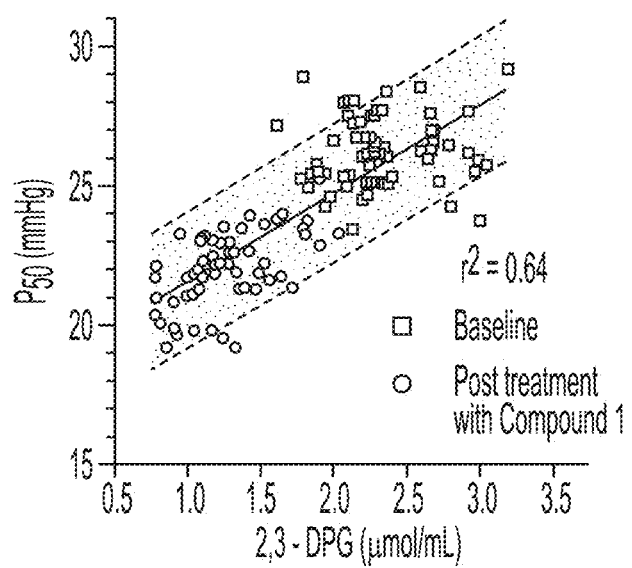
FIG. 43 is a scatter plot of 2,3-DPG levels and p50 values observed in subjects treated with Compound 1.

FIG. 42 is a scatter plot of 2,3-DPG levels and p50 values observed in healthy volunteers in the SAD and MAD cohorts. Solid symbols represent the observed p50/2,3-DPG levels in healthy volunteers dosed with Compound 1 at 24 h following the last administered dose. Baseline data represents p50/2,3 DPB data obtained either prior to Compound 1 treatment and from healthy volunteers dosed with placebo. A positive correlative relationship between 2,3 DPG and p50 levels was observed for patients receiving various doses. As illustrated in FIG. 43, the increase in oxygen affinity in subjects treated with Compound 1 correlated with the reduction of 2,3-DPG, demonstrating preliminary proof of mechanism in healthy RBCs and supporting further clinical development of Compound 1 in patients with SCD.

Results (SCD Subjects)

Single Dose in SCD Patients

Figure 44:
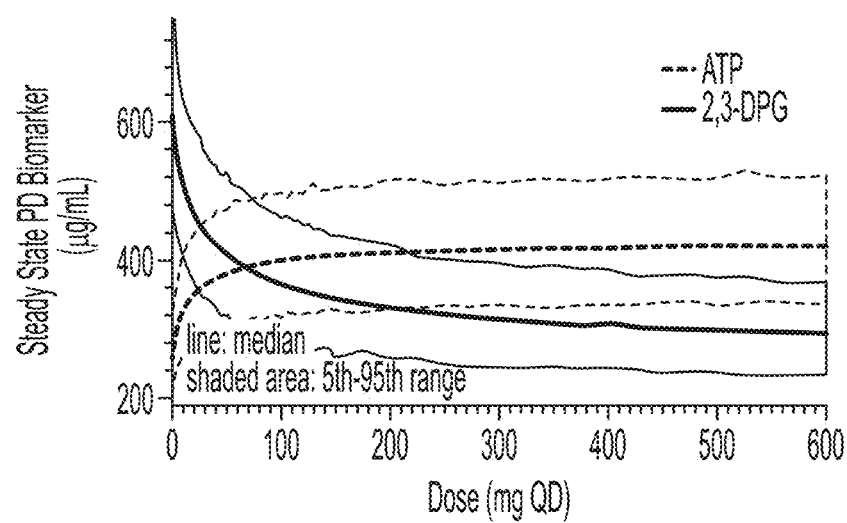
FIG. 44 is a graph depicting a model of the predicted PD response of once daily (QD) doses of Compound 1 in healthy volunteer RBCs.

Modeling of pharmacodynamic response in healthy volunteer RBCs indicated that doses of Compound 1≥150 mg per day result in the maximum ATP response, and ≥400 mg per day maximize the 2,3-DPG response (FIG. 44). A potential exposure to the maximum PD response dose range to evaluate in patients with SCD was identified. Based on the safety and PK/PD profile in healthy volunteer studies, a 700 mg single dose was evaluated in patients with SCD (n=7). A single 700 mg dose of Compound 1 was selected to evaluate in patients with SCD to enable daily dosing cohorts at lower exposures.

In the SCD single dose cohort, seven patients received either Compound 1 (n=5) or placebo (n=2). The baseline characteristics of the SCD patients receiving a single 700 mg dose of Compound 1 or placebo are reported in Tables 21 and 22. All patients had a Hb SS genotype and a mild VOC history but persistent anemia and ongoing hemolysis, despite hydroxyurea therapy.

TABLE 21

Baseline Characteristics of SCD Patients Enrolled in Single Dose Cohort (N = 7)

| | |
|---|---|
| Age, years | 34.7 (15, 48) |
| Male | 2 (29%) |
| Hb SS genotype | 7 (100%) |
| Hydroxyurea therapy | 7 (100%) |
| 12-mo VOC rate | 0 (0, 2) |
| Prior packed RBC transfusion (>30 days) | 1 (14%) |

TABLE 21-continued

Baseline Characteristics of SCD Patients Enrolled in Single Dose Cohort (N = 7)

| Hemoglobin electrophoresis | |
| --- | --- |
| % HbS | 79.4 (70.0, 89.1) |
| % HbF | 14.2 (5.5, 27.5) |
| % F cells | 50.6 (33.3, 91.8) |

TABLE 22

Baseline Characteristics of SCD Patients Enrolled in Single Dose Cohort (N = 7)

| | |
| --- | --- |
| Hb, g/dL | 8.6 (7.4, 10.1) |
| RBC, $10^{12}$/L | 2.4 (1.8, 2.9) |
| ARC, $10^9$/L | 224.6 (148.2, 369.3) |
| Total bilirubin, mg/dL | 3.61 (2.10, 6.60) |
| LDH, U/L | 385.9 (308.0, 576.0) |
| 2,3-DPG, µg/gHb | 5291 (4602, 6137) |
| ATP, µg/gHb | 1845 (1552, 2158) |
| p50, $pO_2$ mmHg | 30.1 (26.1, 34.0) |
| MCV | 108.7 (96.5, 125) |

No serious adverse events (SAEs) or TEAEs leading to pt withdrawal were reported in the SD cohort. In the SD cohort, 7 pts (2 males, 5 females, all HbSS) received 700 mg Compound 1 (n=5) or placebo (n=2).

All SCD patients who received a single 700 mg dose of Compound 1 or placebo were monitored for adverse events for 7 days. The incidence of treatment emergent adverse events (TEAEs) in SCD patients receiving Compound 1 (700 mg) or placebo are reported in Table 23. Six TEAEs were reported in 4 patients; all TEAEs were grade 1 and transient. Specifically, six TEAEs were reported in 4 of 7 (57%) patients, including 3 TEAEs (arthralgia, headache, palpitations) in 2 of 5 (40%) pts receiving Compound 1 and 3 TEAEs (back pain, myalgia, pruritus) in 2 of 2 (100%) pts receiving placebo; all TEAEs were grade 1 and transient. In the Compound 1 cohort, arthralgia, headache, and palpitations each were observed in one patient. One possibly related TEAE (palpitations) occurred about 8 hours post dose. No other symptoms were observed, and the palpitations resolved in <1 minute. In the placebo cohort, backpain, myalgia, and pruritus each were observed in one patient. By comparison, no TEAEs were observed in healthy volunteers who received a single dose of Compound 1 (700 mg) or placebo. The single 700 mg dose of Compound 1 was considered tolerable, and the first multiple dose SCD cohort was initiated.

TABLE 23

Compound 1 is Well Tolerated in Patients with SCD

| | Compound 1 700 mg (N = 5) | Placebo (N = 2) |
| --- | --- | --- |
| Any TEAE, n (%) | 2 (40) | 2 (100) |
| Related to study drug, n (%) | 1 (20) | 0 |

In 3 pts with SCD (3 females, all HbSS) who thus far completed MD-1, 14 days of 300 mg Compound 1 or placebo daily was well tolerated, with 1 pt reporting transient, unrelated Grade 2 TEAEs of nausea/vomiting at the end of the 14-day dosing period.

Figure 45:
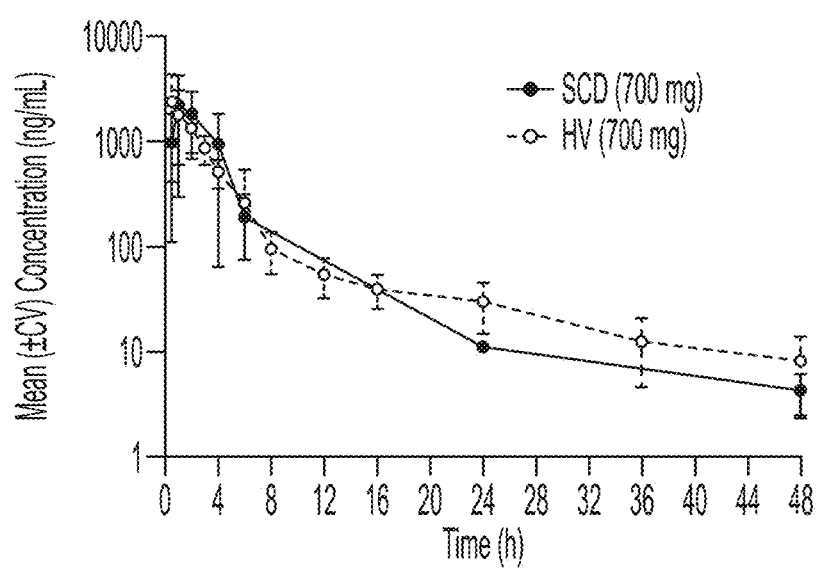
FIG. 45 is a graph of the mean plasma concentration of Compound 1 over time in SCD patients and healthy volunteers following a single 700 mg dose of Compound 1.

As shown in FIG. 45 and Table 24, similar Compound 1 plasma pharmacokinetic profiles were observed in healthy volunteers and SCD patients who received a single 700 mg dose of Compound 1.

TABLE 24

Plasma PK Parameters in Healthy Volunteers and Patients with SCD

| Single Dose (700 mg) | $C_{max}$ ng/mL | $AUC_{inf}$ (h · ng/mL) | $t_{1/2}$ (h) | $T_{max}$ (h) |
| --- | --- | --- | --- | --- |
| HV (N = 6) | 2204 (83.5) | 6995 (30.3) | 13.3 (34.3) | 0.5 (0.5, 6.0) |
| SCD (N = 5) | 2585 (59.9) | 7300 (43.4) | 14.9 (48.7) | 2.0 (1.0, 4.0) |

Values are geometric mean (geometric coefficient of variation) except for $T_{max}$ (Median [Min, Max]).

Figure 46A:
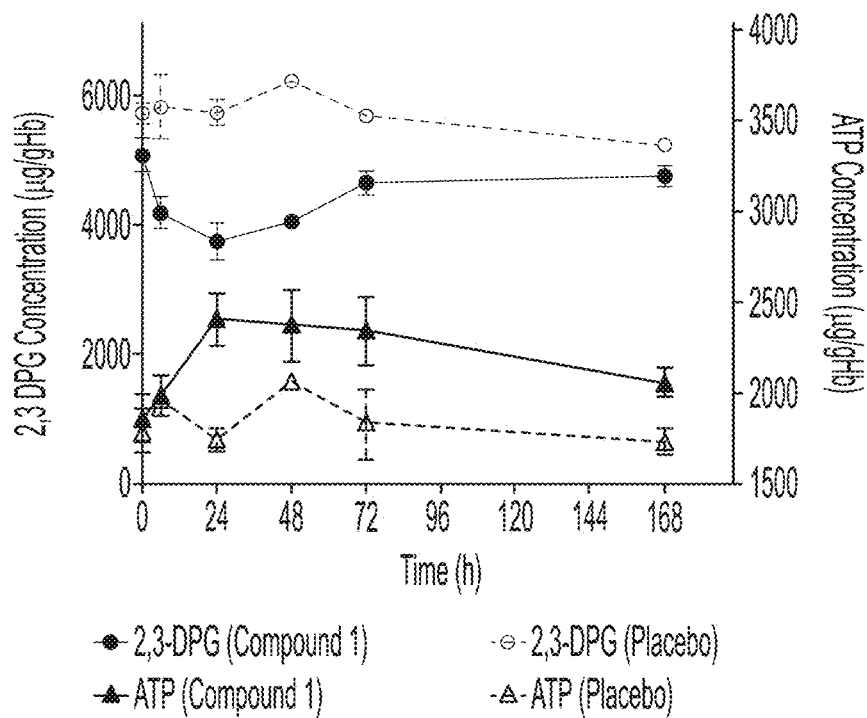
FIG. 46A is a graph of 2,3-DPG and ATP blood concentrations over time in SCD patients following a single 700 mg dose of Compound 1 or placebo.

Biologic activity has been observed in SCD subjects receiving a single dose of Compound 1, demonstrating the PKR enzyme in the SCD RBC is functional and responds to an allosteric PKR activator. As shown in FIG. 46A, 24 hours after a single 700-mg dose of Compound 1 in patients with SCD, ATP blood concentrations increased by 30%, and 2,3-DPG blood concentrations decreased by 26%. Maximum changes were observed at 24 hours. The onset of the increase in ATP blood levels after a single 700 mg dose of Compound 1 was faster in SCD patients than in healthy volunteers, while the onset of the decrease in 2,3-DPG blood levels was slower.

The following table reports the mean percentage change in 2,3-DPG blood levels, relative to baseline, measured over time in SCD patients after a single dose of Compound 1 (700 mg):

| Time After Dose | Percent Change |
| --- | --- |
| 0 | 0 |
| 6 | −16 |
| 24 | −31 |
| 48 | −21 |
| 72 | −8 |

The following table reports the mean percentage change in ATP blood levels, relative to baseline, measured over time in SCD patients after a single dose of Compound 1 (700 mg):

| Time After Dose | Percent Change |
| --- | --- |
| 0 | 0 |
| 6 | 14 |
| 24 | 30 |
| 48 | 30 |
| 72 | 32 |

Figure 54A:
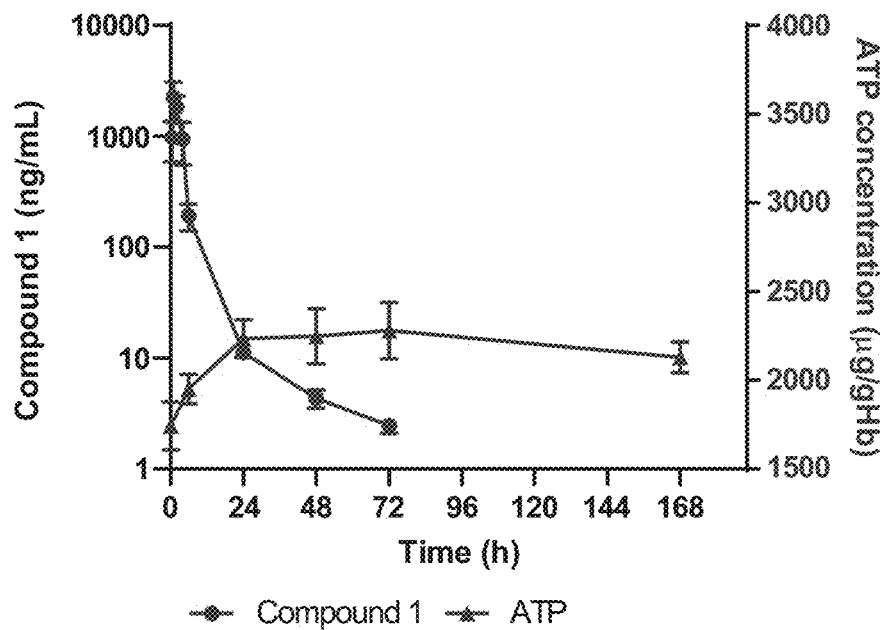
FIG. 54A and FIG. 54B are graphs of ATP blood levels and 2,3-DPG blood levels, respectively, and Compound 1 plasma concentrations, over time, following a single 700 mg dose of Compound 1 in SCD patients.
Figure 54B:
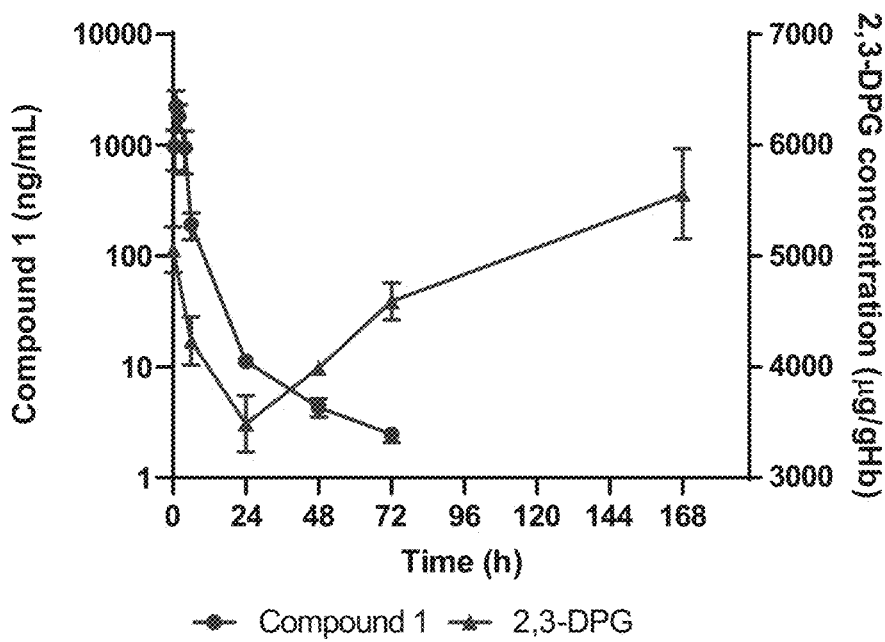

As shown in FIGS. 54A and 54B, the pharmacodynamic maximum effects on blood ATP and 2,3-DPG concentrations lagged behind the pharmacokinetic maximum plasma concentration of Compound 1. Specifically, as shown in FIG. 54A, the pharmacodynamic maximum increase in blood ATP concentration lagged at least about 24 hours behind the pharmakinetic maximum plasma concentration of Compound 1. Likewise, as shown in FIG. 54B, the pharmacodynamic maximum decrease in blood 2,3-DPG concentration lagged about 24 hours behind the pharmakinetic maximum plasma concentration of Compound 1.

Increased $O_2$ affinity (↓P50) with a decreased point of sickling (PoS) and improved HbS RBC deformability were observed in all Compound 1-treated pts. Improved HbS RBC membrane function was also demonstrated with a shift of the osmoscan results towards normal. Improved hematologic parameters, including ~0.9 g/dL Hb increase compared with placebo, were also observed 24 h after a single dose of Compound 1.

Figure 47A:
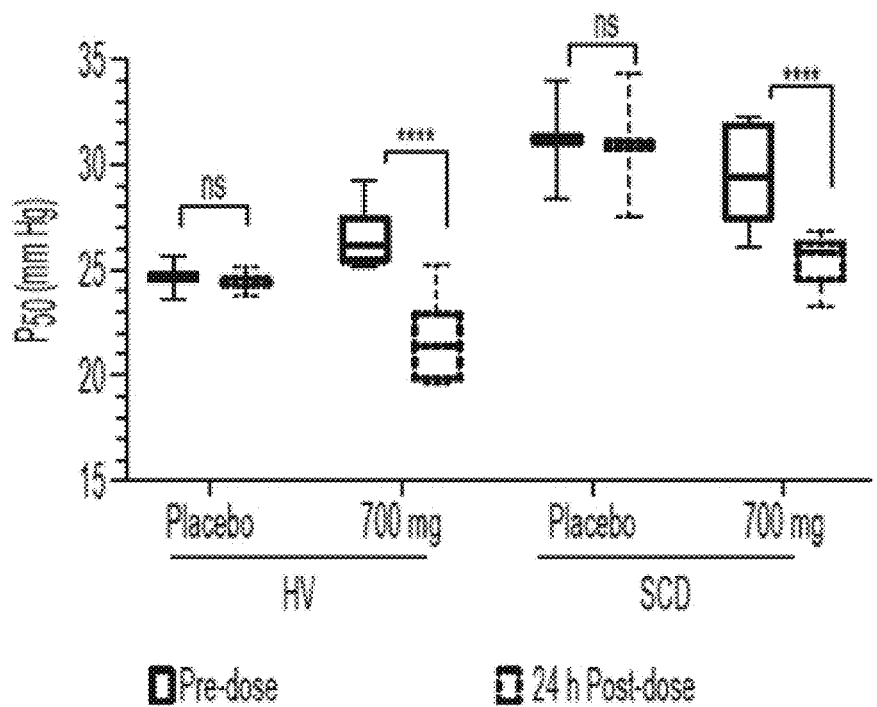
FIG. 47A is a graph of oxygen affinity (p50) before and 24 hours after a single 700 mg dose of Compound 1 in healthy volunteers and SCD patients.

As shown in FIG. 47A, increased hemoglobin 02 affinity (decreased p50) was observed after a single 700 mg dose of Compound 1 in both healthy volunteers (see also FIG. 31) and patients with SCD. In SCD patients, the mean absolute change in p50, relative to baseline, measured 24 hours after a single 700 mg dose of Compound 1, was −4 mmHg.

As shown in FIG. 48A, increased hemoglobin O₂ affinity correlated with a reduction in 2,3-DPG in both healthy volunteers (see also FIG. 37) and patients with SCD.

Figure 49:
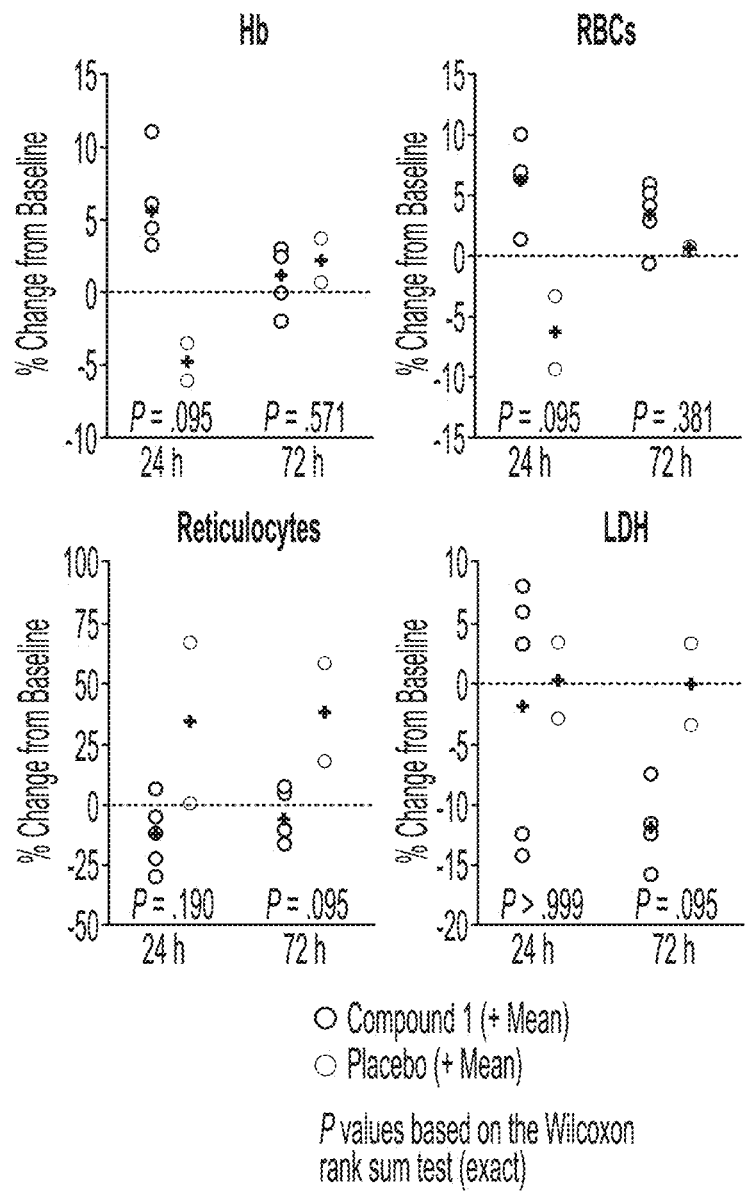
FIG. 49 depicts four graphs showing changes from baseline in hematologic laboratory parameters in SCD patients following a single dose of Compound 1 or placebo.

As shown in FIG. 49, SCD patients treated with Compound 1 demonstrated improved hematologic parameters (increased Hb, increased RBCs, and decreased reticulocytes) 24 hours after Compound 1, when maximum 2,3-DPG and ATP responses were observed (see FIG. 46A), returning to baseline after 72 hours. A single dose of Compound 1 resulted in an increase in Hb of 0.5 g/dL (range: 0.3, 0.9) in Compound 1—treated participants vs. a decrease in Hb of 0.4 g/dL (range: −0.5, −0.3) in placebo-treated participants (decreased Hb potentially due to phlebotomy), as well as a reduction in reticulocytes. Decreased lactate dehydrogenase (LDH) was also observed in Compound 1—treated participants 72 hours after Compound 1 dosing, indicating a reduction in RBC turnover as the source for the transient improvement in RBC parameters. These results suggest that a sustained 2,3-DPG and ATP response may be required for optimal benefit.

Figure 50:
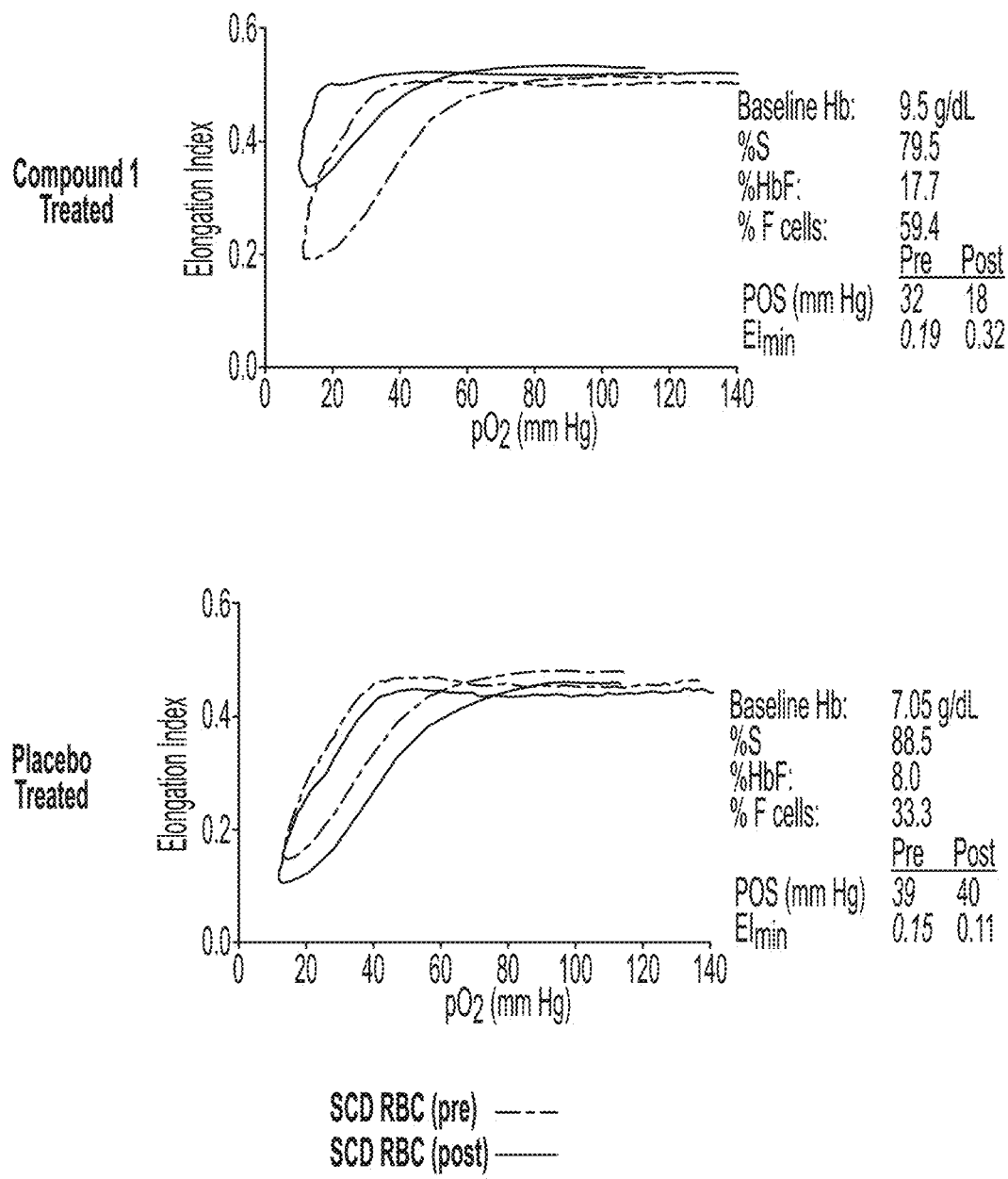
FIG. 50 is a pair of graphs depicting the effects of a single dose of Compound 1 or placebo on oxygen scan in SCD patients.
Figure 51:
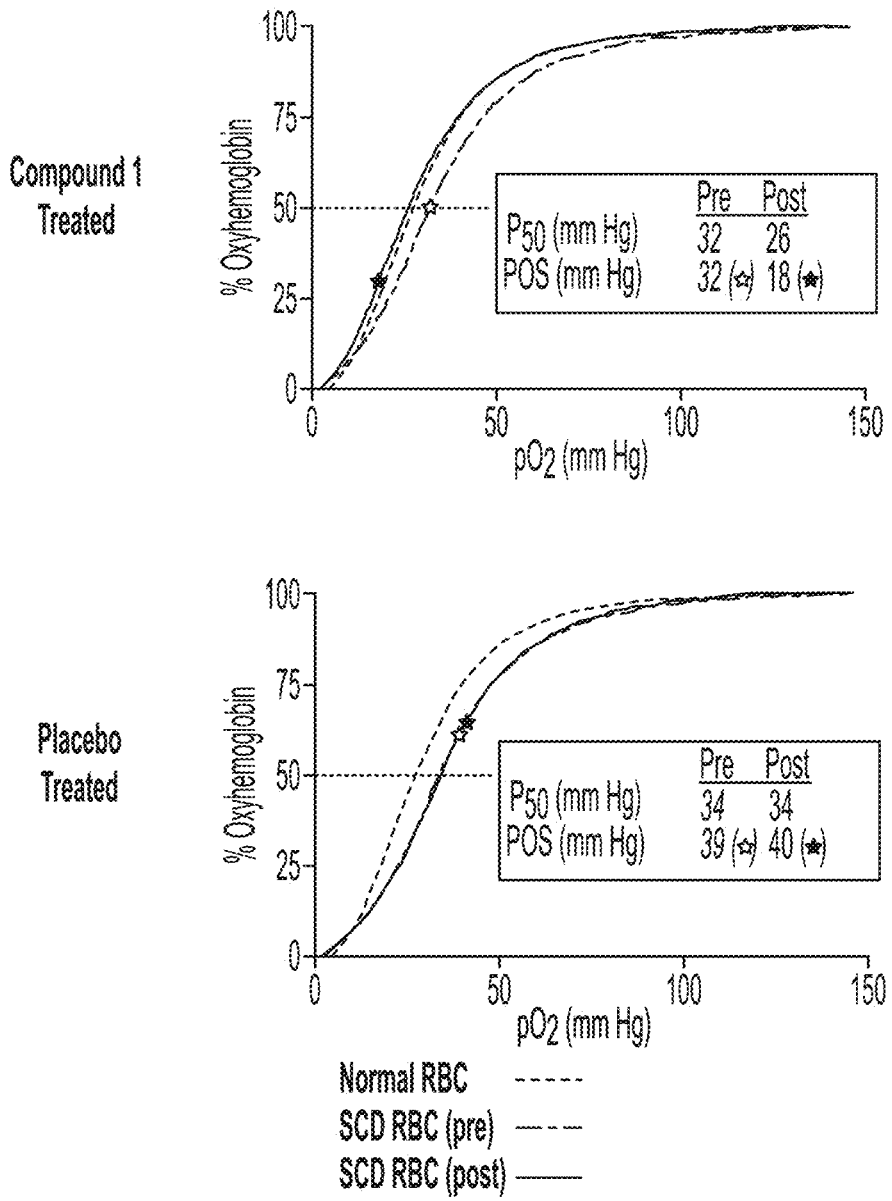
FIG. 51 is a pair of graphs depicting the effects of a single dose of Compound 1 or placebo on oxygen affinity ($PO_{50}$) in SCD patients.
Figure 52:
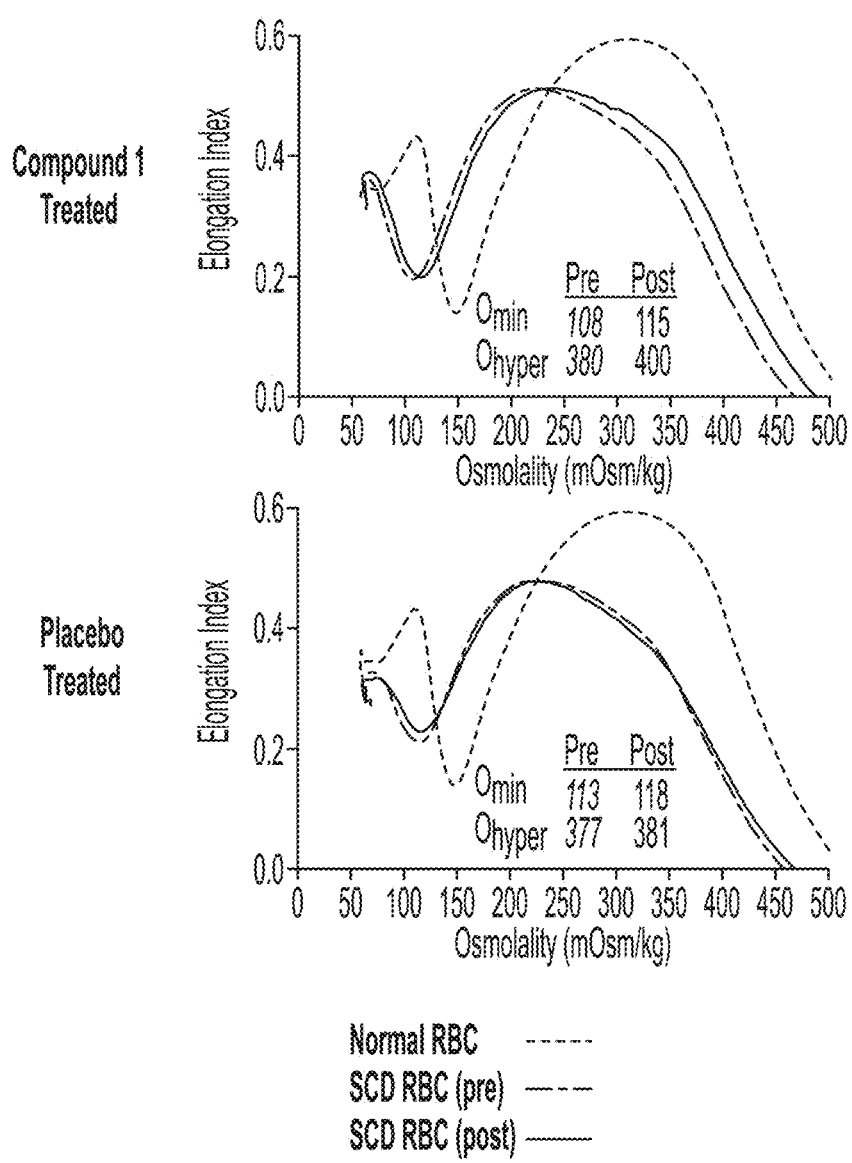
FIG. 52 is a pair of graphs depicting the effects of a single dose of Compound 1 or placebo on osmoscan in SCD patients.

The effects of a single dose of Compound 1 (700 mg) versus placebo on oxygen scan, oxygen affinity (p50), and osmoscan in SCD patients were evaluated. A single dose of Compound 1 decreased the oxygen tension (pO₂) at which HbS started to polymerize and improved the minimum deformability of the deoxygenated sickle RBCs, as demonstrated by trends towards significant reductions from baseline in PoS and increases in EI$_{min}$. At the Point of Sickling (POS or PoS), polymerization of de-oxy HbS can affect the deformability of the RBCs and the elongation Index starts to decrease. The Elmin refers to the lowest level of RBC deformability in the Oxygenscan. The lower the Elmin the lower the deformability of the RBC. As shown in FIG. 50 and Table 25 (Oxygenscan), Compound 1 decreased the deoxygenation HbS polymerization rate and improved sickle RBC 02-dependent deformability, as demonstrated by reductions in POS and increases in EI$_{min}$. This effect was observed in all participants receiving Compound 1. As shown in FIG. 51 and Table 25 (Oxygen affinity curve), Compound 1 increased O₂ affinity (decreased p50) in all participants treated and improved the membrane function of HbS RBCs in all treated patients with SCD, as demonstrated by a shift towards normal in O$_{min}$ and O$_{hyper}$. These effects were transient, with P50 values returning to baseline by the 72-hour measurement. The ability to maintain cellular hydration is a critical function of the RBC membrane. In order to measure the impact of Compound 1 on this critical function, the effect of Compound 1 compared to placebo on the deformability of SCD RBCs across an osmolality gradient was evaluated. As shown in FIG. 52 and Table 25 (Osmoscan), Compound 1 improved osmolality-dependent membrane function in sickle RBCs, as demonstrated by improvements (i.e., shifts toward normal) in O$_{min}$ and O$_{hyper}$. Compound 1 improved the deformability of the SCD RBCs under conditions of both low osmolality (O$_{min}$) and high osmolality (O$_{hyper}$), shifting the response toward normal. These effects were transient, returning to baseline 3 to 7 days after the single dose of Compound 1. SCD RBCs from placebo treated patients showed no change.

TABLE 25

Improvement in Deformability, Oxygen Affinity, and Osmotic Fragility in Sickle RBCs Under Deoxygenation and/or Shear Stress After a Single Dose of Compound 1 (700 mg)

| Parameter | Pre-dose | Post-dose (24 hours) | P Value |
|---|---|---|---|
| POS (Oxygenscan) | 35.4 (27.3, 38.8) | 24.0 (17.9, 31.8) | .063 |
| EI$_{min}$ (Oxygenscan) | 0.193 (0.16, 0.21) | 0.296 (0.26, 0.38) | .125 |
| EI$_{max}$ (Oxygenscan) | 0.445 (0.41, 0.51) | 0.451 (0.42, 0.52) | .250 |
| p50 (Oxygen affinity curve) | 29.4 (26.1, 32.3) | 25.8 (23.3, 26.8) | .063 |
| EI$_{max}$ (Osmoscan) | 0.483 (0.46, 0.57) | 0.478 (0.46, 0.57) | .750 |
| O$_{min}$ (Osmoscan) | 108 (105, 121) | 117 (106, 124) | .063 |
| O$_{hyper}$ (Osmoscan) | 380 (371, 399) | 400 (371, 412) | .125 |

Values presented as median (range).
P values based on the nonparametric Wilcoxon rank sum test for paired data.

Figure 53A:
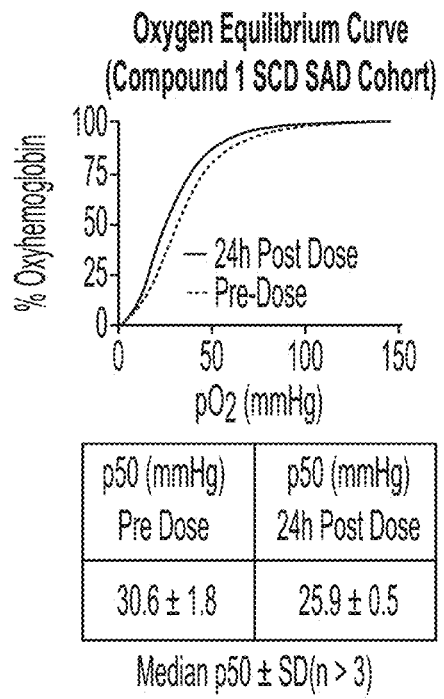
FIG. 53A is a graph of hemoglobin oxygen saturation versus pO2 in SCD subjects before and after a single dose of Compound 1.
Figure 53B:
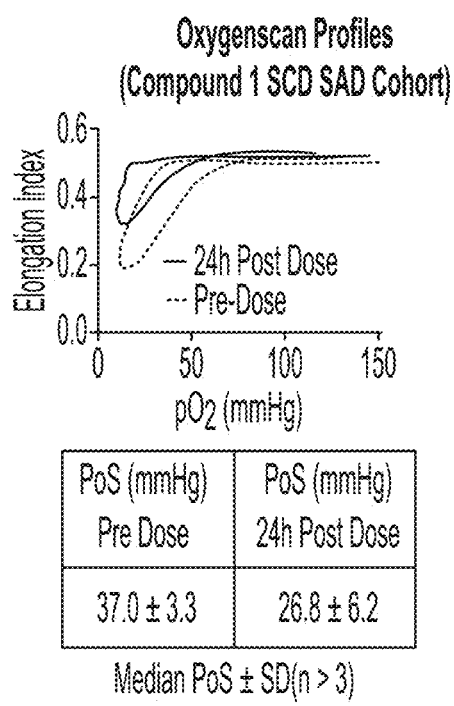
FIG. 53B is a graph of elongation index (EI) versus pP2 in SCD subjects before and after a single dose of Compound 1.

FIGS. 53A and 53B show the effects of Compound 1 on a SCD subject's RBCs, 24 h after Compound 1 dosing. As shown in FIG. 53A, SCD subjects who received a single dose of Compound 1 experienced increased oxygen affinity of HbS, similar to HbA. As shown in FIG. 53B, subjects who received a single dose of Compound 1 experienced a left shift in the point of sickling (PoS) with an increase in the Elmin.

Multiple Ascending Doses (MAD) in SCD Patients

The first MAD cohort in SCD patients (MAD1) had an initial daily dose of 300 mg of Compound 1. This dose was selected from the daily dose range of Compound 1 evaluated in the healthy adult volunteers that was found to be tolerable and pharmacodynamically active. The baseline characteristics of the SCD patients in the MAD cohort receiving 300 mg of Compound 1 or placebo (MAD1, n =9) were as follows:

| | |
|---|---|
| Age, years | 29.7 (19, 43) |
| Male | 3 (33%) |
| Hb SS genotype | 8 (89%) |
| Hb, g/dL | 8.9 (7.1, 10.1) |
| ARC, 109/L | 242.8 (125.6, 329.3) (n = 8) |
| MCV | 112.9 (75.0, 131.5) (n = 8) |
| Total bilirubin, mg/dL | 3.31 (0.60, 11.30) |
| LDH, U/L | 364.8 (180, 610) |
| Hydroxyurea Use | 6 (67%) |
| % HbS | 81.0 (67.0, 92.9) |
| % HbF | 12.1 (3.5, 20.1) |
| % F cells | 41.3 (30.1, 67.2) (n = 6) |

No serious adverse events (SAEs) or TEAEs leading to pt withdrawal were reported in the MAD1 cohort as of Jul. 17, 2020. In 3 pts with SCD (3 females, all HbSS) who thus far completed MAD1, 14 days of 300 mg Compound 1 or placebo daily was well tolerated, with 1 pt reporting transient, unrelated Grade 2 TEAEs of nausea/vomiting at the end of the 14-day dosing period.

Based on data from the MAD1 (300 mg once daily for 14 days), Compound 1 is well-tolerated in patients with SCD. In all, eighteen TEAEs were reported in 7 of 9 patients in the MAD1 (300 mg once daily) cohort (N=9). These included (a) eight Grade 1 TEAEs, including 3 patients c/o headache, 1 each of nausea, constipation, somnolence, increased LDH and increased AST, of which two AEs considered to be possibly related to study treatment were reported by one patient each (1 AE of headache and 1 AE of nausea); (b) six Grade 2 TEAEs, including 3 uncomplicated sickle pain events (in 2 patients), 1 patient with N/V and 1 increased reticulocytes, of which no AEs were considered related to study treatment, all AEs of pain events were considered unrelated and consistent with each patient's SCD pain history, and all AEs were treated with patient's standard home pain medications (no SAE/no hospitalization); and (c) one Grade 4 TEAE of elevated creatine kinase, unrelated to study treatment. Non-treatment-related AEs were consistent with events experienced in this patient population. No treatment-related serious AEs were reported. The TEAEs in MAD1 are summarized in the following table:

| Treatment-Emergent Adverse Events | Compound 1, 300 mg × 14 days (n = 7) | Placebo × 14 days (n = 2) |
|---|---|---|
| Any TEAE, n (%) | 6 (86%) | 1 (50%) |
| Related to study drug, n (%) | 2 (29%) | 0 |
| Any serious adverse event (SAE), n (%) | 0 | 0 |

Figure 46B:
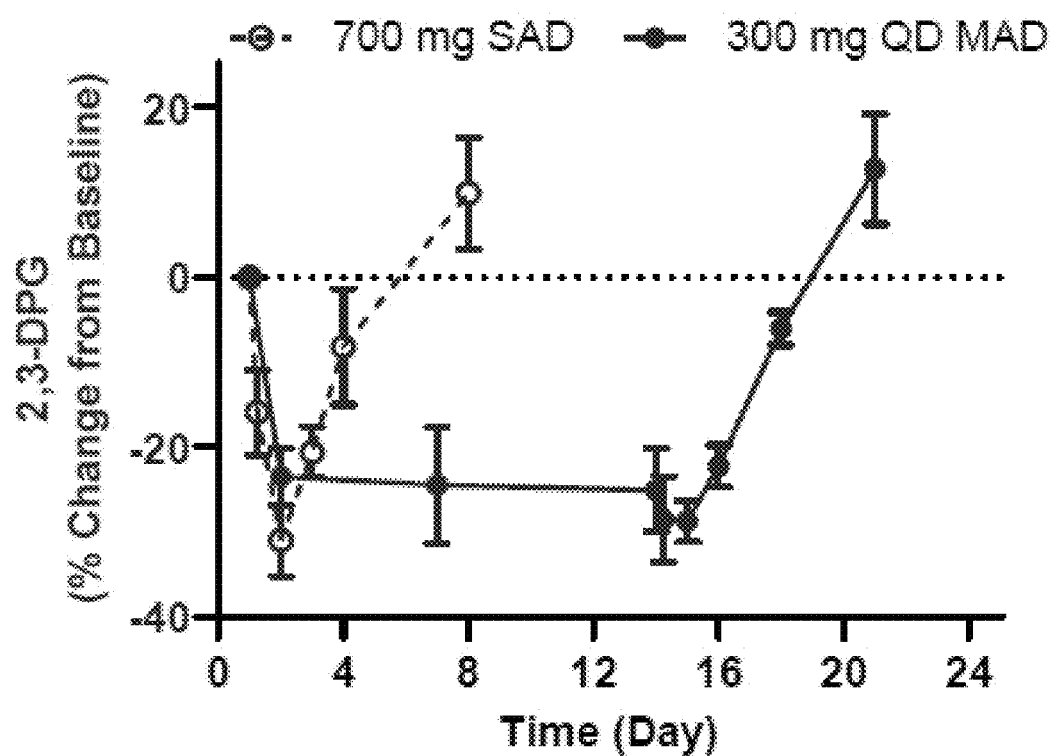
FIG. 46B is a graph of 2,3-DPG levels in red blood cells over time in SCD patients following a single 700 mg dose of Compound 1 or 300 mg QD dosing of Compound 1 over 14 days (MAD1).
Figure 46C:
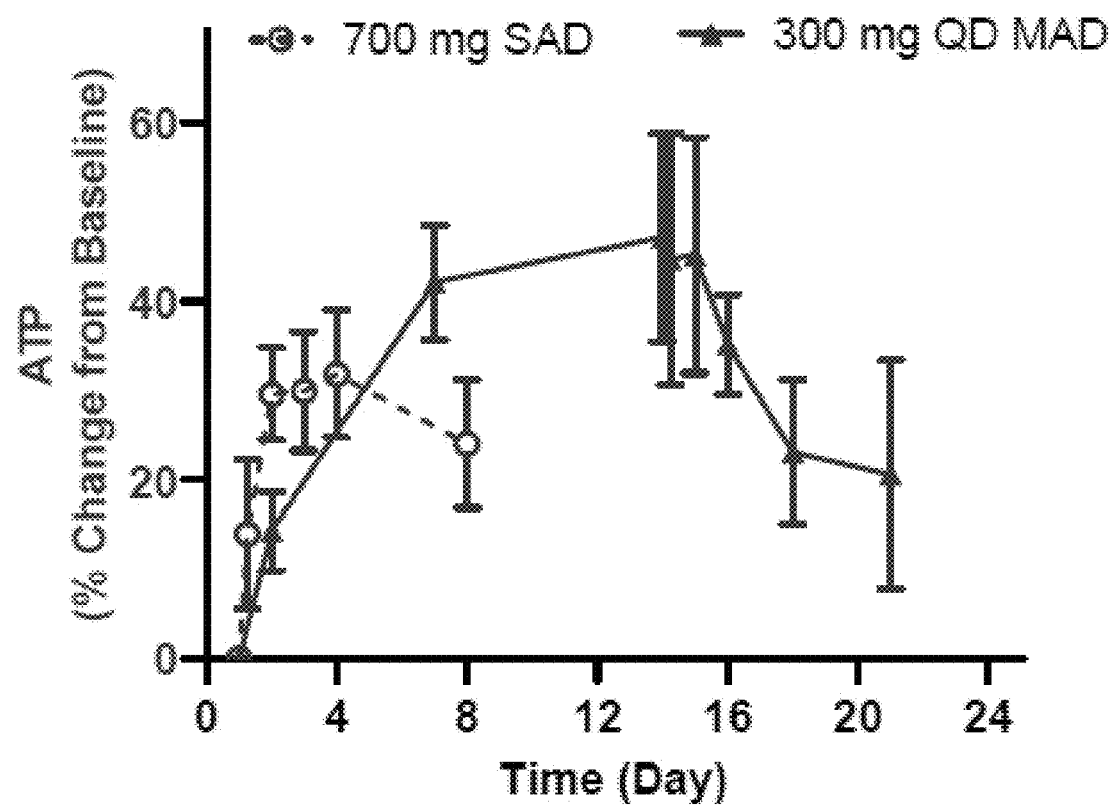
FIG. 46C is a graph of ATP levels in red blood cells over time in SCD patients following a single 700 mg dose of Compound 1 or 300 mg QD dosing of Compound 1 over 14 days (MAD1).

The PK/PD profile of the MAD1 cohort (300 mg once daily for 14 days) supports a dose range of 200 mg to 400 mg once daily. The 2,3-DPG and ATP profiles of the MAD1 (300 mg QD) cohort (along with the corresponding profiles in the 700 mg single dose cohort) are reported in FIGS. 46B and 46C, respectively.

The data show that, from baseline, 2,3-DPG levels were reduced in patients receiving Compound 1, thus increasing oxygen affinity and decreasing sickle hemoglobin polymerization. The following table reports the mean percentage change in 2,3-DPG blood levels, relative to baseline, measured over time after the first dose on days 1 and 14 in SCD patients who received daily doses of Compound 1 (300 mg QD) for 14 days:

| Time After | Day | |
|---|---|---|
| First Daily Dose | 1 | 14 |
| 0 | 0 | −25 |
| 6 |  | −29 |
| 24 | −23 | −29 |
| 48 |  | −22 |

ATP levels were increased from baseline in patients receiving Compound 1, resulting in improved RBC function and reduced hemoloysis. The following table reports the mean percentage change in ATP blood levels, relative to baseline, measured over time after the first dose on days 1 and 14 in SCD patients who received daily doses of Compound 1 (300 mg QD) for 14 days:

| Time After | Day | |
|---|---|---|
| First Daily Dose | 1 | 14 |
| 0 | 0 | 47 |
| 6 |  | 44 |
| 24 | 14 | 45 |
| 48 |  | 35 |

Figure 55A:
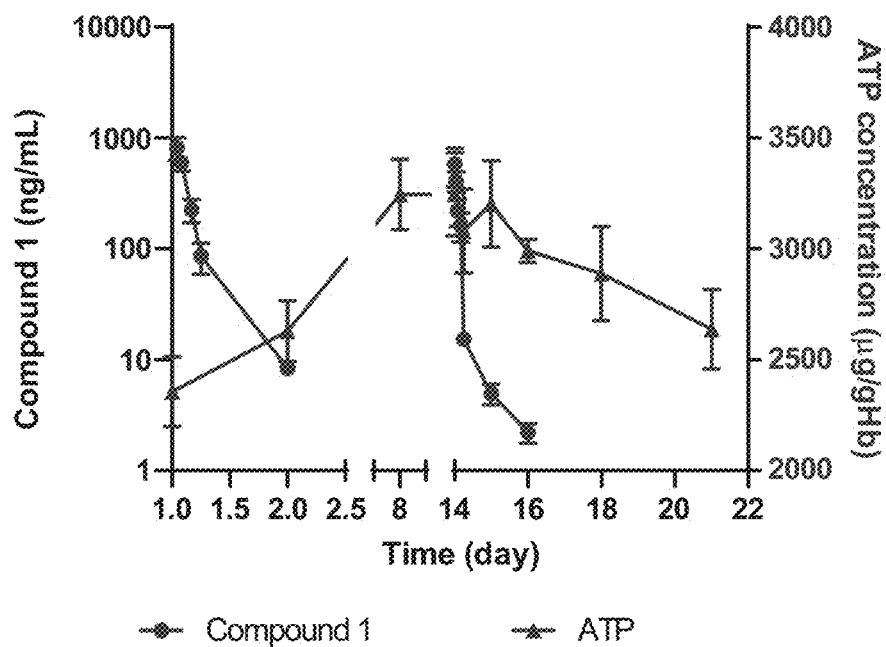
FIG. 55A and FIG. 55B are graphs of ATP blood levels and 2,3-DPG blood levels, respectively, and Compound 1 plasma concentrations, over time, during and after 300 mg QD administration of Compound 1 in SCD patients for 14 days.
Figure 55B:
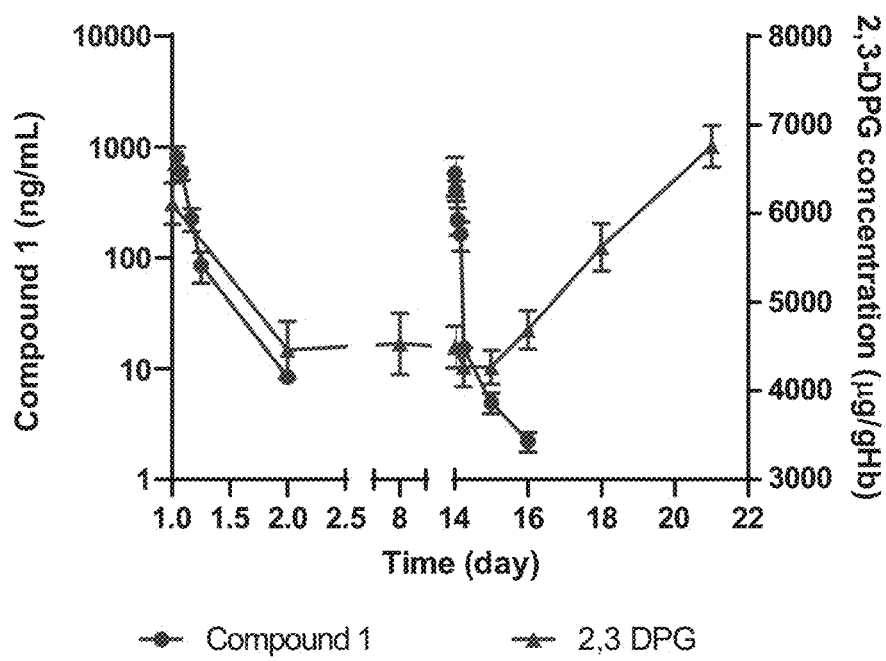

As shown in FIGS. 55A and 55B, stable pharmacodynamic effects on blood ATP and 2,3-DPG concentrations were observed despite fluctuactions the pharmacokinetic plasma concentration of Compound 1 during 300 mg QD dosing in SCD patients. Specifically, a stable increase in blood ATP concentration (FIG. 55A) and a stable decrease in blood 2,3-DPG concentration (FIG. 55B) were observed.

Figure 47B:
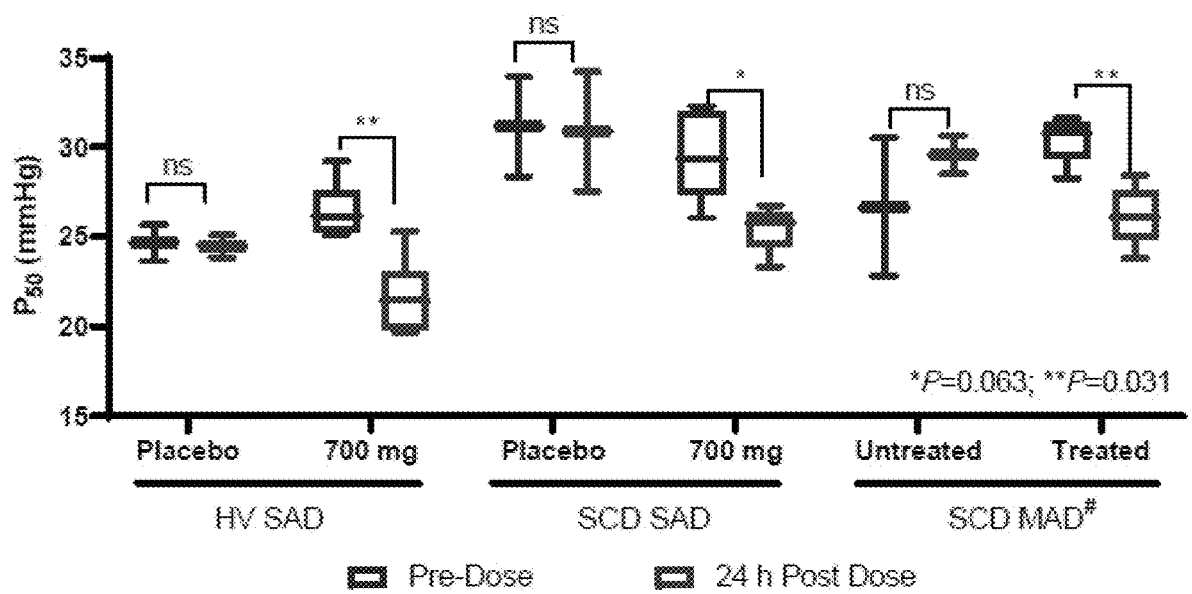
FIG. 47B is a graph of oxygen affinity (p50) (1) before and 24 hours after a single 700 mg dose of Compound 1 in healthy volunteers and SCD patients; and (2) before and after 14 days of treatment with 300 mg of Compound 1 once daily in SCD patients.
Figure 48B:
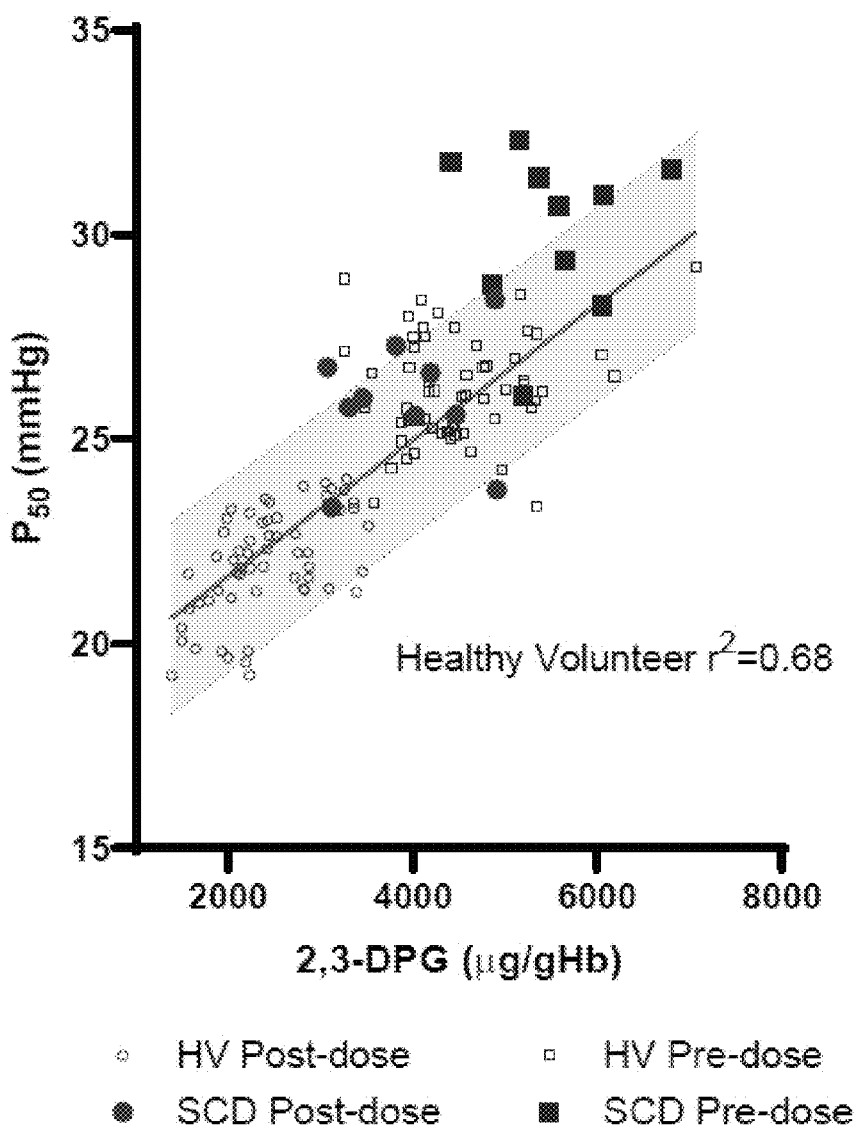

As shown in FIG. 47B, increased hemoglobin 02 affinity (decreased p50) was observed 24 hours after a single 700 mg dose of Compound 1 in both healthy volunteers (HV SAD) and SCD patients (SCD SAD) and after 14 days of Compound 1, 300 mg once daily (SCD MAD). With respect to the bar graphs representing the "Untreated" and "Treated" subjects in the SCD MAD cohort, the bar on the left side represents the P50 measured Pre-Dose, and the bar on the right side represents the P50 measured after 14 days of Compound 1, 300 mg once daily. SCD RBCs have higher P50 at baseline compared to HV RBCs. In the MAD cohort in SCD patients (300 mg QD for 14 days), the mean absolute change in p50, relative to baseline, measured 24 hours after the final dose of Compound 1, was −4 mmHg. As shown in FIG. 48B, change in oxygen affinity correlates with 2,3-DPG response. HbS oxygen affinity appears more sensitive to 2,3-DPG levels than HV oxygen affinity.

Laboratory changes relative to pretreatment for each pt in the MD cohort as of Jul. 17, 2020 are shown in Table 26. In 2 of 3 SCD MD-1 pts treated with Compound 1/placebo (currently blinded), Hb increased by >1 g/dL, % reticulocytes decreased, and markers of hemolysis were improved after 14 days of treatment (compared to pre-treatment levels). Hematologic parameters returned to pre-treatment levels 4 to 7 days post-treatment (data not shown) without clinical AEs. Functional studies in the 2 pts with increased Hb showed improved RBC deformability (↓ PoS) and improved RBC membrane function while on study treatment relative to pre-treatment and/or post-treatment.

TABLE 26

Laboratory Changes in Patients with SCD Receiving 300 mg Compound 1/Placebo Once Daily for 14 Days

| | Hematologic Parameters Hemoglobin, g/dL | | | | | Hemolytic Parameters Indirect Bilirubin, mg/dL | | | | |
|---|---|---|---|---|---|---|---|---|---|---|
| | Screen | Day 1 (Pre-Tx) | Day 7 (on Tx) | Day 14/15 (EOT) | Change from Screen/Pre-Tx to EOT Values (range) | Screen | Day 1 (Pre-Tx) | Day 7 (on Tx) | Day 14/15 (EOT) | Change from Screen/Pre-Tx to EOT Values (range) |
| Pt 1 | 8.1 | 7.9 | 7.9 | 7.5 | ↓ 0.4-0.6 | 4.7 | 2.8 | 2.5 | 3.0 | ↓ 1.7-↑ 0.2 |
| Pt 2 | 9.2 | 9.9 | 10.4 | 11.1 | ↑ 1.2-1.9 | 1.3 | 2.0 | 0.9 | 0.8 | ↓ 0.5-1.2 |
| Pt 3 | 8.7 | 8.1 | 8.8 | 9.2 | ↑ 0.5-1.1 | 1.2 | 1.0 | 0.8 | 1.0 | ↓ 0-0.2 |

| | Reticulocytes, % | | | | | Lactate Dehydrogenase, U/L | | | | |
|---|---|---|---|---|---|---|---|---|---|---|
| | Screen | Day 1 (Pre-Tx) | Day 7 (on Tx) | Day 14/15 (EOT) | Change from Screen/Pre-Tx to EOT Values (range) | Screen | Day 1 (Pre-Tx) | Day 7 (on Tx) | Day 14/15 (EOT) | Change from Screen/Pre-Tx to EOT Values (range) |
| Pt 1 | 8.0 | 10.1 | 12.8 | 11.4 | ↑ 1.3-3.4 | 234 | 180 | 148 | 192 | ↓ 42-↑ 12 |
| Pt 2 | 10.2 | 11.0 | 6.8 | 0.8 | ↓ 9.4-10.2 | 308 | 354 | 257 | 226 | ↓ 82-128 |
| Pt 3 | 8.0 | 16.0 | 5.8 | 4.2 | ↓ 3.8-11.8 | 470 | 473 | 371 | 279 | ↓ 191-194 |

Figure 61A:
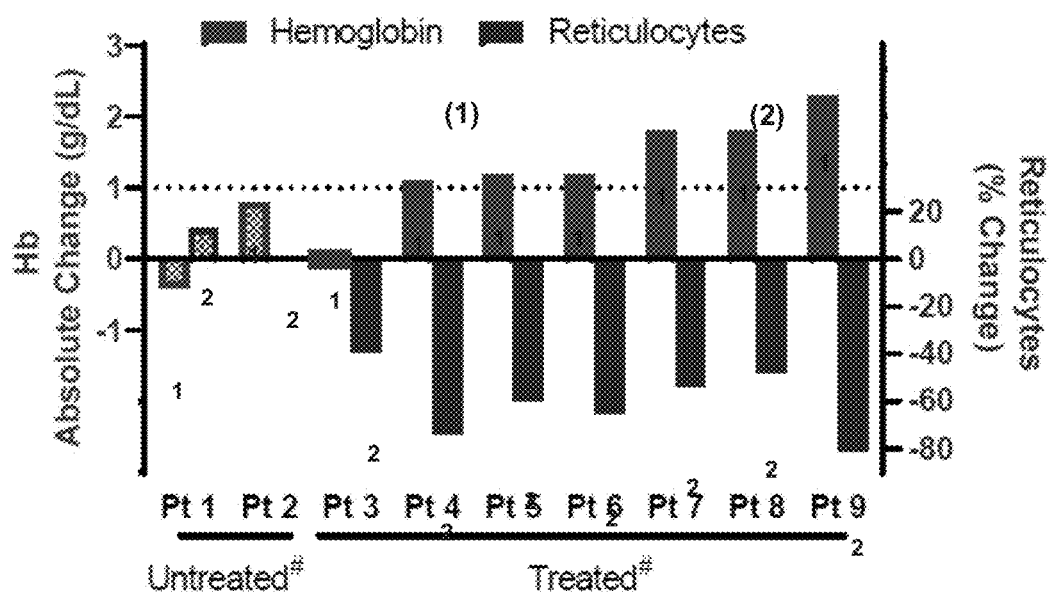
FIG. 61A is a graph showing changes in levels of hemoglobin (indicated with green bars and number (1)) and reticulocytes (indicated with blue bars and number (2)) in SCD patients after 14 days of treatment with 300 mg of Compound 1 once daily.
Figure 61B:
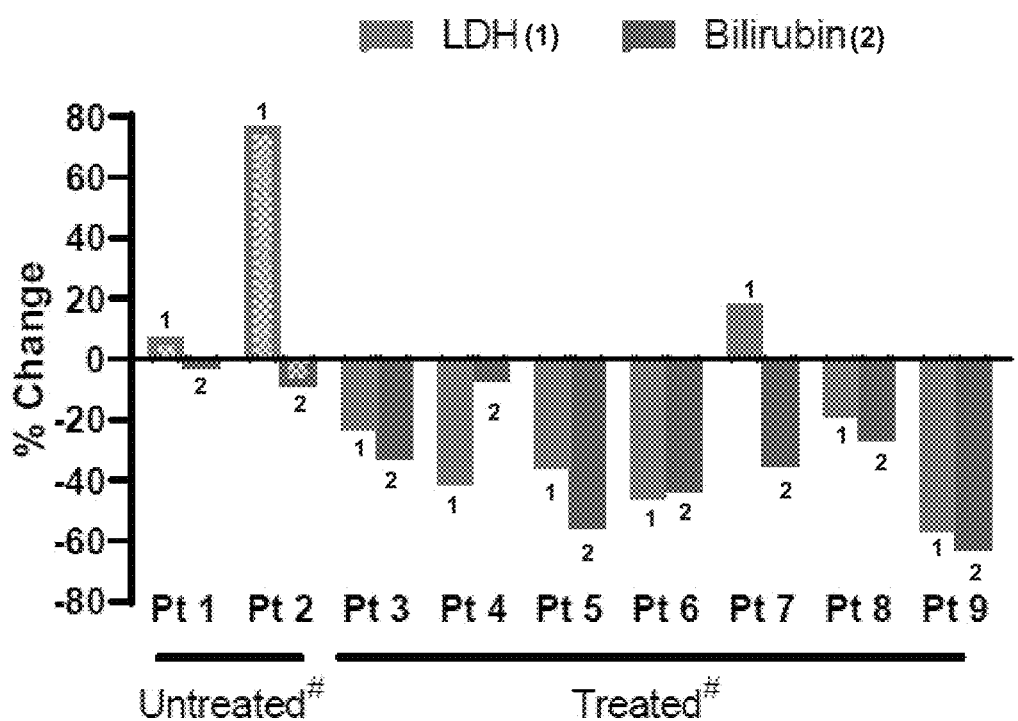
FIG. 61B is a graph showing changes in levels of LDH (indicated with orange bars and number (1)) and bilirubin (indicated with brown bars and number (2)) in SCD patients after 14 days of treatment with 300 mg of Compound 1 once daily.

EOT = end of treatment;
Pre-Tx = pre-treatment;
Pt = patient;
SCD = sickle cell disease;
Tx = treatment Improved hematologic and hemolytic parameters were observed in MAD1 after 14 days of 300 mg Compound 1 once daily (FIG. 61A and 61B). In patients receiving Compound 1, 6 of 7 had a >1 g/dL increase in hemoglobin, and all 7 had a decrease in reticulocytes. A median 1.2 g/dL Hb increase (range 0, 2.3) and a median 60% reticulocyte decrease (range −39%, −81%) over baseline were observed. The onset of the increase in Hb was rapid and continued to increase in most patients through the end of treatment, indicating the potential for additional improvement with extended dosing. In patients receiving Compound 1, 6 of 7 had a decrease in LDH, and all 7 had a decrease in total bilirubin. A median 36% LDH decrease (range +18%, −57%) and a median 35% bilirubin decrease (range −7%, −63%) over baseline were observed, which is consistent with the hypothesis that Compound 1 improves RBC survival and reduces RBC turnover.

Figure 56:
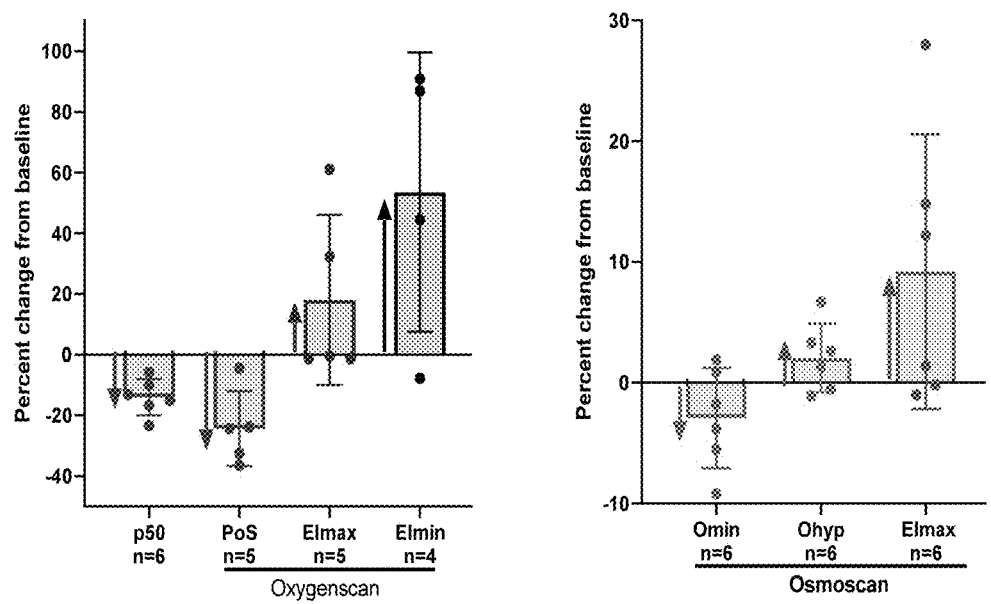
FIG. 56 depicts treatment associated improvements in Hb oxygen affinity, RBC sickling and measures of RBC health in patients with SCD following 14 days of daily dosing.

In SCD patients receiving 300 mg QD Compound 1 for 14 days, analysis of changes from baseline in Hb oxygen affinity (P50) and measures of RBC health (deformability) (FIG. 56) indicated rapid treatment-associated decreases in P50 (increased Hb oxygen affinity) and Point of Sickling (PoS) and improved measures of RBC deformability in all 7 patients receiving Compound for whom results were obtained. Directional changes in each of these parameters all suggest improvement of SCD RBC health.

Figure 57:
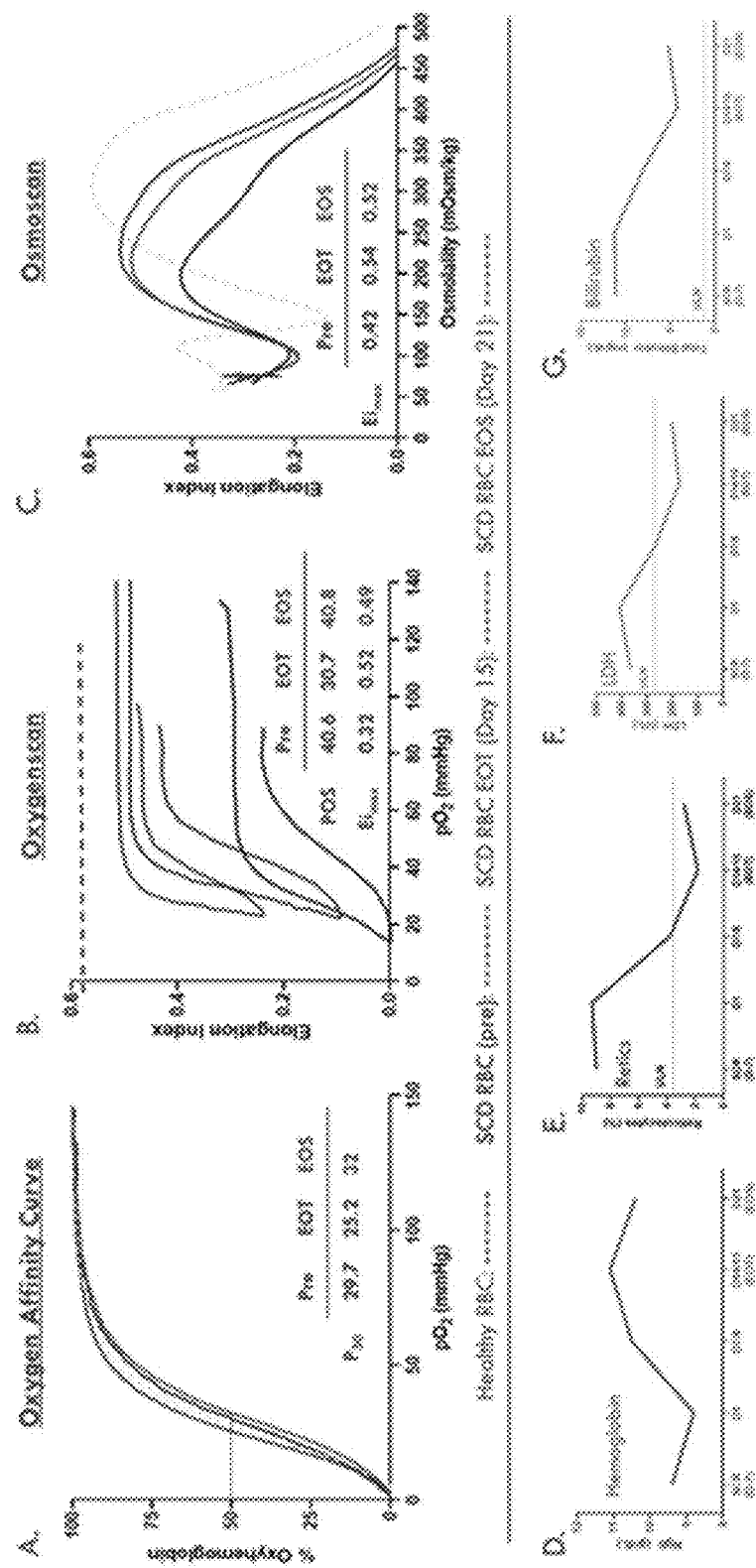
FIG. 57 depicts oxygen affinity, oxygenscan, and osmoscan curves collected from an SCD patient before administration of Compound 1, after 14 days of 300 mg QD Compound 1, and after a 7-day washout.

One patient yielded a complete data set illustrating the potential of Compound 1 to produce sustained improvements in RBC health, decreasing markers of hemolysis and increasing hemoglobin (FIG. 57). As shown FIG. 57A, once daily administration of 300 mg Compound 1 yielded increased Hb oxygen affinity (decreased P50) at end of treatment (day 15), returning to baseline values by day 21. As shown in FIG. 57B, these shifts in oxygen affinity were accompanied by coordinated shifts in the point of sickling (POS) at day 15 and day 21 measured with the oxygenscan. In contrast, the increased in EImax observed at day 15 remained elevated day 21, consistent with improved RBC deformability due to prolonged exposure to Compound 1. As shown in FIG. 57C, findings in the osmoscan exemplify sustained improvement in RBC deformability at day 21. The shift in the day 15 curve to the right and upward relative to pre-treatment, reflected by the increased EImax, is maintained at day 21. As shown in FIG. 57D to 57G, these changes were accompanied by an increase of >2 g/dL in Hb compared with pre-dose on day 1, sustained through day 21. Sustained improvements were also observed in reticulocytes and hemolytic parameters LDH & total bilirubin. This patient was not receiving concomitant hydroxyurea (HU).

Based on the effects observed in SCD patients, oral Compound 1 has the potential to impact both anemia and VOCs in SCD patients. Compound 1 increased Hb >1 g/dL in 6 of 7 patients treated for only 14 days, and decreased bilirubin, LDH and % reticulocytes in all 7 patients (median decreases of 35%, 36%, and 60%, respectively; FIG. 61). Collectively, the encouraging results observed for hemolytic biomarkers and the surrogate endpoint (Hb) in a limited population treated with Compound 1 for 14 days provide preliminary clinical evidence supporting the potential of Compound 1 to produce clinically meaningful outcomes in patients with SCD. These may include improved anemia, decreased VOCs and hospitalizations, and improvement in endothelial dysfunction and systemic vasculopathy which in some SCD subtypes cause greatest risk for earlier morbidity and mortality.

The second MAD cohort in SCD patients (MAD2) received a once-daily (QD) dose of 600 mg of Compound 1 for 14 days.

12-Week Dosing Cohort in SCD Patients

In the 12-week, open-label dosing cohort, SCD patients received a once-daily (QD) dose of 400 mg of Compound 1 for 84 days (12 weeks). The treatment was well-tolerated, with a safety profile consistent with the underlying disease. Increases in ATP levels and hemoglobin levels and a decrease in 2,3-DPG levels were observed and sustained over 12 weeks. An increase in oxygen affinity was also observed. A decrease in the point-of-sickling (lower oxygen pressures) and an increase in deformabiity ($EI_{max}$) were observed via oxygenscan and were sustained over 12 weeks. Improved sickle RBC hydration was observed via osmoscan and was sustained over 12 weeks. Based on preliminary data, improvements in downstream markers of SCD pathophysiology (inflammation, hypercoagulability, and tissue hypoxia) were also observed over 12 weeks of treatment. A sustained increase in RBC lifespan and decrease in hemolysis were observed, as evidenced by sustained decreases in reticulocytes, bilirubin, and lactate dehydrogenase (LDH). A decrease in VOCs was also observed.

Summary/Conclusion

Compound 1 has a favorable safety profile and has demonstrated PD activity after a single dose or after multiple daily doses in HS. In healthy volunteer studies, Compound 1 was well tolerated, demonstrating physiologic responses ($\downarrow$2,3-DPG and $\uparrow$ ATP) with biologic effects including $\uparrow O_2$ affinity, $\downarrow$ reticulocytes (P<0.001) and $\uparrow$ Hb (ns).

Compound 1 has a favorable safety profile in healthy subjects. Compound 1 demonstrates linear and time-independent PK. Reduction in 2,3-DPG and increase in ATP levels in RBCs of healthy volunteers confirms PKR activation by Compound 1. Compound 1 demonstrates proof of mechanism with increased Hb oxygen affinity in healthy volunteer RBCs, consistent with observations from in vitro mixing studies in healthy and sickle RBCs. These results support further clinical development of Compound 1, a PKR activator, in patients with SCD.

Compound 1 has a favorable safety profile in pts with SCD receiving a single dose or up to 14 days of dosing. The single dose studies in SCD subjects show an acceptable safety profile with evidence of PD activity translating into favorable biologic effects of increased oxygen affinity with a shift in the PoS to lower oxygen tensions and improved membrane deformability of sickle RBCs. Compound 1 exhibited linear and time-independent PK, leading to decreased 2,3-DPG and increased ATP levels. These results confirm that the PKR enzyme is functional and responsive to PKR activation in SCD RBCs. A single dose of Compound 1 resulted in favorable biological effects of: (1) improved oxygen affinity, decreased point of sickling and improved deformability; and (2) improved membrane function, demonstrated by an improved response to an osmotic gradient. Specifically, a single dose of Compound 1 led to decreased 2,3-DPG and increased ATP, resulting in increased O2 affinity, decreased PoS, improved RBC deformability, and improved RBC membrane function. A single dose of Compound 1 resulted in improvements in hemoglobin, RBCs, and reticulocytes occurred when maximum PD effects were observed. These improvements indicate that a sustained 2,3-DPG reduction and increased ATP production may improve the hemolytic anemia and frequency of VOCs that characterize SCD.

Additional studies further evaluate the safety, PK/PD, and clinical activity of Compound 1 following daily administration in patients with SCD. A 2-wk SCD/MAD cohort is performed to evaluate the effects of Compound 1 on hemoglobin, inflammation and RBC metabolomics. A 12-wk dosing cohort to further characterize the effects of chronic PKR-activation on the pathophysiology of SCD is performed to evaluate the 2-wk MAD studies.

Initial blinded results of daily dosing with 300 mg Compound 1/placebo over 14 days show improvement in both hematologic and hemolytic parameters in 2 of 3 pts with SCD, along with improved RBC functional studies, suggesting the pharmacodynamic consequences of PKR activation may be of clinical benefit in SCD. Multiple-dose further evaluate the safety, PK/PD, and biological activity of Compound 1 following daily administration in pts with SCD.

The results observed in the MAD1 cohort demonstrated proof of concept for daily administration of Compound 1 (300 mg once daily) for 14 days. PKR activation increased hemoglobin >1 g/dL in 6/7 patients, and 7/7 patients had a decrease in reticulocytes and a decrease in hemolysis. A median Hb increase of 1.2 g/dL and a median reduction in % reticulocyte of 60% were observed. A median reduction in total bilirubin of 35% and median reduction of LDH of 36% were also observed. A MAD2 cohort (600 mg Compound 1 or placebo once daily for 14 days) and an open label cohort (400 mg Compound 1 once daily for 12 weeks) further evaluate the safety, PK/PD, and biological activity of Compound 1 in patients with SCD.

Evaluation of Compound 1 for Aromatase Activity

To assess potential effects on steroidogenesis, Compound 1 was screened for steroid modulation in vitro using the H295R adreno-cortical carcinoma cell line (at 200 to 0.0002 µM) and in an assay to monitor cell viability (MTT Kit). Compound 1 indicated steroid modulation potential (% over vehicle) only at 200 µM, the top concentration tested, with 100% cellular viability at concentrations ≤20 µM (90% viability at 200 µM). Based on these results, Compound 1 demonstrated no significant risk for interference with steroidogenesis considering the predicted maximum exposure (1,500 mg; $C_{max}$ (free)=0.004 µM; $AUC_{0-inf}$ (free)=0.002 µM·hr) of Compound 1 in human studies, Effects on circulating levels of estradiol and testosterone in male and female healthy subjects receiving Compound 1 or placebo for a treatment period of 14 days were evaluated. Compound 1 was administered twice daily (BID) at dose levels of 100 mg, 200 mg, and 300 mg, and once daily (QD) at a dose level of 400 mg. Each dosing cohort was comprised of 9 subjects treated with Compound 1 and 3 subjects treated with placebo. Testosterone and estradiol levels were assessed prior to dosing (baseline), and then on days 8, 14 and 17. Evaluation of the change from baseline for testosterone and estradiol levels confirmed no statistically significant changes and no clinically meaningful trends, consistent with non-clinical testing indicating absence of aromatase inhibition by Compound 1.

Evaluation of Compound 1 for CYP-Mediated Activity

When evaluated for its potential towards major human CYP-mediated drug-drug interactions, Compound 1 concentrations up to 30 µM did not reversibly inhibit any of the major cytochrome P450 (CYP) isoforms in human liver microsomes (Table 27). In primary cultured hepatocytes, increases in messenger ribonucleic acid (mRNA) levels for CYP3A4, CYP1A2 and CYP2B6 at Compound 1 concentrations of 10 micromolar were low, and at clinically relevant unbound exposures (unbound human $C_{max}$), no induction above 2-fold was observed in cultured human hepatocytes across the 3 CYP isoforms tested (Table 28).

Taken together, the interaction risk for Compound 1 as a CYP inducer or reversible inhibitor of concomitant medications predominantly cleared by CYP metabolism is categorized as low. Furthermore, following 14 days of dosing in healthy subjects in the clinical trial of Example 8, the observed clearance on day 1 and day 14 was unchanged, providing clinical evidence that the PK of Compound 1 is time-independent and not a substrate of auto-induction or auto-inhibition at the doses tested.

TABLE 27

Summary of IC$_{50}$ values of cytochrome p450 enzymes data for Compound 1 in single Substrate DDI assay

| Compound ID | Lot # | IC$_{50}$ (µM) (n = 3) | | | | |
|---|---|---|---|---|---|---|
| | | CYP1A2 | CYP2C9 | CYP2C19 | CYP2D6 | CYP3A4 |
| Compound 1 | 9 | >30 | >30 | >30 | >30 | >30 |
| Furafylline | | 1.251 ± 0.061 | | | | |
| Sulfaphenazole | | | 0.863 ± 0.056 | | | |
| Ticlopidine | | | | 1.504 ± 0.024 | | |
| Quinidine | | | | | 0.0516 ± 0.00114 | |
| Ketoconazole | | | | | | 0.0343 ± 0.0023 |

TABLE 28

Fold Induction, EC50 and Emax Values of CYP mRNA by Test Compound 1 and Positive Controls in Cultured Human Hepatocytes From Three Donors (Mean [n = 3)])

| Test Compound | Donor ID | Isoform | Concentrations (µM)/mRNA Fold Induction | | | | | | EC50 (µM) | Emax (Fold Induction) |
|---|---|---|---|---|---|---|---|---|---|---|
| | | | 0.033 | 0.1 | 0.33 | 1 | 3.3 | 10 | | |
| Compound 1 | AIH | CYP1A2 | 0.989 | 0.958 | 1.10 | 1.20 | 1.24 | 1.33 | N/A | N/A |
| | EUJ | | 1.23 | 1.05 | 1.20 | 1.14 | 1.11 | 1.25 | N/A | N/A |
| | HC5-40 | | 1.07 | 0.942 | 0.887 | 0.911 | 0.892 | 1.02 | N/A | N/A |
| | AIH | CYP2B6 | 0.982 | 1.01 | 1.00 | 1.07 | 1.25 | 1.70 | N/A | N/A |
| | EUJ | | 1.17 | 1.23 | 1.10 | 1.29 | 1.26 | 1.43 | N/A | N/A |
| | HC5-40 | | 1.17 | 1.06 | 0.964 | 1.00 | 1.24 | 1.21 | N/A | N/A |
| | AIH | CYP3A4 | 0.940 | 1.13 | 1.11 | 1.41 | 1.84 | 3.60 | N/A | N/A |
| | EUJ | | 1.09 | 0.875 | 1.18 | 1.07 | 1.25 | 2.23 | N/A | N/A |
| | HC5-40 | | 1.25 | 0.889 | 0.836 | 1.18 | 1.62 | 1.29 | N/A | N/A |

Example 9: A SAD/MAD Study to Assess the Safety, Pharmacokinetics, and Pharmacodynamics of Compound 1 in Healthy Volunteers and Sickle Cell Disease Patients Pending the results of the SAD/MAD study described in Example 8, Compound 1 can be evaluated in a registration-enabling global adaptive randomized, placebo-controlled, double blind, parallel group, multicenter trial in patients, ages 12 to 65 years, with SCD. The trial can utilize hemoglobin response as a primary endpoint while collecting additional endpoints around rates of VOC to verify clinical benefit.

Example 10: An Adaptive, Randomized, Placebo-Controlled, Double-Blind, Multi-Center Study of Oral Compound 1, a Pyruvate Kinase Activator in Patients with Sickle Cell Disease (PRAISE)

The hallmark of sickle cell disease (SCD) is hemoglobin S (HbS) polymerization upon deoxygenation, resulting in red blood cell (RBC) sickling, oxidative damage, membrane damage, hemolysis, chronic anemia, cell adhesion, vaso-occlusion and inflammation. Exacerbating the pathogenesis of SCD, the HbS RBC has increased (↑) levels of 2,3-diphosphoglycerate (2,3-DPG), resulting in reduced (↓) Hb oxygen affinity (↑P$_{50}$), and reduced (↓) levels of ATP, essential for RBC homeostasis.

Compound 1 is a potent, selective, and orally bioavailable allosteric activator of erythrocyte pyruvate kinase (PKR) that increases PKR activity, resulting in reduced (↓) 2,3-DPG levels and increased (↑) ATP levels in RBCs. Preliminary data from a study in healthy volunteers and patients with SCD indicate that Compound 1 is well tolerated, has no effect on steroidogenesis, and exhibits linear and time-independent pharmacokinetics (PK) and associated pharmacodynamic (PD) responses (↓2,3-DPG and ↑ ATP). Furthermore, in patients with SCD, a single dose of Compound 1 demonstrated favorable biologic effects, including increased Hb oxygen affinity (↓ P$_{50}$), decreased point of sickling (PoS), improved RBC deformability, and improved RBC membrane function, indicative of overall improved RBC health. Treatment of patients with Sickle Cell Disease (SCD) for 14 days with once-daily Compound 1 resulted in an increase in hemoglobin (Hb) O$_2$ affinity, decrease in red blood cell (RBC) sickling, improved measures of RBC health, and improved hematologic and hemolytic parameters (Example 8).

Figure 58:
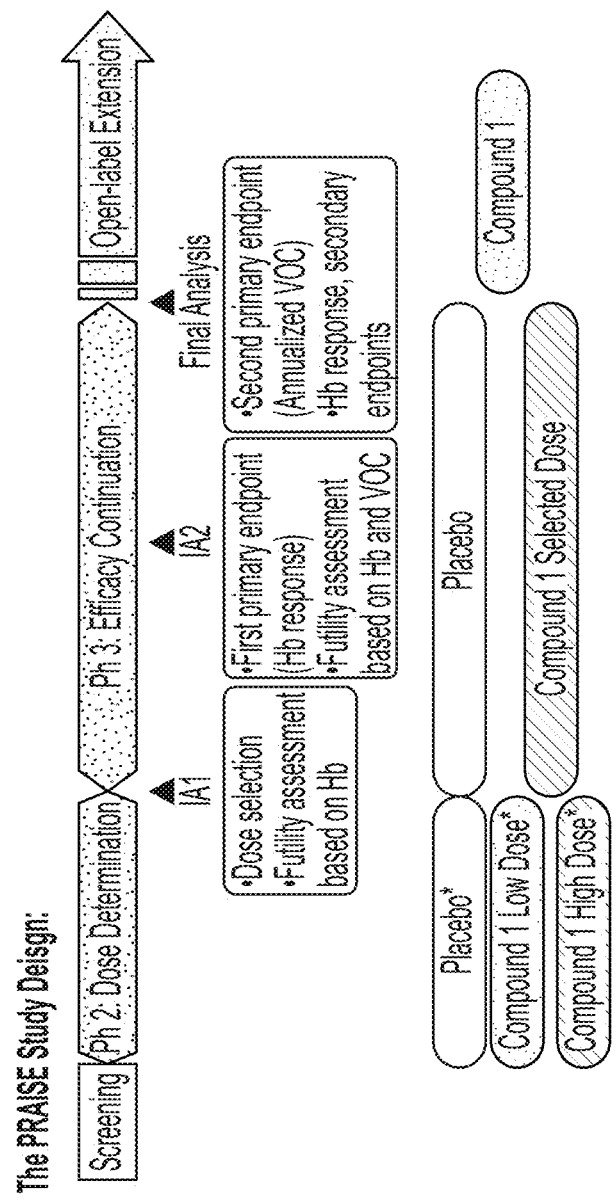
FIG. 58 is a summary of a phase 2/3, randomized, double-blind, placebo-controlled global study (PRAISE) to investigate the safety and efficacy of Compound 1 in patients with SCD.
Figure 62:
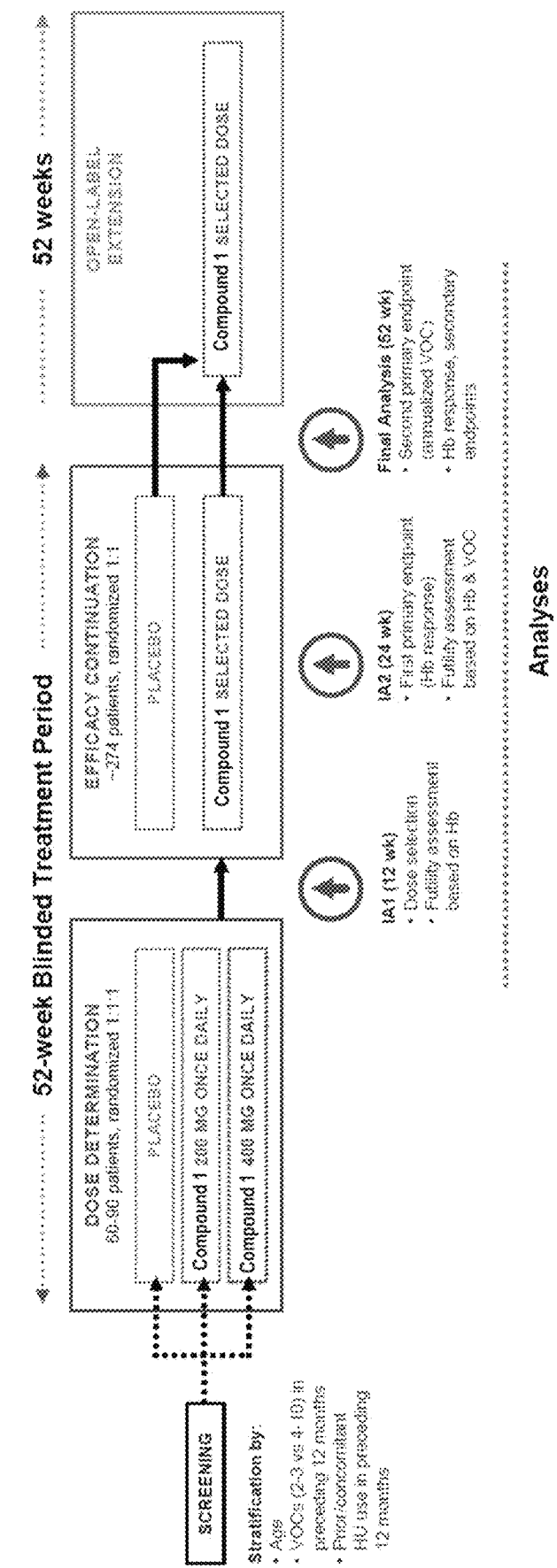
FIG. 62 is a summary of a phase 2/3, randomized, double-blind, placebo-controlled global study to investigate the safety and efficacy of Compound 1 in patients with SCD.

Accordingly, a phase 2/3, randomized, double-blind, placebo-controlled global study (PRAISE) was designed to investigate the safety and efficacy of Compound 1 in patients with SCD. This study is a randomized, placebo-controlled, double-blind, multicenter Phase 2/3 study of patients age 12 years (inclusive), with sickle cell disease. The PRAISE study can enroll up to 344 adult and adolescent (≥12 years old) patients with SCD, including 60 to 90 patients in the Dose Determination (DD) Group and ~274 patients in the Efficacy Continuation (EC) Group using an adaptive design (see FIG. 58 and FIG. 62). The study may evaluate how well Compound 1 works compared to placebo to improve the amount of hemoglobin in the blood and to reduce the number of vaso-occlusive crises. Eligible patients must have had ≥2 vaso-occlusive crises (VOCs) in the past year, and if receiving hydroxyurea (HU), be on stable therapy for the previous 90 days. Patients with >10 VOCs in the past year, hospitalized for sickle cell crisis/other vaso-occlusive event within 14 days of consent, receiving routine RBC transfusions, or with significant hepatic/renal dysfunction will be excluded. There are two planned interim analyses in this study design. Initially, patients will be randomized at 1:1:1 to one of two dose levels of Compound 1 or placebo. At the first interim analysis, one of the two Compound 1 dose levels will be selected for the Phase 3 portion of the study, in which patients will be randomized at 1:1 to the selected Compound 1 dose or placebo. Efficacy on hemoglobin will be evaluated at the second interim analysis, and then will be tested along with evaluation of efficacy on vaso-occlusive crises at the final analysis. Following completion of 52 weeks of double-blind treatment, patients may enter a 52-week Compound 1 open-label extension period.

Eligibility: Minimum Age: 12 Years; Maximum Age: 65 Years; Sex: All.

Key inclusion criteria: SCD (all genotypes or HbSS, HbSβ$^0$, or other variates), at least 2 vaso-occlusive crises (VOCs) in the past 12 mos, baseline Hb≥5.5 and ≤10 g/dL, stable hydroxyurea (HU) therapy for the previous 90 days (if applicable). Other inclusion criteria may include provision of consent, that female patients of childbearing potential use highly effective methods of contraception, and that male patients use barrier methods of contraception.

Key exclusion criteria: More than 10 VOCs in the past 12 mos, hospitalization for sickle cell crisis or other vaso-occlusive event within 14 days of consent, routine RBC transfusions, significant hepatic or renal dysfunction, history of unstable or deteriorating cardiac or pulmonary disease, or overt stroke within 2 yrs. Other exclusion criteria may include; female who is breast feeding or pregnant; hepatic dysfunction characterized by alanine aminotransferase (ALT) >4.0× upper limit of normal (ULN) or direct bilirubin >3.0 ×ULN; known HIV positive; active hepatitis B or hepatitis C infection; severe renal dysfunction (e.g., estimated glomerular filtration rate <30 mL/min/1.73 m$^2$) or on chronic dialysis; history of unstable or deteriorating cardiac or pulmonary disease within 6 months prior to consent including but not limited to unstable angina pectoris or myocardial infarction or elective coronary intervention, congestive heart failure requiring hospitalization, uncontrolled clinically significant arrhythmias and/or symptomatic pulmonary hypertension; history of overt clinical stroke within previous 2 years or any history of an intracranial hemorrhage; patients receiving regularly scheduled blood (RBC) transfusion therapy (also termed chronic, prophylactic, or preventive transfusion); patients receiving concomitant medications that are strong inducers or moderate/strong inhibitors of CYP3A4/5 within 2 weeks of starting study treatment or anticipated need for such agents during the study; use of voxelotor within 28 days prior to starting study treatment or anticipated need for this agent during the study; use of a selectin antagonist (e.g., crizanlizumab or other monoclonal antibody or small molecule) within 28 days of starting treatment or anticipated need for such agents during the study; use of erythropoietin or other hematopoietic growth factor treatment within 28 days of starting study treatment or anticipated need for such agents during the study; and/or receipt of prior cellular-based therapy (e.g., hematopoietic cell transplant, gene modification therapy).

Endpoints: The key objectives for this study are to assess the efficacy of Compound 1 versus placebo and to assess the continued safety of Compound 1. The co-primary endpoints are (1) Hb response rate at Week 24 (increase of >1 g/dL from baseline) and (2) annualized VOC rate during the blinded treatment period based on adjudicated VOC review. Annualized VOC rate may be determined based on VOCs requiring a medical facility visit with one or more of the following subtypes: (a) uncomplicated VOC requiring treatment with oral or parenteral opioids or parenteral NSAIDs; (b) acute chest syndrome; (c) hepatic sequestration; (d) splenic sequestration; and (e) priapism. Secondary endpoints include measures of hemolysis, time to first VOC, and the PROMIS fatigue scale. During the blinded treatment period, secondary endpoints may also include change from baseline to week 24 in: (a) hemoglobin (Hb); (b) SCD-related clinical laboratory measurements, including % reticulocytes, unconjugated bilirubin, and/or lactate dehydrogenase; and/or (c) patient-reported outcome measurement information system (PROMISE) fatigue scale. Secondary endpoints may also include time to first VOC during the blinded treatment period. Adult patients (ages 18 to 65) may complete the PROMIS® Item Bank v1.0—Fatigue—Short Form 7a. Adolescent patients (ages 12 to 17) may complete the PROMIS® Item Bank v2.0—Fatigue—Short Form 10a. Responses may be graded on a score of 1 to 5 with a higher core indicating a worse outcome. Safety endpoints include the incidence of AEs, concomitant medications, vital signs, ECGs, clinical laboratory measurements, and physical examination.

Design: The study design is a group-sequential, adaptive, phase 2/3 study (see FIG. 58 and FIG. 62). The study may enroll ~344 adult and adolescent patients with SCD. Study sample size may be determined based on both primary endpoints. Patients are stratified by age, number of VOCs (2-3 vs. 4-10) in the preceding 12 mos, and prior/concomitant HU use in the preceding 12 mos. The phase 2 DD portion assesses 2 active doses and placebo with patients randomized 1:1:1. The active doses may include a double blind high dose (e.g., 400 mg once daily) and a double blind low dose (e.g., 200 mg once daily). The dose is chosen at the first interim analysis (IA1) based on safety and Hb response rate at Week 12 of the first 60 DD patients. A futility analysis is also conducted on Hb response at that point.

After dose selection, patients are randomized 1:1 (selected dose of Compound 1:placebo) into the phase 3 EC portion to assess Compound 1 efficacy. Once 110 patients from phase 2 or 3 who have been randomized to the selected dose or placebo have completed 24 weeks of follow-up or have dropped out, a second interim analysis (IA2) is performed to assess both efficacy and futility. IA2 assesses the co-primary endpoint of Hb response rate at Week 24 (p <0.001).

The final analysis after 52 weeks of blinded treatment tests the VOC endpoint, the Hb response rate, and all secondary endpoints. Key secondary endpoints are tested at IA2 and all are tested at the final analysis, when there is adequate power.

Treatment: Patients are randomized to receive Compound 1 or placebo. Compound 1 may be administered in the form of tablets prepared as described in Example 1, Step 9. In the DD phase, two doses are evaluated, and in the EC phase, the selected dose of Compound 1 from the DD phase is evaluated in comparison to placebo. Patients in DD on the unselected dose remain on treatment at that dose level for 52 weeks. Following completion of 52 weeks of double-blind treatment, patients may enter a 52-week open-label extension period to receive Compound 1 at the selected dose.

Example 11: Analysis of ATP and 2,3 DPG in K2EDTA Whole Blood by LC-MS/MS

The following procedures are employed for the analysis of ATP and 2,3-DPG in human whole blood K2EDTA using a protein precipitation extraction procedure and analysis by LC-MS/MS.

This bioanalytical method applies to the parameters described below:

| | |
|---|---|
| Assay Range | 25,000-1,500,000 ng/mL |
| Extraction Volume | 15.0 μL |
| Species/Matrix/Anticoagulant | Water as a surrogate for Human Whole Blood K2EDTA |
| Extraction type | Protein Precipitation |
| Sample Storage | 80° C. |
| Mass Spectrometer | API-5500 |
| Acquisition software | Analyst/Aria System |

The following precautions are followed:
1. Standard and QC samples are prepared on ice and stored in plastic containers.
2. Study samples and QC samples are thawed on ice.
3. Extraction is performed on ice.

The following definitions and abbreviations are employed:

| | |
|---|---|
| CRB | Carryover remediation blanks |
| FT | Freeze-thaw |
| MPA | Mobile phase A |
| MPB | Mobile phase B |
| NA | Not applicable |
| NR | Needle rinse |
| RT | Retention time |
| SIP | Stability in progress |
| TBD | To be determined |

The following chemicals, matrix, and reagents are used:

$K_2$EDTA Human Whole Blood, BioreclamationIVT or equivalent
(Note: BioReclamationIVT and BioIVT are considered equivalent)
Acetonitrile (ACN), HPLC Grade or better
Ammonium Acetate ($NH_4OAc$), HPLC grade or equivalent
Ammonium Hydroxide ($NH_4OH$, 28-30%), ACS grade or better
Dimethylsulfoxide (DMSO), ACS grade or better
Formic Acid (FA), 88% ACS grade
Isopropanol (IPA), HPLC Grade or better
Methanol (MeOH), HPLC Grade or better
Water ($H_2O$), Milli-Q or HPLC Grade
ATP-Analyte, Sponsor or supplier
ATP-IS-IS, Sponsor or supplier
2,3-DPG-Analyte, Sponsor or supplier
2,3-DPG-IS-IS, Sponsor or supplier The following procedures are used for reagent preparation. Any applicable weights and volumes listed are nominal and may be proportionally adjusted as long as the targeted composition is achieved:

| Solution | Final Solution Composition | Nominal Volumes for Solution Preparation | Storage Conditions |
|---|---|---|---|
| Mobile Phase A (MPA) | 10 mM Ammoniumn Acetate in water pH 8.5 | Weigh approximately 770.8 mg of Ammonium Acetate; add to a bottle with 1000 mL of water. Adjust pH to 8.3-8.7 using Ammonium Hydroxide. | Ambient Temperature |
| Mobile Phase B (MPB) | 5:95 MPA:ACN | Add 50.0 mL of MPA to 950 mL of CAN. Mix. | Ambient Temperature |
| Needle Rinse 1 (NR1) | 25:25:25:25:0.1 (v:v:v:v:v) MeOH:ACN:H2O:IPA:$NH_4OH$ | Add 500 mL of MeOH, 500 mL of ACN, 500 mL of $H_2O$, 500 mL of IPA, and 2 mL of $NH_4OH$. Mix. | Ambient Temperature |
| Needle Rings 2 (NR2) | 90:10:0.1 (v:v:v) $H_2O$:MeOH:FA | Add 2 mL of FA to 200 mL of MeOH and 1800 mL of $H_2O$. Mix. | Ambient Temperature |

Calibration standards are prepared using water as the matrix according to the table presented below. The indicated standard is prepared by diluting the indicated spiking volume of stock solution with the indicated matrix volume.

| Calibration Standard | Stock Solution | Stock Conc. (ng/mL) | Spiking Vol. (mL) | Matrix Vol. (mL) | Final Vol. (mL) | Final Conc. (ng/mL) |
|---|---|---|---|---|---|---|
| STD-6 | ATP Stock | 60,000,000 | 0.0100 | 0.380 | 0.400 | 1,500,000 |
| | 2,3-DPG Stock | 60,000,000 | 0.0100 | | | |
| STD-5 | STD-6 | 1,500,000 | 0.100 | 0.200 | 0.300 | 500,000 |
| STD-4 | STD-6 | 1,500,000 | 0.0500 | 0.325 | 0.375 | 200,000 |
| STD-3 | STD-6 | 1,500,000 | 0.0250 | 0.350 | 0.375 | 100,000 |
| STD-2 | STD-5 | 500,000 | 0.0500 | 0.450 | 0.500 | 50,000 |

-continued

| Calibration Standard | Stock Solution | Stock Conc. (ng/mL) | Spiking Vol. (mL) | Matrix Vol. (mL) | Final Vol. (mL) | Final Conc. (ng/mL) |
|---|---|---|---|---|---|---|
| STD-1 | STD-5 | 500,000 | 0.0250 | 0.475 | 0.500 | 25,000 |
| Cond. | STD-5 | 500,000 | 0.0250 | 0.975 | 1.00 | 12,500 |

Quality control standards are prepared using water as the matrix according to the table presented below. The indicated quality control standard is prepared by diluting the indicated spiking volume of stock solution with the indicated matrix volume.

| Quality Control Standard | Stock Solution | Stock Conc. (ng/mL) | Spiking Vol. (mL) | Matrix Vol. (mL) | Final Vol. (mL) | Final Conc. (ng/mL) |
|---|---|---|---|---|---|---|
| QC-High | ATP Stock | 60,000,000 | 0.160 | 7.68 | 8.00 | 1,200,000 |
|  | 2,3-DPG Stock | 60,000,000 | 0.160 |  |  |  |
| QC-Mid | QC-High | 1,200,000 | 1.50 | 4.50 | 6.00 | 300,000 |
| QC-Low | QC-Mid | 300,000 | 1.50 | 4.50 | 6.00 | 75,000 |

An internal standard spiking solution is prepared with a final concentration of 12,500 ng/mL ATP and 2,3-DPG by diluting stock solutions of ATP and 2,3-DPG at concentrations of 1,000,000 ng/mL with water. 0.200 mL each of the ATP and 2,3-DPG stock solutions are diluted with 15.6 mL of water to produce a final volume of 16.0 mL at a final concentration of 12,500 ng/mL of ATP and 2,3-DPG.

The following procedures are used for sample extraction prior to analysis via LC-MS/MS. 15.0 µL of the calibration standards, quality controls, matrix blanks, and samples are aliquoted into a 96-well plate. 50.0 µL of the internal standard spiking solution is added to all samples on the plate, with the exception of the matrix blank samples; 50.0 µL of water is added to the matrix blank samples. Subsequently, 150 µL of water is added to all samples on the plate. The plate is then covered and agitated by vortex at high speed for ten minutes, after which 750 µL of methanol is added to all samples on the plate. The plate is covered and agitated by vortex for approximately 1 minute. The plate is then centrifuged at approximately 3500 RPM at approximately 4° C. for five minutes. After centrifugation, a liquid handler is used to transfer 50 µL of each sample to a new 96-well plate, and 200 µL of acetonitrile is added to all samples on the plate. The newly prepared plate is covered and agitated by vortex for approximately 1 minute. The plate is then centrifuged at approximately 3500 RPM at approximately 4° C. for 2 minutes.

The following LC parameters and gradient conditions are used for analysis of the extracted samples:

| LC Parameters | | |
|---|---|---|
| Analytical Column | Vendor: | SeQuant |
|  | Description: | ZIC-pHILIC |
|  | Dimensions: | 50 mm × 2.1 mm |
|  | Column Heater Temperature: | 40° C. |
| Plate Rack | Position: | Cold Stack |
|  | Cold Stack Set Point: | 5° C. |
| Mobile Phase | Mobile Phase A (MPA) | 10 mM Ammonium Acetate in water pH 8.5 |
|  | Mobile Phase B (MPB) | 5:95 MPA:ACN |
| Injection Volume |  | 5 µL |

| LC Gradient | | | | |
|---|---|---|---|---|
| Step | Time (s) | Flow (mL/min) | Gradient Setting | % MPB |
| 1 | 50 | 0.400 | Step | 5 |
| 2 | 30 | 0.400 | Ramp | 95 |
| 3 | 70 | 0.400 | Step | 5 |

Data is collected starting at 0.08 min and is collected over a data window length of 0.70 min.

The following MS parameters are used for analysis of the extracted samples using an API-5500 Mass Spectrometer:

| Interface: | Turbo Ion Spray Ionization, positive-ion mode |
| Scan Mode: | Multiple Reaction Monitoring (MRM) |

|  | Parent/Product: | Dwell Time (ms): |
|---|---|---|
| Scan Parameters: | 506.0/159.0 | 50 |
|  | 521.0/159.0 | 25 |
|  | 265.0/166.8 | 50 |
|  | 268.0/169.8 | 25 |
| Source Temperature: | 400° C. | |

Example 12: Measuring Oxygen Affinity (p50)

Oxygen reversibly binds to the heme portions of the Hgb molecule. As oxygenated blood flows via capillaries to peripheral tissues and organs that are actively consuming oxygen, PO2 drops and Hgb releases oxygen. The affinity of oxygen for hemoglobin can be measured in a sigmoidal oxygen equilibrium curve. In the scan, the Y-axis plots the percent of hemoglobin oxygenation and the X-axis plots the partial pressure of oxygen in millimeters of mercury (mm Hg). If a horizontal line is drawn from the 50% oxygen saturation point to the scanned curve and a vertical line is drawn from the intersection point of the horizontal line with the curve to the partial pressure X-axis, a value commonly known as the p50 is determined (i.e., this is the pressure in mm Hg when the scanned hemoglobin sample is 50% saturated with oxygen). This relationship can be impacted by temperature, pH, carbon dioxide, and the glycolytic intermediate 2,3-DPG. 2,3-DPG binds within the central cavity of the Hgb tetramer, causes allosteric changes, and reduces Hgb's affinity for oxygen. Under physiological conditions (i.e., 37° C., pH=7.4, and partial carbon dioxide pressure of 40 mm Hg), the p50 value for normal adult hemoglobin (HbA) is around 26.5 mm Hg. If a lower than normal p50 value is obtained for the hemoglobin under test, the scanned curve is considered to be "left-shifted" and the presence of high affinity hemoglobin is indicated. If a higher than normal p50 value is obtained for the hemoglobin under test, the scanned curve is considered to be "right-shifted" and the presence of low affinity hemoglobin is indicated.

The oxygen affinity of RBCs was measured in patient blood using a Hemox Analyzer (TCS Scientific Corp.), an automatic system for the recording of blood oxygen equilibrium curves and related phenomena. The Hemox Analyzer was used according to standard methods to determine the hemoglobin-oxygen dissociation curves for whole blood samples, numerically characterized by the p50, the partial pressure of oxygen at which hemoglobin is 50% saturated. The operating principle of the Hemox-Analyzer is based on dual-wavelength spectrophotometry for the measurement of the optical properties of hemoglobin and a Clark electrode for measuring the oxygen partial pressure in millimeters of mercury. Whole blood is diluted and placed into a special plastic cuvette that is maintained at 37° C. To perform the analysis, a beam of polychromatic light is passed through the cuvette and is made monochromatic prior to reaching the photomultiplier detectors. In the case of hemoglobin, the wavelength of maximum absorbance is the measuring wavelength (560 nm), while the reference wavelength is at the isosbestic point at (570 nm). The absorbance at the isosbestic point remains unchanged during the deoxygenation process of the hemoglobin, however the measuring wavelength (560 nm) undergoes a drastic change in absorbance. This change is detected by the electronic circuitry and is plotted as the log/ratio change between the two wavelengths. The log/ratio measurement at 560 nm and 570 nm is utilized to measure the optical absorbance change during the deoxygenation of the hemoglobin. Simultaneously with the measurement of the hemoglobin absorbance, the oxygen concentration is directly measured in the sample using a Clark electrode. Under normal atmospheric conditions of 760 mm of mercury the oxygen concentration (i.e., the oxygen partial pressure) is 149 mm of mercury. This saturation point is used for full-scale calibration of the computer prior to starting the plotting of the curve. When the oxygen is being replaced by an inert gas (nitrogen) in a continuous procedure, hemoglobin becomes deoxygenated.

Blood samples for testing were obtained and handled as follows. Specimen samples of 3 mL of whole blood are collected in tubes containing EDTA (Lavender). A minimum volume of 500 µL of whole blood is required. Blood collected in Sodium or lithium heparin are acceptable, but EDTA is the preferred anti-coagulant. A control sample drawn from a healthy normal volunteer must be processed with each patient sample. The normal control should be handled in the same manner as patient sample (i.e., date of draw, anti-coagulant used, sample storage conditions).Store all specimens at 2-8° C. upon receipt in the laboratory. Specimens must be shipped overnight with a cold pack to maintain shipping temperature ~4° C. and be accompanied by a normal control. Samples are stable in EDTA anti-coagulated blood held at 2-8° C. for 48 hours. Any clotted samples, samples stored in suboptimal conditions, or samples with less than 200 uL volume and samples greater than 48 hours old are rejected.

The following references provide additional guidance on the method of obtaining oxygen affinity curves and determination of p50 as described above:
1. Operation Manual for the Hemox-Analyzer, TCS Scientific, New Hope, PA, revised Jan. 10, 2007.
2. Ellis S S, Pepple D J. Sildenafil Increases the p50 and Shifts the Oxygen-Hemoglobin Dissociation Curve to the Right. J Sex Med. 2015; 12(12):2229-32. doi: 10.1111/jsm.13038.
3. McKoy M, Allen K, Richards A, Pepple D. Effect of cilostazol on the p50 of the oxygen-hemoglobin dissociation curve. Int J Angiol. 2015; 24(1):67-70. doi: 10.1055/s-0034-1383433.
4. Guarnone R, Centenara E, Barosi G. Performance characteristics of Hemox-Analyzer for assessment of the hemoglobin dissociation curve. Haematologica. 1995 September-October; 80(5):426-30.
5. Vanhille D L, Nussenzveig R H, Glezos C, Perkins S, Agarwal AM. Best practices for use of the HEMOX analyzer in the clinical laboratory: quality control determination and choice of anticoagulant. Lab Hematol. 2012; 18(3):17-9.

Example 13: Oral Bioavailability of Compound 1 Pharmaceutical Compositions

The systemic exposure of Compound 1 in rats and mice was evaluated by dosing a spray dried dispersion (SDD) obtained from Step 6 of Example 1, containing Compound 1 and HPMC AS-MG (1:3) dispersed in an aqueous vehicle (0.5% Hydroxypropylmethyl Cellulose in water).

For comparison, a crystalline form (designated Type A) of Compound 1 was also prepared and characterized. Type A was characterized by XRPD (Method A), TGA, DSC, and DVS analysis.

The XRPD pattern for Compound 1 solid form Type A obtained by Method A above was characterized by the XRPD 2-theta peaks and d-spacing summarized in the following table:

| Pos. [°2 Th.] | d-spacing [Å] |
|---|---|
| 4.61 | 19.19 |
| 5.80 | 15.24 |
| 7.22 | 12.25 |
| 7.68 | 11.50 |
| 11.21 | 7.89 |
| 12.31 | 7.19 |
| 14.44 | 6.13 |
| 15.66 | 5.66 |
| 16.95 | 5.23 |
| 18.02 | 4.92 |
| 19.20 | 4.62 |
| 20.48 | 4.34 |
| 21.35 | 4.16 |
| 21.66 | 4.10 |
| 22.47 | 3.96 |
| 23.19 | 3.84 |
| 24.76 | 3.60 |
| 26.73 | 3.34 |
| 28.01 | 3.19 |
| 28.49 | 3.13 |
| 29.35 | 3.04 |
| 30.25 | 2.95 |
| 32.14 | 2.79 |
| 34.12 | 2.63 |
| 36.46 | 2.46 |

The TGA and DSC curves for solid form Type A of Compound 1 showed 1.9% weight loss up to 100° C. by TGA and two endotherms at 85.9° C. (peak temperature) and 146.0° C. (onset temperature) by DSC. Type A was analyzed by DSC by heating to 120° C. and cooled to 25° C., then heated up to 300° C. No endotherm below 100° C. was observed in the second heating cycle. XRPD analysis after DSC cycling showed no form change compared to Type A. DVS results of Type A of Compound 1 showed a 3.4% water uptake up to 40% RH (ambient condition), and 1.0% water uptake from 40% RH to 80% RH at RT, indicating that Type A is hygroscopic. No form change was observed for Type A before and after DVS test at RT, as determined by XRPD. Based on the foregoing analytical data, Type A is believed to be a channel hydrate.

Figure 59:
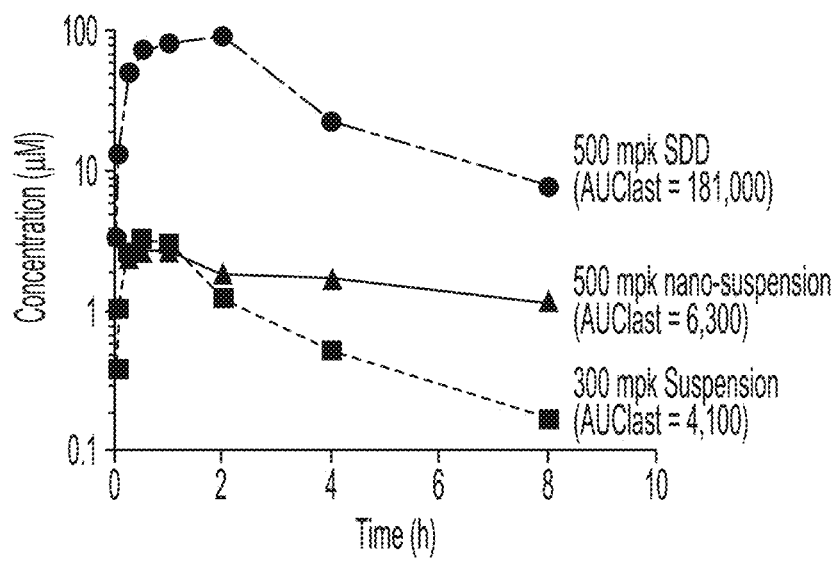
FIG. 59 is a graph showing the concentration of Compound 1 administered in different compositions, measured over time measured in rats in the bioavailability experiment of Example 13.

The SDD formulation ("500 mpk SDD" made up of 50 mg/mL of Compound 1 SDD (SDD made up of Compound 1 and HPMC AS-MG (1:3)) in 0.5% HPMC in water) dosed at 500 mg/kg to rats showed an AUClast that was 40× greater than the maximum exposure obtained with the standard formulation ("300 mpk Suspension" made up of Compound 1 (Type A) in 10% Propylene Glycol, 10% Cremophore, 80% Water), as shown in the data in the Table below, and exceeded the predicted exposure target for efficacy. Additionally, the exposure of a 500 mpk Nano-Suspension made up of nanoparticles of Compound 1 (Type A) was evaluated. Robust exposure was observed with SDD formulation in mouse as well. Results are shown in FIG. 59.

| Animal | $t_{1/2}$ (h) | $t_{max}$ (h) | $C_{max}$ (ng/mL) | AUClast (h*ng/mL) |
|---|---|---|---|---|
| Rat | 3.22 | 1.67 | 44400 | 180603 |
| Mouse | 2.54 | 0.5 | 75200 | 113369 |

Several formulation compositions of Compound 1, including an SDD made up of Compound 1 and HPMC AS-MG (1:3), were evaluated in monkeys. The compositions of the tested oral dosage formulations are listed in the Table below; Compound 1 exposure results for each formulation are shown in FIG. 60.

| Formulation | Dosage Form | Composition |
|---|---|---|
| Formulation #1 (with Bile Salt) | Capsule; Size 0 White Opaque Gelatin | Compound 1 (Type A), micronized 49.9% Avicel PH101 23.5% AcDiSol 5.0% SLS 10.1% Na Taurocholate 10.0% Mg Stearate 0.5% Silicon Dioxide 1.0% |
| Formulation #2 (Formulated Capsule) | Capsule; Size 0 White Opaque Gelatin | Compound 1 (Type A) micronized API 49.9% Avicel PH101 33.3% AcDiSol 5.0% SLS 10.3% Mg Stearate 0.5% SiO2 1.0% |
| Formulation #3 (Micronized fill) | Capsule; Size 0 White Opaque Gelatin | Compound 1 (Type A) micronized API only |
| Formulation #4 (SDD) | Suspension | Compound 1 Spray Dried Dispersion 0.5% Hydroxypropylmethyl Cellulose in Water |

Figure 60:
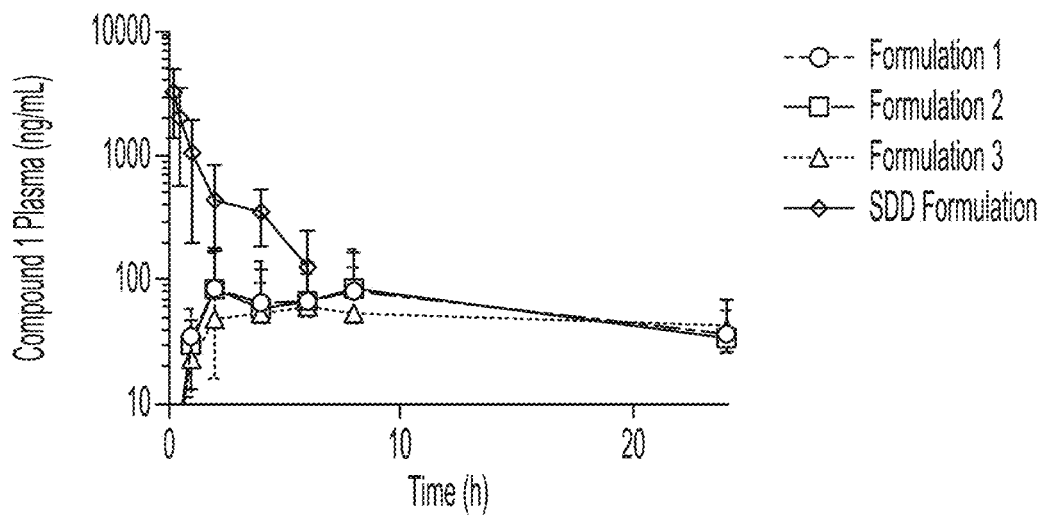
FIG. 60 is a graph showing the exposure (compound 1 plasma concentration in ng/mL over time for 24 hours) of Compound 1 administered non-human primates in different compositions, as described in Example 13.

The formulations were evaluated for pharmacokinetic parameters in monkeys and are shown in FIG. 60. The profiles show that the SDD formulation (Formulation 4) provided a significant enhancement in overall exposure compared to the encapsulated formulations (Formulations 1, 2, and 3). The bioavailability enhancement with the SDD formulation is approximately 50-62%, which is several fold higher compared to the other formulations, at a dose equivalent to 100 mg.

We claim:

1. A method of treating sickle cell disease in a patient, the method comprising repeatedly administering a therapeutically effective amount of Compound 1 to the patient once per day (QD):

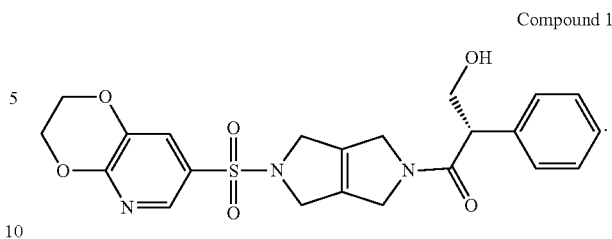

Compound 1

2. The method of claim 1, wherein the patient has a previously confirmed hemoglobin genotype selected from the group consisting of Hgb SS, Hgb Sβ⁺-thalassemia, Hgb Sβ⁰-thalassemia, and Hgb SC.

3. The method of claim 1, wherein the patient has had ≤6 vaso-occlusive crises (VOCs) within the 12 months prior to receiving Compound 1.

4. The method of claim 1, wherein the patient has had no RBC transfusion within 30 days of first receiving Compound 1.

5. The method of claim 1, wherein the patient has received hydroxyurea treatment for at least 90 days prior to first receiving Compound 1.

6. The method of claim 1, wherein the patient has a baseline hemoglobin blood level of 7.0-10.5 g/dL.

7. The method of claim 1, wherein aromatase is not inhibited in the patient.

8. The method of claim 7, wherein the patient is less than 18 years old.

9. A method of treating sickle cell disease in adult patients 18 years of age and older comprising administering to the patient in need thereof a therapeutically effective amount of Compound 1 once daily with or without food:

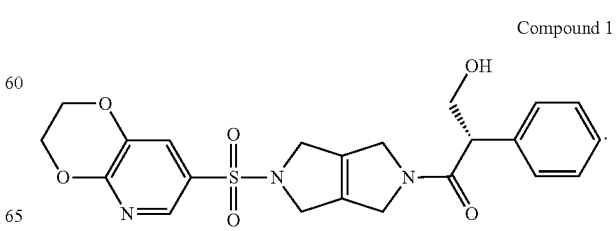

Compound 1

10. The method of claim 9, wherein the Compound 1 is administered as a non-crystalline solid form in a pharmaceutical composition in an oral unit dosage form.

11. The method of claim 10, wherein the oral unit dosage form comprises an active pharmaceutical ingredient consisting of a total of 100 mg or 200 mg of Compound 1.

12. The method of claim 11, wherein the oral unit dosage form further comprises a denucleating agent and the active pharmaceutical ingredient.

13. The method of claim 12, wherein the oral unit dosage form has a total weight of less than 1,000 mg.

14. The method of claim 13, wherein the oral unit dosage form has a total weight of less than 800 mg.

15. The method of claim 14, wherein the total weight of API in the oral unit dosage form is 200 mg.

16. The method of claim 14, wherein the oral unit dosage form comprises up to about 15% by weight of Compound 1.

17. The method of claim 10, wherein the non-crystalline solid form comprises no more than 10% crystalline form detectable by XRPD.

18. The method of claim 17, wherein the oral unit dosage form is a tablet.

19. The method of claim 17, wherein the oral unit dosage form is a capsule.

20. The method of claim 9, wherein the therapeutically effective amount of Compound 1 is selected from the group consisting of 200 mg, 300 mg, 400 mg, and 600 mg.

21. The method of claim 9, wherein the therapeutically effective amount of Compound 1 is 400 mg.

* * * * *